US011787862B2

(12) United States Patent
Sahin et al.

(10) Patent No.: US 11,787,862 B2
(45) Date of Patent: Oct. 17, 2023

(54) BISPECIFIC TRIVALENT ANTIBODIES BINDING TO CLAUDIN6 OR CLAUDIN18.2 AND CD3 FOR TREATMENT OF CLAUDIN EXPRESSING CANCER DISEASES

(71) Applicants: BIONTECH AG, Mainz (DE); Astellas Pharma Inc., Tokyo (JP)

(72) Inventors: Ugur Sahin, Mainz (DE); Christiane Stadler, Bensheim (DE); Leyla Fischer, Gau-Odernheim (DE); Arne Jendretzki, Mainz-Kostheim (DE); Özlem Türeci, Mainz (DE); Fabrice Le Gall, Mainz (DE); Maria Kreuzberg, Aachen (DE)

(73) Assignees: BioNTech SE, Mainz (DE); ASTELLAS PHARMA INC., Tokyo (JP)

( * ) Notice: Subject to any disclaimer, the term of this patent is extended or adjusted under 35 U.S.C. 154(b) by 638 days.

(21) Appl. No.: 16/335,373

(22) PCT Filed: Sep. 20, 2017

(86) PCT No.: PCT/EP2017/073773
§ 371 (c)(1),
(2) Date: Mar. 21, 2019

(87) PCT Pub. No.: WO2018/054973
PCT Pub. Date: Mar. 29, 2018

(65) Prior Publication Data
US 2019/0309067 A1 Oct. 10, 2019

(30) Foreign Application Priority Data
Sep. 23, 2016 (WO) .................. PCT/EP2016/072688

(51) Int. Cl.
| C07K 16/28 | (2006.01) |
| C12N 15/86 | (2006.01) |
| A61P 35/00 | (2006.01) |
| A61K 39/00 | (2006.01) |

(52) U.S. Cl.
CPC .......... *C07K 16/2809* (2013.01); *A61P 35/00* (2018.01); *C07K 16/28* (2013.01); *C12N 15/86* (2013.01); *A61K 2039/505* (2013.01); *A61K 2039/53* (2013.01); *C07K 2317/31* (2013.01); *C07K 2317/35* (2013.01); *C07K 2317/55* (2013.01); *C07K 2317/56* (2013.01); *C07K 2317/622* (2013.01); *C07K 2317/73* (2013.01); *C07K 2317/92* (2013.01); *C07K 2317/94* (2013.01)

(58) Field of Classification Search
CPC .......... C07K 16/2809; C07K 2317/31; C07K 2317/55; C07K 2317/56; C07K 2317/622; C07K 2317/73; A61P 35/00; C12N 15/86
See application file for complete search history.

(56) References Cited

U.S. PATENT DOCUMENTS 10,093,736 B2 * 10/2018 Sahin ................ C07K 16/28
10,717,780 B2 * 7/2020 Sahin ................ C07K 16/2809

FOREIGN PATENT DOCUMENTS

| CN | 1603345 A | 4/2005 |
| CN | 105073776 A | 11/2015 |
| WO | 2014075788 A1 | 5/2014 |
| WO | WO 2014/075697 A1 | 5/2014 |
| WO | WO 2014/075788 A1 | 5/2014 |
| WO | WO 2015/113576 A1 | 8/2015 |
| WO | WO 2016/020444 A1 | 2/2016 |
| WO | WO 2016/087416 A1 | 6/2016 |
| WO | WO 2016/097408 A1 | 6/2016 |
| WO | WO 2016/135239 A1 | 9/2016 |

OTHER PUBLICATIONS

Malia et al, Proteins, 2016, 84:427-434. (Year: 2016).*
Barthelemy et al, Journal of Biological Chemistry, 2008, 283:3639-3654. (Year: 2008).*
Beiboer et al., Journal of Molecular Biology, 2000, 296:833-849. (Year: 2000).*
Choi et al, 2011, Molecular Biosystems, 2011, 7:3327-3334. (Year: 2011).*
De Genst et al, Developmental and Comparative Immunology, 2006, 30:187-98. (Year: 2006).*
Griffiths et al, The EMBO Journal, 1993, 12:725-734. (Year: 1993).*
Klimka et al, British Journal of Cancer, 2000, 83:252-260. (Year: 2000).*
Ward et al, Nature, 1989, 341:544-546. (Year: 1989).*
Mertens, N., Bispecific Antibodies, 2011, pp. 135-149.
Berensmeier, *Appl. Microbiol. Biotechnol.*, 73: 495-504 (2006).
Coligan, John E.; Bierer, Barbara E.; Margulies, David H.; Shevach, Ethan M.; Strober, Warren (2001a): Current Protocols in Immunology. Hoboken, NJ, USA: John Wiley & Sons, Inc.
Coligan, John E.; Dunn, Ben M.; Speicher, David W.; Wingfield, Paul T. (2001b): Current Protocols in Protein Science. Hoboken, NJ, USA: John Wiley & Sons, Inc.
Gallie et al., *Gene*, 165: 233-238 (1995).
Grudzien-Nogalska et al., *Methods in Molecular Biology*, 969: 55-72 (2013).

(Continued)

*Primary Examiner* — Meera Natarajan
*Assistant Examiner* — Cheom-Gil Cheong
(74) *Attorney, Agent, or Firm* — Neal, Gerber & Eisenberg LLP

(57) ABSTRACT

The present invention provides binding agents comprising at least three binding domains, wherein a first binding domain binds to a T cell-specific antigen and a second binding domain and a third binding domain bind to a claudin, and methods of using these binding agents or nucleic acids encoding therefor for treating cancer.

32 Claims, 39 Drawing Sheets
Specification includes a Sequence Listing.

(56) References Cited

OTHER PUBLICATIONS

Holtkamp et al., *Blood*, 108: 4009-4017 (2006).
Kuhn et al., *Gene Therapy*, 1-11 (2010).
Lanzavecchia et al., *Eur. J. Immunol.*, 17: 105-111 (1987).
Lutterbuese et al., *PNAS*, 107 (28): 12605-12610 (2010).
Rothlisberger et al., *J. Mol. Biol.*, 347: 773-789 (2005).
Weingarten-Gabbay et al., *Science*, 351 (6270): aad4939-1 to aad4939-13 (2016).
Woll et al., *International Journal of Cancer*, 134: 731-739 (2014).
Zeenko et al., *The Journal of Biological Chemistry*, 280 (29): 26813-26824 (2005).
Diamond et al., *Proc. Natl. Acad. Sci.*, 81: 5841-5844 (1984).
Finkelstein, *Protein Physics*, 524: 23 (2012).
Ohno et al., *Proc. Natl. Acad. Sci.*, 82: 2945-2949 (1985).
Rudikoff et al., *Proc. Natl. Acad. Sci.*, 79: 1979-1983 (1982).
Viola et al., *Expert Opin. Drug Deliv.*, 7(6): 721-735 (2010).
Yarilin, *Principals of Immunology*, 172-174 (1999).
The International Bureau of WIPO, Notification Concerning Transmittal of International Preliminary Report on Patentability in International Application No. PCT/EP2017/073773 (dated Apr. 4, 2019).
Shen et al., *Molecular Aspects of Medicine*, 34(1):39-58 (2013).
Stadler et al., *Oncoimmunology*, 5(3) e1091555 (12 pages) (2016).
European Patent Office, International Search Report in International Application No. PCT/EP2017/073773 (dated Nov. 29, 2017).
European Patent Office, Written Opinion of The International Searching Authority in International Application No. PCT/EP2017/073773 (dated Nov. 29, 2017).
Ching Chen et al., Enhancement and destruction of antibody function by somatic mutation: unequal occurrence is controlled by V gene combinatorial associations, The EMBO Journal, vol. 14, No. 12, pp. 2784-2794, 1995.
Pakula A. A. et al., Genetic analysis of protein stability and function. Annu. Rev. Genet., 1989 n 23, pp. 289-310.
Schoonjans R. et al., Fab Chains As an Efficient Heterodimerization Scaffold for the Production of Recombinant Bispecific and Trispecific Antibody Derivatives. J. Immunol., 2000, 165, pp. 7050-7057.

* cited by examiner

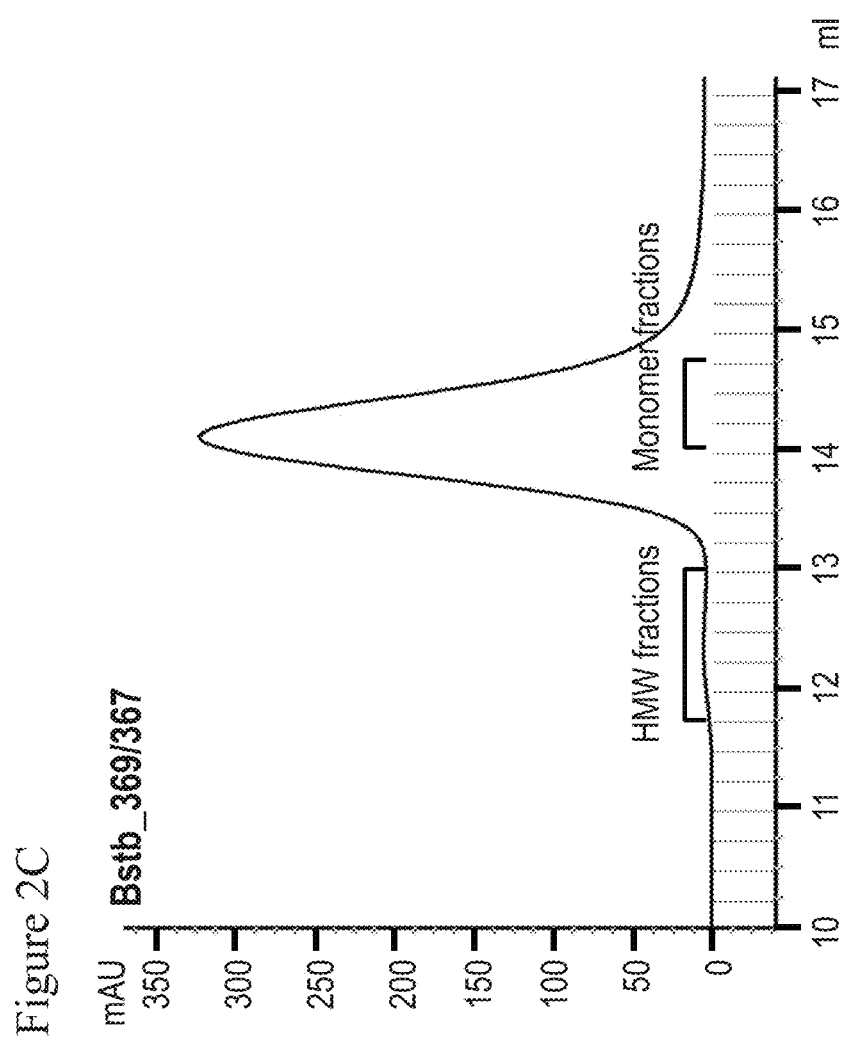

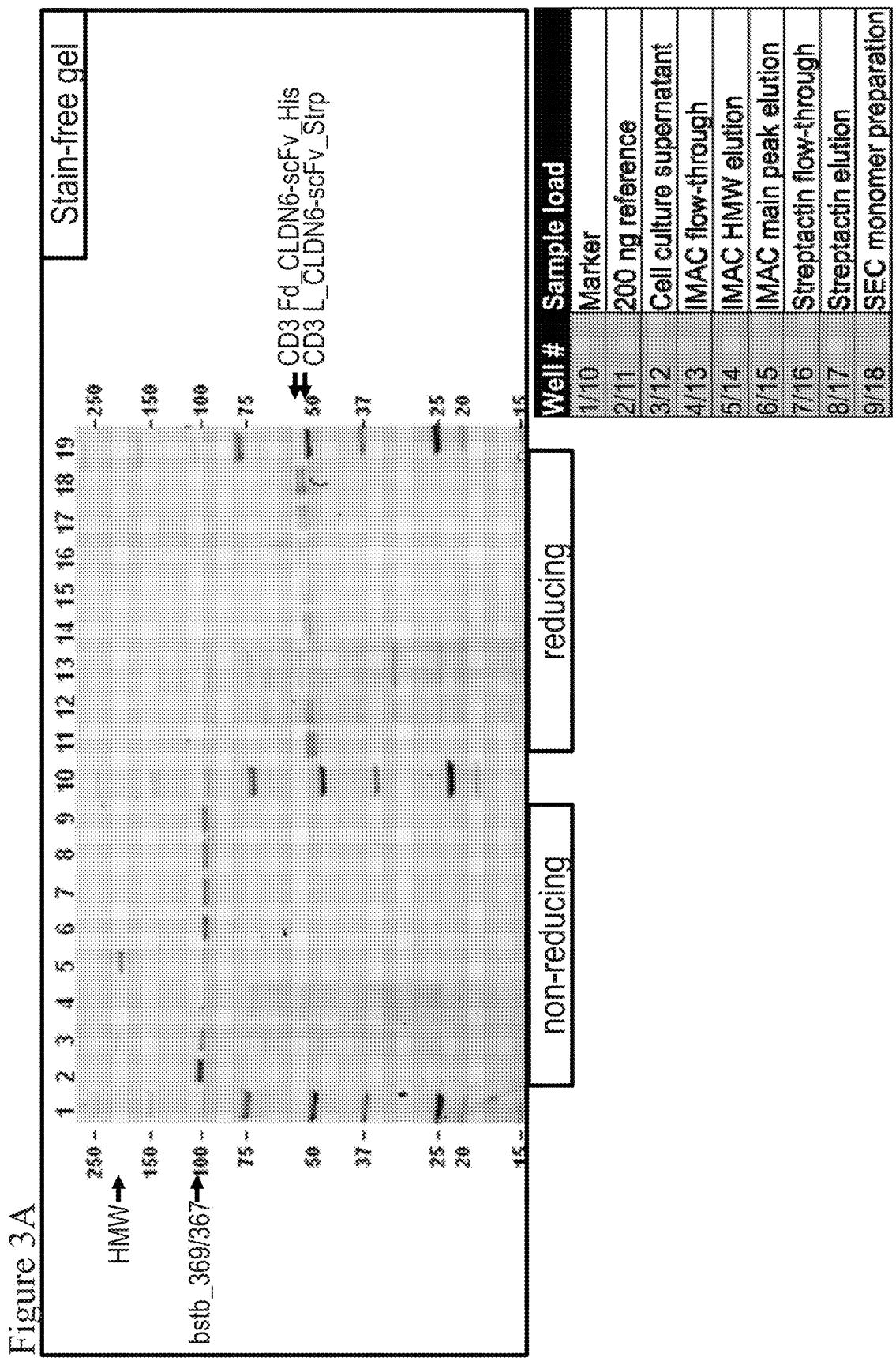

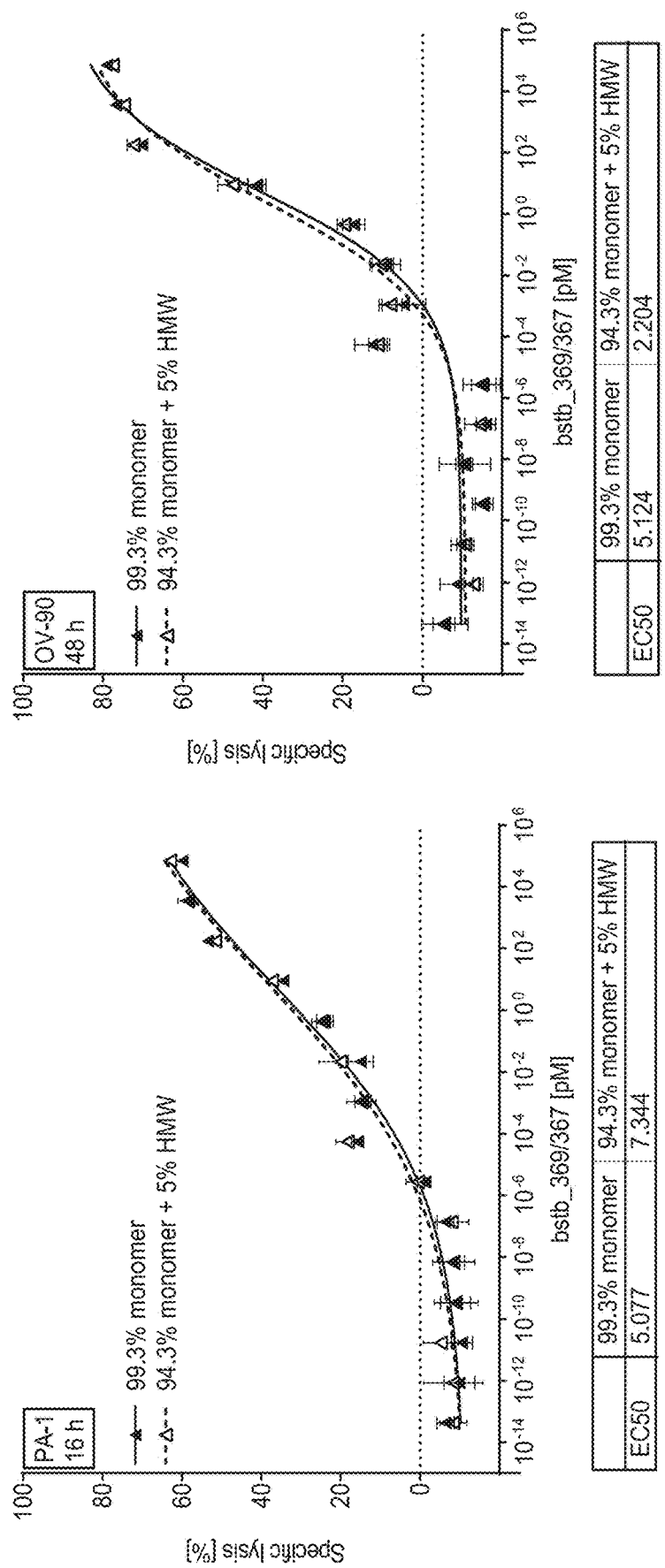

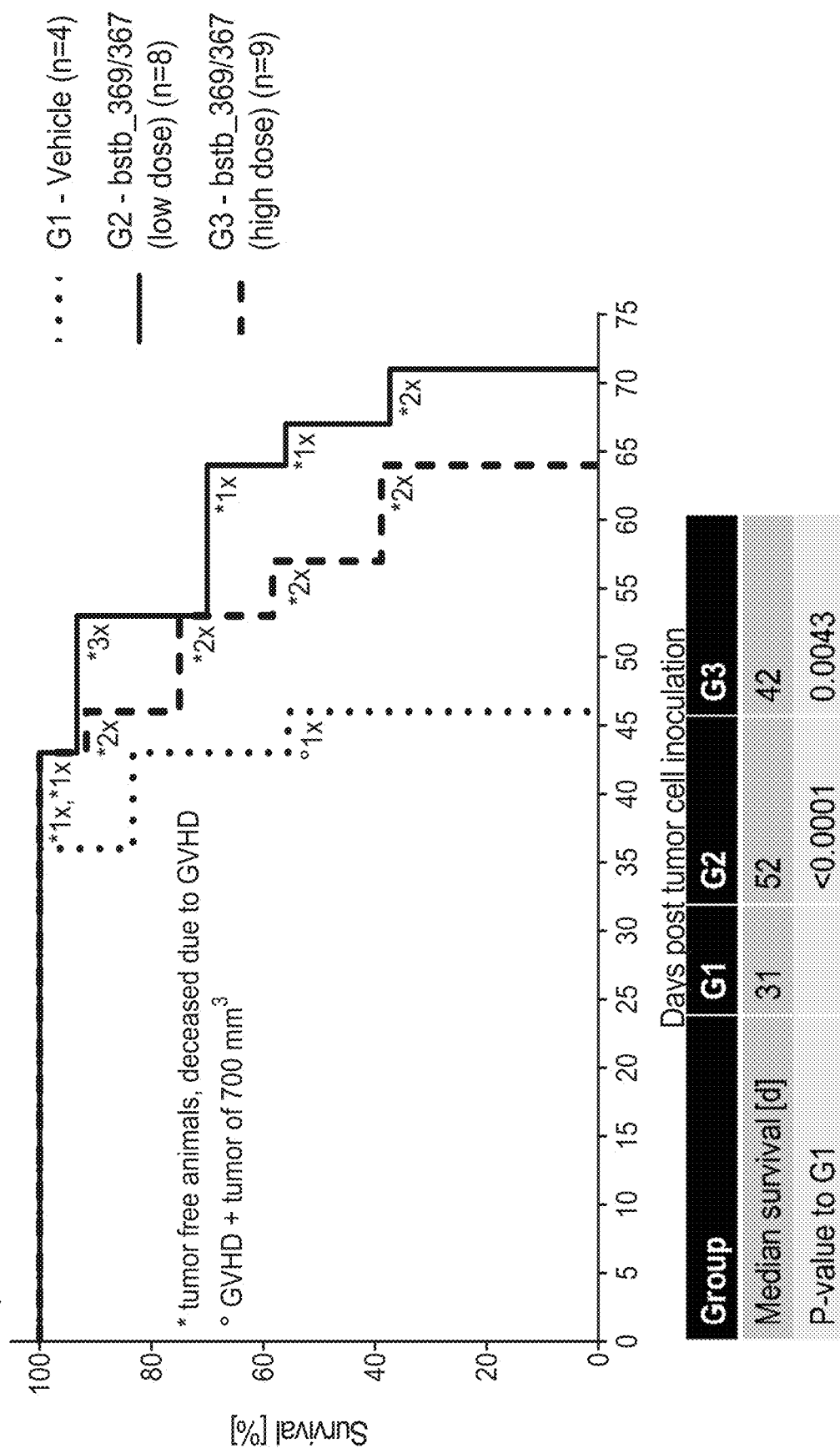

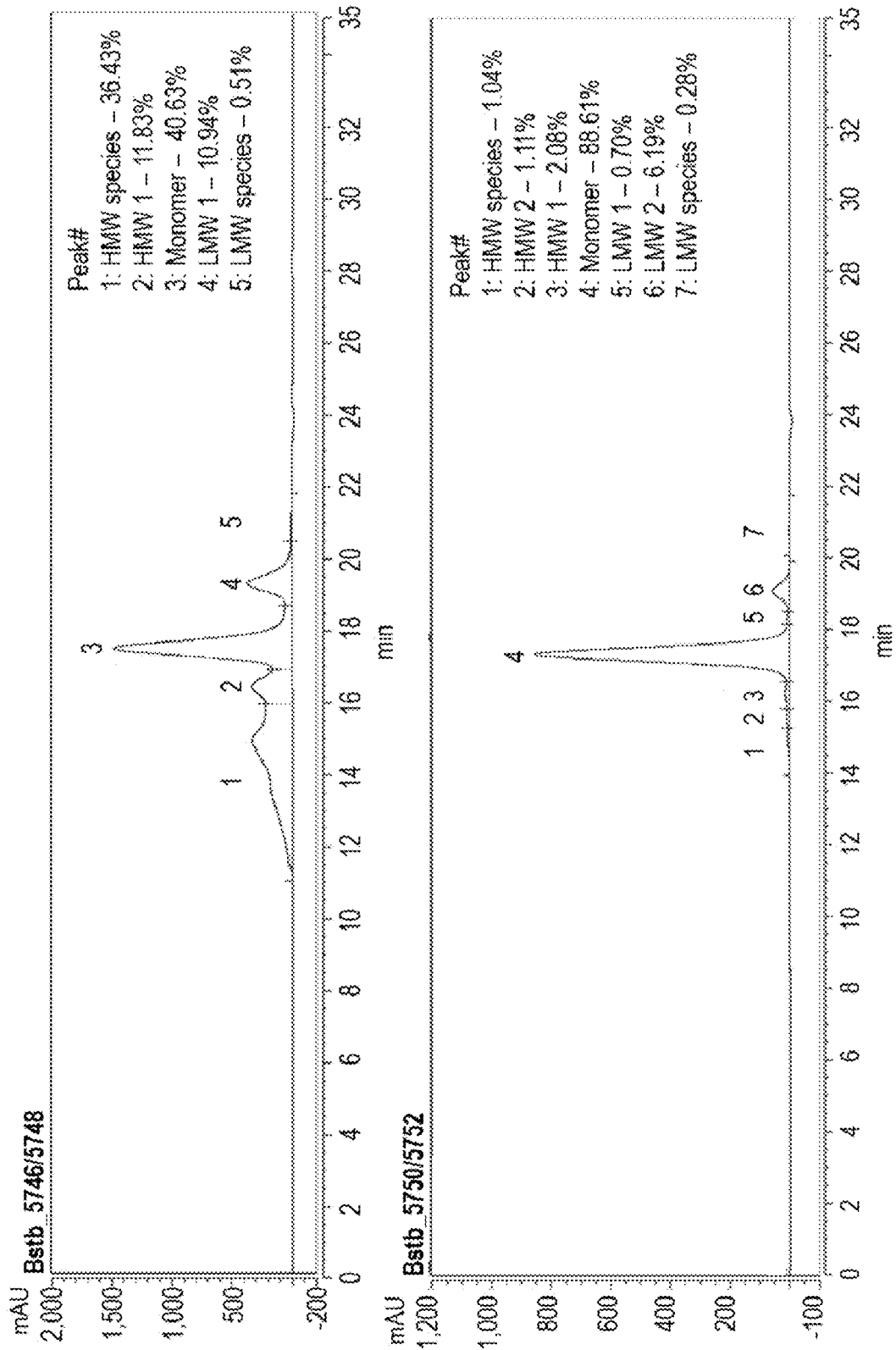

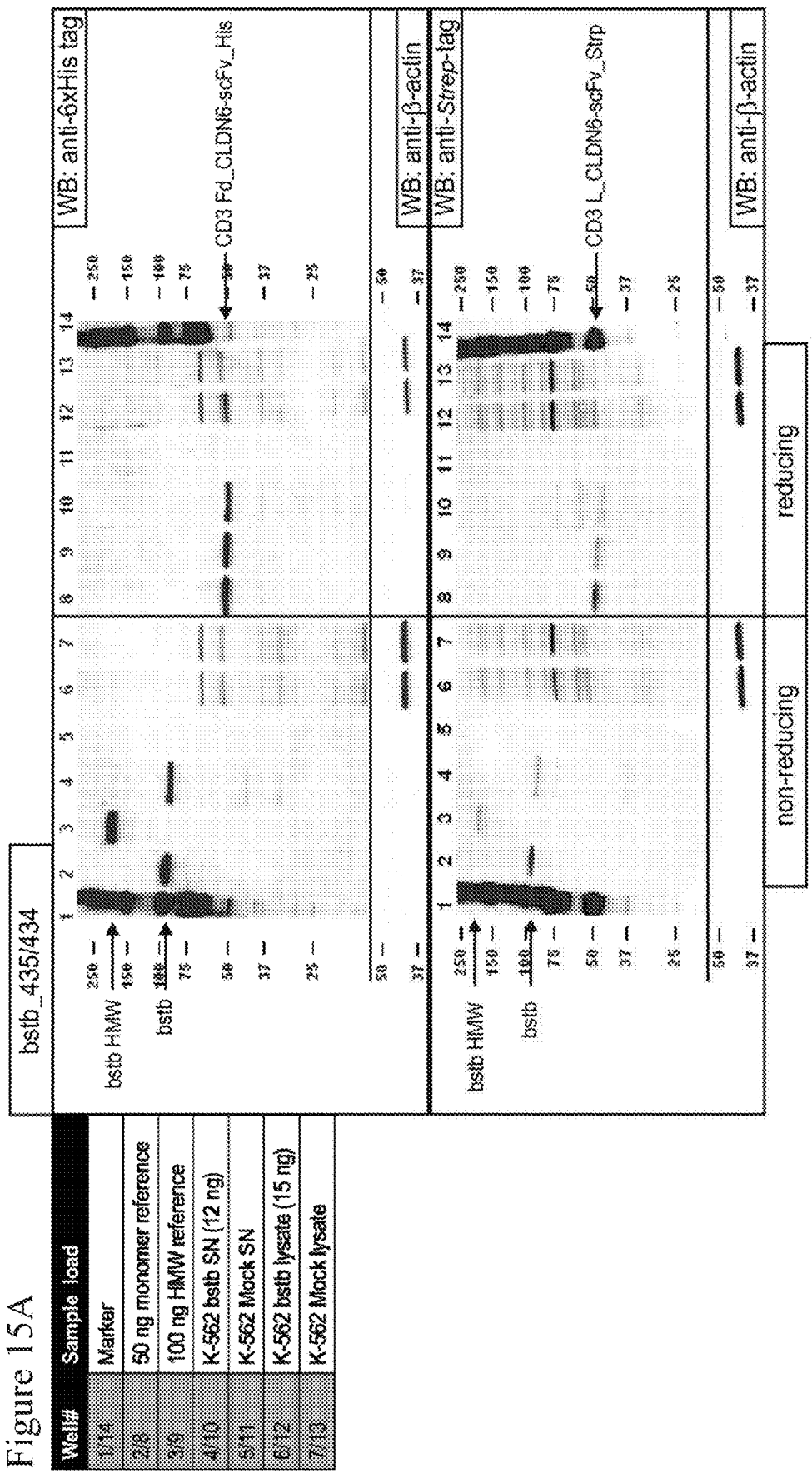

Figure 18A

Anti-TAA

| | FR1-IMGT (1-26) | | | | | CDR1-IMGT (27-38) | FR2-IMGT (39-55) | | CDR2-IMGT (56-65) | | FR3-IMGT (66-104) | | | | | | CDR3-IMGT (105-117) | | FR4-IMGT (118-128) | |
|---|---|---|---|---|---|---|---|---|---|---|---|---|---|---|---|---|---|---|---|---|
| | A | B | | | | BC | C | C' | C'C" | C" | | D | | E | F | | FG | | G | |
| | 1...5....10...15...16...23 26 | | | | | 27....38 | 39 41 46 47 | 55 | 56 | 65 | 66 | 74 75 | 84 85 | 89 | 96 97 | 104 | 105 | 117 | 118 | 128 |
| 1 | EVQLQQSGP.ELVKP.GASMKISCKAS | | | | | GYSF....TGYT | MNWVKQSH.GKCLEWIGL | | INFY..NGGT | | IYNQKFK.G | KATLTVDKSS | STAYMELLSLTS | | EDSAVYYC | | ARDYG...FVLDY | | WGQGTTLTVSS | |
| 2 | QIVLTQSPSIMSVSP.GEKVTITCSAS | | | | | SSV......SY | MRWFQQKP.GTSPKLWIY | | ST......S | | NLASGVP.A | RFSGRG..SG | TSYSLTISRVAA | | EDAATYYC | | QQRSN...YPPWT | | FGCGTKLEIK | |
| 3 | QVQLQQPGA.ELVRP.GASVKLSCKAS | | | | | GYTF....TSYW | INWVKQRP.SQGLEWIGN | | IYPS..DSYT | | NYNQKFK.D | KATLTVDKSS | STAYMQLSSPTS | | EDSAVYYC | | TRSWRG..NSFDY | | WGQGTTLTVSS | |
| 4 | QVQLQQPGA.ELVRP.GASVRLSCKAS | | | | | GYTF....TSYW | GQCLEWIGN | | IYPS..DSYT | | NYNQKFK.D | KATLTVDKSS | STAYMQLSSPTS | | EDSAVYYC | | TRSWRG..NSFDY | | WGQGTTLTVSS | |
| 5 | DIVMTQSPSSLTVTA.GEKVTMSCKSS | | | | | QSLLNSGNQKNY | LTWYQQKP.GQPPKLLIY | | WA......S | | TRESGVP.D | RFTGSG..SG | TDFTLTISSVQA | | EDLAVYYC | | QNDYS...YPFT | | FGSGTRLEIK | |
| 6 | DIVMHQSPSSLTVTA.GEKVTMSCKSS | | | | | QSLLNSGNQRNY | LTWYQQKP.GQPPKLLIY | | WA......S | | HRESGVP.D | RFTGSG..SG | TDFTLTISSVQA | | EDLAVYYC | | QNDYS...YPFT | | FGCGTKLEIK | |

Domain
1: VH (IMAB206 (N49C), IMAB027 (N49C)) SEQ ID NO: 8
2: VL (IMAB206 (C53W,G126C)) SEQ ID NO: 10
3: VH (IMAB362) SEQ ID NO: 20
4: VH (IMAB362 (G49C)) SEQ ID NO: 21
5: VL (IMAB362) SEQ ID NO: 22
6: VL (IMAB362 (S12GC)) SEQ ID NO: 23

Anti-CD3

SEQUENCE LISTING

```
<160> NUMBER OF SEQ ID NOS: 101

<210> SEQ ID NO 1
<211> LENGTH: 261
<212> TYPE: PRT
<213> ORGANISM: Homo sapiens

<400> SEQUENCE: 1

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60
```

```
Gly Tyr Phe Thr Leu Leu Gly Leu Pro Ala Met Leu Gln Ala Val Arg
 65                  70                  75                  80

Ala Leu Met Ile Val Gly Ile Val Leu Gly Ala Ile Gly Leu Leu Val
                 85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 2
<211> LENGTH: 220
<212> TYPE: PRT
<213> ORGANISM: Homo sapiens

<400> SEQUENCE: 2

Met Ala Ser Ala Gly Met Gln Ile Leu Gly Val Val Leu Thr Leu Leu
 1               5                  10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
        50                  55                  60

Lys Val Tyr Asp Ser Leu Leu Ala Leu Pro Gln Asp Leu Gln Ala Ala
 65                 70                  75                  80

Arg Ala Leu Cys Val Ile Ala Leu Leu Val Ala Leu Phe Gly Leu Leu
                 85                 90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Ile Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
```

```
                165                 170                 175
Gly Gly Gly Leu Leu Cys Cys Thr Cys Pro Ser Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220

<210> SEQ ID NO 3
<211> LENGTH: 220
<212> TYPE: PRT
<213> ORGANISM: Homo sapiens

<400> SEQUENCE: 3

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Val Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220

<210> SEQ ID NO 4
<211> LENGTH: 207
<212> TYPE: PRT
<213> ORGANISM: Homo sapiens

<400> SEQUENCE: 4

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
```

```
                    50                  55                  60
Asn Ile Gly Gly Asp Glu Asp Lys Asn Ile Gly Ser Asp Glu Asp
 65                  70                  75                  80

His Leu Ser Leu Lys Glu Phe Ser Glu Leu Glu Gln Ser Gly Tyr Tyr
                 85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
        130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 5
<211> LENGTH: 119
<212> TYPE: PRT
<213> ORGANISM: Artificial Sequence
<220> FEATURE:
<223> OTHER INFORMATION: Antibody-derived sequence

<400> SEQUENCE: 5

Gln Val Gln Leu Gln Gln Ser Gly Ala Glu Leu Ala Arg Pro Gly Ala
 1               5                  10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
                100                 105                 110

Thr Thr Leu Thr Val Ser Ser
        115

<210> SEQ ID NO 6
<211> LENGTH: 106
<212> TYPE: PRT
<213> ORGANISM: Artificial Sequence
<220> FEATURE:
<223> OTHER INFORMATION: Antibody-derived sequence

<400> SEQUENCE: 6

Gln Ile Val Leu Thr Gln Ser Pro Ala Ile Met Ser Ala Ser Pro Gly
 1               5                  10                  15

Glu Lys Val Thr Met Thr Cys Arg Ala Ser Ser Ser Val Ser Tyr Met
                20                  25                  30
```

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys
            100                 105

<210> SEQ ID NO 7
<211> LENGTH: 117
<212> TYPE: PRT
<213> ORGANISM: Artificial Sequence
<220> FEATURE:
<223> OTHER INFORMATION: Antibody-derived sequence

<400> SEQUENCE: 7

Glu Val Gln Leu Gln Gln Ser Gly Pro Glu Leu Val Lys Pro Gly Ala
 1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Ile Tyr Asn Gln Lys Phe
     50                  55                  60

Lys Gly Lys Ala Thr Leu Thr Val Asp Lys Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Asp Tyr Gly Phe Val Leu Asp Tyr Trp Gly Gln Gly Thr Thr
            100                 105                 110

Leu Thr Val Ser Ser
        115

<210> SEQ ID NO 8
<211> LENGTH: 117
<212> TYPE: PRT
<213> ORGANISM: Artificial Sequence
<220> FEATURE:
<223> OTHER INFORMATION: Antibody-derived sequence

<400> SEQUENCE: 8

Glu Val Gln Leu Gln Gln Ser Gly Pro Glu Leu Val Lys Pro Gly Ala
 1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Cys Leu Glu Trp Ile
            35                  40                  45

Gly Leu Ile Asn Pro Tyr Asn Gly Gly Thr Ile Tyr Asn Gln Lys Phe
     50                  55                  60

Lys Gly Lys Ala Thr Leu Thr Val Asp Lys Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Asp Tyr Gly Phe Val Leu Asp Tyr Trp Gly Gln Gly Thr Thr
            100                 105                 110

Leu Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Antibody-derived sequence

<400> SEQUENCE: 9

Gln Ile Val Leu Thr Gln Ser Pro Ser Ile Met Ser Val Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Cys Ile Tyr
        35                  40                  45

Ser Thr Ser Asn Leu Ala Ser Gly Val Pro Ala Arg Phe Ser Gly Arg
    50                  55                  60

Gly Ser Gly Thr Ser Tyr Ser Leu Thr Ile Ser Arg Val Ala Ala Glu
65                  70                  75                  80

Asp Ala Ala Thr Tyr Tyr Cys Gln Gln Arg Ser Asn Tyr Pro Pro Trp
                85                  90                  95

Thr Phe Gly Gly Gly Thr Lys Leu Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Antibody-derived sequence

<400> SEQUENCE: 10

Gln Ile Val Leu Thr Gln Ser Pro Ser Ile Met Ser Val Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Arg
    50                  55                  60

Gly Ser Gly Thr Ser Tyr Ser Leu Thr Ile Ser Arg Val Ala Ala Glu
65                  70                  75                  80

Asp Ala Ala Thr Tyr Tyr Cys Gln Gln Arg Ser Asn Tyr Pro Pro Trp
                85                  90                  95

Thr Phe Gly Cys Gly Thr Lys Leu Glu Ile Lys
            100                 105

<210> SEQ ID NO 11
<211> LENGTH: 117
<212> TYPE: PRT
<213> ORGANISM: Artificial Sequence
<220> FEATURE:
<223> OTHER INFORMATION: Antibody-derived sequence

<400> SEQUENCE: 11

Glu Val Gln Leu Gln Gln Ser Gly Pro Glu Leu Val Lys Pro Gly Ala
1               5                   10                  15

```
Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Lys Phe
    50                  55                  60

Lys Gly Lys Ala Thr Leu Thr Ile Asp Lys Ser Ser Thr Ala Tyr
65                  70                  75                  80

Met Glu Leu Leu Ser Leu Thr Ser Glu Asp Ser Ala Val Tyr Tyr Cys
            85                  90                  95

Ala Arg Asp Tyr Gly Tyr Val Leu Asp Tyr Trp Gly Gln Gly Thr Thr
            100                 105                 110

Leu Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: Antibody-derived sequence

<400> SEQUENCE: 12

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Leu
            20                  25                  30

His Trp Phe Gln Gln Lys Pro Gly Thr Ser Pro Lys Leu Trp Val Tyr
        35                  40                  45

Ser Thr Ser Asn Leu Pro Ser Gly Val Pro Ala Arg Phe Gly Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ile Tyr Pro Pro Trp
            85                  90                  95

Thr Phe Gly Gly Gly Thr Lys Leu Glu Ile Lys
            100                 105

<210> SEQ ID NO 13
<211> LENGTH: 244
<212> TYPE: PRT
<213> ORGANISM: Artificial Sequence
<220> FEATURE:
<223> OTHER INFORMATION: Antibody-derived sequence

<400> SEQUENCE: 13

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Cys Leu Glu Trp Ile
        35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
            85                  90                  95
```

```
Ala Arg Asp Tyr Gly Phe Val Leu Asp Tyr Trp Gly Gln Gly Thr Thr
            100                 105                 110

Leu Thr Val Ser Ser Gly Gly Gly Ser Gly Gly Gly Gly Ser Gly
            115                 120                 125

Gly Gly Gly Ser Gly Gly Gly Ser Gln Ile Val Leu Thr Gln Ser
            130                 135                 140

Pro Ser Ile Met Ser Val Ser Pro Gly Glu Lys Val Thr Ile Thr Cys
145                 150                 155                 160

Ser Ala Ser Ser Ser Val Ser Tyr Met His Trp Phe Gln Gln Lys Pro
                165                 170                 175

Gly Thr Ser Pro Lys Leu Trp Ile Tyr Ser Thr Ser Asn Leu Ala Ser
            180                 185                 190

Gly Val Pro Ala Arg Phe Ser Gly Arg Gly Ser Gly Thr Ser Tyr Ser
            195                 200                 205

Leu Thr Ile Ser Arg Val Ala Ala Glu Asp Ala Ala Thr Tyr Tyr Cys
            210                 215                 220

Gln Gln Arg Ser Asn Tyr Pro Pro Trp Thr Phe Gly Cys Gly Thr Lys
225                 230                 235                 240

Leu Glu Ile Lys

<210> SEQ ID NO 14
<211> LENGTH: 493
<212> TYPE: PRT
<213> ORGANISM: Artificial Sequence
<220> FEATURE:
<223> OTHER INFORMATION: Antibody-derived sequence

<400> SEQUENCE: 14

Gln Val Gln Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205
```

Ser Asn Thr Lys Val Asp Lys Arg Val Glu Pro Lys Ser Cys Ser Gly
    210                 215                 220

Pro Gly Gly Gly Arg Ser Gly Gly Gly Ser Gly Gly Gly Gly Ser
225                 230                 235                 240

Glu Val Gln Leu Gln Gln Ser Gly Pro Glu Leu Val Lys Pro Gly Ala
                    245                 250                 255

Ser Met Lys Ile Ser Cys Lys Ala Ser Gly Tyr Ser Phe Thr Gly Tyr
                260                 265                 270

Thr Met Asn Trp Val Lys Gln Ser His Gly Lys Cys Leu Glu Trp Ile
            275                 280                 285

Gly Leu Ile Asn Pro Tyr Asn Gly Gly Thr Ile Tyr Asn Gln Lys Phe
290                 295                 300

Lys Gly Lys Ala Thr Leu Thr Val Asp Lys Ser Ser Ser Thr Ala Tyr
305                 310                 315                 320

Met Glu Leu Leu Ser Leu Thr Ser Glu Asp Ser Ala Val Tyr Tyr Cys
                325                 330                 335

Ala Arg Asp Tyr Gly Phe Val Leu Asp Tyr Trp Gly Gln Gly Thr Thr
                340                 345                 350

Leu Thr Val Ser Ser Gly Gly Gly Gly Ser Gly Gly Gly Gly Ser Gly
            355                 360                 365

Gly Gly Ser Gly Gly Gly Gly Ser Gln Ile Val Leu Thr Gln Ser
370                 375                 380

Pro Ser Ile Met Ser Val Ser Pro Gly Glu Lys Val Thr Ile Thr Cys
385                 390                 395                 400

Ser Ala Ser Ser Ser Val Ser Tyr Met His Trp Phe Gln Gln Lys Pro
                405                 410                 415

Gly Thr Ser Pro Lys Leu Trp Ile Tyr Ser Thr Ser Asn Leu Ala Ser
                420                 425                 430

Gly Val Pro Ala Arg Phe Ser Gly Arg Gly Ser Gly Thr Ser Tyr Ser
                435                 440                 445

Leu Thr Ile Ser Arg Val Ala Ala Glu Asp Ala Ala Thr Tyr Tyr Cys
            450                 455                 460

Gln Gln Arg Ser Asn Tyr Pro Pro Trp Thr Phe Gly Cys Gly Thr Lys
465                 470                 475                 480

Leu Glu Ile Lys Gly Gly Ser His His His His His His
                485                 490

<210> SEQ ID NO 15
<211> LENGTH: 493
<212> TYPE: PRT
<213> ORGANISM: Artificial Sequence
<220> FEATURE:
<223> OTHER INFORMATION: Antibody-derived sequence

<400> SEQUENCE: 15

Gln Val Gln Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

-continued

```
Met Gln Leu Ser Ser Leu Thr Ser Glu Asp Ser Ala Val Tyr Tyr Cys
                85                  90                  95
Ala Arg Tyr Tyr Asp Asp His Tyr Ser Leu Asp Tyr Trp Gly Gln Gly
            100                 105                 110
Thr Thr Leu Thr Val Ser Ser Ala Ser Thr Lys Gly Pro Ser Val Phe
        115                 120                 125
Pro Leu Ala Pro Cys Ser Lys Ser Thr Ser Glu Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Asn Phe Gly Thr Gln Thr Tyr Thr Cys Asn Val Asp His Lys Pro
        195                 200                 205
Ser Asn Thr Lys Val Asp Lys Thr Val Glu Pro Lys Ser Ala Ser Gly
    210                 215                 220
Pro Gly Gly Gly Arg Ser Gly Gly Gly Ser Gly Gly Gly Gly Ser
225                 230                 235                 240
Glu Val Gln Leu Gln Gln Ser Gly Pro Glu Leu Val Lys Pro Gly Ala
                245                 250                 255
Ser Met Lys Ile Ser Cys Lys Ala Ser Gly Tyr Ser Phe Thr Gly Tyr
            260                 265                 270
Thr Met Asn Trp Val Lys Gln Ser His Gly Lys Cys Leu Glu Trp Ile
        275                 280                 285
Gly Leu Ile Asn Pro Tyr Asn Gly Gly Thr Ile Tyr Asn Gln Lys Phe
    290                 295                 300
Lys Gly Lys Ala Thr Leu Thr Val Asp Lys Ser Ser Ser Thr Ala Tyr
305                 310                 315                 320
Met Glu Leu Leu Ser Leu Thr Ser Glu Asp Ser Ala Val Tyr Tyr Cys
                325                 330                 335
Ala Arg Asp Tyr Gly Phe Val Leu Asp Tyr Trp Gly Gln Gly Thr Thr
            340                 345                 350
Leu Thr Val Ser Ser Gly Gly Gly Gly Ser Gly Gly Gly Gly Ser Gly
        355                 360                 365
Gly Gly Gly Ser Gly Gly Gly Gly Ser Gln Ile Val Leu Thr Gln Ser
    370                 375                 380
Pro Ser Ile Met Ser Val Ser Pro Gly Glu Lys Val Thr Ile Thr Cys
385                 390                 395                 400
Ser Ala Ser Ser Ser Val Ser Tyr Met His Trp Phe Gln Gln Lys Pro
                405                 410                 415
Gly Thr Ser Pro Lys Leu Trp Ile Tyr Ser Thr Ser Asn Leu Ala Ser
            420                 425                 430
Gly Val Pro Ala Arg Phe Ser Gly Arg Gly Ser Gly Thr Ser Tyr Ser
        435                 440                 445
Leu Thr Ile Ser Arg Val Ala Ala Glu Asp Ala Ala Thr Tyr Tyr Cys
    450                 455                 460
Gln Gln Arg Ser Asn Tyr Pro Pro Trp Thr Phe Gly Cys Gly Thr Lys
465                 470                 475                 480
Leu Glu Ile Lys Gly Gly Ser His His His His His His
                485                 490
```

```
<210> SEQ ID NO 16
<211> LENGTH: 473
<212> TYPE: PRT
<213> ORGANISM: Artificial Sequence
<220> FEATURE:
<223> OTHER INFORMATION: Antibody-derived sequence

<400> SEQUENCE: 16
```

Gln Ile Val Leu Thr Gln Ser Pro Ala Ile Met Ser Ala Ser Pro Gly
1               5                   10                  15

Glu Lys Val Thr Met Thr Cys Arg Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Asp Val Pro Gly Gly Ser Glu Val Gln Leu Gln
    210                 215                 220

Gln Ser Gly Pro Glu Leu Val Lys Pro Gly Ala Ser Met Lys Ile Ser
225                 230                 235                 240

Cys Lys Ala Ser Gly Tyr Ser Phe Thr Gly Tyr Thr Met Asn Trp Val
                245                 250                 255

Lys Gln Ser His Gly Lys Cys Leu Glu Trp Ile Gly Leu Ile Asn Pro
            260                 265                 270

Tyr Asn Gly Gly Thr Ile Tyr Asn Gln Lys Phe Lys Gly Lys Ala Thr
        275                 280                 285

Leu Thr Val Asp Lys Ser Ser Ser Thr Ala Tyr Met Glu Leu Leu Ser
    290                 295                 300

Leu Thr Ser Glu Asp Ser Ala Val Tyr Tyr Cys Ala Arg Asp Tyr Gly
305                 310                 315                 320

Phe Val Leu Asp Tyr Trp Gly Gln Gly Thr Thr Leu Thr Val Ser Ser
                325                 330                 335

Gly Gly Gly Gly Ser Gly Gly Gly Ser Gly Gly Gly Gly Ser Gly
            340                 345                 350

Gly Gly Gly Ser Gln Ile Val Leu Thr Gln Ser Pro Ser Ile Met Ser
        355                 360                 365

Val Ser Pro Gly Glu Lys Val Thr Ile Thr Cys Ser Ala Ser Ser Ser

```
                 370                 375                 380
Val Ser Tyr Met His Trp Phe Gln Gln Lys Pro Gly Thr Ser Pro Lys
385                 390                 395                 400

Leu Trp Ile Tyr Ser Thr Ser Asn Leu Ala Ser Gly Val Pro Ala Arg
                405                 410                 415

Phe Ser Gly Arg Gly Ser Gly Thr Ser Tyr Ser Leu Thr Ile Ser Arg
            420                 425                 430

Val Ala Ala Glu Asp Ala Ala Thr Tyr Tyr Cys Gln Gln Arg Ser Asn
        435                 440                 445

Tyr Pro Pro Trp Thr Phe Gly Cys Gly Thr Lys Leu Glu Ile Lys Ser
    450                 455                 460

Ala Trp Ser His Pro Gln Phe Glu Lys
465                 470

<210> SEQ ID NO 17
<211> LENGTH: 484
<212> TYPE: PRT
<213> ORGANISM: Artificial Sequence
<220> FEATURE:
<223> OTHER INFORMATION: Antibody-derived sequence

<400> SEQUENCE: 17

Gln Val Gln Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Ser Gly
    210                 215                 220

Pro Gly Gly Gly Arg Ser Gly Gly Gly Gly Ser Gly Gly Gly Gly Ser
225                 230                 235                 240

Glu Val Gln Leu Gln Gln Ser Gly Pro Glu Leu Val Lys Pro Gly Ala
                245                 250                 255

Ser Met Lys Ile Ser Cys Lys Ala Ser Gly Tyr Ser Phe Thr Gly Tyr
```

-continued

```
                260                 265                 270
Thr Met Asn Trp Val Lys Gln Ser His Gly Lys Cys Leu Glu Trp Ile
        275                 280                 285
Gly Leu Ile Asn Pro Tyr Asn Gly Gly Thr Ile Tyr Asn Gln Lys Phe
        290                 295                 300
Lys Gly Lys Ala Thr Leu Thr Val Asp Lys Ser Ser Ser Thr Ala Tyr
305                 310                 315                 320
Met Glu Leu Leu Ser Leu Thr Ser Glu Asp Ser Ala Val Tyr Tyr Cys
                325                 330                 335
Ala Arg Asp Tyr Gly Phe Val Leu Asp Tyr Trp Gly Gln Gly Thr Thr
                340                 345                 350
Leu Thr Val Ser Ser Gly Gly Gly Ser Gly Gly Gly Ser Gly
                355                 360                 365
Gly Gly Gly Ser Gly Gly Gly Ser Gln Ile Val Leu Thr Gln Ser
        370                 375                 380
Pro Ser Ile Met Ser Val Ser Pro Gly Glu Lys Val Thr Ile Thr Cys
385                 390                 395                 400
Ser Ala Ser Ser Ser Val Ser Tyr Met His Trp Phe Gln Gln Lys Pro
                405                 410                 415
Gly Thr Ser Pro Lys Leu Trp Ile Tyr Ser Thr Ser Asn Leu Ala Ser
                420                 425                 430
Gly Val Pro Ala Arg Phe Ser Gly Arg Gly Ser Gly Thr Ser Tyr Ser
                435                 440                 445
Leu Thr Ile Ser Arg Val Ala Ala Glu Asp Ala Ala Thr Tyr Tyr Cys
                450                 455                 460
Gln Gln Arg Ser Asn Tyr Pro Pro Trp Thr Phe Gly Cys Gly Thr Lys
465                 470                 475                 480
Leu Glu Ile Lys

<210> SEQ ID NO 18
<211> LENGTH: 484
<212> TYPE: PRT
<213> ORGANISM: Artificial Sequence
<220> FEATURE:
<223> OTHER INFORMATION: Antibody-derived sequence

<400> SEQUENCE: 18

Gln Val Gln Leu Gln Gln Ser Gly Ala Glu Leu Ala Arg Pro Gly Ala
1               5                   10                  15
Ser Val Lys Met Ser Cys Lys Thr Ser Gly Tyr Thr Phe Thr Arg Tyr
                20                  25                  30
Thr Met His Trp Val Lys Gln Arg Pro Gly Gln Gly Leu Glu Trp Ile
            35                  40                  45
Gly Tyr Ile Asn Pro Ser Arg Gly Tyr Thr Asn Tyr Asn Gln Lys Phe
        50                  55                  60
Lys Asp Lys Ala Thr Leu Thr Thr Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Tyr Tyr Asp Asp His Tyr Ser Leu Asp Tyr Trp Gly Gln Gly
                100                 105                 110
Thr Thr Leu Thr Val Ser Ser Ala Ser Thr Lys Gly Pro Ser Val Phe
            115                 120                 125
Pro Leu Ala Pro Cys Ser Lys Ser Thr Ser Glu Gly Thr Ala Ala Leu
        130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Asn Phe Gly Thr Gln Thr Tyr Thr Cys Asn Val Asp His Lys Pro
    195                 200                 205

Ser Asn Thr Lys Val Asp Lys Thr Val Glu Pro Lys Ser Ala Ser Gly
210                 215                 220

Pro Gly Gly Gly Arg Ser Gly Gly Gly Ser Gly Gly Gly Gly Gly Ser
225                 230                 235                 240

Glu Val Gln Leu Gln Gln Ser Gly Pro Glu Leu Val Lys Pro Gly Ala
            245                 250                 255

Ser Met Lys Ile Ser Cys Lys Ala Ser Gly Tyr Ser Phe Thr Gly Tyr
        260                 265                 270

Thr Met Asn Trp Val Lys Gln Ser His Gly Lys Cys Leu Glu Trp Ile
    275                 280                 285

Gly Leu Ile Asn Pro Tyr Asn Gly Gly Thr Ile Tyr Asn Gln Lys Phe
290                 295                 300

Lys Gly Lys Ala Thr Leu Thr Val Asp Lys Ser Ser Ser Thr Ala Tyr
305                 310                 315                 320

Met Glu Leu Leu Ser Leu Thr Ser Glu Asp Ser Ala Val Tyr Tyr Cys
            325                 330                 335

Ala Arg Asp Tyr Gly Phe Val Leu Asp Tyr Trp Gly Gln Gly Thr Thr
        340                 345                 350

Leu Thr Val Ser Ser Gly Gly Gly Ser Gly Gly Gly Gly Ser Gly
    355                 360                 365

Gly Gly Gly Ser Gly Gly Gly Gly Ser Gln Ile Val Leu Thr Gln Ser
370                 375                 380

Pro Ser Ile Met Ser Val Ser Pro Gly Glu Lys Val Thr Ile Thr Cys
385                 390                 395                 400

Ser Ala Ser Ser Ser Val Ser Tyr Met His Trp Phe Gln Gln Lys Pro
            405                 410                 415

Gly Thr Ser Pro Lys Leu Trp Ile Tyr Ser Thr Ser Asn Leu Ala Ser
        420                 425                 430

Gly Val Pro Ala Arg Phe Ser Gly Arg Gly Ser Gly Thr Ser Tyr Ser
    435                 440                 445

Leu Thr Ile Ser Arg Val Ala Ala Glu Asp Ala Ala Thr Tyr Tyr Cys
    450                 455                 460

Gln Gln Arg Ser Asn Tyr Pro Pro Trp Thr Phe Gly Cys Gly Thr Lys
465                 470                 475                 480

Leu Glu Ile Lys

<210> SEQ ID NO 19
<211> LENGTH: 463
<212> TYPE: PRT
<213> ORGANISM: Artificial Sequence
<220> FEATURE:
<223> OTHER INFORMATION: Antibody-derived sequence

<400> SEQUENCE: 19

Gln Ile Val Leu Thr Gln Ser Pro Ala Ile Met Ser Ala Ser Pro Gly
1               5                   10                  15

-continued

```
Glu Lys Val Thr Met Thr Cys Arg Ala Ser Ser Val Ser Tyr Met
                 20                  25                  30

Asn Trp Tyr Gln Gln Lys Ser Gly Thr Ser Pro Lys Arg Trp Ile Tyr
             35                  40                  45

Asp Thr Ser Lys Val Ala Ser Gly Val Pro Tyr Arg Phe Ser Gly Ser
         50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Asp Val Pro Gly Gly Ser Glu Val Gln Leu Gln
    210                 215                 220

Gln Ser Gly Pro Glu Leu Val Lys Pro Gly Ala Ser Met Lys Ile Ser
225                 230                 235                 240

Cys Lys Ala Ser Gly Tyr Ser Phe Thr Gly Tyr Thr Met Asn Trp Val
                245                 250                 255

Lys Gln Ser His Gly Lys Cys Leu Glu Trp Ile Gly Leu Ile Asn Pro
            260                 265                 270

Tyr Asn Gly Gly Thr Ile Tyr Asn Gln Lys Phe Lys Gly Lys Ala Thr
        275                 280                 285

Leu Thr Val Asp Lys Ser Ser Ser Thr Ala Tyr Met Glu Leu Leu Ser
    290                 295                 300

Leu Thr Ser Glu Asp Ser Ala Val Tyr Tyr Cys Ala Arg Asp Tyr Gly
305                 310                 315                 320

Phe Val Leu Asp Tyr Trp Gly Gln Gly Thr Thr Leu Thr Val Ser Ser
                325                 330                 335

Gly Gly Gly Gly Ser Gly Gly Gly Ser Gly Gly Gly Gly Ser Gly
            340                 345                 350

Gly Gly Gly Ser Gln Ile Val Leu Thr Gln Ser Pro Ser Ile Met Ser
        355                 360                 365

Val Ser Pro Gly Glu Lys Val Thr Ile Thr Cys Ser Ala Ser Ser Ser
    370                 375                 380

Val Ser Tyr Met His Trp Phe Gln Gln Lys Pro Gly Thr Ser Pro Lys
385                 390                 395                 400

Leu Trp Ile Tyr Ser Thr Ser Asn Leu Ala Ser Gly Val Pro Ala Arg
                405                 410                 415

Phe Ser Gly Arg Gly Ser Gly Thr Ser Tyr Ser Leu Thr Ile Ser Arg
            420                 425                 430

Val Ala Ala Glu Asp Ala Ala Thr Tyr Tyr Cys Gln Gln Arg Ser Asn
```

```
                435                 440                 445
Tyr Pro Pro Trp Thr Phe Gly Cys Gly Thr Lys Leu Glu Ile Lys
    450                 455                 460

<210> SEQ ID NO 20
<211> LENGTH: 118
<212> TYPE: PRT
<213> ORGANISM: Artificial Sequence
<220> FEATURE:
<223> OTHER INFORMATION: Antibody-derived sequence

<400> SEQUENCE: 20

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
        50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser
        115

<210> SEQ ID NO 21
<211> LENGTH: 118
<212> TYPE: PRT
<213> ORGANISM: Artificial Sequence
<220> FEATURE:
<223> OTHER INFORMATION: Antibody-derived sequence

<400> SEQUENCE: 21

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Ile Asn Trp Val Lys Gln Arg Pro Gly Gln Cys Leu Glu Trp Ile
            35                  40                  45

Gly Asn Ile Tyr Pro Ser Asp Ser Tyr Thr Asn Tyr Asn Gln Lys Phe
        50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser
        115

<210> SEQ ID NO 22
<211> LENGTH: 113
<212> TYPE: PRT
<213> ORGANISM: Artificial Sequence
<220> FEATURE:
```

<223> OTHER INFORMATION: Antibody-derived sequence

<400> SEQUENCE: 22

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys

<210> SEQ ID NO 23
<211> LENGTH: 113
<212> TYPE: PRT
<213> ORGANISM: Artificial Sequence
<220> FEATURE:
<223> OTHER INFORMATION: Antibody-derived sequence

<400> SEQUENCE: 23

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Cys Gly Thr Lys Leu Glu Ile
            100                 105                 110

Lys

<210> SEQ ID NO 24
<211> LENGTH: 116
<212> TYPE: PRT
<213> ORGANISM: Artificial Sequence
<220> FEATURE:
<223> OTHER INFORMATION: Antibody-derived sequence

<400> SEQUENCE: 24

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Phe
        50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Leu Gly Phe Gly Asn Ala Met Asp Tyr Trp Gly Gln Gly Thr
            100                 105                 110

Ser Val Thr Val
        115

<210> SEQ ID NO 25
<211> LENGTH: 113
<212> TYPE: PRT
<213> ORGANISM: Artificial Sequence
<220> FEATURE:
<223> OTHER INFORMATION: Antibody-derived sequence

<400> SEQUENCE: 25

Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Leu
            100                 105                 110

Lys

<210> SEQ ID NO 26
<211> LENGTH: 251
<212> TYPE: PRT
<213> ORGANISM: Artificial Sequence
<220> FEATURE:
<223> OTHER INFORMATION: Antibody-derived sequence

<400> SEQUENCE: 26

Gln Val Gln Leu Gln Gln Pro Gly Ala Glu Leu Val Arg Pro Gly Ala
 1               5                  10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
 50                  55                  60

Lys Asp Lys Ala Thr Leu Thr Val Asp Lys Ser Ser Ser Thr Ala Tyr
 65                  70                  75                  80

Met Gln Leu Ser Ser Pro Thr Ser Glu Asp Ser Ala Val Tyr Tyr Cys
                 85                  90                  95

Thr Arg Ser Trp Arg Gly Asn Ser Phe Asp Tyr Trp Gly Gln Gly Thr
            100                 105                 110

```
Thr Leu Thr Val Ser Ser Gly Gly Gly Gly Ser Gly Gly Gly Ser
        115                 120                 125

Gly Gly Gly Gly Ser Gly Gly Gly Ser Asp Ile Val Met Thr Gln
        130                 135                 140

Ser Pro Ser Ser Leu Thr Val Thr Ala Gly Glu Lys Val Thr Met Ser
145                 150                 155                 160

Cys Lys Ser Ser Gln Ser Leu Leu Asn Ser Gly Asn Gln Lys Asn Tyr
                165                 170                 175

Leu Thr Trp Tyr Gln Gln Lys Pro Gly Gln Pro Pro Lys Leu Leu Ile
                180                 185                 190

Tyr Trp Ala Ser Thr Arg Glu Ser Gly Val Pro Asp Arg Phe Thr Gly
                195                 200                 205

Ser Gly Ser Gly Thr Asp Phe Thr Leu Thr Ile Ser Ser Val Gln Ala
        210                 215                 220

Glu Asp Leu Ala Val Tyr Tyr Cys Gln Asn Asp Tyr Ser Tyr Pro Phe
225                 230                 235                 240

Thr Phe Gly Ser Gly Thr Lys Leu Glu Ile Lys
                245                 250

<210> SEQ ID NO 27
<211> LENGTH: 256
<212> TYPE: PRT
<213> ORGANISM: Artificial Sequence
<220> FEATURE:
<223> OTHER INFORMATION: Antibody-derived sequence

<400> SEQUENCE: 27

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys Gly Gly Gly Gly Ser Gly Gly Gly Gly Ser Gly Gly Gly Gly Ser
        115                 120                 125

Gly Gly Gly Gly Ser Gly Gly Gly Ser Gln Val Gln Leu Gln Gln
        130                 135                 140

Pro Gly Ala Glu Leu Val Arg Pro Gly Ala Ser Val Lys Leu Ser Cys
145                 150                 155                 160

Lys Ala Ser Gly Tyr Thr Phe Thr Ser Tyr Trp Ile Asn Trp Val Lys
                165                 170                 175

Gln Arg Pro Gly Gln Gly Leu Glu Trp Ile Gly Asn Ile Tyr Pro Ser
            180                 185                 190

Asp Ser Tyr Thr Asn Tyr Asn Gln Lys Phe Lys Asp Lys Ala Thr Leu
            195                 200                 205

Thr Val Asp Lys Ser Ser Ser Thr Ala Tyr Met Gln Leu Ser Ser Pro
        210                 215                 220
```

```
Thr Ser Glu Asp Ser Ala Val Tyr Tyr Cys Thr Arg Ser Trp Arg Gly
225                 230                 235                 240

Asn Ser Phe Asp Tyr Trp Gly Gln Gly Thr Thr Leu Thr Val Ser Ser
            245                 250                 255

<210> SEQ ID NO 28
<211> LENGTH: 251
<212> TYPE: PRT
<213> ORGANISM: Artificial Sequence
<220> FEATURE:
<223> OTHER INFORMATION: Antibody-derived sequence

<400> SEQUENCE: 28

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Cys Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Gly Gly Gly Gly Ser Gly Gly Gly Gly Ser
        115                 120                 125

Gly Gly Gly Gly Ser Gly Gly Gly Ser Asp Ile Val Met Thr Gln
    130                 135                 140

Ser Pro Ser Ser Leu Thr Val Thr Ala Gly Glu Lys Val Thr Met Ser
145                 150                 155                 160

Cys Lys Ser Ser Gln Ser Leu Leu Asn Ser Gly Asn Gln Lys Asn Tyr
                165                 170                 175

Leu Thr Trp Tyr Gln Gln Lys Pro Gly Gln Pro Pro Lys Leu Leu Ile
            180                 185                 190

Tyr Trp Ala Ser Thr Arg Glu Ser Gly Val Pro Asp Arg Phe Thr Gly
        195                 200                 205

Ser Gly Ser Gly Thr Asp Phe Thr Leu Thr Ile Ser Ser Val Gln Ala
    210                 215                 220

Glu Asp Leu Ala Val Tyr Tyr Cys Gln Asn Asp Tyr Ser Tyr Pro Phe
225                 230                 235                 240

Thr Phe Gly Cys Gly Thr Lys Leu Glu Ile Lys
                245                 250

<210> SEQ ID NO 29
<211> LENGTH: 256
<212> TYPE: PRT
<213> ORGANISM: Artificial Sequence
<220> FEATURE:
<223> OTHER INFORMATION: Antibody-derived sequence

<400> SEQUENCE: 29

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30
```

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Cys Gly Thr Lys Leu Glu Ile
            100                 105                 110

Lys Gly Gly Gly Ser Gly Gly Gly Ser Gly Gly Gly Ser
            115                 120                 125

Gly Gly Gly Ser Gly Gly Gly Ser Gln Val Gln Leu Gln Gln
            130                 135                 140

Pro Gly Ala Glu Leu Val Arg Pro Gly Ala Ser Val Lys Leu Ser Cys
145                 150                 155                 160

Lys Ala Ser Gly Tyr Thr Phe Thr Ser Tyr Trp Ile Asn Trp Val Lys
                165                 170                 175

Gln Arg Pro Gly Gln Cys Leu Glu Trp Ile Gly Asn Ile Tyr Pro Ser
            180                 185                 190

Asp Ser Tyr Thr Asn Tyr Asn Gln Lys Phe Lys Asp Lys Ala Thr Leu
            195                 200                 205

Thr Val Asp Lys Ser Ser Thr Ala Tyr Met Gln Leu Ser Ser Pro
    210                 215                 220

Thr Ser Glu Asp Ser Ala Val Tyr Tyr Cys Thr Arg Ser Trp Arg Gly
225                 230                 235                 240

Asn Ser Phe Asp Tyr Trp Gly Gln Gly Thr Thr Leu Thr Val Ser Ser
            245                 250                 255

<210> SEQ ID NO 30
<211> LENGTH: 500
<212> TYPE: PRT
<213> ORGANISM: Artificial Sequence
<220> FEATURE:
<223> OTHER INFORMATION: Antibody-derived sequence

<400> SEQUENCE: 30

Gln Val Gln Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Asp Asp His Tyr Ser Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Arg Val Glu Pro Lys Ser Cys Ser Gly
210                 215                 220

Pro Gly Gly Gly Arg Ser Gly Gly Gly Ser Gly Gly Gly Gly Gly Ser
225                 230                 235                 240

Gln Val Gln Leu Gln Gln Pro Gly Ala Glu Leu Val Arg Pro Gly Ala
                245                 250                 255

Ser Val Lys Leu Ser Cys Lys Ala Ser Gly Tyr Thr Phe Thr Ser Tyr
            260                 265                 270

Trp Ile Asn Trp Val Lys Gln Arg Pro Gly Gln Gly Leu Glu Trp Ile
        275                 280                 285

Gly Asn Ile Tyr Pro Ser Asp Ser Tyr Thr Asn Tyr Asn Gln Lys Phe
    290                 295                 300

Lys Asp Lys Ala Thr Leu Thr Val Asp Lys Ser Ser Ser Thr Ala Tyr
305                 310                 315                 320

Met Gln Leu Ser Ser Pro Thr Ser Glu Asp Ser Ala Val Tyr Tyr Cys
                325                 330                 335

Thr Arg Ser Trp Arg Gly Asn Ser Phe Asp Tyr Trp Gly Gln Gly Thr
            340                 345                 350

Thr Leu Thr Val Ser Ser Gly Gly Gly Ser Gly Gly Gly Gly Gly Ser
        355                 360                 365

Gly Gly Gly Gly Ser Gly Gly Gly Ser Asp Ile Val Met Thr Gln
    370                 375                 380

Ser Pro Ser Ser Leu Thr Val Thr Ala Gly Glu Lys Val Thr Met Ser
385                 390                 395                 400

Cys Lys Ser Ser Gln Ser Leu Leu Asn Ser Gly Asn Gln Lys Asn Tyr
                405                 410                 415

Leu Thr Trp Tyr Gln Gln Lys Pro Gly Gln Pro Pro Lys Leu Leu Ile
            420                 425                 430

Tyr Trp Ala Ser Thr Arg Glu Ser Gly Val Pro Asp Arg Phe Thr Gly
        435                 440                 445

Ser Gly Ser Gly Thr Asp Phe Thr Leu Thr Ile Ser Ser Val Gln Ala
    450                 455                 460

Glu Asp Leu Ala Val Tyr Tyr Cys Gln Asn Asp Tyr Ser Tyr Pro Phe
465                 470                 475                 480

Thr Phe Gly Ser Gly Thr Lys Leu Glu Ile Lys Gly Gly Ser His His
                485                 490                 495

His His His His
        500

<210> SEQ ID NO 31
<211> LENGTH: 500
<212> TYPE: PRT
<213> ORGANISM: Artificial Sequence
<220> FEATURE:
<223> OTHER INFORMATION: Antibody-derived sequence

<400> SEQUENCE: 31

```
Gln Val Gln Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
            50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Asp Asp His Tyr Ser Leu Asp Tyr Trp Gly Gln Gly
            100                 105                 110

Thr Thr Leu Thr Val Ser Ser Ala Ser Thr Lys Gly Pro Ser Val Phe
            115                 120                 125

Pro Leu Ala Pro Cys Ser Lys Ser Thr Ser Glu Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Pro Lys Ser Ala Ser Gly
            210                 215                 220

Pro Gly Gly Gly Arg Ser Gly Gly Gly Ser Gly Gly Gly Gly Gly Ser
225                 230                 235                 240

Gln Val Gln Leu Gln Gln Pro Gly Ala Glu Leu Val Arg Pro Gly Ala
            245                 250                 255

Ser Val Lys Leu Ser Cys Lys Ala Ser Gly Tyr Thr Phe Thr Ser Tyr
            260                 265                 270

Trp Ile Asn Trp Val Lys Gln Arg Pro Gly Gln Gly Leu Glu Trp Ile
            275                 280                 285

Gly Asn Ile Tyr Pro Ser Asp Ser Tyr Thr Asn Tyr Asn Gln Lys Phe
            290                 295                 300

Lys Asp Lys Ala Thr Leu Thr Val Asp Lys Ser Ser Ser Thr Ala Tyr
305                 310                 315                 320

Met Gln Leu Ser Ser Pro Thr Ser Glu Asp Ser Ala Val Tyr Tyr Cys
            325                 330                 335

Thr Arg Ser Trp Arg Gly Asn Ser Phe Asp Tyr Trp Gly Gln Gly Thr
            340                 345                 350

Thr Leu Thr Val Ser Ser Gly Gly Gly Gly Ser Gly Gly Gly Gly Ser
            355                 360                 365

Gly Gly Gly Gly Ser Gly Gly Gly Gly Ser Asp Ile Val Met Thr Gln
            370                 375                 380

Ser Pro Ser Ser Leu Thr Val Thr Ala Gly Glu Lys Val Thr Met Ser
385                 390                 395                 400

Cys Lys Ser Ser Gln Ser Leu Leu Asn Ser Gly Asn Gln Lys Asn Tyr
            405                 410                 415
```

```
Leu Thr Trp Tyr Gln Gln Lys Pro Gly Gln Pro Pro Lys Leu Leu Ile
            420                 425                 430

Tyr Trp Ala Ser Thr Arg Glu Ser Gly Val Pro Asp Arg Phe Thr Gly
        435                 440                 445

Ser Gly Ser Gly Thr Asp Phe Thr Leu Thr Ile Ser Ser Val Gln Ala
    450                 455                 460

Glu Asp Leu Ala Val Tyr Tyr Cys Gln Asn Asp Tyr Ser Tyr Pro Phe
465                 470                 475                 480

Thr Phe Gly Ser Gly Thr Lys Leu Glu Ile Lys Gly Ser His His
                485                 490                 495

His His His His
        500
```

<210> SEQ ID NO 32
<211> LENGTH: 480
<212> TYPE: PRT
<213> ORGANISM: Artificial Sequence
<220> FEATURE:
<223> OTHER INFORMATION: Antibody-derived sequence

<400> SEQUENCE: 32

```
Gln Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Asp Val Pro Gly Gly Ser Gln Val Gln Leu Gln
    210                 215                 220

Gln Pro Gly Ala Glu Leu Val Arg Pro Gly Ala Ser Val Lys Leu Ser
225                 230                 235                 240

Cys Lys Ala Ser Gly Tyr Thr Phe Thr Ser Tyr Trp Ile Asn Trp Val
                245                 250                 255

Lys Gln Arg Pro Gly Gln Gly Leu Glu Trp Ile Gly Asn Ile Tyr Pro
            260                 265                 270
```

Ser Asp Ser Tyr Thr Asn Tyr Asn Gln Lys Phe Lys Asp Lys Ala Thr
            275                 280                 285

Leu Thr Val Asp Lys Ser Ser Thr Ala Tyr Met Gln Leu Ser Ser
290                 295                 300

Pro Thr Ser Glu Asp Ser Ala Val Tyr Tyr Cys Thr Arg Ser Trp Arg
305                 310                 315                 320

Gly Asn Ser Phe Asp Tyr Trp Gly Gln Gly Thr Thr Leu Thr Val Ser
            325                 330                 335

Ser Gly Gly Gly Gly Ser Gly Gly Gly Ser Gly Gly Gly Gly Ser
            340                 345                 350

Gly Gly Gly Gly Ser Asp Ile Val Met Thr Gln Ser Pro Ser Ser Leu
            355                 360                 365

Thr Val Thr Ala Gly Glu Lys Val Thr Met Ser Cys Lys Ser Ser Gln
370                 375                 380

Ser Leu Leu Asn Ser Gly Asn Gln Lys Asn Tyr Leu Thr Trp Tyr Gln
385                 390                 395                 400

Gln Lys Pro Gly Gln Pro Pro Lys Leu Leu Ile Tyr Trp Ala Ser Thr
            405                 410                 415

Arg Glu Ser Gly Val Pro Asp Arg Phe Thr Gly Ser Gly Ser Gly Thr
            420                 425                 430

Asp Phe Thr Leu Thr Ile Ser Ser Val Gln Ala Glu Asp Leu Ala Val
            435                 440                 445

Tyr Tyr Cys Gln Asn Asp Tyr Ser Tyr Pro Phe Thr Phe Gly Ser Gly
            450                 455                 460

Thr Lys Leu Glu Ile Lys Ser Ala Trp Ser His Pro Gln Phe Glu Lys
465                 470                 475                 480

<210> SEQ ID NO 33
<211> LENGTH: 503
<212> TYPE: PRT
<213> ORGANISM: Artificial Sequence
<220> FEATURE:
<223> OTHER INFORMATION: Antibody-derived sequence

<400> SEQUENCE: 33

Gln Val Gln Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Ser Gly
        210                 215                 220

Pro Gly Gly Gly Arg Ser Gly Gly Gly Ser Gly Gly Gly Gly Gly Ser
225                 230                 235                 240

Asp Ile Val Met Thr Gln Ser Pro Ser Ser Leu Thr Val Thr Ala Gly
            245                 250                 255

Glu Lys Val Thr Met Ser Cys Lys Ser Ser Gln Ser Leu Leu Asn Ser
            260                 265                 270

Gly Asn Gln Lys Asn Tyr Leu Thr Trp Tyr Gln Gln Lys Pro Gly Gln
            275                 280                 285

Pro Pro Lys Leu Leu Ile Tyr Trp Ala Ser Thr Arg Glu Ser Gly Val
            290                 295                 300

Pro Asp Arg Phe Thr Gly Ser Gly Ser Gly Thr Asp Phe Thr Leu Thr
305                 310                 315                 320

Ile Ser Ser Val Gln Ala Glu Asp Leu Ala Val Tyr Tyr Cys Gln Asn
            325                 330                 335

Asp Tyr Ser Tyr Pro Phe Thr Phe Gly Ser Gly Thr Lys Leu Glu Ile
            340                 345                 350

Lys Gly Gly Gly Gly Ser Gly Gly Gly Gly Ser Gly Gly Gly Gly Ser
            355                 360                 365

Gly Gly Gly Gly Ser Gly Gly Gly Gly Ser Gln Val Gln Leu Gln Gln
            370                 375                 380

Pro Gly Ala Glu Leu Val Arg Pro Gly Ala Ser Val Lys Leu Ser Cys
385                 390                 395                 400

Lys Ala Ser Gly Tyr Thr Phe Thr Ser Tyr Trp Ile Asn Trp Val Lys
            405                 410                 415

Gln Arg Pro Gly Gln Gly Leu Glu Trp Ile Gly Asn Ile Tyr Pro Ser
            420                 425                 430

Asp Ser Tyr Thr Asn Tyr Asn Gln Lys Phe Lys Asp Lys Ala Thr Leu
            435                 440                 445

Thr Val Asp Lys Ser Ser Ser Thr Ala Tyr Met Gln Leu Ser Ser Pro
        450                 455                 460

Thr Ser Glu Asp Ser Ala Val Tyr Tyr Cys Thr Arg Ser Trp Arg Gly
465                 470                 475                 480

Asn Ser Phe Asp Tyr Trp Gly Gln Gly Thr Thr Leu Thr Val Ser Ser
            485                 490                 495

Ser His His His His His His
            500

<210> SEQ ID NO 34
<211> LENGTH: 503
<212> TYPE: PRT
<213> ORGANISM: Artificial Sequence
<220> FEATURE:
<223> OTHER INFORMATION: Antibody-derived sequence

<400> SEQUENCE: 34

Gln Val Gln Leu Gln Gln Ser Gly Ala Glu Leu Ala Arg Pro Gly Ala
1               5                   10                  15

```
Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Cys Ser Lys Ser Thr Ser Glu Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Pro Lys Ser Ala Ser Gly
    210                 215                 220

Pro Gly Gly Gly Arg Ser Gly Gly Gly Ser Gly Gly Gly Gly Gly Ser
225                 230                 235                 240

Asp Ile Val Met Thr Gln Ser Pro Ser Ser Leu Thr Val Thr Ala Gly
                245                 250                 255

Glu Lys Val Thr Met Ser Cys Lys Ser Ser Gln Ser Leu Leu Asn Ser
            260                 265                 270

Gly Asn Gln Lys Asn Tyr Leu Thr Trp Tyr Gln Gln Lys Pro Gly Gln
        275                 280                 285

Pro Pro Lys Leu Leu Ile Tyr Trp Ala Ser Thr Arg Glu Ser Gly Val
    290                 295                 300

Pro Asp Arg Phe Thr Gly Ser Gly Ser Gly Thr Asp Phe Thr Leu Thr
305                 310                 315                 320

Ile Ser Ser Val Gln Ala Glu Asp Leu Ala Val Tyr Tyr Cys Gln Asn
                325                 330                 335

Asp Tyr Ser Tyr Pro Phe Thr Phe Gly Ser Gly Thr Lys Leu Glu Ile
            340                 345                 350

Lys Gly Gly Gly Gly Ser Gly Gly Gly Gly Ser Gly Gly Gly Gly Ser
        355                 360                 365

Gly Gly Gly Gly Ser Gly Gly Gly Ser Gln Val Gln Leu Gln Gln
    370                 375                 380

Pro Gly Ala Glu Leu Val Arg Pro Gly Ala Ser Val Lys Leu Ser Cys
385                 390                 395                 400

Lys Ala Ser Gly Tyr Thr Phe Thr Ser Tyr Trp Ile Asn Trp Val Lys
                405                 410                 415

Gln Arg Pro Gly Gln Gly Leu Glu Trp Ile Gly Asn Ile Tyr Pro Ser
            420                 425                 430

Asp Ser Tyr Thr Asn Tyr Asn Gln Lys Phe Lys Asp Lys Ala Thr Leu
```

```
                    435                 440                 445
Thr Val Asp Lys Ser Ser Thr Ala Tyr Met Gln Leu Ser Ser Pro
            450                 455                 460

Thr Ser Glu Asp Ser Ala Val Tyr Tyr Cys Thr Arg Ser Trp Arg Gly
465                 470                 475                 480

Asn Ser Phe Asp Tyr Trp Gly Gln Gly Thr Thr Leu Thr Val Ser Ser
                    485                 490                 495

Ser His His His His His
            500

<210> SEQ ID NO 35
<211> LENGTH: 485
<212> TYPE: PRT
<213> ORGANISM: Artificial Sequence
<220> FEATURE:
<223> OTHER INFORMATION: Antibody-derived sequence

<400> SEQUENCE: 35

Gln Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Asp Val Pro Gly Gly Ser Asp Ile Val Met Thr
    210                 215                 220

Gln Ser Pro Ser Ser Leu Thr Val Thr Ala Gly Glu Lys Val Thr Met
225                 230                 235                 240

Ser Cys Lys Ser Ser Gln Ser Leu Leu Asn Ser Gly Asn Gln Lys Asn
                245                 250                 255

Tyr Leu Thr Trp Tyr Gln Gln Lys Pro Gly Gln Pro Pro Lys Leu Leu
            260                 265                 270

Ile Tyr Trp Ala Ser Thr Arg Glu Ser Gly Val Pro Asp Arg Phe Thr
        275                 280                 285

Gly Ser Gly Ser Gly Thr Asp Phe Thr Leu Thr Ile Ser Ser Val Gln
```

```
                290                 295                 300
Ala Glu Asp Leu Ala Val Tyr Tyr Cys Gln Asn Asp Tyr Ser Tyr Pro
305                 310                 315                 320

Phe Thr Phe Gly Ser Gly Thr Lys Leu Glu Ile Lys Gly Gly Gly Gly
                325                 330                 335

Ser Gly Gly Gly Gly Ser Gly Gly Gly Ser Gly Gly Gly Gly Gly Ser
                340                 345                 350

Gly Gly Gly Gly Ser Gln Val Gln Leu Gln Gln Pro Gly Ala Glu Leu
            355                 360                 365

Val Arg Pro Gly Ala Ser Val Lys Leu Ser Cys Lys Ala Ser Gly Tyr
        370                 375                 380

Thr Phe Thr Ser Tyr Trp Ile Asn Trp Val Lys Gln Arg Pro Gly Gln
385                 390                 395                 400

Gly Leu Glu Trp Ile Gly Asn Ile Tyr Pro Ser Asp Ser Tyr Thr Asn
                405                 410                 415

Tyr Asn Gln Lys Phe Lys Asp Lys Ala Thr Leu Thr Val Asp Lys Ser
            420                 425                 430

Ser Ser Thr Ala Tyr Met Gln Leu Ser Ser Pro Thr Ser Glu Asp Ser
        435                 440                 445

Ala Val Tyr Tyr Cys Thr Arg Ser Trp Arg Gly Asn Ser Phe Asp Tyr
    450                 455                 460

Trp Gly Gln Gly Thr Thr Leu Thr Val Ser Ser Ala Trp Ser His
465                 470                 475                 480

Pro Gln Phe Glu Lys
                485

<210> SEQ ID NO 36
<211> LENGTH: 491
<212> TYPE: PRT
<213> ORGANISM: Artificial Sequence
<220> FEATURE:
<223> OTHER INFORMATION: Antibody-derived sequence

<400> SEQUENCE: 36

Gln Val Gln Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                    165                 170                 175
Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Ser Gly
        210                 215                 220

Pro Gly Gly Gly Arg Ser Gly Gly Gly Ser Gly Gly Gly Gly Ser
225                 230                 235                 240

Gln Val Gln Leu Gln Gln Pro Gly Ala Glu Leu Val Arg Pro Gly Ala
                245                 250                 255

Ser Val Lys Leu Ser Cys Lys Ala Ser Gly Tyr Thr Phe Thr Ser Tyr
            260                 265                 270

Trp Ile Asn Trp Val Lys Gln Arg Pro Gly Gln Gly Leu Glu Trp Ile
        275                 280                 285

Gly Asn Ile Tyr Pro Ser Asp Ser Tyr Thr Asn Tyr Asn Gln Lys Phe
    290                 295                 300

Lys Asp Lys Ala Thr Leu Thr Val Asp Lys Ser Ser Ser Thr Ala Tyr
305                 310                 315                 320

Met Gln Leu Ser Ser Pro Thr Ser Glu Asp Ser Ala Val Tyr Tyr Cys
                325                 330                 335

Thr Arg Ser Trp Arg Gly Asn Ser Phe Asp Tyr Trp Gly Gln Gly Thr
            340                 345                 350

Thr Leu Thr Val Ser Ser Gly Gly Gly Gly Ser Gly Gly Gly Gly Ser
        355                 360                 365

Gly Gly Gly Gly Ser Gly Gly Gly Ser Asp Ile Val Met Thr Gln
    370                 375                 380

Ser Pro Ser Ser Leu Thr Val Thr Ala Gly Glu Lys Val Thr Met Ser
385                 390                 395                 400

Cys Lys Ser Ser Gln Ser Leu Leu Asn Ser Gly Asn Gln Lys Asn Tyr
                405                 410                 415

Leu Thr Trp Tyr Gln Gln Lys Pro Gly Gln Pro Pro Lys Leu Leu Ile
            420                 425                 430

Tyr Trp Ala Ser Thr Arg Glu Ser Gly Val Pro Asp Arg Phe Thr Gly
        435                 440                 445

Ser Gly Ser Gly Thr Asp Phe Thr Leu Thr Ile Ser Ser Val Gln Ala
    450                 455                 460

Glu Asp Leu Ala Val Tyr Tyr Cys Gln Asn Asp Tyr Ser Tyr Pro Phe
465                 470                 475                 480

Thr Phe Gly Ser Gly Thr Lys Leu Glu Ile Lys
                485                 490

<210> SEQ ID NO 37
<211> LENGTH: 470
<212> TYPE: PRT
<213> ORGANISM: Artificial Sequence
<220> FEATURE:
<223> OTHER INFORMATION: Antibody-derived sequence

<400> SEQUENCE: 37

Gln Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
                20                  25                  30

Asn Trp Tyr Gln Gln Lys Ser Gly Thr Ser Pro Lys Arg Trp Ile Tyr
```

```
                35                  40                  45
Asp Thr Ser Lys Val Ala Ser Gly Val Pro Tyr Arg Phe Ser Gly Ser
 50                  55                  60
Gly Ser Gly Thr Ser Tyr Ser Leu Thr Ile Ser Ser Met Glu Ala Glu
 65                  70                  75                  80
Asp Ala Ala Thr Tyr Tyr Cys Gln Gln Trp Ser Ser Asn Pro Leu Thr
                 85                  90                  95
Phe Gly Ala Gly Thr Lys Leu Glu Leu Lys Arg Thr Val Ala Ala Pro
            100                 105                 110
Ser Val Phe Ile Phe Pro Pro Ser Asp Glu Gln Leu Lys Ser Gly Thr
            115                 120                 125
Ala Ser Val Val Cys Leu Leu Asn Asn Phe Tyr Pro Arg Glu Ala Lys
            130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
            195                 200                 205
Asn Arg Gly Glu Cys Asp Val Pro Gly Gly Ser Gln Val Gln Leu Gln
210                 215                 220
Gln Pro Gly Ala Glu Leu Val Arg Pro Gly Ala Ser Val Lys Leu Ser
225                 230                 235                 240
Cys Lys Ala Ser Gly Tyr Thr Phe Thr Ser Tyr Trp Ile Asn Trp Val
                245                 250                 255
Lys Gln Arg Pro Gly Gln Gly Leu Glu Trp Ile Gly Asn Ile Tyr Pro
            260                 265                 270
Ser Asp Ser Tyr Thr Asn Tyr Asn Gln Lys Phe Lys Asp Lys Ala Thr
            275                 280                 285
Leu Thr Val Asp Lys Ser Ser Ser Thr Ala Tyr Met Gln Leu Ser Ser
            290                 295                 300
Pro Thr Ser Glu Asp Ser Ala Val Tyr Tyr Cys Thr Arg Ser Trp Arg
305                 310                 315                 320
Gly Asn Ser Phe Asp Tyr Trp Gly Gln Gly Thr Thr Leu Thr Val Ser
                325                 330                 335
Ser Gly Gly Gly Gly Ser Gly Gly Gly Ser Gly Gly Gly Gly Ser
            340                 345                 350
Gly Gly Gly Gly Ser Asp Ile Val Met Thr Gln Ser Pro Ser Ser Leu
            355                 360                 365
Thr Val Thr Ala Gly Glu Lys Val Thr Met Ser Cys Lys Ser Ser Gln
            370                 375                 380
Ser Leu Leu Asn Ser Gly Asn Gln Lys Asn Tyr Leu Thr Trp Tyr Gln
385                 390                 395                 400
Gln Lys Pro Gly Gln Pro Pro Lys Leu Leu Ile Tyr Trp Ala Ser Thr
                405                 410                 415
Arg Glu Ser Gly Val Pro Asp Arg Phe Thr Gly Ser Gly Ser Gly Thr
            420                 425                 430
Asp Phe Thr Leu Thr Ile Ser Ser Val Gln Ala Glu Asp Leu Ala Val
            435                 440                 445
Tyr Tyr Cys Gln Asn Asp Tyr Ser Tyr Pro Phe Thr Phe Gly Ser Gly
            450                 455                 460
```

```
Thr Lys Leu Glu Ile Lys
465                 470

<210> SEQ ID NO 38
<211> LENGTH: 496
<212> TYPE: PRT
<213> ORGANISM: Artificial Sequence
<220> FEATURE:
<223> OTHER INFORMATION: Antibody-derived sequence

<400> SEQUENCE: 38

Gln Val Gln Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Ser Gly
    210                 215                 220

Pro Gly Gly Gly Arg Ser Gly Gly Gly Ser Gly Gly Gly Gly Ser
225                 230                 235                 240

Asp Ile Val Met Thr Gln Ser Pro Ser Ser Leu Thr Val Thr Ala Gly
                245                 250                 255

Glu Lys Val Thr Met Ser Cys Lys Ser Ser Gln Ser Leu Leu Asn Ser
            260                 265                 270

Gly Asn Gln Lys Asn Tyr Leu Thr Trp Tyr Gln Gln Lys Pro Gly Gln
        275                 280                 285

Pro Pro Lys Leu Leu Ile Tyr Trp Ala Ser Thr Arg Glu Ser Gly Val
    290                 295                 300

Pro Asp Arg Phe Thr Gly Ser Gly Ser Gly Thr Asp Phe Thr Leu Thr
305                 310                 315                 320

Ile Ser Ser Val Gln Ala Glu Asp Leu Ala Val Tyr Tyr Cys Gln Asn
                325                 330                 335

Asp Tyr Ser Tyr Pro Phe Thr Phe Gly Ser Gly Thr Lys Leu Glu Ile
            340                 345                 350
```

```
Lys Gly Gly Gly Gly Ser Gly Gly Gly Ser Gly Gly Gly Ser
        355                 360                 365

Gly Gly Gly Gly Ser Gly Gly Gly Ser Gln Val Gln Leu Gln Gln
    370                 375                 380

Pro Gly Ala Glu Leu Val Arg Pro Gly Ala Ser Val Lys Leu Ser Cys
385                 390                 395                 400

Lys Ala Ser Gly Tyr Thr Phe Thr Ser Tyr Trp Ile Asn Trp Val Lys
                405                 410                 415

Gln Arg Pro Gly Gln Gly Leu Glu Trp Ile Gly Asn Ile Tyr Pro Ser
                420                 425                 430

Asp Ser Tyr Thr Asn Tyr Asn Gln Lys Phe Lys Asp Lys Ala Thr Leu
                435                 440                 445

Thr Val Asp Lys Ser Ser Ser Thr Ala Tyr Met Gln Leu Ser Ser Pro
                450                 455                 460

Thr Ser Glu Asp Ser Ala Val Tyr Tyr Cys Thr Arg Ser Trp Arg Gly
465                 470                 475                 480

Asn Ser Phe Asp Tyr Trp Gly Gln Gly Thr Thr Leu Thr Val Ser Ser
                485                 490                 495

<210> SEQ ID NO 39
<211> LENGTH: 475
<212> TYPE: PRT
<213> ORGANISM: Artificial Sequence
<220> FEATURE:
<223> OTHER INFORMATION: Antibody-derived sequence

<400> SEQUENCE: 39

Gln Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys Asp Val Pro Gly Gly Ser Asp Ile Val Met Thr
        210                 215                 220
```

```
Gln Ser Pro Ser Ser Leu Thr Val Thr Ala Gly Glu Lys Val Thr Met
225                 230                 235                 240

Ser Cys Lys Ser Ser Gln Ser Leu Leu Asn Ser Gly Asn Gln Lys Asn
            245                 250                 255

Tyr Leu Thr Trp Tyr Gln Gln Lys Pro Gly Gln Pro Pro Lys Leu Leu
                260                 265                 270

Ile Tyr Trp Ala Ser Thr Arg Glu Ser Gly Val Pro Asp Arg Phe Thr
            275                 280                 285

Gly Ser Gly Ser Gly Thr Asp Phe Thr Leu Thr Ile Ser Ser Val Gln
        290                 295                 300

Ala Glu Asp Leu Ala Val Tyr Tyr Cys Gln Asn Asp Tyr Ser Tyr Pro
305                 310                 315                 320

Phe Thr Phe Gly Ser Gly Thr Lys Leu Glu Ile Lys Gly Gly Gly Gly
                325                 330                 335

Ser Gly Gly Gly Gly Ser Gly Gly Gly Ser Gly Gly Gly Gly Ser
            340                 345                 350

Gly Gly Gly Gly Ser Gln Val Gln Leu Gln Gln Pro Gly Ala Glu Leu
        355                 360                 365

Val Arg Pro Gly Ala Ser Val Lys Leu Ser Cys Lys Ala Ser Gly Tyr
370                 375                 380

Thr Phe Thr Ser Tyr Trp Ile Asn Trp Val Lys Gln Arg Pro Gly Gln
385                 390                 395                 400

Gly Leu Glu Trp Ile Gly Asn Ile Tyr Pro Ser Asp Ser Tyr Thr Asn
                405                 410                 415

Tyr Asn Gln Lys Phe Lys Asp Lys Ala Thr Leu Thr Val Asp Lys Ser
            420                 425                 430

Ser Ser Thr Ala Tyr Met Gln Leu Ser Ser Pro Thr Ser Glu Asp Ser
        435                 440                 445

Ala Val Tyr Tyr Cys Thr Arg Ser Trp Arg Gly Asn Ser Phe Asp Tyr
450                 455                 460

Trp Gly Gln Gly Thr Thr Leu Thr Val Ser Ser
465                 470                 475

<210> SEQ ID NO 40
<211> LENGTH: 491
<212> TYPE: PRT
<213> ORGANISM: Artificial Sequence
<220> FEATURE:
<223> OTHER INFORMATION: Antibody-derived sequence

<400> SEQUENCE: 40

Gln Val Gln Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110
```

```
Thr Thr Leu Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Ser Gly
210                 215                 220

Pro Gly Gly Gly Arg Ser Gly Gly Gly Ser Gly Gly Gly Gly Ser
225                 230                 235                 240

Gln Val Gln Leu Gln Gln Pro Gly Ala Glu Leu Val Arg Pro Gly Ala
                245                 250                 255

Ser Val Lys Leu Ser Cys Lys Ala Ser Gly Tyr Thr Phe Thr Ser Tyr
            260                 265                 270

Trp Ile Asn Trp Val Lys Gln Arg Pro Gly Gln Cys Leu Glu Trp Ile
        275                 280                 285

Gly Asn Ile Tyr Pro Ser Asp Ser Tyr Thr Asn Tyr Asn Gln Lys Phe
    290                 295                 300

Lys Asp Lys Ala Thr Leu Thr Val Asp Lys Ser Ser Ser Thr Ala Tyr
305                 310                 315                 320

Met Gln Leu Ser Ser Pro Thr Ser Glu Asp Ser Ala Val Tyr Tyr Cys
                325                 330                 335

Thr Arg Ser Trp Arg Gly Asn Ser Phe Asp Tyr Trp Gly Gln Gly Thr
            340                 345                 350

Thr Leu Thr Val Ser Ser Gly Gly Gly Gly Ser Gly Gly Gly Gly Ser
        355                 360                 365

Gly Gly Gly Gly Ser Gly Gly Gly Ser Asp Ile Val Met Thr Gln
    370                 375                 380

Ser Pro Ser Ser Leu Thr Val Thr Ala Gly Glu Lys Val Thr Met Ser
385                 390                 395                 400

Cys Lys Ser Ser Gln Ser Leu Leu Asn Ser Gly Asn Gln Lys Asn Tyr
                405                 410                 415

Leu Thr Trp Tyr Gln Gln Lys Pro Gly Gln Pro Pro Lys Leu Leu Ile
            420                 425                 430

Tyr Trp Ala Ser Thr Arg Glu Ser Gly Val Pro Asp Arg Phe Thr Gly
        435                 440                 445

Ser Gly Ser Gly Thr Asp Phe Thr Leu Thr Ile Ser Ser Val Gln Ala
    450                 455                 460

Glu Asp Leu Ala Val Tyr Tyr Cys Gln Asn Asp Tyr Ser Tyr Pro Phe
465                 470                 475                 480

Thr Phe Gly Cys Gly Thr Lys Leu Glu Ile Lys
                485                 490

<210> SEQ ID NO 41
<211> LENGTH: 470
<212> TYPE: PRT
<213> ORGANISM: Artificial Sequence
<220> FEATURE:
```

<223> OTHER INFORMATION: Antibody-derived sequence

<400> SEQUENCE: 41

```
Gln Ile Val Leu Thr Gln Ser Pro Ala Ile Met Ser Ala Ser Pro Gly
1               5                   10                  15

Glu Lys Val Thr Met Thr Cys Arg Ala Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys Asp Val Pro Gly Gly Ser Gln Val Gln Leu Gln
        210                 215                 220

Gln Pro Gly Ala Glu Leu Val Arg Pro Gly Ala Ser Val Lys Leu Ser
225                 230                 235                 240

Cys Lys Ala Ser Gly Tyr Thr Phe Thr Ser Tyr Trp Ile Asn Trp Val
                245                 250                 255

Lys Gln Arg Pro Gly Gln Cys Leu Glu Trp Ile Gly Asn Ile Tyr Pro
            260                 265                 270

Ser Asp Ser Tyr Thr Asn Tyr Asn Gln Lys Phe Lys Asp Lys Ala Thr
        275                 280                 285

Leu Thr Val Asp Lys Ser Ser Thr Ala Tyr Met Gln Leu Ser Ser
290                 295                 300

Pro Thr Ser Glu Asp Ser Ala Val Tyr Tyr Cys Thr Arg Ser Trp Arg
305                 310                 315                 320

Gly Asn Ser Phe Asp Tyr Trp Gly Gln Gly Thr Thr Leu Thr Val Ser
                325                 330                 335

Ser Gly Gly Gly Gly Ser Gly Gly Gly Ser Gly Gly Gly Gly Ser
            340                 345                 350

Gly Gly Gly Gly Ser Asp Ile Val Met Thr Gln Ser Pro Ser Ser Leu
        355                 360                 365

Thr Val Thr Ala Gly Glu Lys Val Thr Met Ser Cys Lys Ser Ser Gln
        370                 375                 380

Ser Leu Leu Asn Ser Gly Asn Gln Lys Asn Tyr Leu Thr Trp Tyr Gln
385                 390                 395                 400
```

Gln Lys Pro Gly Gln Pro Pro Lys Leu Leu Ile Tyr Trp Ala Ser Thr
                    405                 410                 415

Arg Glu Ser Gly Val Pro Asp Arg Phe Thr Gly Ser Gly Ser Gly Thr
                420                 425                 430

Asp Phe Thr Leu Thr Ile Ser Ser Val Gln Ala Glu Asp Leu Ala Val
            435                 440                 445

Tyr Tyr Cys Gln Asn Asp Tyr Ser Tyr Pro Phe Thr Phe Gly Cys Gly
        450                 455                 460

Thr Lys Leu Glu Ile Lys
465                 470

<210> SEQ ID NO 42
<211> LENGTH: 496
<212> TYPE: PRT
<213> ORGANISM: Artificial Sequence
<220> FEATURE:
<223> OTHER INFORMATION: Antibody-derived sequence

<400> SEQUENCE: 42

Gln Val Gln Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Ser Gly
    210                 215                 220

Pro Gly Gly Gly Arg Gly Gly Gly Ser Gly Gly Gly Gly Gly Gly Ser
225                 230                 235                 240

Asp Ile Val Met Thr Gln Ser Pro Ser Ser Leu Thr Val Thr Ala Gly
                245                 250                 255

Glu Lys Val Thr Met Ser Cys Lys Ser Ser Gln Ser Leu Leu Asn Ser
            260                 265                 270

Gly Asn Gln Lys Asn Tyr Leu Thr Trp Tyr Gln Gln Lys Pro Gly Gln
        275                 280                 285

```
Pro Pro Lys Leu Leu Ile Tyr Trp Ala Ser Thr Arg Glu Ser Gly Val
            290                 295                 300
Pro Asp Arg Phe Thr Gly Ser Gly Ser Gly Thr Asp Phe Thr Leu Thr
305                 310                 315                 320
Ile Ser Ser Val Gln Ala Glu Asp Leu Ala Val Tyr Tyr Cys Gln Asn
                325                 330                 335
Asp Tyr Ser Tyr Pro Phe Thr Phe Gly Cys Gly Thr Lys Leu Glu Ile
                340                 345                 350
Lys Gly Gly Gly Gly Ser Gly Gly Gly Ser Gly Gly Gly Gly Ser
                355                 360                 365
Gly Gly Gly Gly Ser Gly Gly Gly Ser Gln Val Gln Leu Gln Gln
            370                 375                 380
Pro Gly Ala Glu Leu Val Arg Pro Gly Ala Ser Val Lys Leu Ser Cys
385                 390                 395                 400
Lys Ala Ser Gly Tyr Thr Phe Thr Ser Tyr Trp Ile Asn Trp Val Lys
                405                 410                 415
Gln Arg Pro Gly Gln Cys Leu Glu Trp Ile Gly Asn Ile Tyr Pro Ser
                420                 425                 430
Asp Ser Tyr Thr Asn Tyr Asn Gln Lys Phe Lys Asp Lys Ala Thr Leu
                435                 440                 445
Thr Val Asp Lys Ser Ser Ser Thr Ala Tyr Met Gln Leu Ser Ser Pro
450                 455                 460
Thr Ser Glu Asp Ser Ala Val Tyr Tyr Cys Thr Arg Ser Trp Arg Gly
465                 470                 475                 480
Asn Ser Phe Asp Tyr Trp Gly Gln Gly Thr Thr Leu Thr Val Ser Ser
                485                 490                 495

<210> SEQ ID NO 43
<211> LENGTH: 475
<212> TYPE: PRT
<213> ORGANISM: Artificial Sequence
<220> FEATURE:
<223> OTHER INFORMATION: Antibody-derived sequence

<400> SEQUENCE: 43

Gln Ile Val Leu Thr Gln Ser Pro Ala Ile Met Ser Ala Ser Pro Gly
1               5                   10                  15
Glu Lys Val Thr Met Thr Cys Arg Ala Ser Ser Ser Val Ser Tyr Met
                20                  25                  30
Asn Trp Tyr Gln Gln Lys Ser Gly Thr Ser Pro Lys Arg Trp Ile Tyr
                35                  40                  45
Asp Thr Ser Lys Val Ala Ser Gly Val Pro Tyr Arg Phe Ser Gly Ser
            50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ser Ser Asn Pro Leu Thr
                85                  90                  95
Phe Gly Ala Gly Thr Lys Leu Glu Leu Lys Arg Thr Val Ala Ala Pro
                100                 105                 110
Ser Val Phe Ile Phe Pro Pro Ser Asp Glu Gln Leu Lys Ser Gly Thr
                115                 120                 125
Ala Ser Val Val Cys Leu Leu Asn Asn Phe Tyr Pro Arg Glu Ala Lys
            130                 135                 140
Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
            195                 200                 205
Asn Arg Gly Glu Cys Asp Val Pro Gly Gly Ser Asp Ile Val Met Thr
210                 215                 220
Gln Ser Pro Ser Ser Leu Thr Val Thr Ala Gly Glu Lys Val Thr Met
225                 230                 235                 240
Ser Cys Lys Ser Ser Gln Ser Leu Leu Asn Ser Gly Asn Gln Lys Asn
            245                 250                 255
Tyr Leu Thr Trp Tyr Gln Gln Lys Pro Gly Gln Pro Pro Lys Leu Leu
            260                 265                 270
Ile Tyr Trp Ala Ser Thr Arg Glu Ser Gly Val Pro Asp Arg Phe Thr
            275                 280                 285
Gly Ser Gly Ser Gly Thr Asp Phe Thr Leu Thr Ile Ser Ser Val Gln
            290                 295                 300
Ala Glu Asp Leu Ala Val Tyr Tyr Cys Gln Asn Asp Tyr Ser Tyr Pro
305                 310                 315                 320
Phe Thr Phe Gly Cys Gly Thr Lys Leu Glu Ile Lys Gly Gly Gly Gly
            325                 330                 335
Ser Gly Gly Gly Gly Ser Gly Gly Gly Ser Gly Gly Gly Gly Ser
            340                 345                 350
Gly Gly Gly Gly Ser Gln Val Gln Leu Gln Pro Gly Ala Glu Leu
            355                 360                 365
Val Arg Pro Gly Ala Ser Val Lys Leu Ser Cys Lys Ala Ser Gly Tyr
370                 375                 380
Thr Phe Thr Ser Tyr Trp Ile Asn Trp Val Lys Gln Arg Pro Gly Gln
385                 390                 395                 400
Cys Leu Glu Trp Ile Gly Asn Ile Tyr Pro Ser Asp Ser Tyr Thr Asn
            405                 410                 415
Tyr Asn Gln Lys Phe Lys Asp Lys Ala Thr Leu Thr Val Asp Lys Ser
            420                 425                 430
Ser Ser Thr Ala Tyr Met Gln Leu Ser Ser Pro Thr Ser Glu Asp Ser
            435                 440                 445
Ala Val Tyr Tyr Cys Thr Arg Ser Trp Arg Gly Asn Ser Phe Asp Tyr
            450                 455                 460
Trp Gly Gln Gly Thr Thr Leu Thr Val Ser Ser
465                 470                 475

<210> SEQ ID NO 44
<211> LENGTH: 8
<212> TYPE: PRT
<213> ORGANISM: Artificial Sequence
<220> FEATURE:
<223> OTHER INFORMATION: CDR sequence

<400> SEQUENCE: 44

Gly Tyr Ser Phe Thr Gly Tyr Thr
1               5

<210> SEQ ID NO 45
<211> LENGTH: 8
<212> TYPE: PRT
<213> ORGANISM: Artificial Sequence
<220> FEATURE:
```

```
<223> OTHER INFORMATION: CDR sequence

<400> SEQUENCE: 45

Ile Asn Pro Tyr Asn Gly Gly Thr
1               5

<210> SEQ ID NO 46
<211> LENGTH: 10
<212> TYPE: PRT
<213> ORGANISM: Artificial Sequence
<220> FEATURE:
<223> OTHER INFORMATION: CDR sequence

<400> SEQUENCE: 46

Ala Arg Asp Tyr Gly Phe Val Leu Asp Tyr
1               5                   10

<210> SEQ ID NO 47
<211> LENGTH: 10
<212> TYPE: PRT
<213> ORGANISM: Artificial Sequence
<220> FEATURE:
<223> OTHER INFORMATION: CDR sequence

<400> SEQUENCE: 47

Ala Arg Asp Tyr Gly Tyr Val Leu Asp Tyr
1               5                   10

<210> SEQ ID NO 48
<211> LENGTH: 8
<212> TYPE: PRT
<213> ORGANISM: Artificial Sequence
<220> FEATURE:
<223> OTHER INFORMATION: CDR sequence
<220> FEATURE:
<221> NAME/KEY: MISC_FEATURE
<222> LOCATION: (8)..(8)
<223> OTHER INFORMATION: Any amino acid, preferably Thr, Ser or Ile,
      most preferably Thr

<400> SEQUENCE: 48

Ile Asn Pro Tyr Asn Gly Gly Xaa
1               5

<210> SEQ ID NO 49
<211> LENGTH: 10
<212> TYPE: PRT
<213> ORGANISM: Artificial Sequence
<220> FEATURE:
<223> OTHER INFORMATION: CDR sequence
<220> FEATURE:
<221> NAME/KEY: MISC_FEATURE
<222> LOCATION: (4)..(4)
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (6)..(6)
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (8)..(8)
<223> OTHER INFORMATION: Any amino acid, preferably Leu or Phe, more
      preferably Leu

<400> SEQUENCE: 49

Ala Arg Asp Xaa Gly Xaa Val Xaa Asp Tyr
1               5                   10
```

```
<210> SEQ ID NO 50
<211> LENGTH: 5
<212> TYPE: PRT
<213> ORGANISM: Artificial Sequence
<220> FEATURE:
<223> OTHER INFORMATION: CDR sequence

<400> SEQUENCE: 50

Ser Ser Val Ser Tyr
1               5

<210> SEQ ID NO 51
<211> LENGTH: 3
<212> TYPE: PRT
<213> ORGANISM: Artificial Sequence
<220> FEATURE:
<223> OTHER INFORMATION: CDR sequence

<400> SEQUENCE: 51

Ser Thr Ser
1

<210> SEQ ID NO 52
<211> LENGTH: 10
<212> TYPE: PRT
<213> ORGANISM: Artificial Sequence
<220> FEATURE:
<223> OTHER INFORMATION: CDR sequence

<400> SEQUENCE: 52

Gln Gln Arg Ser Asn Tyr Pro Pro Trp Thr
1               5                   10

<210> SEQ ID NO 53
<211> LENGTH: 10
<212> TYPE: PRT
<213> ORGANISM: Artificial Sequence
<220> FEATURE:
<223> OTHER INFORMATION: CDR sequence

<400> SEQUENCE: 53

Gln Gln Arg Ser Ile Tyr Pro Pro Trp Thr
1               5                   10

<210> SEQ ID NO 54
<211> LENGTH: 5
<212> TYPE: PRT
<213> ORGANISM: Artificial Sequence
<220> FEATURE:
<223> OTHER INFORMATION: CDR sequence
<220> FEATURE:
<221> NAME/KEY: MISC_FEATURE
<222> LOCATION: (4)..(4)
<223> OTHER INFORMATION: Any amino acid, preferably Ser or Asn, most
      preferably Ser

<400> SEQUENCE: 54

Ser Ser Val Xaa Tyr
1               5

<210> SEQ ID NO 55
<211> LENGTH: 10
<212> TYPE: PRT
<213> ORGANISM: Artificial Sequence
<220> FEATURE:
<223> OTHER INFORMATION: CDR sequence
<220> FEATURE:
<221> NAME/KEY: MISC_FEATURE
```

```
<222> LOCATION: (4)..(4)
<223> OTHER INFORMATION: Any amino acid, preferably Ser or Asn, most
      preferably Ser
<220> FEATURE:
<221> NAME/KEY: MISC_FEATURE
<222> LOCATION: (5)..(5)
<223> OTHER INFORMATION: Any amino acid, preferably Tyr, Ser, Ile, Asn
      or Thr, more preferably Ile, Asn or Thr, most preferably Ile or
      Asn
<220> FEATURE:
<221> NAME/KEY: MISC_FEATURE
<222> LOCATION: (6)..(6)
<223> OTHER INFORMATION: Any amino acid, preferably Ser or Tyr, more
      preferably Tyr

<400> SEQUENCE: 55

Gln Gln Arg Xaa Xaa Xaa Pro Pro Trp Thr
1               5                   10

<210> SEQ ID NO 56
<211> LENGTH: 8
<212> TYPE: PRT
<213> ORGANISM: Artificial Sequence
<220> FEATURE:
<223> OTHER INFORMATION: CDR sequence

<400> SEQUENCE: 56

Gly Tyr Thr Phe Thr Ser Tyr Trp
1               5

<210> SEQ ID NO 57
<211> LENGTH: 8
<212> TYPE: PRT
<213> ORGANISM: Artificial Sequence
<220> FEATURE:
<223> OTHER INFORMATION: CDR sequence

<400> SEQUENCE: 57

Ile Tyr Pro Ser Asp Ser Tyr Thr
1               5

<210> SEQ ID NO 58
<211> LENGTH: 11
<212> TYPE: PRT
<213> ORGANISM: Artificial Sequence
<220> FEATURE:
<223> OTHER INFORMATION: CDR sequence

<400> SEQUENCE: 58

Thr Arg Ser Trp Arg Gly Asn Ser Phe Asp Tyr
1               5                   10

<210> SEQ ID NO 59
<211> LENGTH: 8
<212> TYPE: PRT
<213> ORGANISM: Artificial Sequence
<220> FEATURE:
<223> OTHER INFORMATION: CDR sequence

<400> SEQUENCE: 59

Gly Tyr Thr Phe Thr Asn Tyr Gly
1               5

<210> SEQ ID NO 60
<211> LENGTH: 8
<212> TYPE: PRT
<213> ORGANISM: Artificial Sequence
<220> FEATURE:
<223> OTHER INFORMATION: CDR sequence
```

<400> SEQUENCE: 60

Ile Asn Thr Asn Thr Gly Glu Pro
1               5

<210> SEQ ID NO 61
<211> LENGTH: 11
<212> TYPE: PRT
<213> ORGANISM: Artificial Sequence
<220> FEATURE:
<223> OTHER INFORMATION: CDR sequence

<400> SEQUENCE: 61

Ala Arg Leu Gly Phe Gly Asn Ala Met Asp Tyr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: CDR sequence

<400> SEQUENCE: 62

Gln Ser Leu Leu Asn Ser Gly Asn Gln Lys Asn Tyr
1               5                   10

<210> SEQ ID NO 63
<211> LENGTH: 3
<212> TYPE: PRT
<213> ORGANISM: Artificial Sequence
<220> FEATURE:
<223> OTHER INFORMATION: CDR sequence

<400> SEQUENCE: 63

Trp Ala Ser
1

<210> SEQ ID NO 64
<211> LENGTH: 9
<212> TYPE: PRT
<213> ORGANISM: Artificial Sequence
<220> FEATURE:
<223> OTHER INFORMATION: CDR sequence

<400> SEQUENCE: 64

Gln Asn Asp Tyr Ser Tyr Pro Phe Thr
1               5

<210> SEQ ID NO 65
<211> LENGTH: 9
<212> TYPE: PRT
<213> ORGANISM: Artificial Sequence
<220> FEATURE:
<223> OTHER INFORMATION: CDR sequence

<400> SEQUENCE: 65

Gln Asn Asp Tyr Ser Tyr Pro Leu Thr
1               5

<210> SEQ ID NO 66
<211> LENGTH: 18
<212> TYPE: PRT
<213> ORGANISM: Artificial Sequence
<220> FEATURE:
<223> OTHER INFORMATION: Linker sequence

```
<400> SEQUENCE: 66

Ser Gly Pro Gly Gly Arg Ser Gly Gly Gly Ser Gly Gly
1               5                   10                  15

Gly Ser

<210> SEQ ID NO 67
<211> LENGTH: 6
<212> TYPE: PRT
<213> ORGANISM: Artificial Sequence
<220> FEATURE:
<223> OTHER INFORMATION: Linker sequence

<400> SEQUENCE: 67

Asp Val Pro Gly Gly Ser
1               5

<210> SEQ ID NO 68
<211> LENGTH: 20
<212> TYPE: PRT
<213> ORGANISM: Artificial Sequence
<220> FEATURE:
<223> OTHER INFORMATION: Linker sequence

<400> SEQUENCE: 68

Gly Gly Gly Gly Ser Gly Gly Gly Ser Gly Gly Gly Ser Gly
1               5                   10                  15

Gly Gly Gly Ser
            20

<210> SEQ ID NO 69
<211> LENGTH: 25
<212> TYPE: PRT
<213> ORGANISM: Artificial Sequence
<220> FEATURE:
<223> OTHER INFORMATION: Linker sequence

<400> SEQUENCE: 69

Gly Gly Gly Gly Ser Gly Gly Gly Ser Gly Gly Gly Ser Gly
1               5                   10                  15

Gly Gly Ser Gly Gly Gly Gly Ser
        20                  25

<210> SEQ ID NO 70
<211> LENGTH: 5
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(5)
<223> OTHER INFORMATION: Sequence repeated x times, wherein x is 3, 4,
      5 or 6

<400> SEQUENCE: 70

Gly Gly Gly Gly Ser
1               5

<210> SEQ ID NO 71
<211> LENGTH: 19
<212> TYPE: PRT
<213> ORGANISM: Artificial Sequence
<220> FEATURE:
<223> OTHER INFORMATION: Secretion signal

<400> SEQUENCE: 71
```

```
Met Gly Trp Ser Cys Ile Ile Leu Phe Leu Val Ala Thr Ala Thr Gly
1               5                   10                  15

Val His Ser

<210> SEQ ID NO 72
<211> LENGTH: 9
<212> TYPE: PRT
<213> ORGANISM: Artificial Sequence
<220> FEATURE:
<223> OTHER INFORMATION: His tag

<400> SEQUENCE: 72

Gly Gly Ser His His His His His His
1               5

<210> SEQ ID NO 73
<211> LENGTH: 6
<212> TYPE: PRT
<213> ORGANISM: Artificial Sequence
<220> FEATURE:
<223> OTHER INFORMATION: His tag

<400> SEQUENCE: 73

His His His His His His
1               5

<210> SEQ ID NO 74
<211> LENGTH: 494
<212> TYPE: PRT
<213> ORGANISM: Artificial Sequence
<220> FEATURE:
<223> OTHER INFORMATION: Antibody-derived sequence

<400> SEQUENCE: 74

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
```

```
            195                 200                 205
Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ser Gly Gly Gly Gly Ser Glu Val Gln Leu Gln Gln Ser
                245                 250                 255

Gly Pro Glu Leu Val Lys Pro Gly Ala Ser Met Lys Ile Ser Cys Lys
                260                 265                 270

Ala Ser Gly Tyr Ser Phe Thr Gly Tyr Thr Met Asn Trp Val Lys Gln
                275                 280                 285

Ser His Gly Lys Asn Leu Glu Trp Ile Gly Leu Ile Asn Pro Tyr Asn
    290                 295                 300

Gly Gly Thr Ile Tyr Asn Gln Lys Phe Lys Gly Lys Ala Thr Leu Thr
305                 310                 315                 320

Val Asp Lys Ser Ser Ser Thr Ala Tyr Met Glu Leu Leu Ser Leu Thr
                325                 330                 335

Ser Glu Asp Ser Ala Val Tyr Tyr Cys Ala Arg Asp Tyr Gly Phe Val
                340                 345                 350

Leu Asp Tyr Trp Gly Gln Gly Thr Thr Leu Thr Val Ser Ser Gly Gly
                355                 360                 365

Gly Gly Ser Gly Gly Gly Gly Ser Gly Gly Gly Gly Ser Asp Ile Val
                370                 375                 380

Leu Thr Gln Ser Pro Ser Ile Met Ser Val Ser Pro Gly Glu Lys Val
385                 390                 395                 400

Thr Ile Thr Cys Ser Ala Ser Ser Ser Val Ser Tyr Met His Trp Phe
                405                 410                 415

Gln Gln Lys Pro Gly Thr Ser Pro Lys Leu Leu Ile Tyr Ser Thr Ser
                420                 425                 430

Asn Leu Ala Ser Gly Val Pro Ala Arg Phe Ser Gly Arg Gly Ser Gly
                435                 440                 445

Thr Ser Tyr Ser Leu Thr Ile Ser Arg Val Ala Ala Glu Asp Ala Ala
                450                 455                 460

Thr Tyr Tyr Cys Gln Gln Arg Ser Asn Tyr Pro Pro Trp Thr Phe Gly
465                 470                 475                 480

Gly Gly Thr Lys Leu Glu Ile Lys His His His His His His
                485                 490
```

<210> SEQ ID NO 75
<211> LENGTH: 495
<212> TYPE: PRT
<213> ORGANISM: Artificial Sequence
<220> FEATURE:
<223> OTHER INFORMATION: Antibody-derived sequence

<400> SEQUENCE: 75

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Ile Asn Trp Val Lys Gln Arg Pro Gly Gln Gly Leu Glu Trp Ile
                35                  40                  45

Gly Asn Ile Tyr Pro Ser Asp Ser Tyr Thr Asn Tyr Asn Gln Lys Phe
                50                  55                  60

Lys Asp Lys Ala Thr Leu Thr Val Asp Lys Ser Ser Ser Thr Ala Tyr
```

-continued

```
            65                  70                  75                  80
Met Gln Leu Ser Ser Pro Thr Ser Glu Asp Ser Ala Val Tyr Tyr Cys
                    85                  90                  95

Thr Arg Ser Trp Arg Gly Asn Ser Phe Asp Tyr Trp Gly Gln Gly Thr
                100                 105                 110

Thr Leu Thr Val Ser Ser Gly Gly Gly Gly Ser Gly Gly Gly Gly Ser
                115                 120                 125

Gly Gly Gly Gly Ser Asp Ile Val Met Thr Gln Ser Pro Ser Ser Leu
            130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
                180                 185                 190

Arg Glu Ser Gly Val Pro Asp Arg Phe Thr Gly Ser Gly Ser Gly Thr
            195                 200                 205

Asp Phe Thr Leu Thr Ile Ser Ser Val Gln Ala Glu Asp Leu Ala Val
            210                 215                 220

Tyr Tyr Cys Gln Asn Asp Tyr Ser Tyr Pro Phe Thr Phe Gly Ser Gly
225                 230                 235                 240

Thr Lys Leu Glu Ile Lys Ser Gly Gly Gly Ser Asp Ile Lys Leu
                245                 250                 255

Gln Gln Ser Gly Ala Glu Leu Ala Arg Pro Gly Ala Ser Val Lys Met
            260                 265                 270

Ser Cys Lys Thr Ser Gly Tyr Thr Phe Thr Arg Tyr Thr Met His Trp
            275                 280                 285

Val Lys Gln Arg Pro Gly Gln Gly Leu Glu Trp Ile Gly Tyr Ile Asn
            290                 295                 300

Pro Ser Arg Gly Tyr Thr Asn Tyr Asn Gln Lys Phe Lys Asp Lys Ala
305                 310                 315                 320

Thr Leu Thr Thr Asp Lys Ser Ser Thr Ala Tyr Met Gln Leu Ser
                325                 330                 335

Ser Leu Thr Ser Glu Asp Ser Ala Val Tyr Tyr Cys Ala Arg Tyr Tyr
                340                 345                 350

Asp Asp His Tyr Ser Leu Asp Tyr Trp Gly Gln Gly Thr Thr Leu Thr
            355                 360                 365

Val Ser Ser Val Glu Gly Gly Ser Gly Gly Ser Gly Gly
            370                 375                 380

Ser Gly Gly Val Asp Asp Ile Gln Leu Thr Gln Ser Pro Ala Ile Met
385                 390                 395                 400

Ser Ala Ser Pro Gly Glu Lys Val Thr Met Thr Cys Arg Ala Ser Ser
                405                 410                 415

Ser Val Ser Tyr Met Asn Trp Tyr Gln Gln Lys Ser Gly Thr Ser Pro
                420                 425                 430

Lys Arg Trp Ile Tyr Asp Thr Ser Lys Val Ala Ser Gly Val Pro Tyr
            435                 440                 445

Arg Phe Ser Gly Ser Gly Ser Gly Thr Ser Tyr Ser Leu Thr Ile Ser
            450                 455                 460

Ser Met Glu Ala Glu Asp Ala Ala Thr Tyr Tyr Cys Gln Gln Trp Ser
465                 470                 475                 480

Ser Asn Pro Leu Thr Phe Gly Ala Gly Thr Lys Leu Glu Leu Lys
                485                 490                 495
```

<210> SEQ ID NO 76
<211> LENGTH: 511
<212> TYPE: PRT
<213> ORGANISM: Artificial Sequence
<220> FEATURE:
<223> OTHER INFORMATION: Antibody-derived sequence

<400> SEQUENCE: 76

```
Gln Val Gln Leu Gln Gln Pro Gly Ala Glu Leu Val Arg Pro Gly Ala
 1               5                  10                  15

Ser Val Lys Leu Ser Cys Lys Ala Ser Gly Tyr Thr Phe Thr Ser Tyr
             20                  25                  30

Trp Ile Asn Trp Val Lys Gln Arg Pro Gly Gln Gly Leu Glu Trp Ile
         35                  40                  45

Gly Asn Ile Tyr Pro Ser Asp Ser Tyr Thr Asn Tyr Asn Gln Lys Phe
     50                  55                  60

Lys Asp Lys Ala Thr Leu Thr Val Asp Lys Ser Ser Thr Ala Tyr
 65                  70                  75                  80

Met Gln Leu Ser Ser Pro Thr Ser Glu Asp Ser Ala Val Tyr Tyr Cys
                 85                  90                  95

Thr Arg Ser Trp Arg Gly Asn Ser Phe Asp Tyr Trp Gly Gln Gly Thr
            100                 105                 110

Thr Leu Thr Val Ser Ser Gly Gly Gly Ser Gly Gly Gly Gly Ser
        115                 120                 125

Gly Gly Gly Gly Ser Gly Gly Gly Ser Asp Ile Val Met Thr Gln
    130                 135                 140

Ser Pro Ser Ser Leu Thr Val Thr Ala Gly Glu Lys Val Thr Met Ser
145                 150                 155                 160

Cys Lys Ser Ser Gln Ser Leu Leu Asn Ser Gly Asn Gln Lys Asn Tyr
                165                 170                 175

Leu Thr Trp Tyr Gln Gln Lys Pro Gly Gln Pro Pro Lys Leu Leu Ile
            180                 185                 190

Tyr Trp Ala Ser Thr Arg Glu Ser Gly Val Pro Asp Arg Phe Thr Gly
        195                 200                 205

Ser Gly Ser Gly Thr Asp Phe Thr Leu Thr Ile Ser Ser Val Gln Ala
    210                 215                 220

Glu Asp Leu Ala Val Tyr Tyr Cys Gln Asn Asp Tyr Ser Tyr Pro Phe
225                 230                 235                 240

Thr Phe Gly Ser Gly Thr Lys Leu Glu Ile Lys Ser Gly Gly Gly Gly
                245                 250                 255

Ser Gln Val Gln Leu Gln Gln Ser Gly Ala Glu Leu Ala Arg Pro Gly
            260                 265                 270

Ala Ser Val Lys Met Ser Cys Lys Thr Ser Gly Tyr Thr Phe Thr Arg
        275                 280                 285

Tyr Thr Met His Trp Val Lys Gln Arg Pro Gly Gln Gly Leu Glu Trp
    290                 295                 300

Ile Gly Tyr Ile Asn Pro Ser Arg Gly Tyr Thr Asn Tyr Asn Gln Lys
305                 310                 315                 320

Phe Lys Asp Lys Ala Thr Leu Thr Thr Asp Lys Ser Ser Ser Thr Ala
                325                 330                 335

Tyr Met Gln Leu Ser Ser Leu Thr Ser Glu Asp Ser Ala Val Tyr Tyr
            340                 345                 350

Cys Ala Arg Tyr Tyr Asp Asp His Tyr Ser Leu Asp Tyr Trp Gly Gln
        355                 360                 365
```

```
Gly Thr Thr Leu Thr Val Ser Gly Gly Gly Ser Gly Gly
    370                 375                 380

Gly Ser Gly Gly Gly Ser Gly Gly Gly Ser Gln Ile Val Leu
385                 390                 395                 400

Thr Gln Ser Pro Ala Ile Met Ser Ala Ser Pro Gly Glu Lys Val Thr
                405                 410                 415

Met Thr Cys Arg Ala Ser Ser Ser Val Ser Tyr Met Asn Trp Tyr Gln
                420                 425                 430

Gln Lys Ser Gly Thr Ser Pro Lys Arg Trp Ile Tyr Asp Thr Ser Lys
            435                 440                 445

Val Ala Ser Gly Val Pro Tyr Arg Phe Ser Gly Ser Gly Ser Gly Thr
450                 455                 460

Ser Tyr Ser Leu Thr Ile Ser Ser Met Glu Ala Glu Asp Ala Ala Thr
465                 470                 475                 480

Tyr Tyr Cys Gln Gln Trp Ser Ser Asn Pro Leu Thr Phe Gly Ala Gly
                485                 490                 495

Thr Lys Leu Glu Leu Lys Gly Gly Ser His His His His His
            500                 505                 510
```

<210> SEQ ID NO 77
<211> LENGTH: 516
<212> TYPE: PRT
<213> ORGANISM: Artificial Sequence
<220> FEATURE:
<223> OTHER INFORMATION: Antibody-derived sequence

<400> SEQUENCE: 77

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
                100                 105                 110

Lys Gly Gly Gly Gly Ser Gly Gly Gly Gly Ser Gly Gly Gly Gly Ser
            115                 120                 125

Gly Gly Gly Gly Ser Gly Gly Gly Ser Gln Val Gln Leu Gln Gln
    130                 135                 140

Pro Gly Ala Glu Leu Val Arg Pro Gly Ala Ser Val Lys Leu Ser Cys
145                 150                 155                 160

Lys Ala Ser Gly Tyr Thr Phe Thr Ser Tyr Trp Ile Asn Trp Val Lys
                165                 170                 175

Gln Arg Pro Gly Gln Gly Leu Glu Trp Ile Gly Asn Ile Tyr Pro Ser
            180                 185                 190

Asp Ser Tyr Thr Asn Tyr Asn Gln Lys Phe Lys Asp Lys Ala Thr Leu
        195                 200                 205

Thr Val Asp Lys Ser Ser Ser Thr Ala Tyr Met Gln Leu Ser Ser Pro
210                 215                 220
```

```
Thr Ser Glu Asp Ser Ala Val Tyr Tyr Cys Thr Arg Ser Trp Arg Gly
225                 230                 235                 240

Asn Ser Phe Asp Tyr Trp Gly Gln Gly Thr Thr Leu Thr Val Ser Ser
            245                 250                 255

Ser Gly Gly Gly Gly Ser Gln Val Gln Leu Gln Gln Ser Gly Ala Glu
        260                 265                 270

Leu Ala Arg Pro Gly Ala Ser Val Lys Met Ser Cys Lys Thr Ser Gly
    275                 280                 285

Tyr Thr Phe Thr Arg Tyr Thr Met His Trp Val Lys Gln Arg Pro Gly
290                 295                 300

Gln Gly Leu Glu Trp Ile Gly Tyr Ile Asn Pro Ser Arg Gly Tyr Thr
305                 310                 315                 320

Asn Tyr Asn Gln Lys Phe Lys Asp Lys Ala Thr Leu Thr Thr Asp Lys
            325                 330                 335

Ser Ser Ser Thr Ala Tyr Met Gln Leu Ser Ser Leu Thr Ser Glu Asp
        340                 345                 350

Ser Ala Val Tyr Tyr Cys Ala Arg Tyr Tyr Asp Asp His Tyr Ser Leu
    355                 360                 365

Asp Tyr Trp Gly Gln Gly Thr Thr Leu Thr Val Ser Ser Gly Gly Gly
370                 375                 380

Gly Ser Gly Gly Gly Gly Ser Gly Gly Gly Gly Ser Gly Gly Gly Gly
385                 390                 395                 400

Ser Gln Ile Val Leu Thr Gln Ser Pro Ala Ile Met Ser Ala Ser Pro
            405                 410                 415

Gly Glu Lys Val Thr Met Thr Cys Arg Ala Ser Ser Ser Val Ser Tyr
        420                 425                 430

Met Asn Trp Tyr Gln Gln Lys Ser Gly Thr Ser Pro Lys Arg Trp Ile
    435                 440                 445

Tyr Asp Thr Ser Lys Val Ala Ser Gly Val Pro Tyr Arg Phe Ser Gly
450                 455                 460

Ser Gly Ser Gly Thr Ser Tyr Ser Leu Thr Ile Ser Ser Met Glu Ala
465                 470                 475                 480

Glu Asp Ala Ala Thr Tyr Tyr Cys Gln Gln Trp Ser Ser Asn Pro Leu
            485                 490                 495

Thr Phe Gly Ala Gly Thr Lys Leu Glu Leu Lys Gly Gly Ser His His
        500                 505                 510

His His His His
        515

<210> SEQ ID NO 78
<211> LENGTH: 1479
<212> TYPE: DNA
<213> ORGANISM: Artificial Sequence
<220> FEATURE:
<223> OTHER INFORMATION: Antibody-derived sequence

<400> SEQUENCE: 78
atgggctggt cctgcatcat cctgtttctg gtggctaccg ccaccggcgt gcactctcag      60
atcgtgctga cccagtctcc cgccatcatg tctgctagcc ctggcgagaa agtgacaatg     120
acctgccggg cctcctcctc cgtgtcctac atgaactggt atcagcagaa gtccggcacc     180
tcccccaagc ggtggatcta cgacacctcc aaggtggcct ctggcgtgcc ctacagattc     240
tccggctctg gctctggcac ctcctacagc ctgaccatct ccagcatgga agccgaggat     300
gccgccacct actactgcca gcagtggtcc tccaaccccc tgacctttgg cgctggcacc     360
```

```
aagctggaac tgaagcggac cgtggccgct ccttccgtgt tcatcttccc tccctccgac      420
gagcagctga agtccggcac cgcctccgtg gtgtgcctgc tgaacaactt ctaccctcgg      480
gaggccaagg tgcagtggaa ggtggacaac gccctgcagt ccggcaactc ccaggaaagc      540
gtcaccgagc aggactccaa ggacagcacc tactccctgt cctccaccct gaccctgtcc      600
aaggccgact acgagaagca caaggtgtac gcctgcgagg tgacccacca gggcctgtcc      660
agccctgtga ccaagtcctt caaccggggc gagtgtgacg tgcctggtgg tagcgaagtg      720
cagctgcagc agagcggccc tgagctggtg aaacccggcg ctagcatgaa gatcagctgc      780
aaggccagcg gctacagctt caccggctac accatgaact gggtgaaaca gagccacggc      840
aagtgcctgg aatggatcgg cctgatcaac ccctacaacg gcggcaccat ctacaaccag      900
aagttcaagg gcaaggccac actgaccgtg gacaagagca gcagcaccgc ctacatggaa      960
ctgctgagcc tgaccagcga ggacagcgcc gtgtactact gcgccagaga ctacggcttc     1020
gtgctggact actggggcca gggcaccacc ctgacagtgt ctagcggagg cggaggatct     1080
ggtggtggcg gatctggcgg cggtggaagt ggcggaggtg gtagccagat cgtgctgacc     1140
cagtcccccc tccatcatgt cgtgtctccc ggcgagaaag tgacaattac ctgctccgcc     1200
tcctcctccg tgtcctacat gcactggttc cagcagaagc ccggcaccct ccccaagctg     1260
tggatctact ccacctccaa cctggcctcc ggcgtgcccg ccagattctc cggaagaggc     1320
tccggcacca gctactccct gaccatctcc agagtggccg ccgaggacgc cgccacctac     1380
tactgccagc agcggtccaa ctaccccccc tggaccttg gctgcggcac caagctggaa     1440
atcaagtctg cctggagcca cccacagttc gagaagtga                           1479
```

<210> SEQ ID NO 79
<211> LENGTH: 1539
<212> TYPE: DNA
<213> ORGANISM: Artificial Sequence
<220> FEATURE:
<223> OTHER INFORMATION: Antibody-derived sequence

<400> SEQUENCE: 79

```
atgggctggt cctgcatcat cctgtttctg gtggctaccg ccaccggcgt gcactcccag       60
gtgcagctgc agcagtctgg cgctgagctg gctagacctg gcgcctccgt gaagatgtcc      120
tgcaagacct ccggctacac cttcacccgg tacaccatgc actgggtcaa gcagaggcct      180
ggacagggcc tggaatggat cggctacatc aaccctctcc ggggctacac caactacaac      240
cagaagttca aggacaaggc caccctgaca accgacaagt cctcctccac cgcctacatg      300
cagctgtcct ccctgacctc cgaggactcc gccgtgtact actgcgcccg gtactacgac      360
gaccactact ccctggacta ctggggccag ggcaccacc tgacagtgtc tagcgcctcc      420
accaagggcc cttccgtgtt ccctctggcc ccttcctcca gtccacctc cggcggcacc      480 gccgctctgg gctgcctggt gaaggactac ttccctgagc tgtgaccgt gagctggaac      540 tctggcgccc tgaccagcgg cgtgcacacc ttccctgccg tgctgcagtc ctccggcctg      600
tactccctgt cctccgtggt gaccgtgcct tcctcctccc tgggcaccca gacctacatc      660
tgcaacgtga accacaagcc ttccaacacc aaggtggaca agcgggtgga gcctaagtcc      720
tgctccggcc ctggggcgg acgcagcggc ggaggcggat ccggcggagg aggctctgaa      780
gtgcagctgc agcagagcgg ccctgagctg gtgaaacccg cgctagcat gaagatcagc      840 tgcaaggcca gcggctacag cttcaccggc tacaccatga actgggtgaa acagagccac      900
```

```
ggcaagtgcc tggaatggat cggcctgatc aaccccctaca acggcggcac catctacaac    960
cagaagttca agggcaaggc cacactgacc gtggacaaga gcagcagcac cgcctacatg   1020
gaactgctga gcctgaccag cgaggacagc gccgtgtact actgcgccag agactacggc   1080
ttcgtgctgg actactgggg ccagggcacc accctgacag tgtctagcgg aggcggagga   1140
tctggtggtg gcggatctgg cggcggtgga agtggcggag gtggtagcca gatcgtgctg   1200
acccagtccc cctccatcat gtccgtgtct cccggcgaga aagtgacaat tacctgctcc   1260
gcctcctcct ccgtgtccta catgcactgg ttccagcaga agcccggcac ctcccccaag   1320
ctgtggatct actccacctc caacctggcc tccggcgtgc ccgccagatt ctccggaaga   1380
ggctccggca ccagctactc cctgaccatc tccagagtgg ccgccgagga cgccgccacc   1440
tactactgcc agcagcggtc caactacccc cctggaccct ttggctgcgg caccaagctg   1500
gaaatcaagg gcggctccca ccaccaccat caccactga                           1539

<210> SEQ ID NO 80
<211> LENGTH: 1539
<212> TYPE: DNA
<213> ORGANISM: Artificial Sequence
<220> FEATURE:
<223> OTHER INFORMATION: Antibody-derived sequence

<400> SEQUENCE: 80
atgggctggt cctgcatcat cctgtttctg gtggctaccg ccaccggcgt gcactcccag     60
gtgcagctgc agcagtctgg cgctgagctg ctagacctg cgcctccgt gaagatgtcc      120 tgcaagacct ccggctacac cttcacccgg tacaccatgc actgggtcaa gcagaggcct    180
ggacagggcc tggaatggat cggctacatc aaccccctccc ggggctacac caactacaac   240
cagaagttca aggacaaggc caccctgaca accgacaagt cctcctccac cgcctacatg    300
cagctgtcct ccctgaccct cgaggactcc gccgtgtact actgcgcccg gtactacgac    360
gaccactact ccctggacta ctggggccag ggcaccacac tgacagtgtc tagcgcctcc    420
accaagggcc cttccgtgtt ccctctggcc ccttgctcca gtccaccctc cgaaggcacc    480
gccgctctgg gctgcctggt gaaggactac ttccctgagc ctgtgaccgt gagctggaac    540
tctggcgccc tgaccagcgg cgtgcacacc ttccctgccg tgctgcagtc ctccggcctg    600
tactccctgt cctccgtggt gaccgtgcct tcctccaact tcggcaccca gacctacacc    660
tgcaacgtgg accacaagcc ttccaacacc aaggtggaca gaccgtggaa gcctaagtcc    720
gcctccggcc tggggggcgg acgcagcggc ggaggcggat ccggcggagg aggctctgaa    780
gtgcagctgc agcagagcgg ccctgagctg gtgaaacccg gcgctagcat gaagatcagc    840
tgcaaggcca gcggctacag cttcacccgg tacaccatga ctgggtgaa acagagccac    900 ggcaagtgcc tggaatggat cggcctgatc aaccccctaca acggcggcac catctacaac    960
cagaagttca agggcaaggc cacactgacc gtggacaaga gcagcagcac cgcctacatg   1020
gaactgctga gcctgaccag cgaggacagc gccgtgtact actgcgccag agactacggc   1080
ttcgtgctgg actactgggg ccagggcacc accctgacag tgtctagcgg aggcggagga   1140
tctggtggtg gcggatctgg cggcggtgga agtggcggag gtggtagcca gatcgtgctg   1200
acccagtccc cctccatcat gtccgtgtct cccggcgaga aagtgacaat tacctgctcc   1260
gcctcctcct ccgtgtccta catgcactgg ttccagcaga agcccggcac ctcccccaag   1320
ctgtggatct actccacctc caacctggcc tccggcgtgc ccgccagatt ctccggaaga   1380
ggctccggca ccagctactc cctgaccatc tccagagtgg ccgccgagga cgccgccacc   1440
```

| | |
|---|---|
| tactactgcc agcagcggtc caactacccc ccctggacct ttggctgcgg caccaagctg | 1500 |
| gaaatcaagg gcggctccca ccaccaccat caccactga | 1539 |

<210> SEQ ID NO 81
<211> LENGTH: 1449
<212> TYPE: DNA
<213> ORGANISM: Artificial Sequence
<220> FEATURE:
<223> OTHER INFORMATION: Antibody-derived sequence

<400> SEQUENCE: 81

| | |
|---|---|
| atgggctggt cctgcatcat cctgtttctg gtggctaccg ccaccggcgt gcactctcag | 60 |
| atcgtgctga cccagtctcc cgccatcatg tctgctagcc ctggcgagaa agtgacaatg | 120 |
| acctgccggg cctcctcctc cgtgtcctac atgaactggt atcagcagaa gtccggcacc | 180 |
| tcccccaagc ggtggatcta cgacacctcc aaggtggcct ctggcgtgcc ctacagattc | 240 |
| tccggctctg gctctggcac ctcctacagc ctgaccatct ccagcatgga agccgaggat | 300 |
| gccgccacct actactgcca gcagtggtcc tccaaccccc tgacctttgg cgctggcacc | 360 |
| aagctggaac tgaagcggac cgtggccgct ccttccgtgt tcatcttccc tccctccgac | 420 |
| gagcagctga agtccggcac cgcctccgtg gtgtgcctgc tgaacaactt ctaccctcgg | 480 |
| gaggccaagg tgcagtggaa ggtggacaac gccctgcagt ccggcaactc ccaggaaagc | 540 |
| gtcaccgagc aggactccaa ggacagcacc tactccctgt cctccaccct gaccctgtcc | 600 |
| aaggccgact acgagaagca caaggtgtac gcctgcgagg tgacccacca gggcctgtcc | 660 |
| agccctgtga ccaagtcctt caaccggggc gagtgtgacg tgcctggtgg tagcgaagtg | 720 |
| cagctgcagc agagcggccc tgagctggtg aaacccggcg ctagcatgaa gatcagctgc | 780 |
| aaggccagcg gctacagctt caccggctac accatgaact gggtgaaaca gagccacggc | 840 |
| aagtgcctgg aatggatcgg cctgatcaac ccctacaacg gcggcaccat ctacaaccag | 900 |
| aagttcaagg gcaaggccac actgaccgtg gacaagagca gcagcaccgc ctacatggaa | 960 |
| ctgctgagcc tgaccagcga ggacagcgcc gtgtactact gcgccagaga ctacggcttc | 1020 |
| gtgctggact actggggcca gggcaccacc ctgacagtgt ctagcggagg cggaggatct | 1080 |
| ggtggtggcg gatctggcgg cggtggaagt ggcggaggtg gtagccagat cgtgctgacc | 1140 |
| cagtccccct ccatcatgtc cgtgtctccc ggcgagaaag tgacaattac ctgctccgcc | 1200 |
| tcctcctccg tgtcctacat gcactggttc cagcagaagc ccggcacctc ccccaagctg | 1260 |
| tggatctact ccacctccaa cctggcctcc ggcgtgcccg ccagattctc cggaagaggc | 1320 |
| tccggcacca gctactccct gaccatctcc agagtggccg ccgaggacgc cgccacctac | 1380 |
| tactgccagc agcggtccaa ctaccccccc tggacctttg gctgcggcac caagctggaa | 1440 |
| atcaagtga | 1449 |

<210> SEQ ID NO 82
<211> LENGTH: 1512
<212> TYPE: DNA
<213> ORGANISM: Artificial Sequence
<220> FEATURE:
<223> OTHER INFORMATION: Antibody-derived sequence

<400> SEQUENCE: 82

| | |
|---|---|
| atgggctggt cctgcatcat cctgtttctg gtggctaccg ccaccggcgt gcactcccag | 60 |
| gtgcagctgc agcagtctgg cgctgagctg gctagacctg gcgcctccgt gaagatgtcc | 120 |

| | |
|---|---|
| tgcaagacct ccggctacac cttcacccgg tacaccatgc actgggtcaa gcagaggcct | 180 |
| ggacagggcc tggaatggat cggctacatc aaccccctcc ggggctacac caactacaac | 240 |
| cagaagttca aggacaaggc caccctgaca accgacaagt cctcctccac cgcctacatg | 300 |
| cagctgtcct ccctgacctc cgaggactcc gccgtgtact actgcgcccg gtactacgac | 360 |
| gaccactact ccctggacta ctggggccag ggcaccacac tgacagtgtc tagcgcctcc | 420 |
| accaagggcc cttccgtgtt ccctctggcc ccttcctcca gtccacctc cggcggcacc | 480 |
| gccgctctgg gctgcctggt gaaggactac ttccctgagc ctgtgaccgt gagctggaac | 540 |
| tctggcgccc tgaccagcgg cgtgcacacc ttccctgccg tgctgcagtc ctccggcctg | 600 |
| tactccctgt cctccgtggt gaccgtgcct tcctcctccc tgggcaccca gacctacatc | 660 |
| tgcaacgtga accacaagcc ttccaacacc aaggtggaca gcgggtgga gcctaagtcc | 720 |
| tgctccggcc ctggggcgg acgcagcggc ggaggcggat ccggcggagg aggctctgaa | 780 |
| gtgcagctgc agcagagcgg ccctgagctg gtgaaacccg gcgctagcat gaagatcagc | 840 |
| tgcaaggcca gcggctacag cttcaccggc tacaccatga actgggtgaa acagagccac | 900 |
| ggcaagtgcc tggaatggat cggcctgatc aacccctaca cggcggcac catctacaac | 960 |
| cagaagttca agggcaaggc cacactgacc gtggacaaga gcagcagcac cgcctacatg | 1020 |
| gaactgctga gcctgaccag cgaggacagc gccgtgtact actgcgccag agactacggc | 1080 |
| ttcgtgctgg actactgggg ccagggcacc accctgacag tgtctagcgg aggcggagga | 1140 |
| tctggtggtg gcggatctgg cggcggtgga agtggcggag gtggtagcca gatcgtgctg | 1200 |
| acccagtccc cctccatcat gtccgtgtct cccggcgaga agtgacaat acctgctcc | 1260 |
| gcctcctcct ccgtgtccta catgcactgg ttccagcaga agcccggcac ctcccccaag | 1320 |
| ctgtggatct actccaccctc caacctggcc tccggcgtgc ccgccagatt ctccggaaga | 1380 |
| ggctccggca ccagctactc cctgaccatc tccagagtgg ccgccgagga cgccgccacc | 1440 |
| tactactgcc agcagcggtc caactacccc ccctggacct ttggctgcgg caccaagctg | 1500 |
| gaaatcaagt ga | 1512 |

<210> SEQ ID NO 83
<211> LENGTH: 1512
<212> TYPE: DNA
<213> ORGANISM: Artificial Sequence
<220> FEATURE:
<223> OTHER INFORMATION: Antibody-derived sequence

<400> SEQUENCE: 83

| | |
|---|---|
| atgggctggt cctgcatcat cctgtttctg gtggctaccg ccaccggcgt gcactcccag | 60 |
| gtgcagctgc agcagtctgg cgctgagctg gctagacctg cgcgcctccgt gaagatgtcc | 120 |
| tgcaagacct ccggctacac cttcacccgg tacaccatgc actgggtcaa gcagaggcct | 180 |
| ggacagggcc tggaatggat cggctacatc aaccccctcc ggggctacac caactacaac | 240 |
| cagaagttca aggacaaggc caccctgaca accgacaagt cctcctccac cgcctacatg | 300 |
| cagctgtcct ccctgacctc cgaggactcc gccgtgtact actgcgcccg gtactacgac | 360 |
| gaccactact ccctggacta ctggggccag ggcaccacac tgacagtgtc tagcgcctcc | 420 |
| accaagggcc cttccgtgtt ccctctggcc ccttgctcca gtccacctc cgaaggcacc | 480 |
| gccgctctgg gctgcctggt gaaggactac ttccctgagc ctgtgaccgt gagctggaac | 540 |
| tctggcgccc tgaccagcgg cgtgcacacc ttccctgccg tgctgcagtc ctccggcctg | 600 |
| tactccctgt cctccgtggt gaccgtgcct tcctccaact tcggcaccca gacctacacc | 660 |

| | |
|---|---|
| tgcaacgtgg accacaagcc ttccaacacc aaggtggaca agaccgtgga gcctaagtcc | 720 |
| gcctccggcc ctggggggcgg acgcagcggc ggaggcggat ccggcggagg aggctctgaa | 780 |
| gtgcagctgc agcagagcgg ccctgagctg gtgaaacccg gcgctagcat gaagatcagc | 840 |
| tgcaaggcca gcggctacag cttcaccggc tacaccatga actgggtgaa acagagccac | 900 |
| ggcaagtgcc tggaatggat cggcctgatc aaccccctaca cggcggcac catctacaac | 960 |
| cagaagttca agggcaaggc cacactgacc gtggacaaga gcagcagcac cgcctacatg | 1020 |
| gaactgctga gcctgaccag cgaggacagc gccgtgtact actgcgccag agactacggc | 1080 |
| ttcgtgctgg actactgggg ccagggcacc accctgacag tgtctagcgg aggcggagga | 1140 |
| tctggtggtg gcggatctgg cggcggtgga agtggcggag gtggtagcca gatcgtgctg | 1200 |
| acccagtccc cctccatcat gtccgtgtct cccggcgaga aagtgacaat tacctgctcc | 1260 |
| gcctcctcct ccgtgtccta catgcactgg ttccagcaga agcccggcac ctcccccaag | 1320 |
| ctgtggatct actccacctc caacctggcc tccggcgtgc ccgccagatt ctccggaaga | 1380 |
| ggctccggca ccagctactc cctgaccatc tccagagtgg ccgccgagga cgccgccacc | 1440 |
| tactactgcc agcagcggtc caactacccc ccctggacct ttggctgcgg caccaagctg | 1500 |
| gaaatcaagt ga | 1512 |

<210> SEQ ID NO 84
<211> LENGTH: 1542
<212> TYPE: DNA
<213> ORGANISM: Artificial Sequence
<220> FEATURE:
<223> OTHER INFORMATION: Antibody-derived sequence

<400> SEQUENCE: 84

| | |
|---|---|
| atgggctggt cctgcatcat cctgtttctg gtggccaccg ccaccggcgt gcacagcgac | 60 |
| atcaagctgc agcagagcgg agccgagctg gccagacctg gggccagcgt gaagatgagc | 120 |
| tgcaagacca gcggctacac cttcacccgg tacaccatgc actgggtgaa acagcggcct | 180 |
| ggacagggcc tggaatggat cggctacatc aacccccagcc ggggctacac caactacaac | 240 |
| cagaagttca aggacaaggc caccctgacc accgacaaga gcagcagcac cgcctacatg | 300 |
| cagctgagca gcctgaccag cgaggacagc gccgtgtact actgcgcccg gtactacgac | 360 |
| gaccactaca gcctggacta ctggggccag ggcaccaccc tgacagtgtc tagcgtggaa | 420 |
| ggaggaagcg gaggatctgg cggctctggg ggaagcggtg gcgtggacga catccagctg | 480 |
| acccagagcc ccgccatcat gtctgccagc cctggcgaga agtgaccat gacctgccgg | 540 |
| gccagcagca gcgtgtccta catgaactgg tatcagcaga agtccggcac cagccccaag | 600 |
| cggtggatct acgacaccag caaggtggca agcggcgtgc cctacagatt cagcggcagc | 660 |
| ggctccggca cctcctactc cctgaccatc agcagcatgg aagccgagga cgccgccacc | 720 |
| tactactgcc agcagtggtc cagcaacccc ctgaccttcg gagccggcac caagctggaa | 780 |
| ctgaagtctg gcgggggagg atccgaggtg cagctgcagc agtccggccc tgagctggtg | 840 |
| aaacccggcg ctagcatgaa gatctcttgc aaggcctccg gctacagctt taccggctac | 900 |
| acaatgaatt gggtgaagca gagccacggc aagaatctgg aatggattgg cctgatcaac | 960 |
| ccttacaacg gcggcacaat ctataatcag aagtttaaag gaaggccac actgacagtg | 1020 |
| gacaagtcca gctccacagc ctacatggaa ctgctgagcc tgacctccga ggactctgcc | 1080 |
| gtgtattact gtgccagaga ctacggcttc gtgctggatt attggggaca gggaacaaca | 1140 |

| | |
|---|---|
| ctgaccgtgt cctccggggg aggggatca ggtgggggag gtagtggggg tggcggctct | 1200 |
| gatatcgtgc tgacccagtc ccctagcatc atgagcgtgt ccccaggcga aaaagtgaca | 1260 |
| atcacttgca gcgccagctc ctccgtgtct tatatgcatt ggttccagca gaagcctggc | 1320 |
| acatccccca aactgttaat ctacagcacc tccaacctgg cttccggcgt gcccgccaga | 1380 |
| ttttctggca gaggcagcgg caccagctac agcctgacaa tcagccgggt ggccgccgaa | 1440 |
| gatgccgcca catattattg tcagcagcgg agcaactacc cccctggac attcggggga | 1500 |
| ggaacaaagc tggaaatcaa gcaccaccac caccaccact ga | 1542 |

<210> SEQ ID NO 85
<211> LENGTH: 1500
<212> TYPE: DNA
<213> ORGANISM: Artificial Sequence
<220> FEATURE:
<223> OTHER INFORMATION: Antibody-derived sequence

<400> SEQUENCE: 85

| | |
|---|---|
| atgggctggt cctgcatcat cctgtttctg gtggctaccg ccaccggcgt gcactctcag | 60 |
| atcgtgctga cccagtctcc cgccatcatg tctgctagcc ctggcgagaa agtgacaatg | 120 |
| acctgccggg cctcctcctc cgtgtcctac atgaactggt atcagcagaa gtccggcacc | 180 |
| tcccccaagc ggtggatcta cgacacctcc aaggtggcct ctggcgtgcc ctacagattc | 240 |
| tccggctctg gctctggcac ctcctacagc ctgaccatct ccagcatgga agccgaggat | 300 |
| gccgccacct actactgcca gcagtggtcc tccaaccccc tgacctttgg cgctggcacc | 360 |
| aagctggaac tgaagcggac cgtggccgct ccttccgtgt tcatcttccc tcctccgac | 420 |
| gagcagctga gtccggcac cgcctccgtg gtgtgcctgc tgaacaactt ctaccctcgg | 480 |
| gaggccaagg tgcagtggaa ggtggacaac gccctgcagt ccggcaactc ccaggaaagc | 540 |
| gtcaccgagc aggactccaa ggacagcacc tactccctgt cctccaccct gaccctgtcc | 600 |
| aaggccgact acgagaagca caaggtgtac gcctgcgagg tgacccacca gggcctgtcc | 660 |
| agccctgtga ccaagtcctt caaccggggc gagtgtgacg tgcctggtgg tagccaggtg | 720 |
| cagctgcagag agcctggcgc tgaactggtc cgacctggcg cctccgtgaa gctgtcctgc | 780 |
| aaggcctccg gctacacctt caccagctac tggatcaact gggtcaagca gcggcctggc | 840 |
| cagggcctgg aatggatcgg caacatctac ccctccgact cctacaccaa ctacaaccag | 900 |
| aagttcaagg acaaggccac cctgaccgtg gacaagtcct cctccaccgc ctacatgcag | 960 |
| ctgtccagcc ccacctccga ggactccgcc gtgtactact gcaccggtc ctggcggggc | 1020 |
| aactccttcg actattgggg ccagggcacc accctgacag tgtcctctgg aggcggagga | 1080 |
| tctggtggtg gcggatctgg cggcggtgga agtggcggag gtggtagcga catcgtgatg | 1140 |
| acccagtccc cctccagcct gaccgtgacc gctggcgaga aagtgaccat gagctgcaag | 1200 |
| tcctcccagt ccctgctgaa ctccggcaac cagaagaact acctgacctg gtatcagcag | 1260 |
| aagcccggcc agcccccaa gctgctgatc tactgggcct ccacccgcga gtctggcgtg | 1320 |
| cccgatagat tcaccggctc cggcagcggc accgacttta ccctgaccat ctccagcgtg | 1380 |
| caggccgagg acctggccgt gtattactgt cagaacgact actcctaccc cttcaccttc | 1440 |
| ggctctggca ccaagctgga aatcaagtct gcctggagcc acccacagtt cgagaagtga | 1500 |

<210> SEQ ID NO 86
<211> LENGTH: 1515
<212> TYPE: DNA
<213> ORGANISM: Artificial Sequence

```
<220> FEATURE:
<223> OTHER INFORMATION: Antibody-derived sequence

<400> SEQUENCE: 86
atgggctggt cctgcatcat cctgtttctg gtggctaccg ccaccggcgt gcactctcag      60
atcgtgctga cccagtctcc cgccatcatg tctgctagcc ctggcgagaa agtgacaatg     120
acctgccggg cctcctcctc cgtgtcctac atgaactggt atcagcagaa gtccggcacc     180
tcccccaagc ggtggatcta cgacacctcc aaggtggcct ctggcgtgcc ctacagattc     240
tccggctctg gctctggcac ctcctacagc ctgaccatct ccagcatgga agccgaggat     300
gccgccacct actactgcca gcagtggtcc tccaacccccc tgacctttgg cgctggcacc     360
aagctggaac tgaagcggac cgtggccgct ccttccgtgt tcatcttccc tccctccgac     420
gagcagctga gtccggcac cgcctccgtg gtgtgcctgc tgaacaactt ctaccctcgg     480
gaggccaagg tgcagtggaa ggtggacaac gccctgcagt ccggcaactc ccaggaaagc     540
gtcaccgagc aggactccaa ggacagcacc tactccctgt cctccaccct gaccctgtcc     600
aaggccgact acgagaagca caaggtgtac gcctgcgagg tgacccacca gggcctgtcc     660
agccctgtga ccaagtcctt caaccggggc gagtgtgacg tgcctggtgg tagcgacatc     720
gtgatgaccc agtccccctc cagcctgacc gtgaccgctg gcgagaaagt gaccatgagc     780
tgcaagtcct cccagtccct gctgaactcc ggcaaccaga gaactacct gacctggtat     840 cagcagaagc ccggccagcc ccccaagctg ctgatctact gggcctccac ccgcgagtct     900
ggcgtgcccg atagattcac cggctccggc agcggcaccg actttaccct gaccatctcc     960
agcgtgcagg ccgaggacct ggccgtgtat tactgtcaga cgactactc ctaccccttc    1020 accttcggct ctggcaccaa gctggaaatc aaggggaggcg tgggttcagg cggcggaggc    1080
agcggtggag gtggtagtgg cggtggcggt tcaggggggag gtggctcgca ggtgcagctg    1140
cagcagcctg cgctgaact ggtccgacct ggcgcctccg tgaagctgtc ctgcaaggcc    1200
tccggctaca ccttcaccag ctactggatc aactgggtca gcagcggcc tggccagggc    1260 ctggaatgga tcggcaacat ctaccccctcc gactcctaca ccaactacaa ccagaagttc    1320
aaggacaagg ccaccctgac cgtggacaag tcctcctcca ccgcctacat gcagctgtcc    1380
agccccacct ccgaggactc cgccgtgtac tactgcaccc ggtcctggcg gggcaactcc    1440
ttcgactatt ggggccaggg caccaccctg acagtgtcct cttctgcctg gagccaccca    1500
cagttcgaga agtga                                                    1515

<210> SEQ ID NO 87
<211> LENGTH: 1560
<212> TYPE: DNA
<213> ORGANISM: Artificial Sequence
<220> FEATURE:
<223> OTHER INFORMATION: Antibody-derived sequence

<400> SEQUENCE: 87
atgggctggt cctgcatcat cctgtttctg gtggctaccg ccaccggcgt gcactcccag      60
gtgcagctgc agcagtctgg cgctgagctg gctagacctg gcgcctccgt gaagatgtcc     120
tgcaagacct ccggctacac cttcacccgg tacaccatg actgggtcaa gcagaggcct     180
ggacagggcc tggaatggat cggctacatc aacccctccc ggggctacac caactacaac     240
cagaagttca aggacaaggc caccctgaca accgacaagt cctcctccac cgcctacatg     300
cagctgtcct ccctgacctc cgaggactcc gccgtgtact actgcgcccg gtactacgac     360
```

```
gaccactact ccctggacta ctggggccag ggcaccacac tgacagtgtc tagcgcctcc    420
accaagggcc cttccgtgtt ccctctggcc ccttcctcca agtccacctc cggcggcacc    480
gccgctctgg gctgcctggt gaaggactac ttccctgagc ctgtgaccgt gagctggaac    540
tctggcgccc tgaccagcgg cgtgcacacc ttccctgccg tgctgcagtc ctccggcctg    600
tactccctgt cctccgtggt gaccgtgcct cctcctcccc tgggcaccca gacctacatc    660
tgcaacgtga accacaagcc ttccaacacc aaggtggaca gcgggtgga gcctaagtcc     720 tgctccggcc tgggggcgg acgcagcggc ggaggcggat ccggcggagg aggctctcag    780
gtgcagctgc agcagcctgg cgctgaactg gtccgacctg cgcctccgt gaagctgtcc    840 tgcaaggcct ccggctacac cttcaccagc tactggatca actgggtcaa gcagcggcct    900 ggccagggc tggaatggat cggcaacatc tacccctccg actcctacac caactacaac    960
cagaagttca aggacaaggc caccctgacc gtggacaagt cctcctccac cgcctacatg    1020
cagctgtcca gccccacctc cgaggactcc gccgtgtact actgcacccg gtcctggcgg    1080
ggcaactcct tcgactattg gggccagggc accaccctga cagtgtcctc tggaggcgga    1140
ggatctggtg gtggcggatc tggcggcggt ggaagtggcg gaggtggtag cgacatcgtg    1200
atgacccagt ccccctccag cctgaccgtg accgctggcg agaaagtgac catgagctgc    1260
aagtcctccc agtccctgct gaactccggc aaccagaaga actacctgac ctggtatcag    1320
cagaagcccg gccagccccc caagctgctg atctactggg cctccacccg cgagtctggc    1380
gtgcccgata gattcaccgg ctccggcagc ggcaccgact taccctgac catctccagc    1440 gtgcaggccg aggacctggc cgtgtattac tgtcagaacg actactccta ccccttcacc    1500
ttcggctctg gcaccaagct ggaaatcaag ggcggctccc accaccacca tcaccactga    1560
```

<210> SEQ ID NO 88
<211> LENGTH: 1569
<212> TYPE: DNA
<213> ORGANISM: Artificial Sequence
<220> FEATURE:
<223> OTHER INFORMATION: Antibody-derived sequence

<400> SEQUENCE: 88

```
atgggctggt cctgcatcat cctgtttctg gtggctaccg ccaccggcgt gcactcccag    60
gtgcagctgc agcagtctgg cgctgagctg gctagacctg cgcctccgt gaagatgtcc    120 tgcaagacct ccggctacac cttcacccgg tacaccatgc actgggtcaa gcagaggcct    180
ggacagggcc tggaatggat cggctacatc aaccccctccc ggggctacac caactacaac    240
cagaagttca aggacaaggc caccctgaca accgacaagt cctcctccac cgcctacatg    300
cagctgtcct ccctgacctc cgaggactcc gccgtgtact actgcgcccg gtactacgac    360
gaccactact ccctggacta ctggggccag ggcaccacac tgacagtgtc tagcgcctcc    420
accaagggcc cttccgtgtt ccctctggcc ccttcctcca agtccacctc cggcggcacc    480
gccgctctgg gctgcctggt gaaggactac ttccctgagc ctgtgaccgt gagctggaac    540
tctggcgccc tgaccagcgg cgtgcacacc ttccctgccg tgctgcagtc ctccggcctg    600
tactccctgt cctccgtggt gaccgtgcct cctcctcccc tgggcaccca gacctacatc    660
tgcaacgtga accacaagcc ttccaacacc aaggtggaca gcgggtgga gcctaagtcc     720 tgctccggcc tgggggcgg acgcagcggc ggaggcggat ccggcggagg aggctctgac    780
atcgtgatga cccagtcccc ctccagcctg accgtgaccg ctggcgagaa agtgaccatg    840
agctgcaagt cctcccagtc cctgctgaac tccggcaacc agaagaacta cctgacctgg    900
```

| | |
|---|---|
| tatcagcaga agcccggcca gccccccaag ctgctgatct actgggcctc cacccgcgag | 960 |
| tctggcgtgc ccgatagatt caccggctcc ggcagcggca ccgactttac cctgaccatc | 1020 |
| tccagcgtgc aggccgagga cctggccgtg tattactgtc agaacgacta ctcctacccc | 1080 |
| ttcaccttcg gctctggcac caagctggaa atcaagggag cggtggttc aggcggcgga | 1140 |
| ggcagcggtg gaggtggtag tggcggtggc ggttcagggg aggtggctc gcaggtgcag | 1200 |
| ctgcagcagc ctggcgctga actggtccga cctggcgcct ccgtgaagct gtcctgcaag | 1260 |
| gcctccggct acaccttcac cagctactgg atcaactggg tcaagcagcg gcctggccag | 1320 |
| ggcctggaat ggatcggcaa catctacccc tccgactcct acaccaacta caaccagaag | 1380 |
| ttcaaggaca aggccaccct gaccgtggac aagtcctcct ccaccgccta catgcagctg | 1440 |
| tccagcccca cctccgagga ctccgccgtg tactactgca cccggtcctg gcggggcaac | 1500 |
| tccttcgact attggggcca gggcaccacc ctgacagtgt cctcttctca ccaccaccat | 1560 |
| caccactga | 1569 |

<210> SEQ ID NO 89
<211> LENGTH: 1560
<212> TYPE: DNA
<213> ORGANISM: Artificial Sequence
<220> FEATURE:
<223> OTHER INFORMATION: Antibody-derived sequence

<400> SEQUENCE: 89

| | |
|---|---|
| atgggctggt cctgcatcat cctgtttctg gtggctaccg ccaccggcgt gcactcccag | 60 |
| gtgcagctgc agcagtctgg cgctgagctg gctagacctg gcgcctccgt gaagatgtcc | 120 |
| tgcaagacct ccggctacac cttcacccgg tacaccatgc actgggtcaa gcagaggcct | 180 |
| ggacagggcc tggaatggat cggctacatc aaccctccc ggggctacac caactacaac | 240 |
| cagaagttca aggacaaggc caccctgaca accgacaagt cctcctccac cgcctacatg | 300 |
| cagctgtcct ccctgaccct cgaggactcc gccgtgtact actgcgcccg gtactacgac | 360 |
| gaccactact ccctggacta ctggggccag ggcaccacac tgacagtgtc tagcgcctcc | 420 |
| accaagggcc cttccgtgtt ccctctggcc ccttgctcca gtcccactc cgaaggcacc | 480 |
| gccgctctgg gctgcctggt gaaggactac ttccctgagc ctgtgaccgt gagctggaac | 540 |
| tctggcgccc tgaccagcgg cgtgcacacc ttccctgccg tgctgcagtc ctccggcctg | 600 |
| tactccctgt cctccgtggt gaccgtgcct tcctccaact tcggcaccca gacctacacc | 660 |
| tgcaacgtga ccacaagcc ttccaacacc aaggtggaca gaccgtgga gcctaagtcc | 720 |
| gcctccggcc ctggggggcgg acgcagcggc ggaggcggat ccggcggagg aggctctcag | 780 |
| gtgcagctgc agcagcctgg cgctgaactg gtccgacctg gcgcctccgt gaagctgtcc | 840 |
| tgcaaggcct ccggctacac cttcaccagc tactggatca actgggtcaa gcagcggcct | 900 |
| ggccagggcc tggaatggat cggcaacatc taccctccg actcctacac caactacaac | 960 |
| cagaagttca aggacaaggc caccctgacc gtggacaagt cctcctccac cgcctacatg | 1020 |
| cagctgtcca gccccacctc cgaggactcc gccgtgtact actgcacccg gtcctggcgg | 1080 |
| ggcaactcct tcgactattg gggccagggc accaccctga cagtgtcctc tggaggcgga | 1140 |
| ggatctggtg gtggcggatc tggcggcggt ggaagtggcg gaggtggtag cgacatcgtg | 1200 |
| atgacccagt ccccctccag cctgaccgtg accgctggcg agaaagtgac catgagctgc | 1260 |
| aagtcctccc agtccctgct gaactccggc aaccagaaga actacctgac ctggtatcag | 1320 |

| | |
|---|---|
| cagaagcccg gccagccccc caagctgctg atctactggg cctccacccg cgagtctggc | 1380 |
| gtgcccgata gattcaccgg ctccggcagc ggcaccgact ttaccctgac catctccagc | 1440 |
| gtgcaggccg aggacctggc cgtgtattac tgtcagaacg actactccta ccccttcacc | 1500 |
| ttcggctctg gcaccaagct ggaaatcaag ggcggctccc accaccacca tcaccactga | 1560 |

<210> SEQ ID NO 90
<211> LENGTH: 1569
<212> TYPE: DNA
<213> ORGANISM: Artificial Sequence
<220> FEATURE:
<223> OTHER INFORMATION: Antibody-derived sequence

<400> SEQUENCE: 90

| | |
|---|---|
| atgggctggt cctgcatcat cctgtttctg gtggctaccg ccaccggcgt gcactcccag | 60 |
| gtgcagctgc agcagtctgg cgctgagctg gctagacctg gcgcctccgt gaagatgtcc | 120 |
| tgcaagacct ccggctacac cttcacccgg tacaccatgc actgggtcaa gcagaggcct | 180 |
| ggacagggcc tggaatggat cggctacatc aaccccctcc ggggctacac caactacaac | 240 |
| cagaagttca aggacaaggc cacccctgaca accgacaagt cctcctccac cgcctacatg | 300 |
| cagctgtcct ccctgacctc cgaggactcc gccgtgtact actgcgcccg gtactacgac | 360 |
| gaccactact ccctggacta ctggggccag ggcaccacac tgacagtgtc tagcgcctcc | 420 |
| accaagggcc cttccgtgtt ccctctggcc ccttgctcca gtccacctc cgaaggcacc | 480 |
| gccgctctgg gctgcctggt gaaggactac ttccctgagc tgtgaccgt gagctggaac | 540 |
| tctggcgccc tgaccagcgg cgtgcacacc ttccctgccg tgctgcagtc ctccggcctg | 600 |
| tactccctgt cctccgtggt gaccgtgcct cctccaact tcggcaccca gacctacacc | 660 |
| tgcaacgtgg accacaagcc ttccaacacc aaggtggaca gaccgtgga gcctaagtcc | 720 |
| gcctccggcc ctggggcgg acgcagcggc ggaggcggat ccggcggagg aggctctgac | 780 |
| atcgtgatga cccagtcccc ctccagcctg accgtgaccg ctggcgagaa agtgaccatg | 840 |
| agctgcaagt cctcccagtc cctgctgaac tccggcaacc agaagaacta cctgacctgg | 900 |
| tatcagcaga agccccggcca gcccccaag ctgctgatct actgggcctc cacccgcgag | 960 |
| tctggcgtgc ccgatagatt caccggctcc ggcagcggca ccgactttac cctgaccatc | 1020 |
| tccagcgtgc aggccgagga cctggccgtg tattactgtc agaacgacta ctcctacccc | 1080 |
| ttcaccttcg gctctggcac caagctggaa atcaagggag gcggtggttc aggcggcgga | 1140 |
| ggcagcggtg gaggtggtag tggcggtggc ggttcagggg gaggtggctc gcaggtgcag | 1200 |
| ctgcagcagc ctggcgctga actggtccga cctggcgcct ccgtgaagct gtcctgcaag | 1260 |
| gcctccggct acaccttcac cagctactgg atcaactggg tcaagcagcg gcctggccag | 1320 |
| ggcctggaat ggatcggcaa catctacccc tccgactcct acaccaacta caaccagaag | 1380 |
| ttcaaggaca aggccaccct gaccgtggac aagtcctcct ccaccgccta catgcagctg | 1440 |
| tccagcccca cctccgagga ctccgccgtg tactactgca cccggtcctg gcggggcaac | 1500 |
| tccttcgact attggggcca gggcaccacc ctgacagtgt cctcttctca ccaccaccat | 1560 |
| caccactga | 1569 |

<210> SEQ ID NO 91
<211> LENGTH: 1533
<212> TYPE: DNA
<213> ORGANISM: Artificial Sequence
<220> FEATURE:
<223> OTHER INFORMATION: Antibody-derived sequence

<400> SEQUENCE: 91

```
atgggctggt cctgcatcat cctgtttctg gtggctaccg ccaccggcgt gcactcccag        60
gtgcagctgc agcagtctgg cgctgagctg gctagacctg gcgcctccgt gaagatgtcc       120
tgcaagacct ccggctacac cttcacccgg tacaccatgc actgggtcaa gcagaggcct       180
ggacagggcc tggaatggat cggctacatc aaccctcc ggggctacac caactacaac         240
cagaagttca aggacaaggc caccctgaca accgacaagt cctcctccac cgcctacatg       300
cagctgtcct ccctgacctc cgaggactcc gccgtgtact actgcgcccg gtactacgac       360
gaccactact ccctggacta ctggggccag ggcaccacac tgacagtgtc tagcgcctcc       420
accaagggcc cttccgtgtt ccctctggcc ccttcctcca gtccacctc cggcggcacc        480
gccgctctgg gctgcctggt gaaggactac ttccctgagc ctgtgaccgt gagctggaac       540
tctggcgccc tgaccagcgg cgtgcacacc ttccctgccg tgctgcagtc ctccggcctg       600
tactccctgt cctccgtggt gaccgtgcct tcctcctccc tgggcaccca gacctacatc       660
tgcaacgtga accacaagcc ttccaacacc aaggtggaca gcgggtgga gcctaagtcc        720
tgctccggcc ctggggcgg acgcagcggc ggaggcggat ccggcggagg aggctctcag        780
gtgcagctgc agcagcctgg cgctgaactg gtccgacctg gcgcctccgt gaagctgtcc       840
tgcaaggcct ccggctacac cttcaccagc tactggatca actgggtcaa gcagcggcct       900
ggccagggcc tggaatggat cggcaacatc taccctccg actcctacac caactacaac        960
cagaagttca aggacaaggc caccctgacc gtggacaagt cctcctccac cgcctacatg      1020
cagctgtcca gccccacctc cgaggactcc gccgtgtact actgcacccg gtcctggcgg      1080
ggcaactcct tcgactattg gggccagggc accaccctga cagtgtcctc tggaggcgga      1140
ggatctggtg gtggcggatc tggcggcggt ggaagtggcg gaggtggtag cgacatcgtg      1200
atgacccagt cccctccag cctgaccgtg accgctggcg agaaagtgac catgagctgc      1260
aagtcctccc agtccctgct gaactccggc aaccagaaga ctacctgac ctggtatcag      1320
cagaagcccg gccagccccc caagctgctg atctactggg cctccacccg cgagtctggc      1380
gtgcccgata gattcaccgg ctccggcagc ggcaccgact taccctgac catctccagc      1440
gtgcaggccg aggacctggc cgtgtattac tgtcagaacg actactccta ccccttcacc      1500
ttcggctctg gcaccaagct ggaaatcaag tga                                   1533
```

<210> SEQ ID NO 92
<211> LENGTH: 1548
<212> TYPE: DNA
<213> ORGANISM: Artificial Sequence
<220> FEATURE:
<223> OTHER INFORMATION: Antibody-derived sequence

<400> SEQUENCE: 92

```
atgggctggt cctgcatcat cctgtttctg gtggctaccg ccaccggcgt gcactcccag        60
gtgcagctgc agcagtctgg cgctgagctg gctagacctg gcgcctccgt gaagatgtcc       120
tgcaagacct ccggctacac cttcacccgg tacaccatgc actgggtcaa gcagaggcct       180
ggacagggcc tggaatggat cggctacatc aaccctccc ggggctacac caactacaac        240
cagaagttca aggacaaggc caccctgaca accgacaagt cctcctccac cgcctacatg       300
cagctgtcct ccctgacctc cgaggactcc gccgtgtact actgcgcccg gtactacgac       360
gaccactact ccctggacta ctggggccag ggcaccacac tgacagtgtc tagcgcctcc       420
```

| | |
|---|---:|
| accaagggcc cttccgtgtt ccctctggcc ccttcctcca agtccacctc cggcggcacc | 480 |
| gccgctctgg gctgcctggt gaaggactac ttccctgagc ctgtgaccgt gagctggaac | 540 |
| tctggcgccc tgaccagcgg cgtgcacacc ttccctgccg tgctgcagtc ctccggcctg | 600 |
| tactccctgt cctccgtggt gaccgtgcct cctcctcccc tgggcaccca gacctacatc | 660 |
| tgcaacgtga accacaagcc ttccaacacc aaggtggaca gcgggtgga gcctaagtcc | 720 |
| tgctccggcc ctggggcgg acgcagcggc ggaggcggat ccggcggagg aggtctgac | 780 |
| atcgtgatga cccagtcccc ctccagcctg accgtgaccg ctggcgagaa agtgaccatg | 840 |
| agctgcaagt cctcccagtc cctgctgaac tccggcaacc agaagaacta cctgacctgg | 900 |
| tatcagcaga agcccggcca gccccccaag ctgctgatct actgggcctc caccgcgag | 960 |
| tctggcgtgc ccgatagatt caccggctcc ggcagcggca ccgactttac cctgaccatc | 1020 |
| tccagcgtgc aggccgagga cctggccgtg tattactgtc agaacgacta ctcctacccc | 1080 |
| ttcaccttcg gctctggcac caagctggaa atcaagggag gcgtggttc aggcggcgga | 1140 |
| ggcagcggtg gaggtggtag tggcggtggc ggttcagggg gaggtggctc gcaggtgcag | 1200 |
| ctgcagcagc ctggcgctga actggtccga cctggcgcct ccgtgaagct gtcctgcaag | 1260 |
| gcctccggct acaccttcac cagctactgg atcaactggg tcaagcagcg gcctggccag | 1320 |
| ggcctggaat ggatcggcaa catctacccc tccgactcct acaccaacta caaccagaag | 1380 |
| ttcaaggaca aggccaccct gaccgtggac aagtcctcct ccaccgccta catgcagctg | 1440 |
| tccagcccca cctccgagga ctccgccgtg tactactgca cccggtcctg gcggggcaac | 1500 |
| tccttcgact attggggcca gggcaccacc ctgacagtgt cctcttga | 1548 |

<210> SEQ ID NO 93
<211> LENGTH: 1470
<212> TYPE: DNA
<213> ORGANISM: Artificial Sequence
<220> FEATURE:
<223> OTHER INFORMATION: Antibody-derived sequence

<400> SEQUENCE: 93

| | |
|---|---:|
| atgggctggt cctgcatcat cctgtttctg gtggctaccg ccaccggcgt gcactctcag | 60 |
| atcgtgctga cccagtctcc cgccatcatg tctgctagcc ctggcgagaa agtgacaatg | 120 |
| acctgccggg cctcctcctc cgtgtcctac atgaactggt atcagcagaa gtccggcacc | 180 |
| tcccccaagc ggtggatcta cgacacctcc aaggtggcct ctggcgtgcc ctacagattc | 240 |
| tccggctctg gctctggcac ctcctacagc ctgaccatct ccagcatgga agccgaggat | 300 |
| gccgccacct actactgcca gcagtggtcc tccaaccccc tgaccttggg cgctggcacc | 360 |
| aagctggaac tgaagcggac cgtggccgct ccttccgtgt tcatcttccc tcctccgac | 420 |
| gagcagctga gtccggcac cgcctccgtg gtgtgcctgc tgaacaactt ctaccctcgg | 480 |
| gaggccaagg tgcagtggaa ggtggacaac gccctgcagt ccggcaactc ccaggaaagc | 540 |
| gtcaccgagc aggactccaa ggacagcacc tactccctgt cctccaccct gaccctgtcc | 600 |
| aaggccgact acgagaagca caaggtgtac gcctgcgagg tgacccacca gggcctgtcc | 660 |
| agccctgtga ccaagtcctt caaccggggc gagtgtgacg tgcctggtgg tagccaggtg | 720 |
| cagctgcagc agcctggcgc tgaactggtc cgacctggcg cctccgtgaa gctgtcctgc | 780 |
| aaggcctccg gctacacctt caccagctac tggatcaact gggtcaagca gcggcctggc | 840 |
| cagggcctga atggatcgg caacatctac ccctccgact cctacaccaa ctacaaccag | 900 |
| aagttcaagg acaaggccac cctgaccgtg gacaagtcct cctccaccgc ctacatgcag | 960 |

```
ctgtccagcc ccacctccga ggactccgcc gtgtactact gcacccggtc ctggcggggc    1020
aactccttcg actattgggg ccagggcacc accctgacag tgtcctctgg aggcggagga    1080
tctggtggtg gcggatctgg cggcggtgga agtggcggag gtggtagcga catcgtgatg    1140
acccagtccc cctccagcct gaccgtgacc gctggcgaga agtgaccat gagctgcaag    1200 tcctcccagt ccctgctgaa ctccggcaac cagaagaact acctgacctg gtatcagcag    1260
aagcccggcc agcccccaa gctgctgatc tactgggcct ccacccgcga gtctggcgtg    1320
cccgatagat tcaccggctc cggcagcggc accgacttta ccctgaccat ctccagcgtg    1380
caggccgagg acctggccgt gtattactgt cagaacgact actcctaccc cttcaccttc    1440
ggctctggca ccaagctgga aatcaagtga                                     1470
```

<210> SEQ ID NO 94
<211> LENGTH: 1485
<212> TYPE: DNA
<213> ORGANISM: Artificial Sequence
<220> FEATURE:
<223> OTHER INFORMATION: Antibody-derived sequence

<400> SEQUENCE: 94

```
atgggctggt cctgcatcat cctgtttctg gtggctaccg ccaccggcgt gcactctcag      60
atcgtgctga cccagtctcc cgccatcatg tctgctagcc ctggcgagaa agtgacaatg     120
acctgccggg cctcctcctc cgtgtcctac atgaactggt atcagcagaa gtccggcacc     180
tcccccaagc ggtggatcta cgacacctcc aaggtggcct ctggcgtgcc ctacagattc     240
tccggctctg gctctggcac ctcctacagc ctgaccatct ccagcatgga agccgaggat     300
gccgccacct actactgcca gcagtggtcc tccaaccccc tgacctttgg cgctggcacc     360
aagctggaac tgaagcggac cgtggccgct ccttccgtgt tcatcttccc tcccctccgac    420 gagcagctga gtccggcac cgcctccgtg tgtgcctgc tgaacaactt ctaccctcgg      480
gaggccaagg tgcagtggaa ggtggacaac gccctgcagt ccggcaactc ccaggaaagc    540
gtcaccgagc aggactccaa ggacagcacc tactccctgt cctccaccct gaccctgtcc    600
aaggccgact acgagaagca caaggtgtac gcctgcgagg tgacccacca gggcctgtcc    660
agccctgtga ccaagtcctt caaccggggc gagtgtgacg tgcctggtgg tagcgacatc    720
gtgatgaccc agtccccctc cagcctgacc gtgaccgctg gcgagaaagt gaccatgagc    780
tgcaagtcct cccagtccct gctgaactcc ggcaaccaga gaactacct gacctggtat     840 cagcagaagc ccggccagcc ccccaagctg ctgatctact gggcctccac ccgcgagtct    900
ggcgtgcccg atagattcac cggctccggc agcggcaccg actttaccct gaccatctcc    960
agcgtgcagg ccgaggacct ggccgtgtat tactgtcaga acgactactc ctaccccttc   1020
accttcggct ctggcaccaa gctggaaatc aagggaggcg tggttcagg cggcggaggc   1080 agcggtggag gtggtagtgg cggtggcggt tcagggggag gtggctcgca ggtgcagctg    1140
cagcagcctg gcgctgaact ggtccgacct ggcgcctccg tgaagctgtc ctgcaaggcc    1200
tccggctaca ccttcaccag ctactggatc aactgggtca agcagcggcc tggccagggc    1260
ctggaatgga tcgcaacat ctaccctcc gactcctaca ccaactacaa ccagaagttc     1320
aaggacaagg ccaccctgac cgtggacaag tcctcctcca ccgcctacat gcagctgtcc    1380
agccccacct ccgaggactc cgccgtgtac tactgcaccc ggtcctggcg gggcaactcc    1440
ttcgactatt ggggccaggg caccaccctg acagtgtcct cttga                     1485
```

<210> SEQ ID NO 95
<211> LENGTH: 1533
<212> TYPE: DNA
<213> ORGANISM: Artificial Sequence
<220> FEATURE:
<223> OTHER INFORMATION: Antibody-derived sequence

<400> SEQUENCE: 95

```
atgggctggt cctgcatcat cctgtttctg gtggctaccg ccaccggcgt gcactcccag      60
gtgcagctgc agcagtctgg cgctgagctg gctagacctg gcgcctccgt gaagatgtcc     120
tgcaagacct ccggctacac cttcacccgg tacaccatgc actgggtcaa gcagaggcct     180
ggacagggcc tggaatggat cggctacatc aaccctcc   ggggctacac caactacaac     240
cagaagttca aggacaaggc caccctgaca accgacaagt cctcctccac cgcctacatg     300
cagctgtcct ccctgacctc cgaggactcc gccgtgtact actgcgcccg gtactacgac     360
gaccactact ccctggacta ctggggccag ggcaccacac tgacagtgtc tagcgcctcc     420
accaagggcc cttccgtgtt ccctctggcc ccttcctcca gtccacctc  cggcggcacc     480
gccgctctgg gctgcctggt gaaggactac ttccctgagc ctgtgaccgt gagctggaac     540
tctggcgccc tgaccagcgg cgtgcacacc ttccctgccg tgctgcagtc ctccggcctg     600
tactccctgt cctccgtggt gaccgtgcct cctcctccc  tgggcaccca gacctacatc     660
tgcaacgtga accacaagcc ttccaacacc aaggtggaca gcggggtgga gcctaagtcc     720
tgctccggcc tgggggcgg  acgcagcggc ggaggcggat ccggcggagg aggctctcag     780
gtgcagctgc agcagcctgg cgctgaactg gtccgacctg gcgcctccgt gaagctgtcc     840
tgcaaggcct ccggctacac cttccaccagc tactggatca actgggtcaa gcagcggcct     900
ggccagtgcc tggaatggat cggcaacatc tacccctccg actcctacac caactacaac     960
cagaagttca aggacaaggc caccctgacc gtggacaagt cctcctccac cgcctacatg    1020
cagctgtcca gccccacctc cgaggactcc gccgtgtact actgcacccg gtcctggcgg    1080
ggcaactcct tcgactattg gggccagggc accaccctga gtgtcctc  tggaggcgga    1140
ggatctggtg gtggcggatc tggcggcggt ggaagtggcg gaggtggtag cgacatcgtg    1200
atgacccagt cccccctccag cctgaccgtg accgctggcg agaaagtgac catgagctgc    1260
aagtcctccc agtccctgct gaactccggc aaccagaaga actacctgac ctggtatcag    1320
cagaagcccg gccagccccc caagctgctg atctactggg cctccacccg cgagtctggc    1380
gtgcccgata gattcaccgg ctccggcagc ggcaccgact taccctgac  catctccagc    1440
gtgcaggccg aggacctggc cgtgtattac tgtcagaacg actactccta ccccttcacc    1500
ttcggctgcg gcaccaagct ggaaatcaag tga                                 1533
```

<210> SEQ ID NO 96
<211> LENGTH: 1548
<212> TYPE: DNA
<213> ORGANISM: Artificial Sequence
<220> FEATURE:
<223> OTHER INFORMATION: Antibody-derived sequence

<400> SEQUENCE: 96

```
atgggctggt cctgcatcat cctgtttctg gtggctaccg ccaccggcgt gcactcccag      60
gtgcagctgc agcagtctgg cgctgagctg gctagacctg gcgcctccgt gaagatgtcc     120
tgcaagacct ccggctacac cttcacccgg tacaccatgc actgggtcaa gcagaggcct     180
ggacagggcc tggaatggat cggctacatc aaccctcc   ggggctacac caactacaac     240
```

```
cagaagttca aggacaaggc caccctgaca accgacaagt cctcctccac cgcctacatg    300
cagctgtcct ccctgacctc cgaggactcc gccgtgtact actgcgcccg gtactacgac    360
gaccactact ccctggacta ctggggccag ggcaccacac tgacagtgtc tagcgcctcc    420
accaagggcc cttccgtgtt ccctctggcc ccttcctcca gtccacctc cggcggcacc     480 gccgctctgg gctgcctggt gaaggactac ttccctgagc tgtgaccgt gagctggaac     540 tctggcgccc tgaccagcgg cgtgcacacc ttccctgccg tgctgcagtc ctccggcctg    600
tactccctgt cctccgtggt gaccgtgcct cctcctccc tgggcaccca gacctacatc     660
tgcaacgtga accacaagcc ttccaacacc aaggtggaca gcgggtgga gcctaagtcc     720 tgctccggcc tgggggcgg acgcagcggc ggaggcggat ccggcggagg aggctctgac    780
atcgtgatga cccagtcccc ctccagcctg accgtgaccg ctggcgagaa agtgaccatg    840
agctgcaagt cctcccagtc cctgctgaac tccggcaacc agaagaacta cctgacctgg    900
tatcagcaga gccccggcca gccccccaag ctgctgatct actgggcctc cacccgcgag    960
tctggcgtgc ccgatagatt caccggctcc ggcagcggca ccgactttac cctgaccatc   1020
tccagcgtgc aggccgagga cctggccgtg tattactgtc agaacgacta ctcctacccc   1080
ttcaccttcg gctgcggcac caagctggaa atcaagggag gcggtggttc aggcggcgga   1140
ggcagcggtg gaggtggtag tggcggtggc ggttcagggg gaggtggctc gcaggtgcag   1200
ctgcagcagc ctggcgctga actggtccga cctggcgcct ccgtgaagct gtcctgcaag   1260
gcctccggct acaccttcac cagctactgg atcaactggg tcaagcagcg gcctggccag   1320
tgcctggaat ggatcggcaa catctacccc tccgactcct acaccaacta caaccagaag   1380
ttcaaggaca aggccaccct gaccgtggac aagtcctcct ccaccgccta catgcagctg   1440
tccagcccca cctccgagga ctccgccgtg tactactgca cccggtcctg gcggggcaac   1500
tccttcgact attggggcca gggcaccacc ctgacagtgt cctcttga              1548
```

<210> SEQ ID NO 97
<211> LENGTH: 1470
<212> TYPE: DNA
<213> ORGANISM: Artificial Sequence
<220> FEATURE:
<223> OTHER INFORMATION: Antibody-derived sequence

<400> SEQUENCE: 97

```
atgggctggt cctgcatcat cctgtttctg gtggctaccg ccaccggcgt gcactctcag     60
atcgtgctga cccagtctcc cgccatcatg tctgctagcc ctggcgagaa agtgacaatg    120
acctgccggg cctcctcctc cgtgtcctac atgaactggt atcagcagaa gtccggcacc    180
tcccccaagc ggtggatcta cgacacctcc aaggtggcct ctggcgtgcc ctacagattc    240
tccggctctg gctctggcac ctcctacagc ctgaccatct ccagcatgga agccgaggat    300
gccgccacct actactgcca gcagtggtcc tccaaccccc tgaccttggg cgctggcacc    360
aagctggaac tgaagcggac cgtggccgct ccttccgtgt tcatcttccc tcctccgac    420 gagcagctga gtccggcac cgcctccgtg gtgtgcctgc tgaacaactt ctaccctcgg    480
gaggccaagg tgcagtggaa ggtggacaac gccctgcagt ccggcaactc ccaggaaagc    540
gtcaccgagc aggactccaa ggacagcacc tactccctgt cctccaccct gaccctgtcc    600
aaggccgact acgagaagca caaggtgtac gcctgcgagg tgacccacca gggcctgtcc    660
agccctgtga ccaagtcctt caaccggggc gagtgtgacg tgcctggtgg tagccaggtg    720
```

| | |
|---|---|
| cagctgcagc agcctggcgc tgaactggtc cgacctggcg cctccgtgaa gctgtcctgc | 780 |
| aaggcctccg gctacacctt caccagctac tggatcaact gggtcaagca gcggcctggc | 840 |
| cagtgcctgg aatggatcgg caacatctac ccctccgact cctacaccaa ctacaaccag | 900 |
| aagttcaagg acaaggccac cctgaccgtg gacaagtcct cctccaccgc ctacatgcag | 960 |
| ctgtccagcc ccacctccga ggactccgcc gtgtactact gcacccggtc ctggcggggc | 1020 |
| aactccttcg actattgggg ccagggcacc accctgacag tgtcctctgg aggcggagga | 1080 |
| tctggtggtg gcggatctgg cggcggtgga agtggcggag gtggtagcga catcgtgatg | 1140 |
| acccagtccc cctccagcct gaccgtgacc gctggcgaga agtgaccat gagctgcaag | 1200 |
| tcctcccagt ccctgctgaa ctccggcaac cagaagaact acctgacctg gtatcagcag | 1260 |
| aagcccggcc agccccccaa gctgctgatc tactgggcct ccacccgcga gtctggcgtg | 1320 |
| cccgatagat tcaccggctc cggcagcggc accgacttta ccctgaccat ctccagcgtg | 1380 |
| caggccgagg acctggccgt gtattactgt cagaacgact actcctaccc cttcaccttc | 1440 |
| ggctgcggca ccaagctgga aatcaagtga | 1470 |

<210> SEQ ID NO 98
<211> LENGTH: 1485
<212> TYPE: DNA
<213> ORGANISM: Artificial Sequence
<220> FEATURE:
<223> OTHER INFORMATION: Antibody-derived sequence

<400> SEQUENCE: 98

| | |
|---|---|
| atgggctggt cctgcatcat cctgtttctg gtggctaccg ccaccggcgt gcactctcag | 60 |
| atcgtgctga cccagtctcc cgccatcatg tctgctagcc ctggcgagaa agtgacaatg | 120 |
| acctgccggg cctcctcctc cgtgtcctac atgaactggt atcagcagaa gtccggcacc | 180 |
| tcccccaagc ggtggatcta cgacacctcc aaggtggcct ctggcgtgcc ctacagattc | 240 |
| tccggctctg gctctggcac ctcctacagc ctgaccatct ccagcatgga agccgaggat | 300 |
| gccgccacct actactgcca gcagtggtcc tccaaccccc tgacctttgg cgctggcacc | 360 |
| aagctggaaa tgaagcggac cgtggccgct ccttccgtgt tcatcttccc tcctccgac | 420 |
| gagcagctga gtccggcac cgcctccgtg gtgtgcctgc tgaacaactt ctaccctcgg | 480 |
| gaggccaagg tgcagtggaa ggtggacaac gccctgcagt ccggcaactc ccaggaaagc | 540 |
| gtcaccgagc aggactccaa ggacagcacc tactccctgt cctccaccct gaccctgtcc | 600 |
| aaggccgact acgagaagca caaggtgtac gcctgcgagg tgacccacca gggcctgtcc | 660 |
| agccctgtga ccaagtcctt caaccggggc gagtgtgacg tgcctggtgg tagcgacatc | 720 |
| gtgatgaccc agtcccctc cagcctgacc gtgaccgctg gcgagaaagt gaccatgagc | 780 |
| tgcaagtcct cccagtccct gctgaactcc ggcaaccaga gaactacct gacctggtat | 840 |
| cagcagaagc ccggccagcc ccccaagctg ctgatctact gggcctccac ccgcgagtct | 900 |
| ggcgtgcccg atagattcac cggctccggc agcggcaccg actttaccct gaccatctcc | 960 |
| agcgtgcagg ccgaggacct ggccgtgtat tactgtcaga acgactactc ctacccttc | 1020 |
| accttcggct gcggcaccaa gctggaaatc aaggaggcg tggttcagg cggcggaggc | 1080 |
| agcggtggag gtggtagtgg cggtggcggt tcaggggag gtggctcgca ggtgcagctg | 1140 |
| cagcagcctg gcgctgaact ggtccgacct ggcgcctccg tgaagctgtc ctgcaaggcc | 1200 |
| tccggctaca ccttcaccag ctactggatc aactgggtca gcagcggcc tggccagtgc | 1260 |
| ctggaatgga tcggcaacat ctacccctcc gactcctaca ccaactacaa ccagaagttc | 1320 |

```
aaggacaagg ccaccctgac cgtggacaag tcctcctcca ccgcctacat gcagctgtcc   1380
agccccacct ccgaggactc cgccgtgtac tactgcaccc ggtcctggcg gggcaactcc   1440
ttcgactatt ggggccaggg caccaccctg acagtgtcct cttga                  1485
```

<210> SEQ ID NO 99
<211> LENGTH: 1593
<212> TYPE: DNA
<213> ORGANISM: Artificial Sequence
<220> FEATURE:
<223> OTHER INFORMATION: Antibody-derived sequence

<400> SEQUENCE: 99

```
atgggctggt cctgcatcat cctgtttctg gtggctaccg ccaccggcgt gcactctcag     60
gtgcagctgc agcagcctgg cgctgaactg gtccgacctg gcgcctccgt gaagctgtcc    120
tgcaaggcct ccggctacac cttcaccagc tactggatca actgggtcaa gcagcggcct    180
ggccagggcc tggaatggat cggcaacatc taccccgccg actcctacac caactacaac    240
cagaagttca aggacaaggc caccctgacc gtggacaagt cctcctccac cgcctacatg    300
cagctgtcca gccccacctc cgaggactcc gccgtgtact actgcacccg gtcctggcgg    360
ggcaactcct tcgactattg gggccagggc accaccctga cagtgtcctc tggaggcgga    420
ggatctggtg gtggcggatc tggcggcggt ggaagtggcg gaggtggtag cgacatcgtg    480
atgacccagt cccctccag cctgaccgtg accgctggcg agaaagtgac catgagctgc    540
aagtcctccc agtccctgct gaactccggc aaccagaaga actacctgac ctggtatcag    600
cagaagcccg gccagccccc caagctgctg atctactggg cctccacccg cgagtctggc    660
gtgcccgata gattcaccgg ctccggcagc ggcaccgact ttaccctgac catctccagc    720
gtgcaggccg aggacctggc cgtgtattac tgtcagaacg actactccta ccccttcacc    780
ttcggctctg gcaccaagct ggaaatcaag tctggcggag cggatccca ggtgcagctg     840 cagcagtctg gcgctgagct ggctagacct ggcgcctccg tgaagatgtc ctgcaagacc    900
tccggctaca ccttcacccg gtacaccatg cactgggtca gcagaggcc tggacagggc    960 ctggaatgga tcggctacat caaccctcc cggggctaca ccaactacaa ccagaagttc   1020
aaggacaagg ccaccctgac aaccgacaag tcctcctcca ccgcctacat gcagctgtcc   1080
tccctgacct ccgaggactc cgccgtgtac tactgcgccc ggtactacga cgaccactac   1140
tccctggact actggggcca gggcaccaca ctgacagtgt ctagcggtgg tgaggaagc    1200 ggaggggtg gtagcggtgg tggaggctct ggcggggag ggagtcagat cgtgctgacc   1260
cagtctcccg ccatcatgtc tgctagccct ggcgagaaag tgacaatgac ctgccgggcc   1320
tcctcctccg tgtcctacat gaactggtat cagcagaagt ccggcacctc ccccaagcgg   1380
tggatctacg acacctccaa ggtggcctct ggcgtgccct acagattctc cggctctggc   1440 tctggcaccct cctacagcct gaccatctcc agcatggaag ccgaggatgc cgccacctac   1500
tactgccagc agtggtcctc caacccctg acctttggcg ctggcaccaa gctggaactg   1560
aagggcggct ctcaccacca ccatcaccac tga                                1593
```

<210> SEQ ID NO 100
<211> LENGTH: 1608
<212> TYPE: DNA
<213> ORGANISM: Artificial Sequence
<220> FEATURE:
<223> OTHER INFORMATION: Antibody-derived sequence

```
<400> SEQUENCE: 100
atgggctggt cctgcatcat cctgtttctg gtggctaccg ccaccggcgt gcactctgac      60
atcgtgatga cccagtcccc ctccagcctg accgtgaccg ctggcgagaa agtgaccatg     120
agctgcaagt cctcccagtc cctgctgaac tccggcaacc agaagaacta cctgacctgg     180
tatcagcaga agcccggcca gccccccaag ctgctgatct actgggcctc caccgcgag      240 tctggcgtgc ccgatagatt caccggctcc ggcagcggca ccgactttac cctgaccatc     300
tccagcgtgc aggccgagga cctggccgtg tattactgtc agaacgacta ctcctacccc     360
ttcaccttcg gctctggcac caagctggaa atcaagggag cggtggttc aggcggcgga     420 ggcagcggtg gaggtggtag tggcggtggc ggttcagggg gaggtggctc gcaggtgcag     480
ctgcagcagc ctggcgctga actggtccga cctggcgcct ccgtgaagct gtcctgcaag     540
gcctccggct acaccttcac cagctactgg atcaactggt caagcagcg gcctggccag     600 ggcctggaat ggatcggcaa catctacccc tccgactcct acaccaacta caaccagaag     660
ttcaaggaca aggccaccct gaccgtggac aagtcctcct ccaccgccta catgcagctg     720
tccagcccca cctccgagga ctccgccgtg tactactgca cccggtcctg gcggggcaac     780
tccttcgact attggggcca gggcaccacc ctgacagtgt cctcttctgg cggaggcgga     840
tcccaggtgc agctgcagca gtctggcgct gagctggcta acctggcgc ctccgtgaag     900 atgtcctgca agacctccgg ctacaccttc acccggtaca ccatgcactg ggtcaagcag     960
aggcctggac agggcctgga atggatcggc tacatcaacc cctcccgggg ctacaccaac    1020
tacaaccaga agttcaagga caaggccacc ctgacaaccg acaagtcctc ctccaccgcc    1080
tacatgcagc tgtcctccct gacctccgag gactccgccg tgtactactg cgcccggtac    1140
tacgacgacc actactccct ggactactgg ggccagggca ccacactgac agtgtctagc    1200
ggaggcggag gatctggtgg tggcggatct ggcggcggtg gaagtggcgg aggtggtagc    1260
cagatcgtgc tgacccagtc tcccgccatc atgtctgcta gccctggcga gaaagtgaca    1320
atgacctgcc gggcctcctc ctccgtgtcc tacatgaact ggtatcagca gaagtccggc    1380
acctccccca gcggtggat ctacgacacc tccaaggtgg cctctggcgt gccctacaga    1440
ttctccggct ctggctctgg cacctcctac agcctgacca tctccagcat ggaagccgag    1500
gatgccgcca cctactactg ccagcagtgg tcctccaacc ccctgacctt tggcgctggc    1560
accaagctgg aactgaaggg cggctctcac caccaccatc accactga                1608

<210> SEQ ID NO 101
<211> LENGTH: 1545
<212> TYPE: DNA
<213> ORGANISM: Artificial Sequence
<220> FEATURE:
<223> OTHER INFORMATION: Antibody-derived sequence

<400> SEQUENCE: 101
atgggatggt cctgcatcat cctgtttctg gtggctaccg ccaccggcgt gcacagccag      60
gtgcagctgc agcagcctgg agctgaactg gtgcggcctg agccagcgt gaagctgtcc     120 tgcaaggcca cggctacac cttcaccagc tactggatca ctgggtgaa gcagcggcct     180 ggacagggcc tggaatggat cggcaacatc taccccagcg acagctacac caactacaac     240
cagaagttca aggacaaggc caccctgacc gtgacaaga gcagcagcac cgcctacatg     300
cagctgtcca gccccacctc cgaggacagc gccgtgtact actgcaccag aagctggcgg     360
ggcaacagct cgactactg gggccagggc accacactga cagtcagcag cggaggaggg     420
```

-continued

```
ggatctggcg ggggaggaag cggaggggg ggaagcgaca tcgtgatgac ccagagcccc    480
agcagcctga ccgtgacagc cggggaaaag gtgaccatga gctgcaagag cagccagagc    540
ctgctgaaca gcggcaacca gaagaactac ctgacctggt atcagcagaa gcccggccag    600 cccccaagc tgctgatcta ctgggccagc acccggaga gcggcgtgcc cgaccggttt    660
accggctccg gctccggcac cgacttcacc ctgaccatca gcagcgtgca ggccgaggac    720
ctggccgtgt attactgtca gaacgactac agctacccct tcaccttcgg cagcggcacc    780
aagctggaaa tcaagagcgg aggggagga tccgatatca gctgcagca gagcggagct    840 gaactggcta ggccaggcgc ctccgtgaag atgagctgta agacctccgg ctataccttt    900
acccggtaca ccatgcactg ggtgaaacag aggcccggac aggggctgga atggattggc    960
tatatcaacc cctcccgggg ctacacaaat tacaatcaga aattcaaaga taaagccaca   1020
ctgacaaccg acaagtccag ctccacagcc tatatgcagc tgtcctccct gaccagcgag   1080
gactctgccg tgtactattg cgcccggtac tacgacgacc actacagcct ggattattgg   1140
gggcagggga caacactgac agtctccagc gtggagggcg gcagcggagg atctggcggg   1200
agcggcggct ctggggggcgt cgacgacatc cagctgaccc agtcccccgc catcatgagc   1260
gccagccctg gcgagaaggt gacaatgacc tgccgggcca gcagcagcgt gagctacatg   1320
aattggtatc agcagaaaag cggcaccagc cccaagcggt ggatctacga caccagcaag   1380
gtggcctccg gcgtgcccta cagattctcc ggctccggct ctggcaccag ctacagcctg   1440
acaatttcta gcatggaagc cgaggacgcc gccacctact actgccagca gtggagcagc   1500
aaccccctga cctttggcgc cggaacaaag ctggaactga agtga                  1545
```

BISPECIFIC TRIVALENT ANTIBODIES BINDING TO CLAUDIN6 OR CLAUDIN18.2 AND CD3 FOR TREATMENT OF CLAUDIN EXPRESSING CANCER DISEASES

This application is a National Stage Entry of International Application Number PCT/EP2017/073773, which was filed on Sep. 20, 2017 and claimed priority to International Application Number PCT/EP2016/072688, which was filed on Sep. 23, 2016. The contents of each of the aforementioned applications are incorporated herein by reference in their entireties.

Claudins are integral membrane proteins located within the tight junctions of epithelia and endothelia. Claudins are predicted to have four transmembrane segments with two extracellular loops, and N- and C-termini located in the cytoplasm. The claudin (CLDN) family of transmembrane proteins plays a critical role in the maintenance of epithelial and endothelial tight junctions and might also play a role in the maintenance of the cytoskeleton and in cell signaling.

CLDN18 exists in two different splice variants, which are described in mouse and in human 15 (Niimi, Mol. Cell. Biol. 21:7380-90, 2001). The splice variants (Genbank accession number: splice variant 1 (CLDN18.1): NP_057453, NM_016369, and splice variant 2 (CLDN18.2): NM_001002026, NP_001002026) have a molecular weight of approximately 27.9/27.72 kD. The splice variants CLDN18.1 and CLDN18.2 differ in the N-terminal portion which comprises the first transmembrane (TM) region and loop1, whereas the primary protein sequence of the C-terminus is identical.

In normal tissues, there is no detectable expression of CLDN18.2 with exception of stomach where CLDN18.2 is expressed exclusively on short-lived differentiated gastric epithelial cells. CLDN18.2 is maintained in the course of malignant transformation and thus frequently displayed on the surface of human gastric cancer cells. Moreover, this pan-tumoral antigen is ectopically activated at significant levels in esophageal, pancreatic and lung adenocarcinomas. The CLDN18.2 protein is also localized in lymph node metastases of gastric cancer adenocarcinomas and in distant metastases especially into the ovary (so-called Krukenberg tumors).

CLDN6 is expressed in a series of different human cancer cells while expression in normal tissues is limited to placenta.

The differential expression of claudins such as CLDN18.2 and CLDN6 between cancer and normal cells, their membrane localization and their absence from the vast majority of toxicity relevant normal tissues makes these molecules attractive targets for cancer immunotherapy and the use of antibody-based therapeutics for targeting claudins in cancer therapy promises a high level of therapeutic specificity.

It has been an object of the invention to provide novel agents and methods for the therapy of cancer diseases.

The solution of the problem underlying the invention is based on the concept of generating a binding agent that comprises two binding domains that are specific for a tumor-associated claudin molecule, i.e., cancer cells. The binding agent also comprises a binding domain that is specific for a T cell-specific antigen such as CD3 allowing to bind to T cells and to pull the T cells into the complex, thus making it possible to target the cytotoxic effect of the T cells to the cancer cells. Formation of this complex can induce signalling in cytotoxic T cells, either on its own or in combination with accessory cells, which leads to the release of cytotoxic mediators.

We report for the first time that binding agents comprising two binding domains targeting a claudin and another binding domain targeting a T cell-specific antigen such as CD3 can induce potent T cell-mediated lysis and are effective in treating tumor diseases.

SUMMARY OF THE INVENTION

The invention provides a binding agent comprising at least three binding domains, wherein a first binding domain binds to a T cell-specific antigen and a second binding domain and a third binding domain bind to a claudin. The binding agent of the invention may bind to a T cell (e.g., by engaging the CD3 receptor) and a cancer cell expressing a claudin to be destroyed as a target.

In one embodiment the binding agent comprises six antibody variable domains with at least three binding domains, wherein at least two binding domains bind to a claudin and at least one binding domain binds to a T cell-specific antigen.

In one embodiment each of the first, second and third binding domains comprises a variable domain of a heavy chain of an immunoglobulin (VH) and a variable domain of a light chain of an immunoglobulin (VL).

In one embodiment the first binding domain comprises a variable domain of a heavy chain of an immunoglobulin (VH) with a specificity for a T cell-specific antigen (VH(T)), and a variable domain of a light chain of an immunoglobulin (VL) with a specificity for a T cell-specific antigen (VL(T)) and the second binding domain and the third binding domain each comprise a variable domain of a heavy chain of an immunoglobulin (VH) with a specificity for a claudin antigen (VH(CLDN)), and a variable domain of a light chain of an immunoglobulin (VL) with a specificity for a claudin antigen (VL(CLDN)).

In one embodiment said heavy chain variable domain (VH) and the corresponding light chain variable domain (VL) of one or more of the binding domains are connected via a peptide linker, in particular a flexible peptide linker such as a glycine-serine peptide linker. In one embodiment, the peptide linker comprises the amino acid sequence $(G_4S)_x$ (SEQ ID NO: 70), wherein x is 3, 4, 5 or 6.

In one embodiment said heavy chain variable domain (VH) and the corresponding light chain variable domain (VL) of one or more of the binding domains have the format of a Fab molecule and/or of an scFv molecule.

In one embodiment the first binding domain has the format of a Fab molecule and/or the second binding domain and the third binding domain have the format of an scFv molecule.

In one embodiment the binding agent of the invention is a dimer composed of two polypeptide chains, in which the first polypeptide comprises a scFv linked to an additional VL domain through a constant domain of a light chain of an immunoglobulin (CL), and the second polypeptide comprises a scFv linked to an additional VH domain through a constant domain 1 of a heavy chain of an immunoglobulin (CH1). The two polypeptide chains are preferably bound together by a disulfide bridge. The disulfide bridge is preferably formed between a Cys residue in the CL domain and a Cys residue in the CH1 domain, such that the additional VL domain of the first polypeptide associates with the additional VH domain of the second polypeptide in an antigen-binding configuration, such that the binding agent as a whole includes three antigen-binding domains. According to the invention, the VH and VL domains in the scFv moieties are preferably connected by peptide linkers such as a peptide linker comprising the amino acid sequence $(G_4S)_x$ (SEQ ID NO: 70), wherein x is 3, 4, 5 or 6, and the Fab chains and the scFv are preferably connected by peptide linkers such as a peptide linker comprising the amino acid sequence $DVPG_2S$ (SEQ ID NO: 67) or $SGPG_3RS(G_4S)_2$ (SEQ ID NO: 66). In one embodiment, the scFv moieties bind to the claudin and the Fab moiety binds to the T cell-specific antigen.

In one embodiment, the first binding domain is comprised by a Fab fragment and the second and third binding domains are each comprised by a scFv wherein each chain of the Fab fragment is linked to one scFv and the scFvs are preferably linked at the C-termini of the Fab fragment.

In one embodiment the binding agent comprises a first and a second polypeptide, said first and second polypeptides comprising a VH domain with a specificity for the T cell-specific antigen (VH(T)), a VL domain with a specificity for the T cell-specific antigen (VL(T)), a first VH domain with a specificity for the claudin (VH(CLDN)), a second VH domain with a specificity for the claudin (VH(CLDN)), a first VL domain with a specificity for the claudin (VL(CLDN)) and a second VL domain with a specificity for the claudin (VL(CLDN)), wherein the first polypeptide and the second polypeptide are associated so as to form the binding agent.

In one embodiment the binding agent comprises
(a) a first polypeptide comprising a VH domain with a specificity for the T cell-specific antigen (VH(T)), a VH domain with a specificity for the claudin (VH(CLDN)) and a VL domain with a specificity for the claudin (VL(CLDN)); and
(b) a second polypeptide comprising a VL domain with a specificity for the T cell-specific antigen (VL(T)), a VH domain with a specificity for the claudin (VH(CLDN)) and a VL domain with a specificity for the claudin (VL(CLDN)), wherein the first polypeptide and the second polypeptide are associated so as to form the binding agent.

In one embodiment the first polypeptide further comprises a constant domain 1 of a heavy chain of an immunoglobulin (CH1) and the second polypeptide further comprises a constant domain of a light chain of an immunoglobulin (CL), wherein both domains are able to associate.

In one embodiment the first polypeptide and the second polypeptide are covalently linked via a disulfide bridge between the CH1 domain and the CL domain.

In one embodiment of the binding agent of the invention, in the first polypeptide and the second polypeptide, the VH domain(s), the VL domain(s), the CH1 domain and the CL domain are arranged, from N-terminus to C-terminus, in the order VH(T)-CH1-VH(CLDN)-VL(CLDN) and VL(T)-CL-VH(CLDN)-VL(CLDN); or
VH(T)-CH1-VL(CLDN)-VH(CLDN) and VL(T)-CL-VL(CLDN)-VH(CLDN); or
VH(T)-CH1-VH(CLDN)-VL-(CLDN) and VL(T)-CL-VL(CLDN)-VH-(CLDN); or
VH(T)-CH1-VL(CLDN)-VH-(CLDN) and VL(T)-CL-VH(CLDN)-VL-(CLDN); or
VH(CLDN)-CH1-VH(T)-VL(T) and VL(CLDN)-CL-VH(CLDN)-VL(CLDN); or
VH(CLDN)-CH1-VL(T)-VH(T) and VL(CLDN)-CL-VL(CLDN)-VH(CLDN); or
VH(CLDN)-CH1-VL(T)-VH(T) and VL(CLDN)-CL-VH(CLDN)-VL(CLDN); or
VH(CLDN)-CH1-VH(T)-VL(T) and VL(CLDN)-CL-VL(CLDN)-VH(CLDN); or
VH(CLDN)-CH1-VH(CLDN)-VL(CLDN) and VL(CLDN)-CL-VH(T)-VL(T); or
VH(CLDN)-CH1-VL(CLDN)-VH(CLDN) and VL(CLDN)-CL-VL(T)-VH(T); or
VH(CLDN)-CH1-VL(CLDN)-VH(CLDN) and VL(CLDN)-CL-VH(T)-VL(T); or
VH(CLDN)-CH1-VH(CLDN)-VL(CLDN) and VL(CLDN)-CL-VL(T)-VH(T).

In one embodiment the most N-terminal VH domain of one chain associates with the most N-terminal VL domain of the other chain so as to form a binding domain and each of the VH-VL or VL-VH domains within one chain forms a binding domain.

In one embodiment the VH-VL or VL-VH domains are connected to the CH1 domain or CL domain via a peptide linker such as a peptide linker comprising the amino acid sequence $DVPG_2S$ (SEQ ID NO: 67) or $SGPG_3RS(G_4S)_2$ (SEQ ID NO: 66).

In one embodiment the VH and VL domains are connected via a peptide linker to form the VH-VL or VL-VH domains such as a peptide linker comprising the amino acid sequence $(G_4S)_x$ (SEQ ID NO: 70), wherein x is 3, 4, 5 or 6.

In the binding agent of the invention a VH domain with a specificity for the T cell-specific antigen (VH(T)) and a VL domain with a specificity for the T cell-specific antigen (VL(T)) are able to associate so as to form a binding domain binding to the T cell-specific antigen.

Furthermore, in the binding agent of the invention a VH domain with a specificity for the claudin (VH(CLDN)) and a VL domain with a specificity for the claudin (VL(CLDN)) are able to associate so as to form a binding domain binding to the claudin. According to the invention, the VH domains with a specificity for the claudin (VH(CLDN)) and the VL domains with a specificity for the claudin (VL(CLDN)) each may be identical or different. In case the binding agent of the invention comprises different VH domains with a specificity for the claudin (VH(CLDN), VH(CLDN)*) and/or different VL domains with a specificity for the claudin (VL(CLDN), VL(CLDN)*), VH(CLDN) and VL(CLDN) are able to associate so as to form a first binding domain binding to the claudin and VH(CLDN)* and VL(CLDN)* are able to associate so as to form a second binding domain binding to the claudin.

In one embodiment the binding agent of the invention is a bispecific dimeric binding agent.

In one embodiment the T cell-specific antigen is expressed on the surface of a T cell.

In one embodiment binding of the binding agent to the T cell-specific antigen on T cells results in proliferation and/or activation of the T cells.

In one embodiment the T cell-specific antigen is CD3.

In one embodiment the first binding domain binds to the epsilon-chain of CD3.

In one embodiment the CD3 is expressed on the surface of a T cell. In one embodiment binding of the binding agent to CD3 on T cells results in proliferation and/or activation of the T cells, wherein said T cells preferably release cytotoxic factors, e.g. performs and granzymes, and initiate cytolysis and apoptosis of cancer cells.

In one embodiment the claudin is expressed on the surface of a cancer cell.

In one embodiment the claudin is selected from the group consisting of claudin 6 and claudin 18.2.

In one embodiment the binding agent binds to an extracellular domain of the claudin.

In one embodiment the binding agent of the invention binds to native epitopes of the claudin present on the surface of living cells. In one embodiment the binding agent binds to the first extracellular loop of the claudin.

In one embodiment the binding to a T cell-specific antigen and/or the binding to a claudin is a specific binding.

In one embodiment the binding agent induces T cell-mediated cytotoxicity against cancer cells expressing the claudin.

In one embodiment the binding agent induces T cell-mediated cytotoxicity against cancer cells expressing the claudin with an EC50 of <10 nM or <1 nM or <500 pM or <250 pM or <100 pM or <50 pM.

In one embodiment the claudin is claudin 6 and the cancer cell(s) is/are from a cancer selected from the group consisting of urinary bladder cancer, ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof.

In one embodiment the claudin is claudin 18.2 and the cancer cell(s) is/are from a cancer selected from the group consisting of gastric cancer, esophageal cancer, pancreatic cancer, lung cancer such as non-small cell lung cancer (NSCLC), breast cancer, ovarian cancer, colon cancer, hepatic cancer, head-neck cancer, cancer of the gallbladder and the metastasis thereof, a Krukenberg tumor, peritoneal metastasis and/or lymph node metastasis.

In one embodiment the T cell-specific antigen is CD3 and VH(T) comprises or consists of an amino acid sequence represented by SEQ ID NO: 5 or a fragment thereof or a variant of the amino acid sequence or fragment and/or VL(T) comprises or consists of an amino acid sequence represented by SEQ ID NO: 6 or a fragment thereof or a variant of the amino acid sequence or fragment.

In one embodiment the claudin is claudin 6 and VH(CLDN) comprises or consists of an amino acid sequence represented by SEQ ID NO: 8 or a fragment thereof or a variant of the amino acid sequence or fragment and/or VL(CLDN) comprises or consists of an amino acid sequence represented by SEQ ID NO: 10 or a fragment thereof or a variant of the amino acid sequence or fragment.

In one embodiment the T cell-specific antigen is CD3, the claudin is claudin 6 and
the first polypeptide comprises or consists of an amino acid sequence represented by SEQ ID NO: 14 or a fragment thereof or a variant of the amino acid sequence or fragment and the second polypeptide comprises or consists of an amino acid sequence represented by SEQ ID NO: 16 or a fragment thereof or a variant of the amino acid sequence or fragment;
the first polypeptide comprises or consists of an amino acid sequence represented by SEQ ID NO: 15 or a fragment thereof or a variant of the amino acid sequence or fragment and the second polypeptide comprises or consists of an amino acid sequence represented by SEQ ID NO: 16 or a fragment thereof or a variant of the amino acid sequence or fragment;
the first polypeptide comprises or consists of an amino acid sequence represented by SEQ ID NO: 17 or a fragment thereof or a variant of the amino acid sequence or fragment and the second polypeptide comprises or consists of an amino acid sequence represented by SEQ ID NO: 19 or a fragment thereof or a variant of the amino acid sequence or fragment; or
the first polypeptide comprises or consists of an amino acid sequence represented by SEQ ID NO: 18 or a fragment thereof or a variant of the amino acid sequence or fragment and the second polypeptide comprises or consists of an amino acid sequence represented by SEQ ID NO: 19 or a fragment thereof or a variant of the amino acid sequence or fragment.

In one embodiment the claudin is claudin 18.2 and (i) VH(CLDN) comprises or consists of an amino acid sequence represented by SEQ ID NO: 20 or a fragment thereof or a variant of the amino acid sequence or fragment and/or VL(CLDN) comprises or consists of an amino acid sequence represented by SEQ ID NO: 22 or a fragment thereof or a variant of the amino acid sequence or fragment or (ii) VH(CLDN) comprises or consists of an amino acid sequence represented by SEQ ID NO: 21 or a fragment thereof or a variant of the amino acid sequence or fragment and/or VL(CLDN) comprises or consists of an amino acid sequence represented by SEQ ID NO: 23 or a fragment thereof or a variant of the amino acid sequence or fragment.

In one embodiment the T cell-specific antigen is CD3, the claudin is claudin 18.2 and
the first polypeptide comprises or consists of an amino acid sequence represented by SEQ ID NO: 30 or a fragment thereof or a variant of the amino acid sequence or fragment and the second polypeptide comprises or consists of an amino acid sequence represented by SEQ ID NO: 32 or a fragment thereof or a variant of the amino acid sequence or fragment;
the first polypeptide comprises or consists of an amino acid sequence represented by SEQ ID NO: 31 or a fragment thereof or a variant of the amino acid sequence or fragment and the second polypeptide comprises or consists of an amino acid sequence represented by SEQ ID NO: 32 or a fragment thereof or a variant of the amino acid sequence or fragment;
the first polypeptide comprises or consists of an amino acid sequence represented by SEQ ID NO: 33 or a fragment thereof or a variant of the amino acid sequence or fragment and the second polypeptide comprises or consists of an amino acid sequence represented by SEQ ID NO: 35 or a fragment thereof or a variant of the amino acid sequence or fragment;
the first polypeptide comprises or consists of an amino acid sequence represented by SEQ ID NO: 34 or a fragment thereof or a variant of the amino acid sequence or fragment and the second polypeptide comprises or consists of an amino acid sequence represented by SEQ ID NO: 35 or a fragment thereof or a variant of the amino acid sequence or fragment;

the first polypeptide comprises or consists of an amino acid sequence represented by SEQ ID NO: 36 or a fragment thereof or a variant of the amino acid sequence or fragment and the second polypeptide comprises or consists of an amino acid sequence represented by SEQ ID NO: 37 or a fragment thereof or a variant of the amino acid sequence or fragment;

the first polypeptide comprises or consists of an amino acid sequence represented by SEQ ID NO: 38 or a fragment thereof or a variant of the amino acid sequence or fragment and the second polypeptide comprises or consists of an amino acid sequence represented by SEQ ID NO: 39 or a fragment thereof or a variant of the amino acid sequence or fragment;

the first polypeptide comprises or consists of an amino acid sequence represented by SEQ ID NO: 40 or a fragment thereof or a variant of the amino acid sequence or fragment and the second polypeptide comprises or consists of an amino acid sequence represented by SEQ ID NO: 41 or a fragment thereof or a variant of the amino acid sequence or fragment;

the first polypeptide comprises or consists of an amino acid sequence represented by SEQ ID NO: 42 or a fragment thereof or a variant of the amino acid sequence or fragment and the second polypeptide comprises or consists of an amino acid sequence represented by SEQ ID NO: 43 or a fragment thereof or a variant of the amino acid sequence or fragment.

In different embodiments, the binding agent of the invention or one or more of the polypeptide chains of the binding agent of the invention comprise or do not comprise secretion signals such as N-terminal secretion signals, in particular immunoglobulin such as IgG secretion signals such as the sequence MGWSCIILFLVATATGVHS (SEQ ID NO: 71) and/or comprise or do not comprise tags, in particular C-terminal tags such as His-tags, in particular the sequence Gly-Gly-Ser-(His)$_6$ (SEQ ID NO: 72) or (His)$_6$ (SEQ ID NO: 73), or a Strep-tag.

The invention also provides a nucleic acid encoding the binding agent of the invention.

The invention also provides a nucleic acid encoding the first polypeptide and/or the second polypeptide as defined herein.

In one embodiment the nucleic acid of the invention is in the form of a vector or in the form of RNA.

In one embodiment the nucleic acid of the invention is a recombinant nucleic acid.

The invention also provides a host cell comprising the nucleic acid of the invention.

The invention also provides the binding agent of the invention, the nucleic acid of the invention or the host cell of the invention for use as a medicament.

The invention also provides the binding agent of the invention, the nucleic acid of the invention or the host cell of the invention for use in treating or preventing cancer.

The invention also provides a pharmaceutical composition comprising the binding agent of the invention, the nucleic acid of the invention or the host cell of the invention.

In one embodiment, the pharmaceutical composition further comprises a pharmaceutically acceptable carrier and/or excipient.

The invention also provides a method of treatment of a disease comprising administering a binding agent of the invention, a nucleic acid of the invention, a host cell of the invention, or a pharmaceutical composition of the invention to a subject in need thereof. In one embodiment, the disease is cancer.

The invention also provides a method of treating or preventing cancer comprising administering the binding agent of the invention, the nucleic acid of the invention, the host cell of the invention or the pharmaceutical composition of the invention to a subject in need thereof.

The invention also provides a use of a binding agent of the invention, a nucleic acid of the invention, a host cell of the invention, or a pharmaceutical composition of the invention for the manufacture of a medicament. In one embodiment, the medicament is for the treatment of cancer.

In one embodiment cells of said cancer express a claudin to which said binding agent is capable of binding.

In one embodiment said claudin is claudin 6 and said cancer is selected from the group consisting of urinary bladder cancer, ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof.

In one embodiment said claudin is claudin 18.2 and said cancer is selected from the group consisting of gastric cancer, esophageal cancer, pancreatic cancer, lung cancer such as non-small cell lung cancer (NSCLC), breast cancer, ovarian cancer, colon cancer, hepatic cancer, head-neck cancer, cancer of the gallbladder and the metastasis thereof, a Krukenberg tumor, peritoneal metastasis and/or lymph node metastasis.

The invention also provides a binding agent, a nucleic acid or a host cell as described herein for use in the methods of treatment described herein. In one embodiment, the invention provides a pharmaceutical composition as described herein for use in the methods of treatment described herein.

According to the invention, claudin 18.2 preferably has the amino acid sequence according to SEQ ID NO: 1 and claudin 6 preferably has the amino acid sequence according to SEQ ID NO: 2 or 3.

Other features and advantages of the instant invention will be apparent from the following detailed description and claims.

Figure 1A:
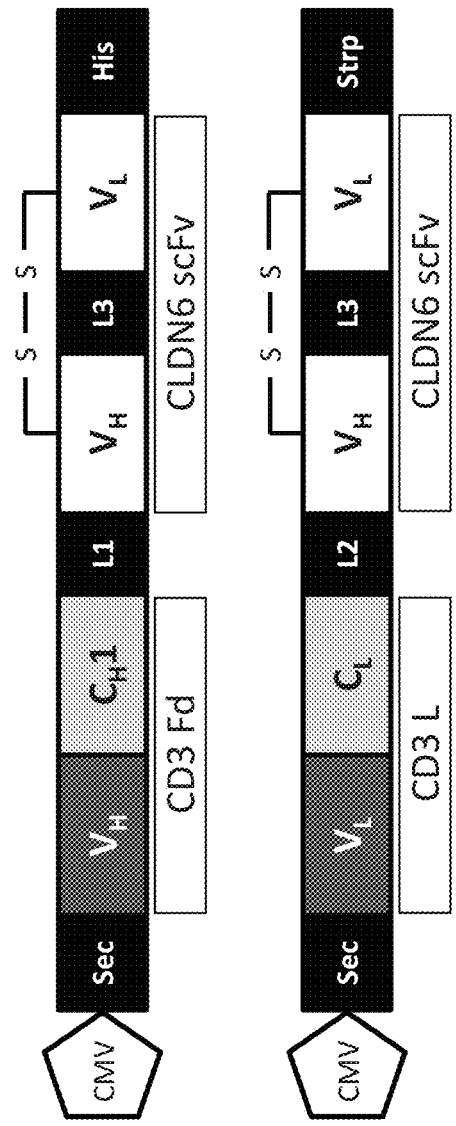
FIG. 1: Modular schemes illustrating the DNA-constructs and the bstb protein targeting TAA CLDN6.

(A) Design of the bstb chains on DNA level. (B) Schematic model of the bstb molecule. $C_H1$ is derived from IgG1 in bstb_369/367 and from IgG2 in bstb_371/367. C indicates constant region; CMV, Cytomegalovirus promoter; Fd, digestible fragment/heavy chain portion of Fab (antigen binding fragment); H, heavy chain; His, 6xHis-tag; L, light chain; L1, SGPG$_3$RS(G$_4$S)$_2$ linker (SEQ ID NO: 66); L2, DVPG$_2$S linker (SEQ ID NO: 67); L3, (G$_4$S)$_4$ linker (SEQ ID NO: 68); S-S, disulfide bridge; scFv, single chain variable fragment; Sec, secretion signal; Strp, Strep-tag; V, variable domain.

FIG. 2: Purification of tagged and tag-free bstb proteins from cell culture supernatant.

Expi293F™ cells were transiently transfected with the respective bstb constructs. Supernatant was harvested seven days post transfection and subjected to purification. (A) Chromatograms showing the first purification step of tagged bstbs via Ni-NTA affinity chromatography (Immobilized metal ion affinity chromatography—IMAC). mAU (milli-absorbance-units) on the y-axis are plotted against the volume in ml on the x-axis. Left, IMAC peaks of bstb_369/367, right, IMAC peaks of bstb_371/367. The respective right peak contains the HMW species and the respective middle peak the monomeric species. The respective left peak shows impurities. 1) specifies the fractions pooled as main peak containing mainly monomeric species, 2) the fractions pooled as HMW species. (B) Chromatograms showing the second purification step of tagged bstbs. IMAC main peak pools were subjected to Strep-Tactin© affinity chromatography. Plot on the left, peak of bstb_369/367, plot on the right, peak of bstb_371/367. (C) Separation of HMW species and monomer species of bstb_369/367 by size exclusion chromatography (SEC). Pooled HMW and pooled monomer fractions are specified by square brackets. (D) SE-HPLC analysis of tag-free bstb_5726/5725 after purification. mAU (milli-absorbance-units) on the y-axis are plotted against the time in minutes on the x-axis.

Bstb indicates bispecific TriMAB; HMW, high molecular weight species; LMW, low molecular weight species.

FIG. 3: SDS-PAGE analysis of CLDN6×CD3 protein bstb_369/367.

Supernatant of Expi293F' cells transiently expressing bstb_369/367 was purified via IMAC. HMW species were separately eluted from the main peak. Main peak species were subsequently subjected to a Strep-Tactin® affinity chromatography. The eluted pool was further separated by SEC to harvest highly monomeric bstb. Aliquots of the cell culture supernatant, a reference and different purification steps were loaded under non-reducing (left) and reducing (right) conditions on a 4-15% Tris-Glycine stain-free gel. (A) Bands were visualized on stain-free gel via fluorescence. (B) Western Blot analysis using anti-His tag detection antibody (upper blot) or StrepMAB detection antibody. Arrows on the left specify the non-reduced monomer and HMW, the arrows on the right the reduced bstb chains. Fd indicates digestible fragment/heavy chain portion of Fab (antigen binding fragment); HMW, high molecular weight species; His, 6xHis tag; IMAC, immobilized metal affinity chromatography; L, light chain; scFv, single chain variable fragment; SEC, size exclusion chromatography; Strp, Strep-tag.

Figure 4A:
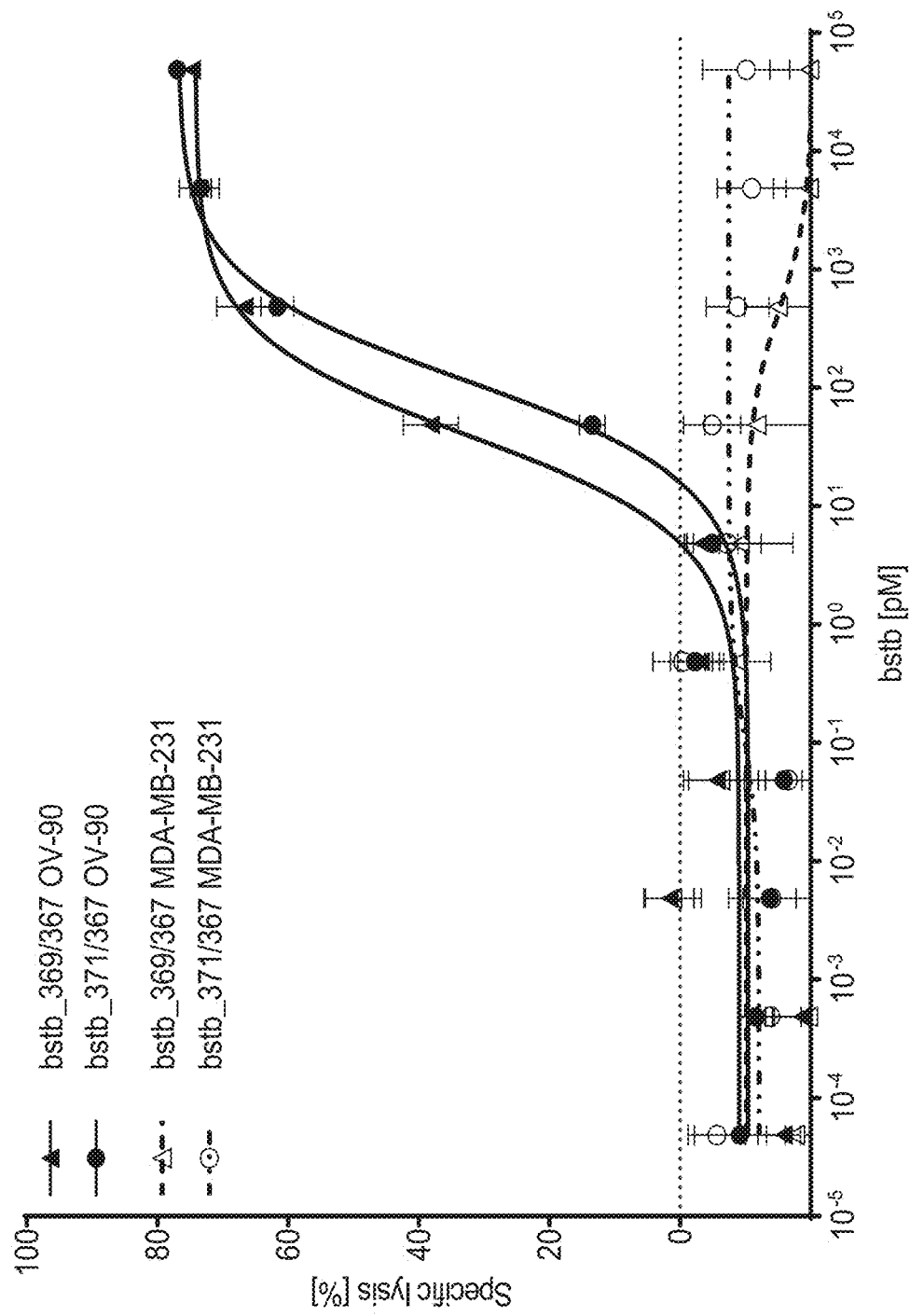
Figure 4B:
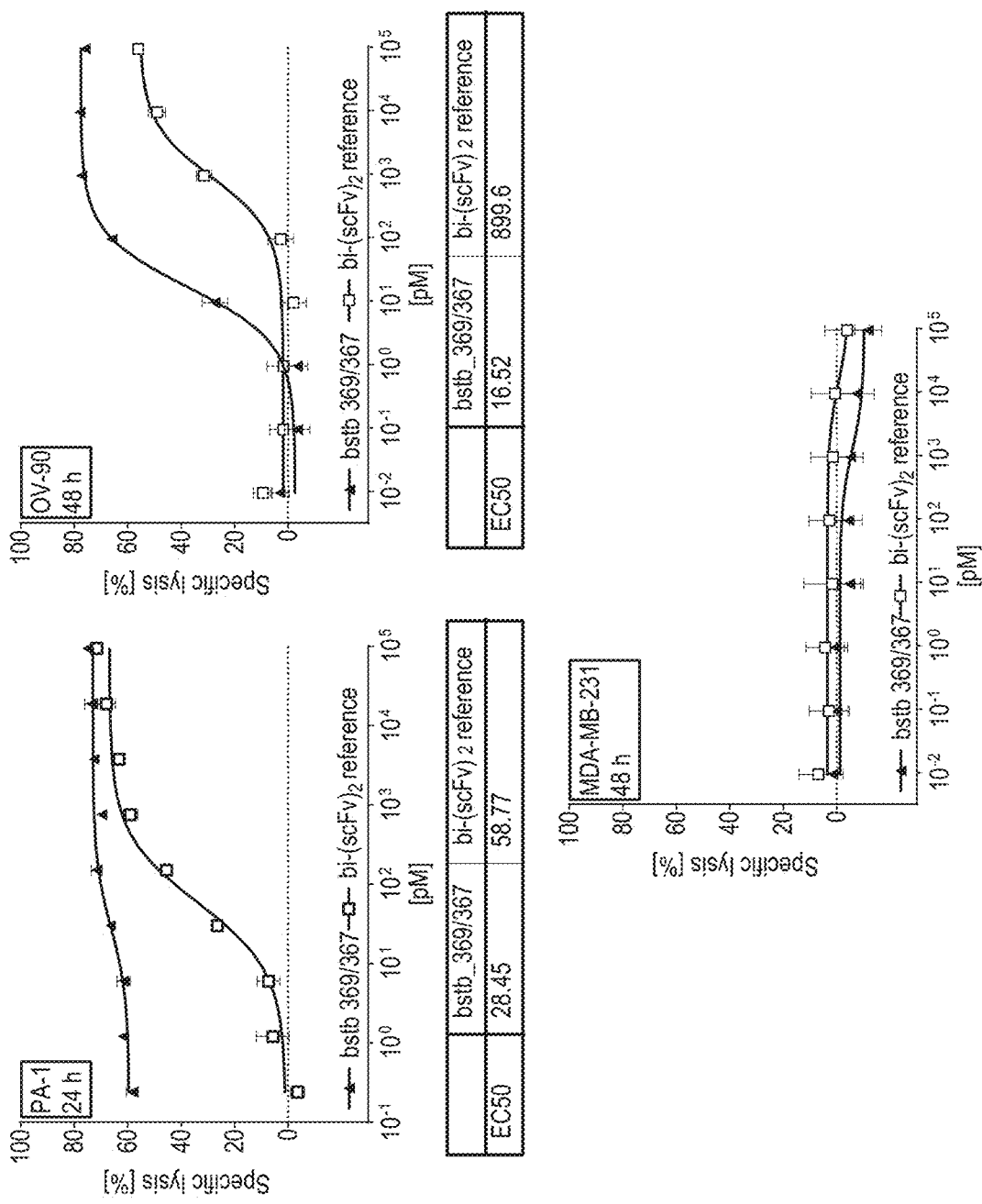

FIG. 4: In vitro cytotoxicity assay to determine the specific lysis mediated by CLDN6×CD3 proteins bstb_369/367 and bstb_371/367.

Human PBMC as effector cells and human stably luciferase transduced carcinoma cells as target cells were used in an effector to target ratio of 5:1 in luciferase-based cytotoxicity assays to determine the specific concentration-dependent lysis. CLDN6$^+$ cell lines PA-1 (ovarian teratocarcinoma) and/or OV-90 (ovarian cancer) served as positive targets and CDLN6$^-$ cell line MDA-MB-231 (breast cancer) as negative target. Mean values of triplicates including standard deviation are shown. Half-maximal lysis values (EC50) are indicated below the corresponding graphs. (A) Specific lysis (standard slope) mediated by bstb_369/367 and bstb_371/367 of CLDN6$^+$ ovarian carcinoma cells OV-90 after 48 h of incubation. (B) Comparison of specific lysis (standard slope) mediated by bstb_369/367 and a CDLN6×CD3specific bi-(scFv)$_2$ reference protein. Cell lines and incubation times are indicated in the single graphs. (C) Specific lysis (variable slope) of bstb_369/367 and the impact of 5% HMW on the activity of bstb_369/367. Left: incubation with PA-1 for 16 h; right: incubation with OV-90 for 48 h. Solid lines specify the lysis curve of monomeric bstb_369/367, dashed lines the lysis curve of monomeric bstb_369/367 spiked with 5% HMW species. (D) Specific lysis (standard slope) of OV-90 after 48 h of incubation. Left plot: Lysis mediated by bstb_369/367 and the tag-free analog bstb_5726/5725 as monomer and spiked with 5% HMW. Right plot: Lysis mediated by bstb_369/367 as reference and by the CH1(IgG2)-carrying variant bstb_5727/5725 as monomer and spiked with 5% HMW. Bstb indicates bispecific TriMAB; bi-(scFv)$_2$, bispecific single chain variable fragment; EC50, half maximal effective concentration; HMW, high molecular weight species.

Figure 5A:
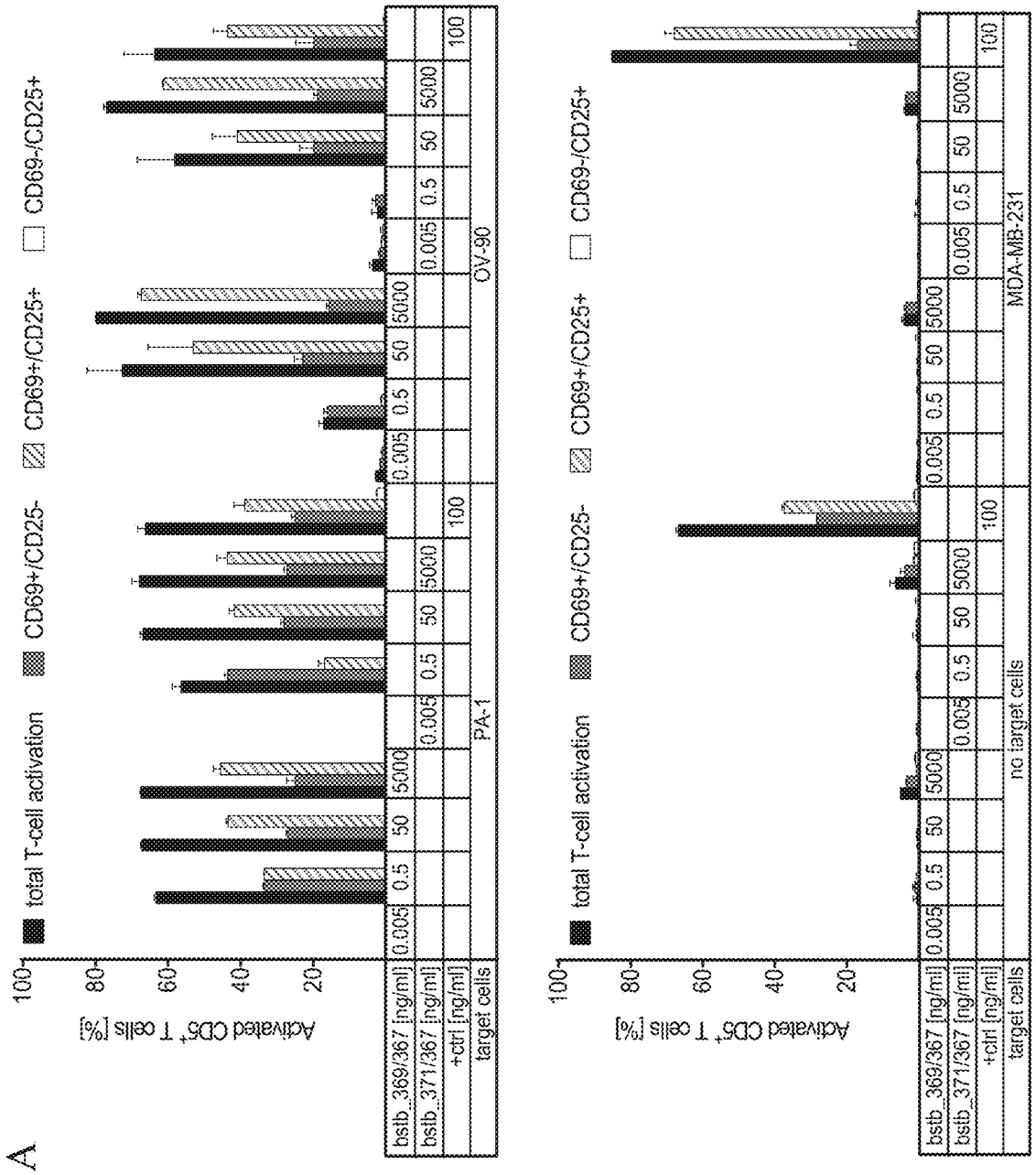
Figure 5B:
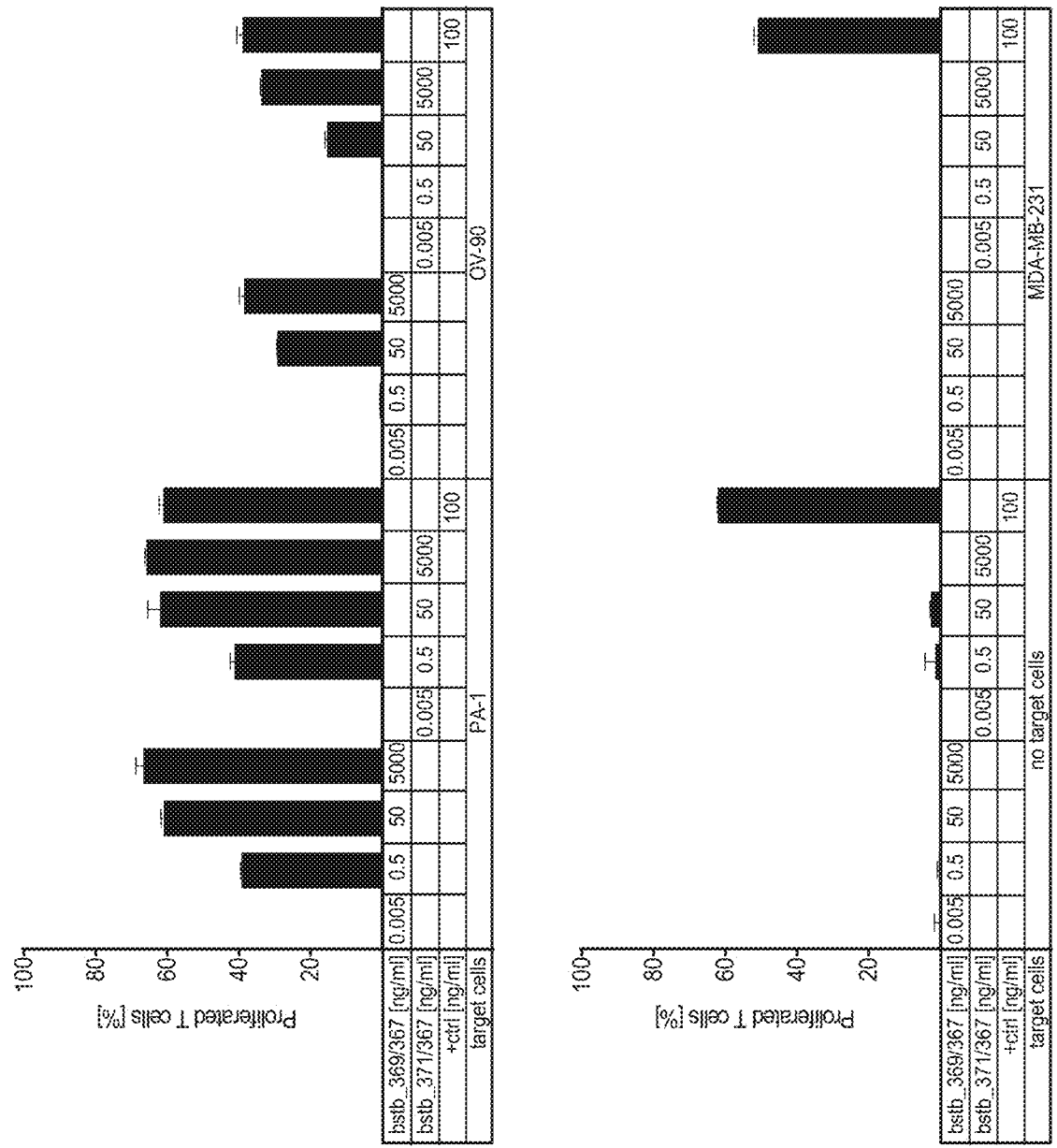

FIG. 5: Target-dependent T-cell modulation mediated by CLDN6×CD3 proteins bstb_369/367 and bstb_371/367

CLDN6$^+$ OV-90 and PA-1 and CLDN6—MDA-MB-231 cancer cell lines were used as target cells. Human PBMC served as effector cells in an E:T ratio of 5:1. Anti-CD3 IgG2a OKT3 was applied in a concentration of 100 ng/ml as activation control. Mock samples were incubated with DPBS to subtract the background signals from analyzed sample values. PBMC without target cells were used as further specificity control. All samples were set up in duplicates in a 24-well format. Escalating concentrations of bstb proteins bstb_369/367 or bstb_371/367 (0.005-5000 ng/ml) were applied. (A) T-cell activation: PBMC were harvested after 48 h of co-incubation and labeled with anti-CD5-PE-Cy7, anti-CD25-PE, anti-CD69-APC and eFluor506 to analyze activation of viable T cells by flow cytometry. (B) T-cell proliferation: Human PBMC were CFSE-stained prior to assay set up. PBMC were harvested after 72 h of co-incubation and labeled with anti-CD5-APC and eFluor506 to exclude non-lymphocytes and dead cells. Decrease of CFSE signal indicating T-cell proliferation was analyzed by flow cytometry. Bstb indicates bispecific TriMAB; ctrl, control.

FIG. 6: Binding of different CLDN6×CD3 bispecific antibodies to the tumor specific antigen CLDN6.

(A) Relative binding affinity of bi-(scFv)$_2$ reference, bstb_369/367 and bstb_5726/5725 was examined by flow cytometry on endogenously CLDN6-expressing PA-1 human carcinoma cells in a concentration range of 9.77 ng/ml to 10 µg/ml. Primary antibodies were detected with Protein L-FITC (4 µg/ml). Data are depicted as mean±standard deviation (n=2 replicates). (B) The impact of high molecular weight (HMW) species on the binding of monomeric bstb_5726/5725 was analyzed in flow cytometry with either monomeric bstb_5726/5725 or monomeric bstb_5726/5725 spiked with ~3% or 5% HMW species (concentration range 9.77 ng/ml to 10 µg/ml). Primary antibodies were detected with Protein L-FITC (4 µg/ml). Data are depicted as mean±standard deviation (n=2 replicates). Bstb indicates bispecific TriMAB; MFI, median fluorescence intensity.

FIG. 7: In vivo efficacy of CLDN6×CD3 protein bstb_369/367 in a mouse xenograft tumor model.

Male and female immunodeficient NSG mice were used. (A) Injection schedule scheme. Mice were inoculated subcutaneously with CLDN6+ human ovarian carcinoma cells OV-90 as target cells and engrafted intraperitoneally (i.p.) with human PBMC as effector cells. Treatment started at a mean tumor volume of ~35 mm³ per group and was conducted i.p. 3-times per week. Group 1 (G1) received vehicle buffer DPBS, group 2 (G2) a low dose bstb_369/367 of 31 μg/kg and group 3 (G3) a higher dose of 308 μg/kg. (B) Tumor growth of all mice and groups over time. Treatment was applied i.p. during the time period highlighted by a border. Top, vehicle group G1; lower left, low bstb_369/367 dose group G2; lower right, higher bstb_369/367 dose group G3. Each line represents an individual mouse. (C) Kaplan-Meier survival plot of all groups from the day of treatment start until the day of euthanasia. The table below indicates the median survival days per group and the significance of survival of G2 and G3 as compared to G1 by log-rank (Mantel-Cox) test.

Bstb indicates bispecific TriMAB; d, days; G, group; GVHD, graft-versus-host disease; i.p., intraperitoneally; PBMC, peripheral blood mononuclear cells; s.c., subcutaneously.

Figure 8:
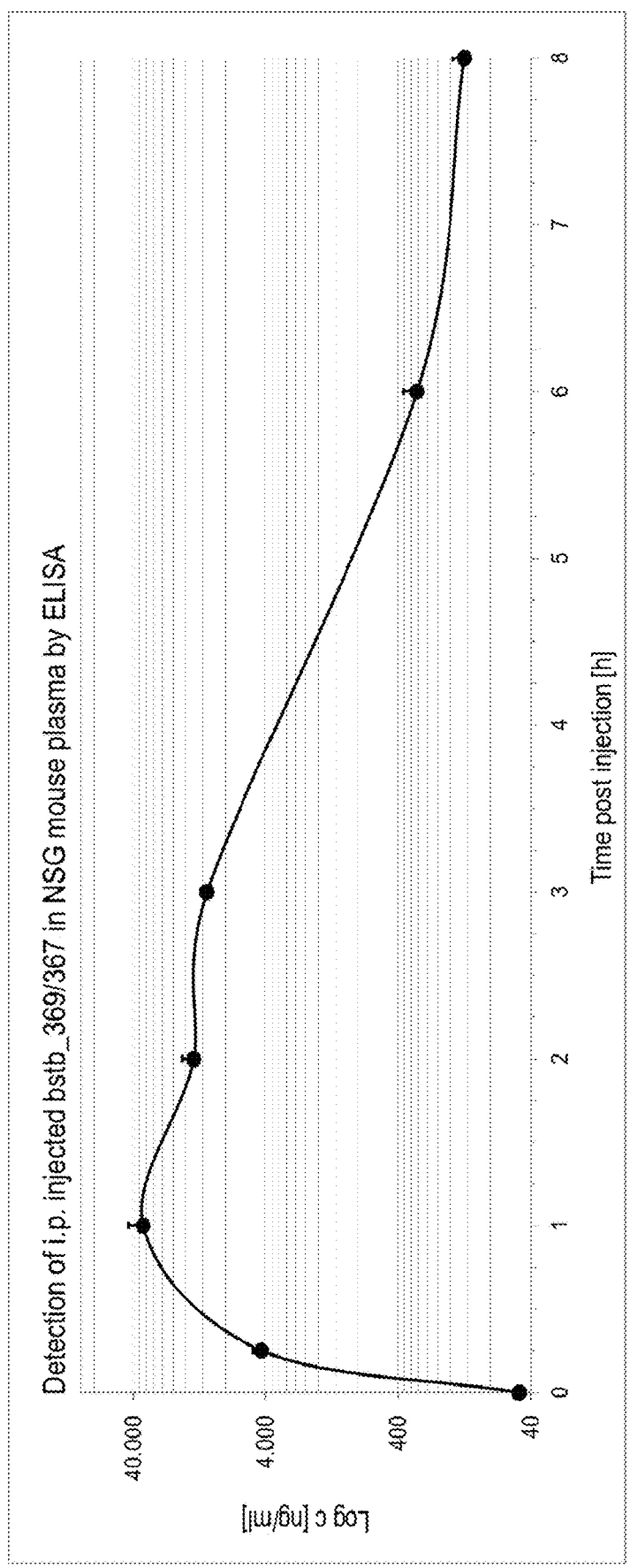

FIG. 8: Estimation of in vivo pharmacokinetics of CLDN6×CD3 protein bstb_369/367.

5 mg/kg bstb_369/367 was injected i.p. into female immunodeficient NSG mice at day 0. DPBS injection ("0 h") served as control before injection. Plasma was harvested 0.25 h, 1 h, 2 h, 3 h, 6 h and 8 h post injection. Bstb_369/367 plasma concentration was detected via ELISA. The concentration is plotted in log scale on the y-axis. Each point represents the mean value with standard deviation of three mice.

I.p. indicates intraperitoneally.

FIG. 9: In vivo dose finding with CLDN6×CD3-bstb protein bstb_5726/5725 in a mouse xenograft tumor model.

Male and female immunodeficient NSG mice were inoculated subcutaneously with CLDN6+ human ovarian carcinoma cells OV-90 as target cells and engrafted intraperitoneally (i.p.) with human PBMC as effector cells. Treatment started at a mean tumor volume of ~150 mm³ per group and was conducted i.p. 3-times per week. (A) Injection schedule scheme. (B) Tumor growth plots. Dosing of groups (n=6) was as indicated in the single plots. Control group G7 (n=8) received DPBS. Plots show tumor growth of all mice and groups over time. The treatment period is highlighted by a border. Each line represents an individual mouse (mouse ID=BIO-####). Bstb indicates bispecific TriMAB; DPBS, Dulbecco's phosphate-buffered saline; i.p., intraperitoneally; PBMC, peripheral blood mononuclear cells; s.c., subcutaneously.

FIG. 10: Modular schemes illustrating the DNA-constructs and the bstb protein targeting TAA CLDN18.2.

(A) Design of the bstb chains on DNA level. Anti-CLDN18.2-scFv is either oriented in the VH-VL order (upper scheme) or in the VL-VH order (lower scheme). Constructs with and without ("+/−") disulfide bridges (S-S) were designed. (B) Theoretic models of exemplified bstb molecules with anti-CLDN18.2 scFv in VH-VL or VL-VH order with tags but without disulfide bridges (S-S) in the scFv moieties (top) and without tags but with S-S(bottom). $C_H1$ is derived from IgG1 or IgG2.

C indicates constant region; CMV, Cytomegalovirus promoter; Fd, digestible fragment/heavy chain portion of Fab (antigen binding fragment); H, heavy chain; His, 6xHis-tag; L, light chain; L1, SGPG$_3$RS(G$_4$S)$_2$ linker (SEQ ID NO: 66); L2, DVPG$_2$S linker (SEQ ID NO: 67); L3, (G$_4$S)$_4$ linker (SEQ ID NO: 68); L4, (G$_4$S)$_5$ linker (SEQ ID NO: 69); S-S, disulfide bridge; scFv, single chain variable fragment; Sec, secretion signal; Strp, Strep-tag; V, variable domain.

Figure 11:
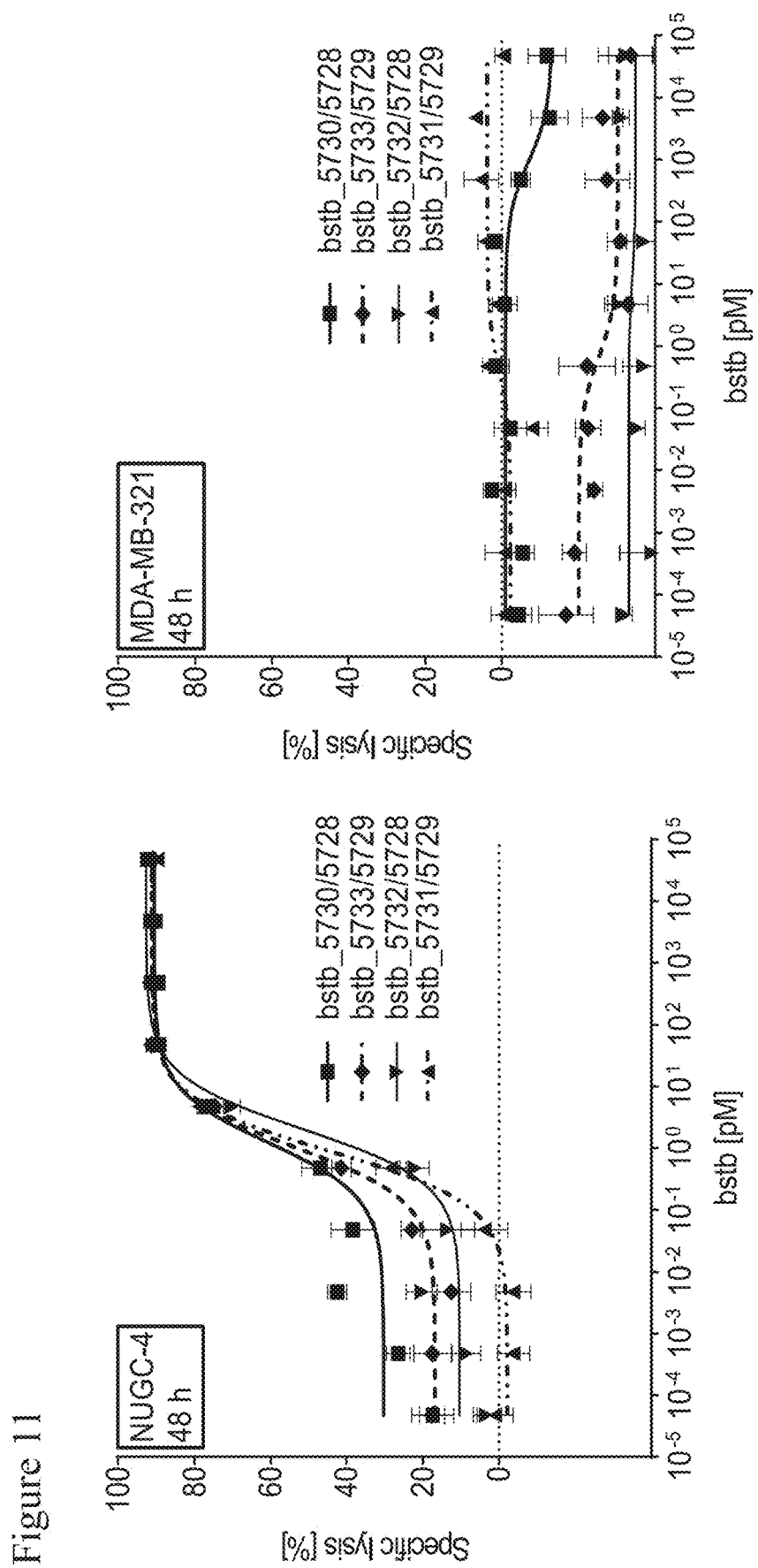

FIG. 11: In vitro cytotoxicity assay to compare the specific lysis mediated by CLDN18.2×CD3-bstb proteins.

Human PBMC as effector cells and human stably luciferase transduced carcinoma cells as target cells were used in an effector to target ratio of 5:1 in a luciferase-based cytotoxicity assay. IMAC and Strep-Tactin® purified bstb test items were used without further enrichment of monomeric species via SEC. Left graph: Specific and concentration-dependent lysis of CLDN18.2+ gastric carcinoma cells NUGC-4_hCLDN18.2 mediated by bstb_5730/5728, bstb_5731/5729, bstb_5732/5728 and bstb_5733/5729 after 48 h of incubation. Right graph: Lysis of CDLN18.2-control cell line MDA-MB-231. Mean values of triplicates including standard deviation are shown. Bstb indicates bispecific TriMAB.

FIG. 12: SE-HPLC analysis of different CLDN18.2×CD3-bstb proteins after purification.

Expi293F™ cells were transiently transfected with bstb_5745/5747, bstb_5749/5751, bstb_5746/5748 or bstb_5750/5752 constructs. Supernatant was harvested seven days post 10 transfection and subjected to purification. (A) SE-HPLC analysis of bstb_5745/5747 (upper plot) and bstb_5749/5751 (lower plot) after purification (lower plot). mAU (milli-absorbance-units) on the y-axis are plotted against the time in minutes on the x-axis. The monomer content is strongly increased in bstb_5749/5751 which contains the extra disulfide bonds within the anti-CLDN18.2 scFv moieties. (B) SE-HPLC analysis of bstb_5746/5748 (upper plot) and bstb_5750/5752 (lower plot) after purification (lower plot). mAU (milli-absorbance-units) on the y-axis are plotted against the time in minutes on the x-axis. The monomer content is strongly increased in bstb_5749/5751 which contains the extra disulfide bonds within the anti-CLDN18.2 scFv moieties.

Bstb indicates bispecific TriMAB; HMW, high molecular weight species; LMW, low molecular weight species.

Figure 13A:
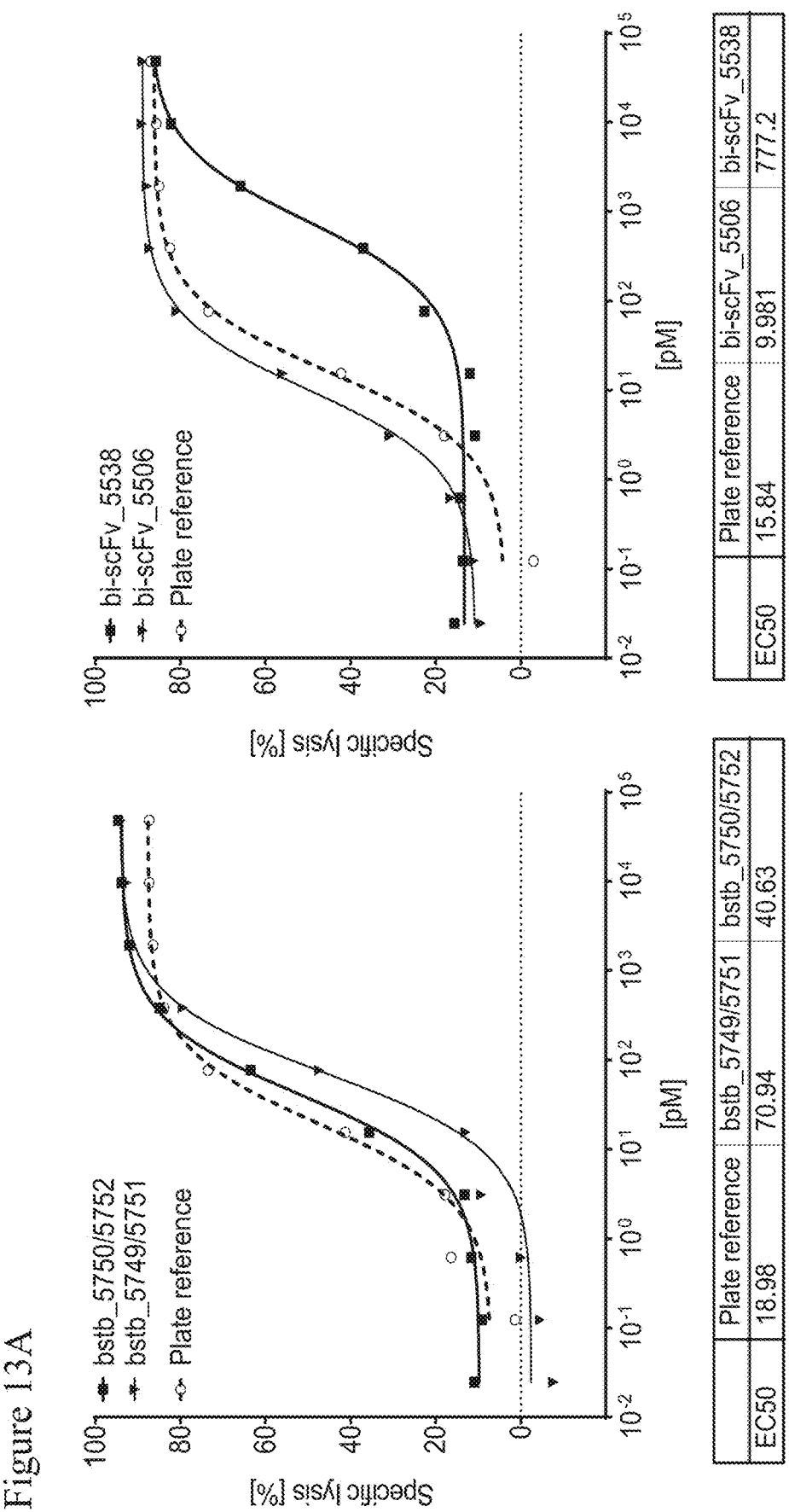

FIG. 13: In vitro cytotoxicity assay to compare the specific lysis mediated by highly monomeric disulfide bridge containing CLDN18.2×CD3-bstb and bi-(scFv)$_2$ proteins.

Human PBMC as effector cells and human stably luciferase transduced CLDN18.2+ gastric carcinoma cells NUGC-4_hCLDN18.2 as target cells were used in an effector to target ratio of 5:1 in a luciferase-based cytotoxicity assay. Monomeric bstb test items separated by SEC and their bi-(scFv)$_2$ protein analogs were used in 10-point, 5-fold serial dilutions. (A) Specific and concentration-dependent lysis mediated by bstb_5749/5751 and bstb_5750/5752 (left graph) and bi-scFv_5506 and bi-scFv_5538 (right graph) after 48 h of incubation. EC50 values are summarized in the tables below. EC50 values of the "plate reference" served for normalization.

(B) Fold difference of the bivalent bstb compared to the related bi-(scFv)$_2$ analogs after normalization to the "plate reference". Related bi-(scFv)$_2$ EC50 values were set to 1 for calculations.

Bi-scFv indicates bispecific single chain variable fragment; bstb, bispecific TriMAB; EC50, half maximal effective concentration.

Figure 14:
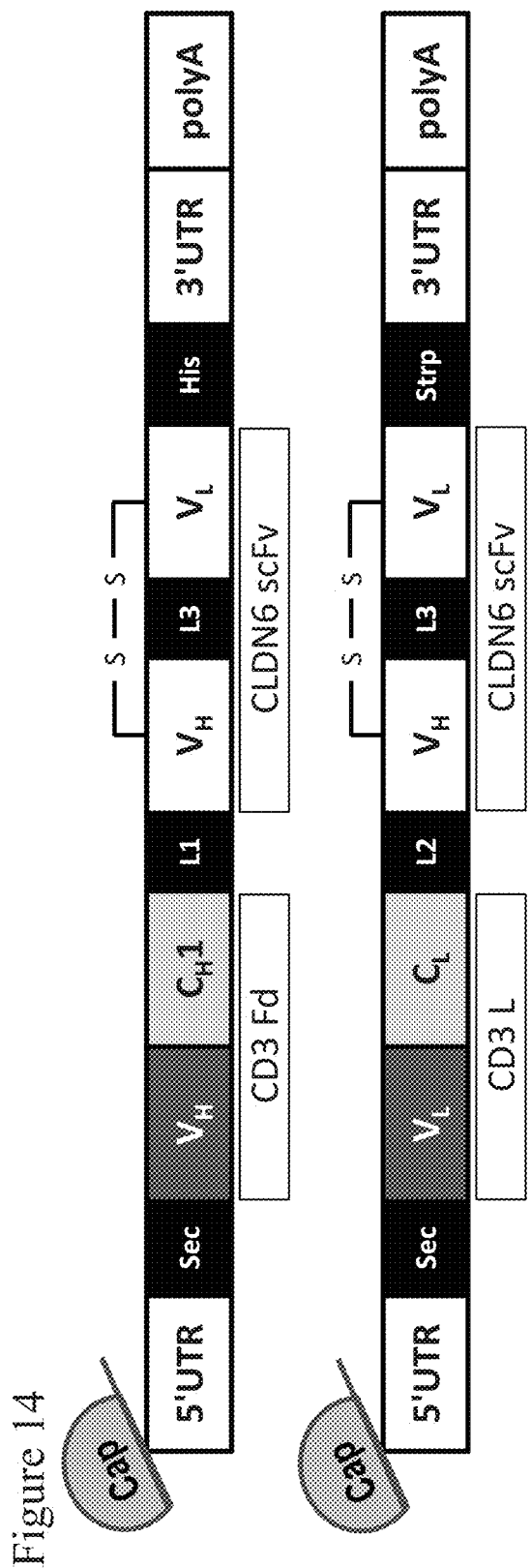

FIG. 14: Modular schemes illustrating the RNA-constructs encoding for CLDN6×CD3 bstb.

Design of the bstb Fd-(top) and L-chain (bottom) on RNA level.

C indicates constant region; CMV, Cytomegalovirus promoter; Fd, digestible fragment/heavy chain portion of Fab (antigen binding fragment); H, heavy chain; His, 6xHis-tag; L, light chain; L1, SGPG$_3$RS(G$_4$S)$_2$ linker (SEQ ID NO: 66); L2, DVPG$_2$S linker (SEQ ID NO: 67); L3, (G$_4$S)$_4$ linker (SEQ ID NO: 68); S-S, disulfide bridge; scFv, single chain variable fragment; Sec, secretion signal; Strp, Strep-tag; V, variable domain.

Figure 15B:
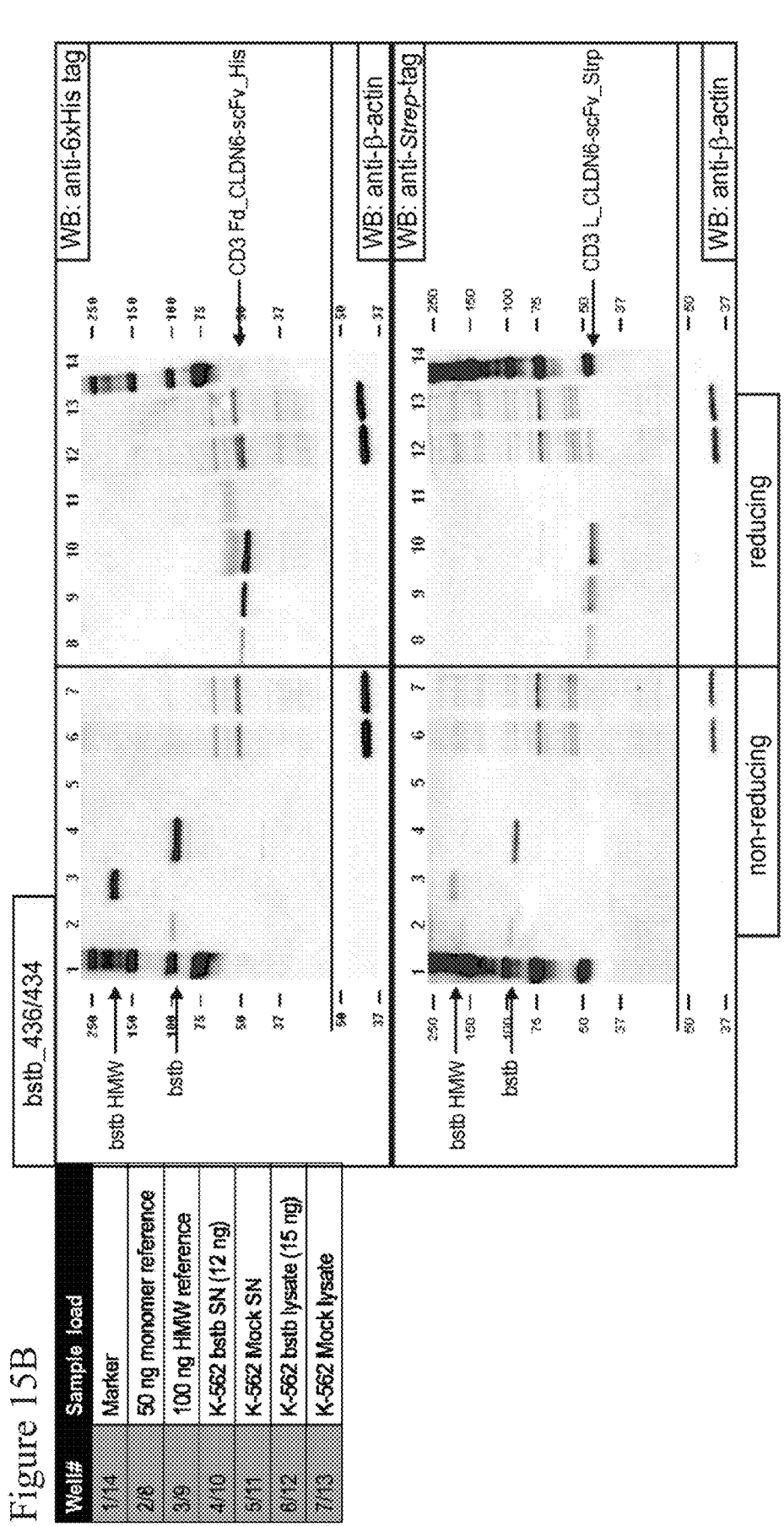
Figure 15C:
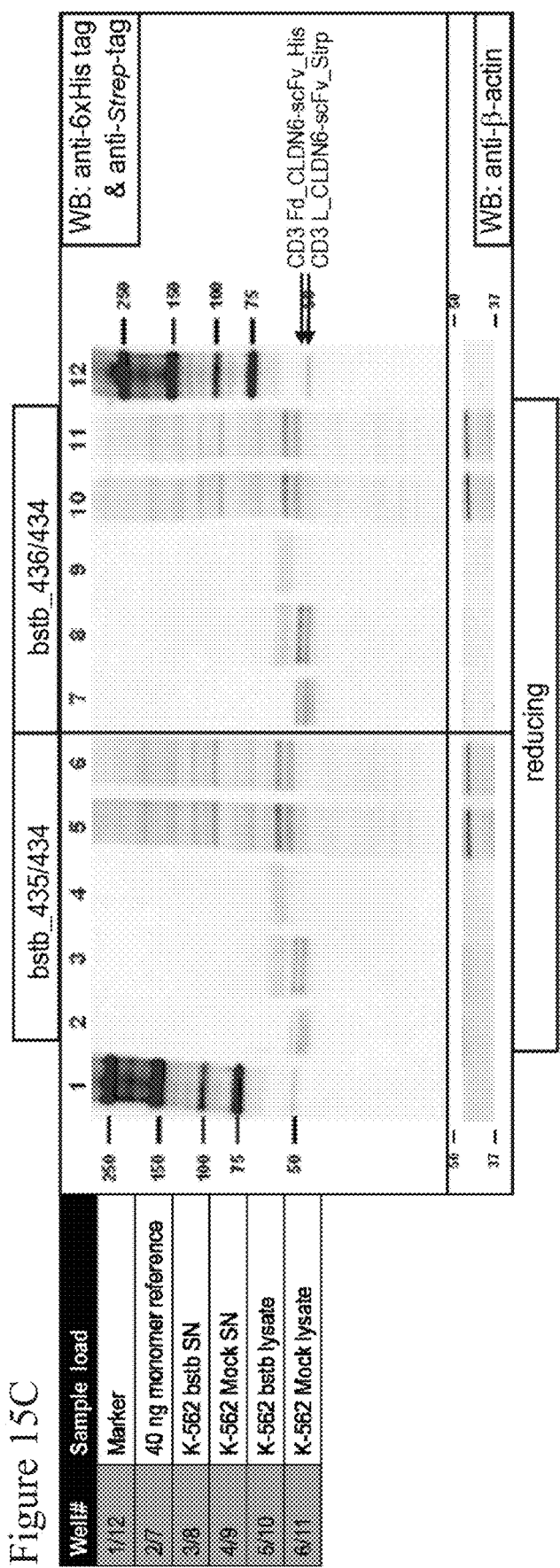

FIG. 15: Western Blot analysis of IVT-mRNA encoded CLDN6×CD3 bstb_435/434 and bstb_436/434 in producer cells.

Human chronic myeloid leukemia cell line K-562 was transiently transfected via electroporation with equal IVT-mRNA amounts of the Fd- and the L-chain or with H$_2$O only (Mock). K-562 supernatants were harvested 48 h post electroporation and cell lysates were generated. As reference the purified protein analogs bstb_369/367 (A) or bstb_371/367 (B) were loaded as monomeric and HMW preparation onto the gels. Gradient SDS-PAGE and Western Blot analysis were performed for the detection of translated and purified protein products.

Both bstb variants ((A) bstb_435/434, (B) bstb_436/434) were detected in K-562 supernatant and cell lysate by anti-6xHis-tag HRP (Fd-part) and anti-Strep-MAB-HRP (L-part). Anti-3-actin 2 0 immunoblotting served as loading control for cell lysates. Samples were loaded as indicated in the attached sample load tables under non-reducing and reducing conditions. Arrow heads indicate the protein bands of interest. (A) bstb_435/434, (B) bstb_436/434. In (C) both bstb variants were detected under reducing conditions with a mixture of anti-6xHis-tag HRP and anti-Strep-MAB-HRP to visualize the heterodimeric state of the antibody derivatives.

Bstb indicates bispecific TriMAB; Fd, digestible fragment/heavy chain portion of Fab (antigen binding fragment); His, 6xHis-tag; HMW, high molecular weight species; HRP, horseradish peroxidase; L, light chain portion of bstb; scFv, single chain variable fragment; SN, supernatant.

Figure 16:
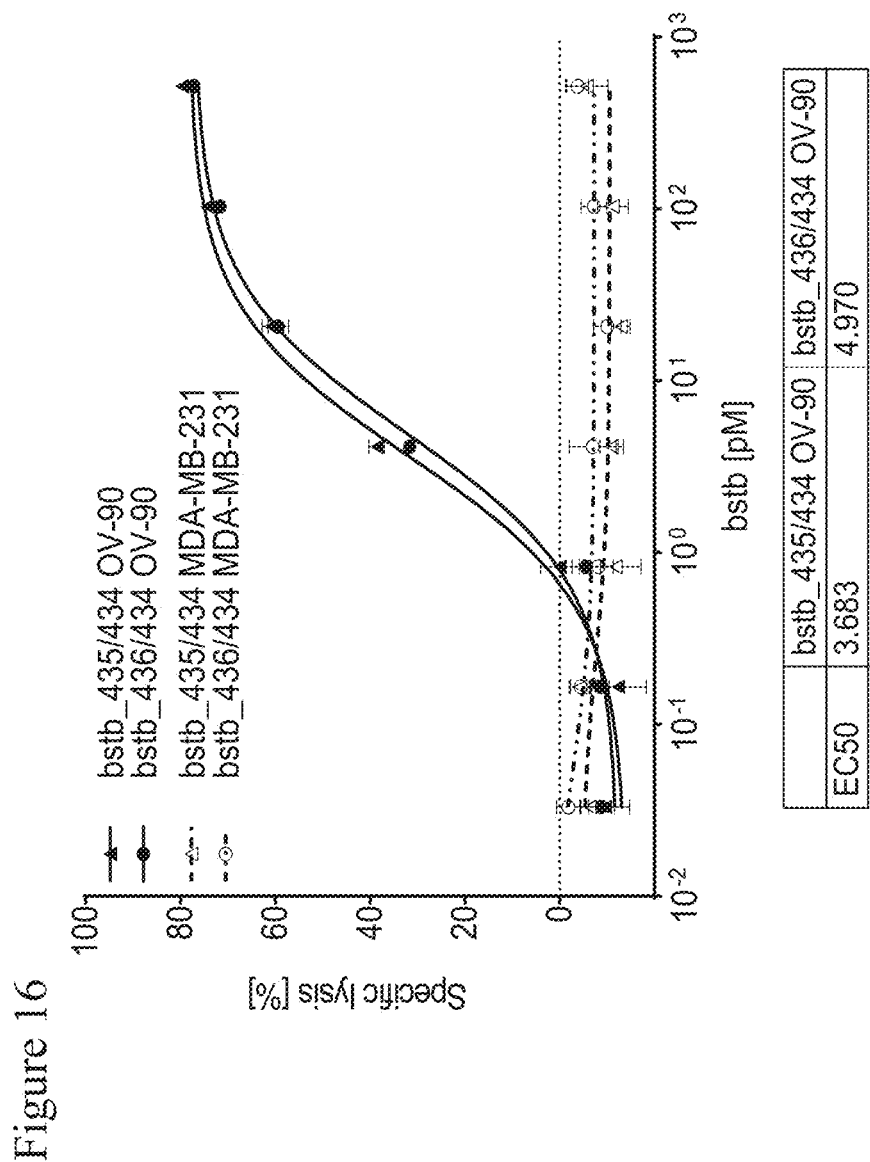

FIG. 16: In vitro cytotoxicity assay to determine the specific lysis mediated by CLDN6× CD3 bstb_435/434 and bstb_436/434.

Human PBMC as effector cells and human stably luciferase transduced carcinoma cells as target cells were used in an effector to target ratio of 5:1 in a luciferase-based cytotoxicity assay. K-562 SN containing RNA-encoded bstb_435/434 or bstb_436/434 was applied in a 7-point, 5-fold serial dilution. The specific concentration-dependent lysis mediated by bstb_435/434 and bstb_436/434 of CLDN6$^+$ ovarian carcinoma cells OV-90 after 48 h of incubation is shown. CDLN6$^-$ breast carcinoma cells MDA-MB-231 served as negative control. Mean values of triplicates including standard deviation are shown.

Bstb indicates bispecific TriMAB; EC50, half maximal effective concentration.

Figure 17A:
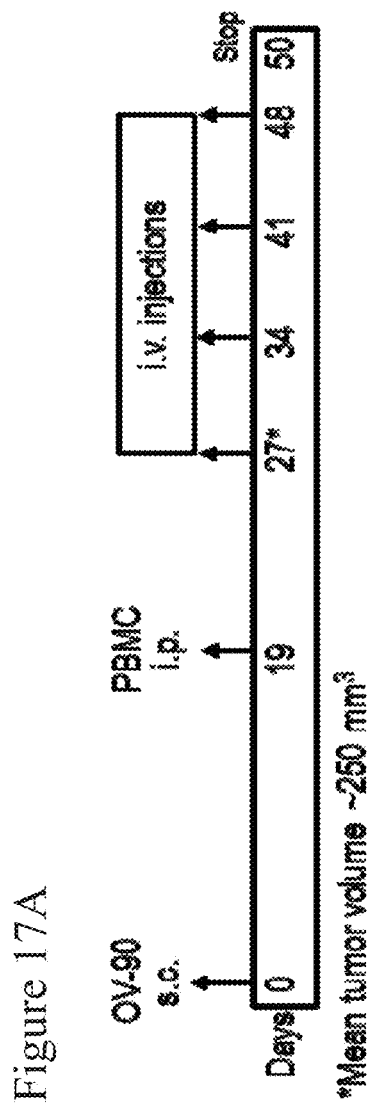

FIG. 17: Comparison of in vivo efficacy of CLDN6×CD3 RNA and protein bstb and bi-(scFv)$_2$ in a mouse xenograft tumor model.

Male (black symbols) and female (white symbols) immunodeficient NSG mice were used. (A) Injection schedule scheme. Mice were inoculated subcutaneously (s.c.) with CLDN6$^+$ human ovarian carcinoma cells OV-90 as target cells and engrafted intraperitoneally (i.p.) with human PBMC as effector cells. Treatment started at a mean tumor volume of ~250 mm$^3$ per group and was conducted intravenously (i.v.) once per week. Group 1 (G1) received RNA control complex (luciferase RNA in TransIT), G2 bstb RNA complex and G3 bi-(scFv)$_2$ RNA complex. Each injection contained a total of 3 μg RNA. G4-6 served as protein control/reference groups: G4 received vehicle buffer (protein formulation buffer), G5 100 μg/kg bstb reference and G6 200 μg/kg bi-(scFv)$_2$ reference. (B) Tumor growth of all mice and groups over time. Treatment was applied i.v. as indicated by arrowheads. The treatment per group is specified in the graph titles. Each line represents an individual mouse. (C) Flow cytometric analysis of human T cells that infiltrated xenograft tumor tissue of mice treated with control RNA (G1), bstb RNA (G2) or bi-(scFv)$_2$ RNA (G3). Each symbol represents an individual mouse, lines the mean value per group. Symbols are in accordance with (B).

Bi-scFv indicates bispecific single chain fragment; bstb, bispecific TriMAB; d, days; G, group; GVHD, graft-versus-host disease; i.p., intraperitoneally; i.v., intravenously; PBMC, peripheral blood mononuclear cells; s.c., subcutaneously.

Figure 18B:
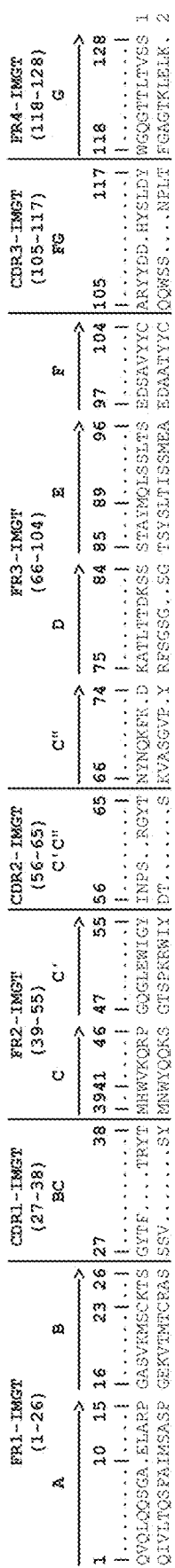

FIG. 18: V$_H$ and V$_L$ amino acid sequences according to IMGT nomenclature.

The amino acid sequences in standard one letter code of the VH and VL domains that were used in the here described bstb molecules are shown. A) VH and VL sequences of anti-CLDN18.2 and anti-CLDN6, B) VH and VL sequences of anti-CD3.

CDR indicates complementarity determining region; FR, framework region; IMGT, the international ImMunoGeneTics information system; VH, variable heavy chain; VL, variable light chain.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, 2nd Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop, termed EC1 or ECL1, consists on average of 53 amino acids, and the second extracellular loop, termed EC2 or ECL2, consists of around 24 amino acids. Cell surface proteins of the claudin family, such as CLDN6 and CLDN18.2, are expressed in tumors of various origins, and are particularly suited as target structures in connection with antibody-mediated cancer immunotherapy due to their selective expression (no expression in a toxicity relevant normal tissue) and localization to the plasma membrane.

In the context of the present invention, the preferred claudins are CLDN6 and CLDN18.2. CLDN6 and CLDN18.2 have been identified as differentially expressed in tumor tissues, with the only normal tissues expressing CLDN18.2 being stomach and the only normal tissue expressing CLDN6 being placenta.

CLDN18.2 is selectively expressed in normal tissues in differentiated epithelial cells of the gastric mucosa. CLDN18.2 is expressed in cancers of various origins such as pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non-small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

CLDN6 has been found to be expressed, for example, in ovarian cancer, lung cancer, gastric cancer, breast cancer, hepatic cancer, pancreatic cancer, skin cancer, melanomas, head neck cancer, sarcomas, bile duct cancer, renal cell cancer, and urinary bladder cancer. CLDN6 is a particularly preferred target for the prevention and/or treatment of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, 2 0 skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof. In one embodiment, the cancer disease associated with CLDN6 expression is selected from the group consisting of ovarian cancer, lung cancer, metastatic ovarian cancer and metastatic lung cancer. Preferably, the ovarian cancer is a carcinoma or an adenocarcinoma. Preferably, the lung cancer is a carcinoma or an adenocarcinoma, and preferably is bronchiolar cancer such as a bronchiolar carcinoma or bronchiolar adenocarcinoma.

The term "claudin" or "CLDN" includes CLDN18.2 and CLDN6. Preferably, a claudin is a human claudin.

The term "claudin 18" or "CLDN18" includes any variants, including claudin 18 splice variant 1 (claudin 18.1 (CLDN18.1)) and claudin 18 splice variant 2 (claudin 18.2 (CLDN18.2)).

The term "claudin 18.2" or "CLDN18.2" preferably relates to human CLDN18.2, and, in particular, to a protein comprising, preferably consisting of the amino acid sequence according to SEQ ID NO: 1 of the sequence listing or a variant of said amino acid sequence. The first extracellular loop of CLDN18.2 preferably comprises amino acids 27 to 81, more preferably amino acids 29 to 78 of the amino acid sequence shown in SEQ ID NO: 1. The second extracellular loop of CLDN18.2 preferably comprises amino acids 140 to 180 or 144 to 167 of the amino acid sequence shown in SEQ ID NO: 1. Said first and second extracellular loops preferably form the extracellular portion of CLDN18.2.

The term "claudin 6" or "CLDN6" preferably relates to human CLDN6, and, in particular, to a protein comprising, preferably consisting of the amino acid sequence of SEQ ID NO: 2 or SEQ ID NO: 3 of the sequence listing or a variant of said amino acid sequence. The first extracellular loop of CLDN6 preferably comprises amino acids 28 to 80 or 29 to 81, more preferably amino acids 28 to 76 of the amino acid sequence shown in SEQ ID NO: 2 or the amino acid sequence shown in SEQ ID NO: 3. The second extracellular loop of CLDN6 preferably comprises amino acids 138 to 160, preferably amino acids 141 to 159, more preferably amino acids 145 to 157 of the amino acid sequence shown in SEQ ID NO: 2 or the amino acid sequence shown in SEQ ID NO: 3. Said first and second extracellular loops preferably form the extracellular portion of CLDN6.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any post translationally modified variants and conformation variants.

The second target molecule of the binding agents described herein is a T cell-specific antigen. A T cell-specific antigen is an antigen on the surface of T cells. A preferred embodiment of such T cell-specific antigen is the CD3 (cluster of differentiation 3) complex.

The CD3 complex denotes an antigen that is expressed on mature human T-cells, thymocytes and a subset of natural killer cells as part of the multimolecular T-cell receptor (TCR) complex. The T-cell co-receptor is a protein complex and is composed of four distinct chains. In mammals, the complex contains a CD3γ chain, a CD3δ chain, and two CD3ε chains. These chains associate with a molecule known as the T-cell receptor (TCR) and the ζ chain to generate an activation signal in T lymphocytes. The TCR, ζ chain, and CD3 molecules together comprise the TCR complex.

The human CD3 epsilon is indicated in GenBank Accession No. NM_000733 and comprises SEQ ID NO: 4. The human CD3 gamma is indicated in GenBank Accession No. NM_000073. The 15 human CD3 delta is indicated in GenBank Accession No. NM_000732. CD3 is responsible for the signal transduction of the TCR. As described by Lin and Weiss, Journal of Cell Science 114, 243-244 (2001), activation of the TCR complex by binding of MHC-presented specific antigen epitopes results in the phosphorylation of immunoreceptor tyrosine-based activation motifs (ITAMs) by Src family kinases, triggering recruitment of further kinases which results in T-cell activation including $Ca^{2+}$ release. Clustering of CD3 on T cells, e.g. by immobilized anti-CD3-antibodies, leads to T-cell activation similar to the engagement of the T-cell receptor, but independent from its clone typical specificity.

As used herein, "CD3" includes human CD3 and denotes an antigen that is expressed on human T cells as part of the multimolecular T-cell receptor complex.

With respect to CD3, the binding agent of the invention preferably recognizes the epsilon-chain of CD3, particular, it recognizes an epitope that corresponds to the first 27 N-terminal amino acids of CD3 epsilon or functional fragments of this 27 amino acid stretch.

According to the invention, the term "claudin positive cancer" or similar terms mean a cancer involving cancer cells expressing a claudin, preferably on the surface of said cancer cells.

"Cell surface" is used in accordance with its normal meaning in the art, and thus includes the outside of the cell which is accessible to binding by proteins and other molecules A claudin is expressed on the surface of cells if it is located at the surface of said cells and is accessible to binding by claudin-specific antibodies added to the cells.

The term "extracellular portion" in the context of the present invention refers to a part of a molecule such as a protein that is facing the extracellular space of a cell and preferably is accessible from the outside of said cell, e.g., by antigen-binding molecules such as antibodies located outside the cell. Preferably, the term refers to one or more extracellular loops or domains or a fragment thereof.

The terms "part" or "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope or peptide is preferably immunologically equivalent to the epitope or peptide it is derived from. A part or fragment of a protein sequence preferably comprises a sequence of at least 4, in particular at least 6, at least 8, at least 12, at least 15, at least 20, at least 30, at least 50, or at least 100 consecutive amino acids of the protein sequence.

According to the invention, CLDN18.2 is not substantially expressed in a cell if the level of expression is lower compared to expression in stomach cells or stomach tissue. Preferably, the level of expression is less than 10%, preferably less than 5%, 3%, 2%, 1%, 0.5%, 0.1% or 0.05% of the expression in stomach cells or stomach tissue or even lower. Preferably, CLDN18.2 is not substantially expressed in a cell if the level of expression exceeds the level of expression in non-cancerous tissue other than stomach by no more than 2-fold, preferably 1.5-fold, and preferably does not exceed the level of expression in said non-cancerous tissue. Preferably, CLDN18.2 is not substantially expressed in a cell if the level of expression is below the detection limit and/or if the level of expression is too low to allow binding by CLDN18.2-specific antibodies added to the cell.

According to the invention, CLDN18.2 is expressed in a cell if the level of expression exceeds the level of expression in non-cancerous tissue other than stomach preferably by more than 2-fold, preferably 10-fold, 100-fold, 1000-fold, or 10000-fold. Preferably, CLDN18.2 is expressed in a cell if the level of expression is above the detection limit and/or if the level of expression is high enough to allow binding by CLDN18.2-specific antibodies added to the cell. Preferably, CLDN18.2 expressed in a cell is expressed or exposed on the surface of said cell.

According to the invention, CLDN6 is not substantially expressed in a cell if the level of expression is lower compared to expression in placenta cells or placenta tissue. Preferably, the level of expression is less than 10%, preferably less than 5%, 3%, 2%, 1%, 0.5%, 0.1% or 0.05% of the expression in placenta cells or placenta tissue or even lower. Preferably, CLDN6 is not substantially expressed in a cell if the level of expression exceeds the level of expression in non-cancerous tissue other than placenta by no more than 2-fold, preferably 1.5-fold, and preferably does not exceed the level of expression in said non-cancerous tissue. Preferably, CLDN6 is not substantially expressed in a cell if the level of expression is below the detection limit and/or if the level of expression is too low to allow binding by CLDN6-specific antibodies added to the cell.

According to the invention, CLDN6 is expressed in a cell if the level of expression exceeds the level of expression in non-cancerous tissue other than placenta preferably by more than 2-fold, preferably 10-fold, 100-fold, 1000-fold, or 10000-fold. Preferably, CLDN6 is expressed in a cell if the level of expression is above the detection limit and/or if the level of expression is high enough to allow binding by CLDN6-specific antibodies added to the cell. Preferably, CLDN6 expressed in a cell is expressed or exposed on the surface of said cell.

According to the invention, the term "disease" refers to any pathological state, including cancer, in particular those forms of cancer described herein. Any reference herein to cancer or particular forms of cancer also includes cancer metastasis thereof. In a preferred embodiment, a disease to be treated according to the present application involves cells expressing claudin (CLDN) such as CLDN18.2 and/or CLDN6.

"Diseases associated with cells expressing a claudin" or similar expressions means according to the invention that a claudin is expressed in cells of a diseased tissue or organ. In one embodiment, expression of a claudin in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases associated with cells expressing a claudin include cancer diseases. Furthermore, according to the invention, cancer diseases preferably are those wherein the cancer cells express a claudin.

As used herein, a "cancer disease" or "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease. Preferably, a "cancer disease" is characterized by cells expressing a claudin and a cancer cell expresses a claudin. A cell expressing a claudin preferably is a cancer cell, preferably of the cancers described herein.

The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis. One particular form of metastasis which is treatable using the therapy of the invention is metastasis originating from gastric cancer as primary site. In preferred embodiments such gastric cancer metastasis is Krukenberg tumors, peritoneal metastasis and/or lymph node metastasis.

Krukenberg tumor is an uncommon metastatic tumor of the ovary accounting for 1% to 2% of all ovarian tumors. Prognosis of Krukenberg tumor is still very poor and there is no established treatment for Krukenberg tumors. Krukenberg tumor is a metastatic signet ring cell adenocarcinoma of the ovary. Stomach is the primary site in most Krukenberg tumor cases (70%). Carcinomas of colon, appendix, and breast (mainly invasive lobular carcinoma) are the next most common primary sites. Rare cases of Krukenberg tumor originating from carcinomas of the gallbladder, biliary tract, pancreas, small intestine, ampulla of Vater, cervix, and urinary bladder/urachus have been reported.

By "treat" is meant to administer a compound or composition or a combination of compounds or compositions to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for cancer would be a candidate for therapy to prevent cancer.

By "being at risk" is meant a subject that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

The term "patient" means according to the invention a subject for treatment, in particular a diseased subject, including human beings, nonhuman primates or another animals, in particular mammals such as cows, horses, pigs, sheeps, goats, dogs, cats or rodents such as mice and rats. In a particularly preferred embodiment, a patient is a human being.

"Target cell" shall mean any undesirable cell such as a cancer cell. In preferred embodiments, the target cell expresses a claudin.

The term "antigen" relates to a molecule such as a protein or peptide comprising an epitope against which an agent is directed and/or is to be directed, preferably to induce an immune response. In a preferred embodiment, an antigen is a tumor-associated antigen, such as CLDN18.2 or CLDN6, i.e., a constituent of cancer cells which may be derived from the cytoplasm, the cell surface and the cell nucleus, in particular those antigens which are produced, preferably in large quantity, intracellular or as surface antigens on cancer cells.

In the context of the present invention, the term "tumor-associated antigen" preferably relates to proteins that are under normal conditions specifically expressed in a limited number of tissues and/or organs or in specific developmental stages and are expressed or aberrantly expressed in one or more tumor or cancer tissues. In the context of the present invention, the tumor-associated antigen is preferably associated with the cell surface of a cancer cell and is preferably not or only rarely expressed in normal tissues.

The term "epitope" refers to an antigenic determinant in a molecule, e.g., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "binding agent", as used herein, refers to any agent capable of binding to desired antigens. In certain embodiments of the invention, the binding agent is an antibody, antibody fragment, or construct thereof. The binding agent may also comprise synthetic, modified or non-naturally occurring moieties, in particular non-peptide moieties. Such moieties may, for example, link desired antigen-binding functionalities or regions such as antibodies or antibody fragments. In one embodiment, the binding agent is a synthetic construct comprising antigen-binding CDRs or variable regions.

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the VL (variable light chain) domain, $C_L$ (constant light chain) domain, and the CH (constant heavy chain) domains $C_H1$, $C_H2$, $C_H3$, and $C_H4$. There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The term "antibody" refers to an immunoglobulin comprising at least two heavy (H) chains and two light (L) chains inter-connected by disulfide bonds, or an antigen binding portion thereof. The term "antibody" includes monoclonal antibodies, recombinant antibodies, human antibodies, humanized antibodies and chimeric antibodies. Each heavy chain is comprised of a heavy chain variable region (abbreviated herein as VH) and a heavy chain constant region. Each light chain is comprised of a light chain variable region (abbreviated herein as VL) and a light chain constant region. The term "region" and the term "domain" are used interchangeably herein. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non-human source. However the definition is not limited to this particular example.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The binding agents such as antibodies described herein are preferably isolated. "Isolated" as used herein, is intended to refer to a binding agent which is substantially free of other agents having different antigenic specificities (e.g., an isolated antibody that specifically binds to CLDN18.2 is substantially free of antibodies that specifically bind antigens other than CLDN18.2). An isolated binding agent that specifically binds to an epitope, isoform or variant of human CLDN18.2 may, however, have cross-reactivity to other related antigens, e.g., from other species (e.g., CLDN18.2 species homologs). Moreover, an isolated binding agent may be substantially free of other cellular material and/or chemicals.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A single-chain variable fragment (scFv) is a fusion protein of the variable regions of the heavy (VH) and light chains (VL) of immunoglobulins, connected with a short linker peptide of usually ten to about 30 amino acids. The linker is usually rich in glycine for flexibility, as well as serine or threonine for solubility, and can either connect the N-terminus of the VH with the C-terminus of the VL, or vice versa. Divalent (or bivalent) single-chain variable fragments (di-scFvs, bi-scFvs) can be engineered by linking two scFvs. This can be done by producing a single peptide chain with two VH and two VL regions, yielding tandem scFvs. The invention also includes multispecific molecules comprising more than two scFvs binding domains. One common flexible linking peptide is (Gly4Ser)$_x$ (SEQ ID NO: 70), wherein x may be 3, 4, 5 or 6. Optionally, the association of the VH and VL can be stabilized by one or more intermolecular disulfide bonds.

As used herein, the term "binding domain" or "antigen-binding domain" refers to the site, e.g. of an antibody, that binds to an antigen and includes the antigen-binding portion of an antibody. The binding domain may be comprised of heavy chain and light chain variable domains (VH and VL), each of which includes four conserved framework regions (FR) and three CDRs. The CDRs vary in sequence and determine the specificity to a particular antigen. The VH and VL domains together may form the site that specifically binds a particular antigen.

Fab (fragment antigen binding) antibody fragments are immunoreactive polypeptides comprising monovalent antigen-binding domains of an antibody composed of a polypeptide consisting of a heavy chain variable region (VH) and heavy chain constant region 1 (CH1) portion and a polypeptide consisting of a light chain variable region (VL) and a light chain constant region (in which the CL and CH1 portions are bound together, preferably by a disulfide bond between Cys residues). Preferably in the Fab fragments described herein the CH1 region and the CL region are of human origin. In one embodiment, the CL region is a kappa-type CL region. In one embodiment, the CH1 region is derived from IgG1 or IgG2.

All antibodies and derivatives of antibodies such as antibody fragments as described herein for the purposes of the invention are encompassed by the term "antibody". The term "antibody derivatives" refers to any modified form of an antibody, e.g., a conjugate of the antibody and another agent or antibody, or an antibody fragment. Furthermore, the antibodies and derivatives of antibodies as described herein are useful for producing binding agents of the invention such as antibody fragments.

Naturally occurring antibodies are generally monospecific, i.e. they bind to a single antigen. The present invention provides binding agents binding to a cytotoxic cell such as a T cell (e.g. by engaging the CD3 receptor) and a target cell such as a cancer cell (by engaging a claudin). The binding agents of the present invention bind to at least two different types of antigen and are at least bispecific or multispecific such as trispecific, tetraspecific and so on.

A binding agent of the present invention may be at least trivalent. As used herein, "valent", "valence", "valencies", or other grammatical variations thereof, mean the number of antigen binding sites or binding domains in a binding agent. Antigen binding sites binding to the same antigen may recognize the same epitope or different epitopes. Trivalent bispecific antibodies and tetravalent bispecific antibodies are known in the art. A binding agent of the present invention may also have valencies higher than 4.

A binding agent described herein is preferably an artificial protein (including protein complexes) that may be composed of fragments of at least two different antibodies (said fragments of at least two different antibodies forming at least two different binding domains) and consequently binds to at least two different types of antigen. A binding agent according to the invention is engineered to simultaneously bind to an immune cell, such as an immune effector cell, in particular a T cell such as a cytotoxic cell (e.g. by binding to CD3) and a target cell like a cancer cell (by binding to the tumor-associated antigen claudin) to be destroyed.

Several types of trivalent antibodies have been developed and all types are within the scope of the present invention. Triplebodies or single-chain triple antibodies (sctbs) are composed of three distinct scFv regions joined by linker sequences. Also, the natural in vivo heterodimerization of the heavy chain ($C_H1$ domain) and light chain (CL domain) may be used to form a scaffold on which multiple scFvs can be added. For example, a scFv specific to one antigen can be linked to a CH1 domain, which is also linked to a scFv specific to another antigen and this chain can interact with another chain containing an scFv specific to either antigen linked to a CL domain (scFv3-CH1/CL). Another example of a trivalent construction involves the use of a Fab fragment specific to one epitope C-terminally linked to two scFvs specific to another epitope, one on each chain (Fab-scFv2). Yet another example of a trivalent (or tetravalent) molecule includes a variety of formats which contain additional binding entities attached to N- or C-termini of antibodies. For example, one format consists of an intact antibody molecule specific to one antigen with a single chain Fab (scFab) linked to the C-terminal end of the molecule (IgG-scFab). The dock-and-lock (DNL) approach has also been used to generate trivalent antibodies (DNL-F(ab)$_3$) (Chang, C.-H. et al. In: Bispecific Antibodies. Kontermann R E (ed.), Springer Heidelberg Dordrecht London New York, pp. 199-216 (2011)). Each of the foregoing antibodies is within the scope of the present invention.

Tetravalent antibodies have also been constructed and all types are within the scope of the present invention. Examples of tetravalent antibodies include, but are not limited to, scFv2-Fc, F(ab')$_2$-scFv2, scFv2-H/L, and scFv-dhlx-scFv molecules. Bispecific scFv2-Fc constructs have an Fc domain with two scFvs specific to one molecule linked to the N-termini of the Fc chains and another two scFvs specific to another molecule linked to the C-termini of the Fc chain. Bispecific F(ab')2-scFv2 constructs include scFv fragments linked to the C-terminal end of an F(ab')2 fragment. scFv2-H/L constructs have scFvs specific to one molecule linked to the heavy chains while scFvs specific to another molecule are linked to the light chains. Finally, scFv-dhlx-scFv constructs contain one type of scFv linked to a helical dimerization domain followed by another type of scFv. Two chains of this type can dimerize, generating a tetravalent antibody.

The binding agent of the invention may be in the format of an antibody molecule or of an antibody-like molecule or of a protein scaffold with antibody-like properties or of a cyclic peptide with at least two binding specificities. Thus, the binding agent may comprise one or more antibodies as described herein or fragments thereof.

In one embodiment the binding agent of the invention comprises the heavy chain (Fd fragment) and light chain (L) of a Fab fragment which are able to heterodimerize and upon which additional binding functions or domains can be incorporated. Such additional binding domains may independently be selected from the group consisting of binding domains comprising two antibody variable regions such as scFv binding domains, i.e. VH-VL or VL-VH, and binding domains comprising one antibody variable region such as VH binding domains and VHH binding domains In one embodiment the binding agent of the invention is in the format of a Fab-scFv2 construct, i.e. a Fab fragment provided with two scFv fragments, preferably at the C-terminus of the constant regions of the Fab fragment. In one embodiment the binding agent of the invention is a dimer composed of two polypeptide chains preferably bound together by a disulfide bridge, in which the first polypeptide comprises an scFv linked to an additional VL domain through a CL polypeptide chain, and the second polypeptide comprises an scFv linked to an additional VH domain through a CH1 polypeptide chain. The disulfide bridge is preferably formed between a Cys residue in the CL and a Cys residue in the CH1, such that the additional VL of the first polypeptide associates with the additional VH of the second polypeptide in an antigen-binding configuration, such that the binding agent as a whole includes three antigen-binding domains. Thus, in one embodiment, the binding agent of the invention comprises the heavy chain (Fd fragment) and light chain (L) of a Fab fragment which are able to heterodimerize and upon which scFv binding domains are incorporated (preferably at the C-terminus of Fd/L). According to the invention, the VH and VL domains in the scFv moieties are preferably connected by peptide linkers and/or the Fab chains and the scFv are preferably connected by peptide linkers. According to the invention, the VH and VL domains in the scFv moieties are preferably connected by peptide linkers comprising the amino acid sequence $(G_4S)_x$ (SEQ ID NO: 70), wherein x is 3, 4, 5 or 6. The Fab chains and the scFv are preferably connected by a peptide linker comprising the amino acid sequence $DVPG_2S$ (SEQ ID NO: 67) or $SGPG_3RS(G_4S)_2$ (SEQ ID NO: 66). In one embodiment, a linker comprising the amino acid sequence $SGPG_3RS(G_4S)_2$ (SEQ ID NO: 66) connects a scFv binding domain to a Fd fragment and a linker comprising the amino acid sequence $DVPG_2S$ (SEQ ID NO: 67) connects a scFv binding domain to an L fragment. In one embodiment, the scFv moieties bind to the claudin and the Fab moiety binds to the T cell-specific antigen.

In one embodiment the binding agent of the invention comprises a first and a second polypeptide, wherein the first polypeptide and the second polypeptide comprises from N-terminus to C-terminus the following domains: VH-$C_H$1-scFv and VL-CL-scFv,
wherein VH and VL are associated so as to form a binding domain.

In one embodiment the binding agent of the invention comprises a first and a second polypeptide, wherein, in the first polypeptide and the second polypeptide, the VH domain(s), the VL domain(s), the CH1 domain and the CL domain are arranged, from N-terminus to C-terminus, in the order
VH(T)-CH1-VH(CLDN)-VL(CLDN) and VL(T)-CL-VH(CLDN)-VL(CLDN); or
VH(T)-CH1-VL(CLDN)-VH(CLDN) and VL(T)-CL-VL(CLDN)-VH(CLDN); or VH(T)-CH1-VH(CLDN)-VL-(CLDN) and VL(T)-CL-VL(CLDN)-VH-(CLDN); or
VH(T)-CH1-VL(CLDN)-VH-(CLDN) and VL(T)-CL-VH(CLDN)-VL-(CLDN); or
VH(CLDN)-CH1-VH(T)-VL(T) and VL(CLDN)-CL-VH(CLDN)-VL(CLDN); or
VH(CLDN)-CH1-VL(T)-VH(T) and VL(CLDN)-CL-VL(CLDN)-VH(CLDN); or
VH(CLDN)-CH1-VH(T)-VL(T) and VL(CLDN)-CL-VH(CLDN)-VL(CLDN); or
VH(CLDN)-CH1-VL(T)-VH(T) and VL(CLDN)-CL-VL(CLDN)-VH(CLDN); or
VH(CLDN)-CH1-VH(CLDN)-VL(CLDN) and VL(CLDN)-CL-VH(T)-VL(T); or
VH(CLDN)-CH1-VL(CLDN)-VH(CLDN) and VL(CLDN)-CL-VL(T)-VH(T); or
VH(CLDN)-CH1-VL(CLDN)-VH(CLDN) and VL(CLDN)-CL-VH(T)-VL(T); or
VH(CLDN)-CH1-VH(CLDN)-VL(CLDN) and VL(CLDN)-CL-VL(T)-VH(T).

The term "linker" refers to any means that serves to join two distinct functional units (e.g. antigen binding moieties). Types of linkers include, but are not limited to, chemical linkers and polypeptide linkers. The sequences of the polypeptide linkers are not limited. Polypeptide linkers are preferably non-immunogenic and flexible, such as those comprising serine and glycine sequences. Depending on the particular construct, the linkers may be long or short.

According to the invention, a linker connecting the VH and VL domains to form VH-VL or VL-VH scFv domains preferably comprises a flexible peptide linker such as a glycine-serine peptide linker. In one embodiment, the linker comprises the amino acid sequence $(G_4S)_x$ (SEQ ID NO: 70), wherein x is 3, 4, 5 or 6. In case of a scFv domain comprising the VH and VL domains in the VH-VL orientation the linker preferably comprises the amino acid sequence $(G_4S)_4$ (SEQ ID NO: 68). In case of a scFv domain comprising the VH and VL domains in the VL-VH orientation the linker preferably comprises the amino acid sequence $(G_4S)_5$ (SEQ ID NO: 69).

According to the invention, a linker connecting a scFv domain and a Fd domain, preferably at the C-terminus of $C_H1$, preferably comprises the amino acid sequence $DVPG_2S$ (SEQ ID NO: 67) or $SGPG_3RS(G_4S)_2$ (SEQ ID NO: 66), preferably $SGPG_3RS(G_4S)_2$ (SEQ ID NO: 66). According to the invention, a linker connecting a scFv domain and a L domain, preferably at the C-terminus of CL, preferably comprises the amino acid sequence $DVPG_2S$ (SEQ ID NO: 67) or $SGPG_3RS(G_4S)_2$ (SEQ ID NO: 66), preferably $DVPG_2S$ (SEQ ID NO: 67).

Binding agents according to the invention may also comprise an amino acid sequence for facilitating secretion of the molecule, such as a N-terminal secretion signal, and/or one or more epitope tags facilitating binding, purification or detection of the molecule.

Preferably, the secretion signal is a signal sequence (e.g. the amino acid sequence MGWSCIILFLVATATGVHS (SEQ ID NO: 71)) that allows a sufficient passage through the secretory pathway and/or secretion of the binding agent or the polypeptide chains thereof into the extracellular environment. Preferably, the secretion signal sequence is cleavable and is removed from the mature binding agent. The secretion signal sequence preferably is chosen with respect to the cell or organism wherein the binding agent is produced in.

The amino acid sequence of an epitope tag may be introduced to any position within the amino acid sequence of the binding agent, and may take the shape of a loop within the encoded protein structure, or it may be N-terminally or C-terminally fused to the binding agent. Preferably, the epitope tag is C-terminally fused to the binding agent. The epitope tag may contain a cleavage site that allows a removal of the tag from the binding agent. Said epitope tag can be any kind of epitope tag that is functional under native and/or denaturing conditions, preferable a histidin tag, most preferable a tag comprising six histidins.

The binding agent of the invention may contain, in addition to said first, second and third binding domains one or more further binding domains which serve e.g. to enhance selectivity for tumor cells. This can be achieved e.g. by providing binding domains that bind to other antigens expressed on tumor cells.

In the context of the present invention, the binding agents generated are preferably capable of eliciting immune effector functions as described herein. Preferably, said immune effector functions are directed against cells carrying the tumor-associated antigen claudin on their surface.

The term "immune effector functions" in the context of the present invention includes any functions mediated by components of the immune system that result e.g. in the inhibition of tumor growth and/or inhibition of tumor development, including inhibition of tumor dissemination and metastasis. Preferably, immune effector functions result in killing of tumor cells. Such functions comprise complement dependent cytotoxicity (CDC), antibody-dependent cell-mediated cytotoxicity (ADCC), antibody-dependent cell-mediated phagocytosis (ADCP), induction of apoptosis in the cells carrying the tumor-associated antigen, cytolysis of the cells carrying the tumor-associated antigen, and/or inhibition of proliferation of the cells carrying the tumor-associated antigen. Binding agents may also exert an effect simply by binding to tumor-associated antigens on the surface of a cancer cell. For example, antibodies may block the function of the tumor-associated antigen or induce apoptosis just by binding to the tumor-associated antigen on the surface of a cancer cell.

The binding agents described herein may be conjugated to a therapeutic moiety or agent, such as a cytotoxin, a drug (e.g., an immunosuppressant) or a radioisotope. A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Suitable therapeutic agents for forming conjugates include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Binding agents also can be conjugated to a radioisotope, e.g., iodine-131, yttrium-90 or indium-111, to generate cytotoxic radiopharmaceuticals.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pincheraet al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

The term "binding" according to the invention preferably relates to a specific binding.

According to the present invention, an agent such as an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An agent is not (substantially) capable of binding to a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 µg/ml or higher. Preferably, an agent has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the agent is capable of binding. For example, if the $K_D$ for binding of an agent to the target to which the agent is capable of binding is 10-7 M, the $K_D$ for binding to a target for which the agent has no significant affinity would be at least $10^{-6}$ M, $10^{-5}$ M, $10^{-4}$ M, $10^{-3}$ M, $10^{-2}$ M, or $10^{-1}$ M.

An agent such as an antibody is specific for a predetermined target if it is capable of binding to said predetermined target while it is not capable of binding to other targets, i.e. has no significant affinity for other targets and does not significantly bind to other targets in standard assays. According to the invention, an agent is specific for a claudin if it is capable of binding to a claudin but is not (substantially) capable of binding to other targets. Preferably, an agent is specific for a claudin if the affinity for and the binding to such other targets does not significantly exceed the affinity for or binding to claudin-unrelated proteins such as bovine serum albumin (BSA), casein, human serum albumin (HSA) or non-claudin transmembrane proteins such as MHC molecules or transferrin receptor or any other specified polypeptide. Preferably, an agent is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an agent to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an agent to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

The term "competes" refers to the competition between two antibodies for binding to a target antigen. If two antibodies do not block each other for binding to a target antigen, such antibodies are non-competing and this is an indication that said antibodies do not bind to the same part, i.e. epitope of the target antigen. It is well known to a person skilled in the art how to test for competition of antibodies for binding to a target antigen. An example of such a method is a so-called cross-competition assay, which may e.g. be performed as an ELISA or by flow-cytometry.

For example an ELISA-based assay may be performed by coating ELISA plate wells with each of the antibodies; adding the competing antibody and His-tagged extracellular domain of the antigen/target and incubate; detecting whether the added antibody inhibited binding of the His-tagged protein to the coated antibody may be performed by adding biotinylated anti-His antibody, followed by Streptavidin-poly-HRP, and further developing the reaction with ABTS and measuring the absorbance at 405 nm. For example a flow-cytometry assay may be performed by incubating cells expressing the antigen/target with an excess of unlabeled antibody, incubating the cells with a sub-optimal concentration of biotin-labeled antibody, followed by incubation with fluorescently labeled streptavidin and analyzing by flow cytometry.

Two antibodies have the "same specificity" if they bind to the same antigen and to the same epitope. Whether an antibody to be tested recognizes the same epitope as a certain antigen-binding antibody, i.e., the antibodies bind to the same epitope, can be analyzed based on their competition for the same epitope. The competition between the antibodies can be detected by a cross-blocking assay. For example, a competitive ELISA assay may be used as a cross-blocking assay. For example, target antigen may be coated on the wells of a microtiter plate and antigen-binding antibody and candidate competing test antibody may be added. The amount of the antigen-binding antibody bound to the antigen in the well indirectly correlates with the binding ability of the candidate competing test antibody that competes therewith for binding to the same epitope. Specifically, the larger the affinity of the candidate competing test antibody is for the same epitope, the smaller the amount of the antigen-binding antibody bound to the antigen-coated well. The amount of the antigen-binding antibody bound to the well can be measured by labeling the antibody with detectable or measurable labeling substances.

An antibody competing for binding to an antigen with another antibody, e.g., an antibody comprising heavy and light chain variable regions as described herein, or an antibody having the specificity for an antigen of another antibody, e.g., an antibody comprising heavy and light chain variable regions as described herein, may be an antibody comprising variants of said heavy and/or light chain variable regions as described herein, e.g. modifications in the CDRs and/or a certain degree of identity as described herein.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombed heptamer/nonamer homology element.

The term "unrearranged" or "germline configuration" as used herein in reference to a V segment refers to the configuration wherein the V segment is not recombined so as to be immediately adjacent to a D or J segment.

In one embodiment, a binding agent of the invention has the ability of binding to CLDN18.2, i.e. the ability of binding to an epitope present in CLDN18.2, preferably an epitope located within the extracellular domains of CLDN18.2, in particular the first extracellular loop, preferably amino acid positions 29 to 78 of CLDN18.2. In particular embodiments, an agent having the ability of binding to CLDN18.2 binds to an epitope on CLDN18.2 which is not present on CLDN18.1.

An agent having the ability of binding to CLDN18.2 preferably binds to CLDN18.2 but not to CLDN18.1. Preferably, an agent having the ability of binding to CLDN18.2 is specific for CLDN18.2. Preferably, an agent having the ability of binding to CLDN18.2 binds to CLDN18.2 expressed on the cell surface. In particular preferred embodiments, an agent having the ability of binding to CLDN18.2 binds to native epitopes of CLDN18.2 present on the surface of living cells.

In a preferred embodiment, a binding domain binding to CLDN18.2 of a binding agent of the invention comprises a heavy chain variable region (VH) comprising an amino acid sequence selected from the group consisting of SEQ ID NOs: 20, 21, 24 or a fragment thereof or a variant of the amino acid sequence or fragment.

In a preferred embodiment, a binding domain binding to CLDN18.2 of a binding agent of the invention comprises alight chain variable region (VL) comprising an amino acid sequence selected from the group consisting of SEQ ID NOs: 22, 23, 25 or a fragment thereof or a variant of the amino acid sequence or fragment.

In certain preferred embodiments, a binding domain binding to CLDN18.2 of a binding agent of the invention comprises a combination of heavy chain variable region (VH) and light chain variable region (VL) selected from the following possibilities:

(i) the VH comprises an amino acid sequence represented by SEQ ID NO: 20 or a fragment thereof 25 or a variant of the amino acid sequence or fragment and the VL comprises an amino acid sequence represented by SEQ ID NO: 22 or a fragment thereof or a variant of the amino acid sequence or fragment, (ii) the VH comprises an amino acid sequence represented by SEQ ID NO: 20 or a fragment thereof or a variant of the amino acid sequence or fragment and the VL comprises an amino acid sequence 30 represented by SEQ ID NO: 23 or a fragment thereof or a variant of the amino acid sequence or fragment, (iii) the VH comprises an amino acid sequence represented by SEQ ID NO: 21 or a fragment thereof or a variant of the amino acid sequence or fragment and the VL comprises an amino acid sequence represented by SEQ ID NO: 22 or a fragment thereof or a variant of the amino acid sequence or fragment, (iv) the VH comprises an amino acid sequence represented by SEQ ID NO: 21 or a fragment thereof or a variant of the amino acid sequence or fragment and the VL comprises an amino acid sequence represented by SEQ ID NO: 23 or a fragment thereof or a variant of the amino acid sequence or fragment, (v) the VH comprises an amino acid sequence represented by SEQ ID NO: 24 or a fragment thereof or a variant of the amino acid sequence or fragment and the VL comprises an amino acid sequence represented by SEQ ID NO: 25 or a fragment thereof or a variant of the amino acid sequence or fragment.

In a particularly preferred embodiment, a binding domain binding to CLDN18.2 of a binding agent of the invention comprises the following combination of heavy chain variable region (VH) and light chain variable region (VL):

the VH comprises an amino acid sequence represented by SEQ ID NO: 20 or a fragment thereof or a variant of the amino acid sequence or fragment and the VL comprises an amino acid sequence represented by SEQ ID NO: 22 or a fragment thereof or a variant of the amino acid sequence or fragment.

In a particularly preferred embodiment, a binding domain binding to CLDN18.2 of a binding agent of the invention comprises the following combination of heavy chain variable region (VH) and light chain variable region (VL):

the VH comprises an amino acid sequence represented by SEQ ID NO: 21 or a fragment thereof or a variant of the amino acid sequence or fragment and the VL comprises an amino acid sequence represented by SEQ ID NO: 23 or a fragment thereof or a variant of the amino acid sequence or fragment.

The term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In one embodiment a binding domain comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of binding agents made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains or protein labels.

In one embodiment a binding domain comprising one or more CDRs, a set of CDRs or a combination of sets of CDRs as described herein comprises said CDRs in a human antibody framework.

In a preferred embodiment, a binding domain binding to CLDN18.2 of a binding agent of the invention comprises the following combination of heavy chain variable region (VH) and light chain variable region (VL):

the VH comprises a heavy chain complementarity determining region 3 (HCDR3) comprising the sequence set forth in SEQ ID NO: 58, and the VL comprises a light chain complementarity determining region 3 (LCDR3) comprising the sequence set forth in SEQ ID NO: 64.

In one embodiment, the VH further comprises a HCDR1 comprising the sequence set forth in SEQ ID NO: 56 and/or a HCDR2 comprising the sequence set forth in SEQ ID NO: 57, and/or the VL further comprises a LCDR1 comprising the sequence set forth in SEQ ID NO: 62, and/or a LCDR2 comprising the sequence set forth in SEQ ID NO: 63.

In a preferred embodiment, a binding domain binding to CLDN18.2 of a binding agent of the invention comprises the following combination of heavy chain variable region (VH) and light chain variable region (VL):

the VH comprises a HCDR1 comprising the sequence set forth in SEQ ID NO: 56, a HCDR2 comprising the sequence set forth in SEQ ID NO: 57 and a HCDR3 comprising the sequence set forth in SEQ ID NO: 58 and the VL comprises a LCDR1 comprising the sequence set forth in SEQ ID NO: 62, a LCDR2 comprising the sequence set forth in SEQ ID NO: 63 and a LCDR3 comprising the sequence set forth in SEQ ID NO: 64.

In a preferred embodiment, a binding domain binding to CLDN18.2 of a binding agent of the invention comprises the following combination of heavy chain variable region (VH) and light chain variable region (VL):

the VH comprises a heavy chain complementarity determining region 3 (HCDR3) comprising the sequence set forth in SEQ ID NO: 61, and the VL comprises a light chain complementarity determining region 3 (LCDR3) comprising the sequence set forth in SEQ ID NO: 65.

In one embodiment, the VH further comprises a HCDR1 comprising the sequence set forth in SEQ ID NO: 59 and/or a HCDR2 comprising the sequence set forth in SEQ ID NO: 60, and/or the VL further comprises a LCDR1 comprising the sequence set forth in SEQ ID NO: 62, and/or a LCDR2 comprising the sequence set forth in SEQ ID NO: 63.

In a preferred embodiment, a binding domain binding to CLDN18.2 of a binding agent of the invention comprises the following combination of heavy chain variable region (VH) and light chain variable region (VL):

the VH comprises a HCDR1 comprising the sequence set forth in SEQ ID NO: 59, a HCDR2 comprising the sequence set forth in SEQ ID NO: 60 and a HCDR3 comprising the sequence set forth in SEQ ID NO: 61 and the VL comprises a LCDR1 comprising the sequence set forth in SEQ ID NO: 62, a LCDR2 comprising the sequence set forth in SEQ ID NO: 63 and a LCDR3 comprising the sequence set forth in SEQ ID NO: 65.

In one embodiment, said heavy and light chain variable regions comprise said complementarity determining regions interspersed within framework regions. In one embodiment, each variable region comprises three complementarity determining regions (CDR1, 2, and 3) and four framework regions (FR1, 2, 3, and 4). In one embodiment, said complementarity determining regions and said framework regions are arranged from amino-terminus to carboxy-terminus in the following order: FR1, CDR1, FR2, CDR2, FR3, CDR3, FR4.

In further embodiments, a binding domain binding to CLDN18.2 of a binding agent of the invention comprises heavy and light chain variable regions of an antibody which (i) competes for CLDN18.2 binding with an antibody comprising heavy and light chain variable regions as described above and/or (ii) has the specificity for CLDN18.2 of an antibody comprising heavy and 5 light chain variable regions as described above.

In one embodiment, the heavy chain variable region (VH) and light chain variable region (VL) of a binding domain binding to CLDN18.2 of a binding agent of the invention has the format of a scFv molecule. In this embodiment, a binding domain binding to CLDN18.2 of a binding agent of 10 the invention comprises an amino acid sequence selected from the group consisting of SEQ ID NOs: 26, 27, 28, 29 or a fragment thereof or a variant of the amino acid sequence or fragment.

It is to be understood that the binding domains binding to CLDN18.2 of a binding agent of the invention may be identical or essentially identical or different and thus may bind to identical or essentially identical epitopes or different epitopes. Thus, both binding domains binding to CLDN18.2 of a binding agent of the invention may correspond or correspond essentially to one of the binding domains binding to CLDN18.2 of a binding agent of the invention described herein or they may be independently selected from the binding domains binding to CLDN18.2 of a binding agent of the invention described herein.

In one embodiment, a binding agent of the invention has the ability of binding to CLDN6, i.e. the ability of binding to an epitope present in CLDN6, preferably an epitope located within the extracellular domains of CLDN6, in particular the first extracellular loop, preferably amino acid positions 28 to 76 or 29 to 81 of CLDN6 or the second extracellular loop, preferably amino acid 25 positions 141 to 159 of CLDN6. In particular embodiments, an agent having the ability of binding to CLDN6 binds to an epitope on CLDN6 which is not present on CLDN9. Preferably, an agent having the ability of binding to CLDN6 binds to an epitope on CLDN6 which is not present on CLDN4 and/or CLDN3. Most preferably, an agent having the ability of binding to CLDN6 binds to an epitope on CLDN6 which is not present on a claudin protein other than CLDN6.

An agent having the ability of binding to CLDN6 preferably binds to CLDN6 but not to CLDN9 and preferably does not bind to CLDN4 and/or CLDN3. Preferably, an agent having the ability of binding to CLDN6 is specific for CLDN6. Preferably, an agent having the ability of binding to CLDN6 binds to CLDN6 expressed on the cell surface. In particular preferred embodiments, an agent having the ability of binding to CLDN6 binds to native epitopes of CLDN6 present on the surface of living cells.

In a preferred embodiment, a binding domain binding to CLDN6 of a binding agent of the invention comprises a heavy chain variable region (VH) comprising an amino acid sequence selected from the group consisting of SEQ ID NOs: 7, 8, 11 or a fragment thereof or a variant of the amino acid sequence or fragment.

In a preferred embodiment, a binding domain binding to CLDN6 of a binding agent of the invention comprises a light chain variable region (VL) comprising an amino acid sequence selected from the group consisting of SEQ ID NOs: 9, 10, 12 or a fragment thereof or a variant of the amino acid sequence or fragment.

In certain preferred embodiments, a binding domain binding to CLDN6 of a binding agent of the invention comprises a combination of heavy chain variable region (VH) and light chain variable region (VL) selected from the following possibilities:

(i) the VH comprises an amino acid sequence represented by SEQ ID NO: 7 or a fragment thereof or a variant of the amino acid sequence or fragment and the VL comprises an amino acid sequence represented by SEQ ID NO: 9 or a fragment thereof or a variant of the amino acid sequence or fragment, (ii) the VH comprises an amino acid sequence represented by SEQ ID NO: 7 or a fragment thereof or a variant of the amino acid sequence or fragment and the VL comprises an amino acid sequence represented by SEQ ID NO: 10 or a fragment thereof or a variant of the amino acid sequence or fragment, (iii) the VH comprises an amino acid sequence represented by SEQ ID NO: 8 or a fragment thereof or a variant of the amino acid sequence or fragment and the VL comprises an amino acid sequence represented by SEQ ID NO: 9 or a fragment thereof or a variant of the amino acid sequence or fragment, (iv) the VH comprises an amino acid sequence represented by SEQ ID NO: 8 or a fragment thereof or a variant of the amino acid sequence or fragment and the VL comprises an amino acid sequence represented by SEQ ID NO: 10 or a fragment thereof or a variant of the amino acid sequence or fragment, (v) the VH comprises an amino acid sequence represented by SEQ ID NO: 11 or a fragment thereof or a variant of the amino acid sequence or fragment and the VL comprises an amino acid sequence represented by SEQ ID NO: 12 or a fragment thereof or a variant of the amino acid sequence or fragment, (vi) the VH comprises an amino acid sequence represented by SEQ ID NO: 7 or a fragment thereof or a variant of the amino acid sequence or fragment and the VL comprises an amino acid sequence represented by SEQ ID NO: 12 or a fragment thereof or a variant of the amino acid sequence or fragment, (vii) the VH comprises an amino acid sequence represented by SEQ ID NO: 8 or a fragment thereof or a variant of the amino acid sequence or fragment and the VL comprises an amino acid sequence represented by SEQ ID NO: 12 or a fragment thereof or a variant of the amino acid sequence or fragment.

In a particularly preferred embodiment, a binding domain binding to CLDN6 of a binding agent of the invention comprises the following combination of heavy chain variable region (V competes for CLDN6 binding with an antibody comprising heavy and light chain variable regions as described above and/or (ii) has the specificity for CLDN6 of an antibody comprising heavy and light chain variable regions as described above.

In one embodiment, the heavy chain variable region (VH) and light chain variable region (VL) of a binding domain binding to CLDN6 of a binding agent of the invention has the format of a scFv molecule. In this embodiment, a binding domain binding to CLDN6 of a binding agent of the invention comprises the amino acid sequence set forth in SEQ ID NO: 13 or a fragment thereof or a variant of the amino acid sequence or fragment.

It is to be understood that the binding domains binding to CLDN6 of a binding agent of the invention may be identical or essentially identical or different and thus may bind to identical or essentially identical epitopes or different epitopes. Thus, both binding domains binding to CLDN6 of a binding agent of the invention may correspond or correspond essentially to one of the binding domains binding to CLDN6 of a binding agent of the invention described herein or they may be independently selected from the binding domains binding to CLDN6 of a binding agent of the invention described herein.

Anti-CD3 antibodies which are useful for providing binding agents according to the invention include but are not limited to UCHT1-HS (humanized mAB), UCHT1-MM (murine mAB), CLB-T3, TR66, 145-2C11.

UCHT1 is a monoclonal IgG1 anti-CD3 monoclonal antibody which detects CD3 in human and primate sample types. CLB-T3 is a mouse monoclonal anti-CD3 antibody which is directed against the CD3 antigen and reacts with 80-90% human peripheral T lymphocytes and medullary thymocytes. TR66 is a mouse IgG1 monoclonal anti-CD3 antibody which recognizes the epsilon-chain of human CD3. 145-2C1 1 is an armenian hamster monoclonal anti-mouse CD3 antibody.

Preferably, the VH and VL regions of the CD3-binding domain are derived from antibodies/antibody molecules and antibody-like molecules which are capable of specifically recognizing the human CD3 in the context of other TCR subunits as present on activated primary human T cells expressing the TCR in its native configuration. The VH and VL regions derived from an antibody specific for the CD3-epsilon chain are most preferred and said (parental) antibodies should be capable of specifically binding epitopes reflecting the native or near-native structure or a conformational epitope of human CD3 presented in the context of the TCR complex.

In a preferred embodiment of the invention, the VH and VL regions of the CD3-binding domain are derived from a CD3-specific antibody selected from the group consisting of UCHT1-HS, UCHT1-MM, CLB-T3 and TR66, preferably TR66.

In a preferred embodiment, a binding domain binding to CD3 of a binding agent of the invention comprises a heavy chain variable region (VH) comprising the amino acid sequence set forth in SEQ ID NO: 5 or a fragment thereof or a variant of the amino acid sequence or fragment.

In a preferred embodiment, a binding domain binding to CD3 of a binding agent of the invention comprises a light chain variable region (VL) comprising the amino acid sequence set forth in SEQ ID NO: 6 or a fragment thereof or a variant of the amino acid sequence or fragment.

In a preferred embodiment, a binding domain binding to CD3 of a binding agent of the invention comprises the following combination of heavy chain variable region (VH) and light chain variable region (VL):

the VH comprises an amino acid sequence represented by SEQ ID NO: 5 or a fragment thereof or a variant of the amino acid sequence or fragment and the VL comprises an amino acid sequence represented by SEQ ID NO: 6 or a fragment thereof or a variant of the amino acid sequence or fragment.

The term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In one embodiment a binding domain comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of binding agents made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains or protein labels.

In one embodiment a binding domain comprising one or more CDRs, a set of CDRs or a combination of sets of CDRs as described herein comprises said CDRs in a human antibody framework.

It is to be understood that the binding agents described herein may be delivered to a patient by administering a nucleic acid such as RNA encoding the agent and/or by administering a host cell comprising a nucleic acid such as RNA encoding the agent. If the binding agent comprises more than one polypeptide chain, the different polypeptide chains may be encoded on the same nucleic acid or on different nucleic acids. Thus, a nucleic to be administered may be a mixture of different nucleic acid molecules. A nucleic acid encoding a binding agent when administered to a patient may be present in naked form or in a suitable delivery vehicle such as in the form of liposomes or nanoparticles or viral particles, or within a host cell. The nucleic acid provided can produce the agent over extended time periods in a sustained manner mitigating the instability at least partially observed for therapeutic antibodies. Nucleic acids to be delivered to a patient can be produced by recombinant means. If a nucleic acid is administered to a patient without being present within a host cell, it is preferably taken up by cells of the patient for expression of the binding agent encoded by the nucleic acid. If a nucleic acid is administered to a patient while being present within a host cell, it is preferably expressed by the host cell within the patient so as to produce the binding agent encoded by the nucleic acid.

The term "recombinant" in the context of the present invention means "made through genetic engineering". Preferably, a "recombinant object" such as a recombinant nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a 0-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In one embodiment of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes at least one of said transgenes encoding the binding agent described herein. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

The genome of alphaviruses is single stranded RNA of positive sense (ssRNA(+)) that encodes two open reading frames (ORF) for large polyproteins. The ORF at the 5'-end of the genome encodes the non-structural proteins nSP1 to nSP4 (nsP1-4), which are translated and processed to an RNA-dependent RNA-polymerase (replicase); the ORF at the 3'-end encodes the structural proteins—capsid and glycoproteins. Both ORFs are separated by the so called subgenomic promoter (SGP), which governs the transcription of the structural ORF. When exploited as gene vectors, the structural proteins behind the SGP are commonly replaced by transgenes. In order to package such vectors into viral particles, the structural proteins are commonly expressed in trans from helper constructs. Alphaviruses replicate in the cytoplasm of infected cells exclusively at the RNA level. After infection, the ssRNA(+) genome acts as mRNA for the translation of the nsP1234 poly-protein precursor which is at early stages of the viral life cycle autoproteolytically processed to the fragments nsP123 and nsP4. Fragments nsP123 and nsP4 form the (−)strand replicase complex that transcribes (−)stranded RNA from the genomic RNA template. At later stages, the nsP1234 polyprotein is completely cleaved to the single proteins which assemble to the (+)strand replicase complex that synthesizes new (+)stranded genomes, as well as subgenomic transcripts that code the structural proteins or transgenes. Subgenomic RNA as well as new genomic RNA is capped and poly-adenylated and thus recognized as mRNA after target cells infection. Only new genomic RNA contains a packaging signal which ensures exclusive packaging of genomic RNA into budding virions. The attractiveness of alphaviral replicons for vectorology is based on the positive orientation of the capped and poly-adenylated RNA genome. Translatable replicon RNA can easily be synthesized in vitro, whereby capping may be achieved with cap-analoga added to the in vitro transcription reaction and poly-A tails may be encoded as poly-T tracks on the plasmid templates. In vitro transcribed (IVT) replicons are transfected by conventional transfection techniques and even low amounts of starting IVT RNA are multiplied rapidly. Within a few hours after transfer, transgenes which are placed downstream of the SGP are transcribed to very high copy numbers of about 40.000 to 200.000 copies of subgenomic RNA per cell, thus it is not surprising that recombinant proteins are strongly expressed. Dependent on the specific aim, IVT replicons may be transfected directly into target cells, or packaged into alphaviral particles with helper vectors that provide structural genes in trans. Transfer into the skin or muscles leads to high and sustained local expression, paralleled by a strong induction of humoral and cellular immune response In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity and/or immunogenicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5'-triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. In addition, incorporation of two or more 3'-non translated regions (UTR) into the 3'-non translated region of an RNA molecule can result in an enhancement in translation efficiency. In one particular embodiment the 3'-UTR is derived from the human β-globin gene.

Preferably, RNA if delivered to, i.e. transfected into, a cell, in particular a cell present in vivo, expresses the protein, peptide or antigen it encodes.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

According to the invention, the term "RNA encoding" means that RNA, if present in the appropriate environment, preferably within a cell, can be expressed to produce a protein or peptide it encodes.

Some aspects of the invention rely on the adoptive transfer of host cells which are transfected in vitro with a nucleic acid such as RNA encoding a binding agent described herein and transferred to recipients such as patients, preferably after ex vivo expansion from low precursor frequencies to clinically relevant cell numbers. The host cells used for treatment according to the invention may be autologous, allogeneic, or syngeneic to a treated recipient.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding to a target or to sustain effector functions. Preferably, a sequence which is a variant with respect to a specific sequence, when it replaces the specific sequence in an antibody retains binding of said antibody to a claudin and/or CD3 and preferably functions of said antibody as described herein, e.g. CDC mediated lysis or ADCC mediated lysis. Furthermore, preferably, a sequence which is a variant with respect to a specific sequence, when it replaces the specific sequence in a binding agent retains binding of said binding agent to a claudin and/or CD3 and preferably functions of said binding agent as described herein, e.g. cytotoxic T-cell mediated lysis.

For example, the sequences shown in the sequence listing can be modified so as to remove one or more, preferably all free cysteine residues, in particular by replacing the cysteine residues by amino acids other than cysteine, preferably serine, alanine, threonine, glycine, tyrosine, tryptophan, leucine or methionine.

It will be appreciated by those skilled in the art that in particular the sequences of the CDR, hypervariable and variable regions can be modified without losing the ability to bind a claudin and/or CD3. For example, CDR regions will be either identical or highly homologous to the regions specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions specifically disclosed herein. In one embodiment, the variable region sequences only deviate in the framework sequences from the variable region sequences specifically disclosed herein.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%7, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The binding agents of the invention can be produced either intracellularly (e.g. in the cytosol, in the periplasma or in inclusion bodies) and then isolated from the host cells and optionally further purified; or they can be produced extracellularly (e.g. in the medium in which the host cells are cultured) and then isolated from the culture medium and optionally further purified. Methods and reagents used for the recombinant production of polypeptides, such as specific suitable expression vectors, transformation or transfection methods, selection markers, methods of induction of protein expression, culture conditions, and the like, are known in the art. Similarly, protein isolation and purification techniques are well known to the skilled person.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid and transferred to a recipient can express the nucleic acid in the recipient. The term "cell" includes bacterial cells; other useful cells are yeast cells, fungal cells or mammalian cells. Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*. Suitable yeast cells include cells from species of *Saccharomyces* (Tor example *Saccharomyces cerevisiae*), *Schizosaccharomyces* (for example Schizo *saccharomyces pombe*), *Pichia* (for example *Pichia pastoris* and *Pichia* methanolicd), and *Hansenula*. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T-cell receptor (TCR).

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more.

Antibody-Dependent Cell-Mediated Cytotoxicity

ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-Dependent Cytotoxicity

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

Antibodies described herein for e.g. providing VL and VH regions can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined specificity e.g. see Babcock et al., 1996; A novel strategy for generating monoclonal antibodies from single, isolated lymphocytes producing antibodies of defined specificities. For details of recombinant antibody engineering see also Welschof and Kraus, Recombinant antibodies for cancer therapy ISBN-O-89603-918-8 and Benny K. C. Lo Antibody Engineering ISBN 1-58829-092-1.

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitoneally or intravenously with antigen expressing cells 3 days before sacrifice and removal of the spleen to increase the rate 10 of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of 15 antigen-specific antibodies. Individual wells can then be screened by ELISA for antibody secreting hybridomas. By immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

Antibodies also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. *E. coli*. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Chimerization

Non-labeled murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerization of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-O-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region.

The ability of antibodies and other binding agents to bind an antigen can be determined using standard binding assays (e.g., ELISA, Western Blot, immunofluorescence and flow cytometric analysis).

To purify antibodies, selected producer cell lines can be grown in two-liter spinner-flasks for recombinant antibody purification. Alternatively, antibodies can be produced in dialysis based bioreactors. Supernatants can be filtered and, if necessary, concentrated before affinity chromatography with protein L-sepharose. Eluted antibodies can be checked by gel electrophoresis and high performance liquid chromatography to ensure purity. The buffer solution can be exchanged into PBS, and the concentration can be determined by OD280 using the respective extinction coefficient. The recombinant antibodies can be aliquoted and stored at −65 to −85° C.

In order to demonstrate binding of monoclonal antibodies to living cells expressing antigen, flow cytometry can be used. Cell lines expressing naturally or after transfection antigen and negative controls lacking antigen expression (grown under standard growth conditions) can be mixed with various concentrations of monoclonal antibodies in hybridoma supernatants or in PBS containing 1% FBS, and can be incubated at 4° C. for 30 min. After washing, the fluorescence-labeled detection reagent (such as fluorescence conjugated anti IgG antibody, anti Fab antibody or Protein-L) can bind to antigen-bound monoclonal antibody under the same conditions as the primary antibody staining. The samples can be analyzed by flow cytometry with a FACS instrument using light and side scatter properties to gate on single, living cells. In order to distinguish antigen-specific monoclonal antibodies from non-specific binders in a single measurement, the method of co-transfection can be employed. Cells transiently transfected with plasmids encoding antigen and a fluorescent marker can be stained as described above. Transfected cells can be detected in a different fluorescence channel than antibody-stained cells. As the majority of transfected cells express both transgenes, antigen-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

In order to demonstrate binding of monoclonal antibodies to living cells expressing antigen, immunofluorescence microscopy analysis can be used. For example, cell lines expressing either spontaneously or after transfection antigen and negative controls lacking antigen expression are grown in chamber slides under standard growth conditions in DMEM/F12 medium, supplemented with 10% fetal calf serum (FCS), 2 mM L-glutamine, 100 IU/ml penicillin and 100 µg/ml streptomycin. Cells can then be fixed with methanol or paraformaldehyde or left untreated. Cells can then be reacted with monoclonal antibodies against the antigen for 30 min. at 25° C. After washing, cells can be reacted with an Alexa555-labeled anti-mouse IgG secondary antibody (Molecular Probes) under the same conditions. Cells can then be examined by fluorescence microscopy.

Cell extracts from cells expressing antigen and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Antibodies can be further tested for reactivity with antigen by immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection antigen. For immunostaining, antibodies reactive to antigen can be incubated followed by horseradish-peroxidase conjugated goat anti-mouse or goat anti-rabbit antibodies (DAKO) according to the vendors instructions.

Preclinical Studies

Binding agents described herein also can be tested in an in vivo model (e.g. in immunodeficient mice carrying xenografted tumors inoculated with cell lines expressing a claudin) to determine their efficacy in controlling growth of claudin-expressing tumor cells.

In vivo studies after xenografting claudin-expressing tumor cells into immunocompromised mice or other animals can be performed using binding agents described herein. Binding agents can be administered to tumor free mice followed by injection of tumor cells to measure the effects of the binding agents to prevent formation of tumors or tumor-related symptoms. Binding agents can be administered to tumor-bearing mice to determine the therapeutic efficacy of respective binding agents to reduce tumor growth, metastasis or tumor related symptoms. Application of binding agents can be combined with application of other substances as cystostatic drugs, growth factor inhibitors, cell cycle blockers, angiogenesis inhibitors or antibodies to determine synergistic efficacy and potential toxicity of combinations. To analyze toxic side effects mediated by binding agents animals can be inoculated with binding agents or control reagents and thoroughly investigated for symptoms possibly related to claudin-binding agent therapy.

Mapping of epitopes recognized by binding agents can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by ISBN-089603-375-9 and in "Epitope Mapping: A Practical Approach" Practical Approach Series, 248 by Olwyn M. R. Westwood, Frank C. Hay.

The compounds and agents described herein may be administered in the form of any suitable pharmaceutical composition.

The pharmaceutical compositions of the invention are preferably sterile and contain an effective amount of the binding agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or non-aqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by an altered expression pattern of a claudin such as CLDN18.2 and/or CLDN6.

For example, in one embodiment, agents described herein can be used to treat a patient with a cancer disease, e.g., a cancer disease such as described herein characterized by the presence of cancer cells expressing a claudin.

The pharmaceutical compositions and methods of treatment described according to the invention may also be used for immunization or vaccination to prevent a disease described herein.

The pharmaceutical composition of the invention may be administered together with 10 supplementing immunity-enhancing substances such as one or more adjuvants and may comprise one or more immunity-enhancing substances to further increase its effectiveness, preferably to achieve a synergistic effect of immunostimulation. The term "adjuvant" relates to compounds which prolong or enhance or accelerate an immune response. Various mechanisms are possible in this respect, depending on the various types of adjuvants. For example, compounds which allow 15 the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, INFα, INF-γ, GM-CSF, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, 25 are also suitable for use as adjuvants in the pharmaceutical composition of the present invention.

The agents and compositions provided herein may be used alone or in combination with conventional therapeutic regimens such as surgery, irradiation, chemotherapy and/or bone marrow transplantation (autologous, syngeneic, allogeneic or unrelated).

Treatment of cancer represents a field where combination strategies are especially desirable since frequently the combined action of two, three, four or even more cancer drugs/therapies generates synergistic effects which are considerably stronger than the impact of a monotherapeutic approach. Thus, in another embodiment of the present invention, a cancer treatment which utilizes immune—or vaccination-based mechanisms such as the methods and pharmaceutical compositions of the present invention may be effectively combined with various other drugs and/or methods targeting similar or other specific mechanisms. Among those are e.g. combinations with conventional tumor therapies, multi-epitope strategies, additional immunotherapy, and treatment approaches targeting angiogenesis or apoptosis (for review see e.g. Andersen et al. 2008: Cancer treatment: the combination of vaccination with other therapies. Cancer Immunology Immunotherapy, 57(11): 1735-1743.) Sequential administration of different agents may inhibit cancer cell growth at different check points, while other agents may e.g. inhibit neo-angiogenesis, survival of malignant cells or metastases, potentially converting cancer into a chronic disease. The following list provides some non-limiting examples of anti-cancer drugs and therapies which can be used in combination with the present invention:

1. Chemotherapy

Chemotherapy is the standard of care for multiple types of cancer. The most common chemotherapy agents act by killing cells that divide rapidly, one of the main properties of cancer cells. Thus, a combination with conventional chemotherapeutic drugs such as e.g. alkylating agents, antimetabolites, anthracyclines, plant alkaloids, topoisomerase inhibitors, and other antitumour agents which either affect cell division or DNA synthesis may significantly improve the therapeutic effects of the present invention by clearing suppressor cells, reboot of the immune system, by rendering tumor cells more susceptible to immune mediated killing, or by additional activation of cells of the immune system. A synergistic anti-cancer action of chemotherapeutic and vaccination-based immunotherapeutic drugs has been demonstrated in multiple studies (see e.g. Quoix et al. 2011: Therapeutic vaccination with TG4010 and first-line chemotherapy in advanced non-small-cell lung cancer: a controlled phase 2B trial. Lancet Oncol. 12(12): 1125-33.; see also Liseth et al. 2010: Combination of intensive chemotherapy and anticancer vaccines in the treatment of human malignancies: the hematological experience. J Biomed Biotechnol. 2010: 6920979; see also Hirooka et al 2009: A combination therapy of gemcitabine with immunotherapy for patients with inoperable locally advanced pancreatic cancer. Pancreas 38(3): e69-74). There are hundreds of chemotherapeutic drugs available which are basically suitable for combination therapies. Some (non-limiting) examples of chemotherapeutic drugs which can be combined with the present invention are carboplatin (Paraplatin), cisplatin (Platinol, Platinol-AQ), cyclophosphamide (Cytoxan, Neosar), docetaxel (Taxotere), doxorubicin (Adriamycin), erlotinib (Tarceva), etoposide (VePesid), fluorouracil (5-FU), gemcitabine (Gemzar), imatinib mesylate (Gleevec), irinotecan (Camptosar), methotrexate (Folex, Mexate, Amethopterin), paclitaxel (Taxol, Abraxane), sorafinib (Nexavar), sunitinib (Sutent), topotecan (Hycamtin), vincristine (Oncovin, Vincasar PFS), and vinblastine (Velban).

2. Surgery

Cancer surgery—an operation to remove the tumor—remains the foundation of cancer treatment. Surgery can be combined with other cancer treatments in order to delete any remaining tumor cells. Combining surgical methods with subsequent immunotherapeutic treatment is a promising approach which has been demonstrated countless times.

3. Radiation

Radiation therapy remains an important component of cancer treatment with approximately 50% of all cancer patients receiving radiation therapy during their course of illness. The main goal of radiation therapy is to deprive cancer cells of their multiplication (cell division) potential. The types of radiation used to treat cancer are photons radiation (x-rays and gamma rays) and particle radiations (electron, proton and neutron beams.) There are two ways to deliver the radiation to the location of the cancer. External beam radiation is delivered from outside the body by aiming high-energy rays (photons, protons or particle radiation) to the location of the tumor. Internal radiation or brachytherapy is delivered from inside the body by radioactive sources, sealed in catheters or seeds directly into the tumor site. Radiation therapy techniques which are applicable in combination with the present invention are e.g. fractionation (radiation therapy delivered in a fractionated regime, e.g. daily fractions of 1.5 to 3 Gy given over several weeks), 3D conformal radiotherapy (3DCRT; delivering radiation to the gross tumor volume), intensity modulated radiation therapy (IMRT; computer-controlled intensity modulation of multiple radiation beams), image guided radiotherapy (IGRT; a technique comprising pre-radiotherapy imaging which allows for correction), and stereotactic body radiation therapy (SRBT, delivers very high individual doses of radiation over only a few treatment fractions). For a radiation therapy review see Baskar et al. 2012: Cancer and radiation therapy: current advances and future directions. Int. J Med Sci. 9(3): 193-199.

4. Antibodies

Antibodies (preferably monoclonal antibodies) achieve their therapeutic effect against cancer cells through various mechanisms. They can have direct effects in producing apoptosis or programmed cell death. They can block components of signal transduction pathways such as e.g. growth factor receptors, effectively arresting proliferation of tumor cells. In cells that express monoclonal antibodies, they can bring about anti-idiotype antibody formation. Indirect effects include recruiting cells that have cytotoxicity, such as monocytes and macrophages. This type of antibody-mediated cell kill is called antibody-dependent cell mediated cytotoxicity (ADCC). Antibodies also bind complement, leading to direct cell toxicity, known as complement dependent cytotoxicity (CDC). Combining surgical methods with immunotherapeutic drugs or methods is a successful approach, as e.g. demonstrated in Gadri et al. 2009: Synergistic effect of dendritic cell vaccination and anti-CD20 antibody treatment in the therapy of murine lymphoma. J Immunother. 32(4): 333-40. The following list provides some non-limiting examples of anti-cancer antibodies and potential antibody targets (in brackets) which can be used in combination with the present invention: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Bavituximab (phosphatidylserine), Bectumomab (CD22), Belimumab (BAFF), Bevacizumab (VEGF-A), Bivatuzumab mertansine (CD44 v6), Blinatumomab (CD19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin av03), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-β), Galiximab (CD80), Ganitumab (IGF−1), Gemtuzumab ozogamicin (CD33), Gevokizumab (IL-1β), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL-5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Narnatumab (RON), Necitumumab (EGFR), Nimotuzumab (EGFR), Nivolumab (IgG4), Ofatumumab (CD20), Olaratumab (PDGF-R a), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzumab (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL-6), Tabalumab (BAFF), Tacatuzumab tetraxetan (alpha-fetoprotein), Taplitumomab paptox (CD19), Tenatumomab (tenascin C), Teprotumumab (CD221), Ticilimumab (CTLA-4), Tigatuzumab (TRAIL-R2), TNX-650 (IL-13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1BB), Volociximab (integrin a5p1), Votumumab (tumor antigen CTAA16.88), Zalutumumab (EGFR), Zanolimumab (CD4).

5. Cytokines, Chemokines, Costimulatory Molecules, Fusion Proteins

Combined usage of the antigen-coding pharmaceutical compositions of the present invention with cytokines, chemokines, costimulatory molecules and/or fusion proteins thereof to evoke beneficial immune modulation or tumor inhibition effects is another embodiment of the present invention. In order to increase the infiltration of immune cells into the tumor and facilitate the movement of antigen-presenting cells to tumor-draining lymph nodes, various chemokines with C, CC, CXC and CX3C structures might be used. Some of the most promising chemokines are e.g CCR7 and its ligands CCL19 and CCL21, furthermore CCL2, CCL3, CCL5, and CCL16. Other examples are CXCR4, CXCR7 and CXCL12. Furthermore, costimulatory or regulatory molecules such as e.g. B7 ligands (B7.1 and B7.2) are useful. Also useful are other cytokines such as e.g. interleukins especially (e.g. IL-1 to IL17), interferons (e.g. IFNalpha1 to IFNalpha8, IFNalpha10, IFNalpha13, IFNalpha14, IFNalpha16, IFNalpha17, IFNalpha2i, IFNbeta1, IFNW, IFNE1 and IFNK), hematopoietic factors, TGFs (e.g. TGF-α, TGF-β, and other members of the TGF family), finally members of the tumor necrosis factor family of receptors and their ligands as well as other stimulatory molecules, comprising but not limited to 4-1BB, 4-1BB-L, CD137, CD137L, CTLA-4GITR, GITRL, Fas, Fas-L, TNFR1, TRAIL-R1, TRAIL-R2, p75NGF-R, DR6, LT.beta.R, RANK, EDARI, XEDAR, Fn114, Troy/Trade, TAJ, TNFRII, HVEM, CD27, CD30, CD40, 4-1BB, OX40, GITR, GITRL, TACI, BAFF-R, BCMA, RELT, and CD95 (Fas/APO-1), glucocorticoid-induced TNFR-related protein, TNF receptor-related apoptosis-mediating protein (TRAMP) and death receptor-6 (DR6). Especially CD40/CD40L and OX40/OX40L are important targets for combined immunotherapy because of their direct impact on T cell survival and proliferation. For a review see Lechner et al. 2011: Chemokines, costimulatory molecules and fusion proteins for the immunotherapy of solid tumors. Immunotherapy 3 (11), 1317-1340.

6. Bacterial Treatments

Researchers have been using anaerobic bacteria, such as *Clostridium novyi*, to consume the interior of oxygen-poor tumours. These should then die when they come in contact with the tumour's oxygenated sides, meaning they would be harmless to the rest of the body. Another strategy is to use anaerobic bacteria that have been transformed with an enzyme that can convert a non-toxic prodrug into a toxic drug. With the proliferation of the bacteria in the necrotic and hypoxic areas of the tumour, the enzyme is expressed solely in the tumour. Thus, a systemically applied prodrug is metabolised to the toxic drug only in the tumour. This has been demonstrated to be effective with the non-pathogenic anaerobe *Clostridium sporogenes*.

7. Kinase Inhibitors

Another large group of potential targets for complementary cancer therapy comprises kinase inhibitors, because the growth and survival of cancer cells is closely interlocked with the deregulation of kinase activity. To restore normal kinase activity and therefor reduce tumor growth a broad range of inhibitors is in use. The group of targeted kinases comprises receptor tyrosine kinases e.g. BCR-ABL, B-Raf, EGFR, HER-2/ErbB2, IGF-IR, PDGFR-a, PDGFR-0, c-Kit, Flt-4, Flt3, FGFR1, FGFR3, FGFR4, CSF1R, c-Met, RON, c-Ret, ALK, cytoplasmic tyrosine kinases e.g. c-SRC, c-YES, Abl, JAK-2, serine/threonine kinases e.g. ATM, Aurora A & B, CDKs, mTOR, PKCi, PLKs, b-Raf, S6K, STK11/LKB1 and lipid kinases e.g. P13K, SKI. Small molecule kinase inhibitors are e.g. PHA-739358, Nilotinib, Dasatinib, and PD166326, NSC 743411, Lapatinib (GW-572016), Canertinib (CI-1033), Semaxinib (SU5416), Vatalanib (PTK787/ZK222584), Sutent (SU11248), Sorafenib (BAY 43-9006) and Leflunomide (SU101). For more information see e.g. Zhang et al. 2009: Targeting cancer with small molecule kinase inhibitors. Nature Reviews Cancer 9, 28-39.

8. Toll-Like Receptors

The members of the Toll-like receptor (TLRs) family are an important link between innate and adaptive immunity and the effect of many adjuvants rely on the activation of TLRs. A large number of established vaccines against cancer incorporate ligands for TLRs for boosting vaccine responses. Besides TLR2, TLR3, TLR4 especially TLR7 and TLR8 have been examined for cancer therapy in passive immunotherapy approaches. The closely related TLR7 and TLR8 contribute to antitumor responses by affecting immune cells, tumor cells, and the tumor microenvironment and may be activated by nucleoside analogue structures. All TLRs have been used as stand-alone immunotherapeutics or cancer vaccine adjuvants and may be synergistically combined with the formulations and methods of the present invention. For more information see van Duin et al. 2005: Triggering TLR signaling in vaccination. Trends in Immunology, 27(1):49-55.

9. Angiogenesis Inhibitors

In addition to therapies which target immune modulatory receptors affected by tumor-mediated escape mechanisms and immune suppression there are therapies which target the tumor environment. Angiogenesis inhibitors prevent the extensive growth of blood vessels (angiogenesis) that tumors require to survive. The angiogenesis promoted by tumor cells to meet their increasing nutrient and oxygen demands for example can be blocked by targeting different molecules. Non-limiting examples of angiogenesis-mediating molecules or angiogenesis inhibitors which may be combined with the present invention are soluble VEGF (VEGF isoforms VEGF121 and VEGF165, receptors VEGFR1, VEGFR2 and co-receptors Neuropilin-1 and Neuropilin-2) 1 and NRP-1, angiopoietin 2, TSP-1 and TSP-2, angiostatin and related molecules, endostatin, vasostatin, calreticulin, platelet factor-4, TIMP and CDAI, Meth-1 and Meth-2, IFN-α, -β and -γ, CXCL10, IL-4 , -12 and -18, prothrombin (kringle domain-2), antithrombin III fragment, prolactin, VEGI, SPARC, osteopontin, maspin, canstatin, proliferin-related protein, restin and drugs like e.g. bevacizumab, itraconazole, carboxyamidotriazole, TNP-470, CM101, IFN-α, platelet factor-4, suramin, SU5416, thrombospondin, VEGFR antagonists, angiostatic steroids+heparin, cartilage-derived angiogenesis inhibitory factor, matrix metalloproteinase inhibitors, 2-methoxyestradiol, tecogalan, tetrathiomolybdate, thalidomide, thrombospondin, prolactin Vβ3 inhibitors, linomide, tasquinimod, for review see e.g. Schoenfeld and Dranoff 2011: Anti-angiogenesis immunotherapy. Hum Vaccin. (9):976-81.

10. Small Molecule Targeted Therapy Drugs

Small molecule targeted therapy drugs are generally inhibitors of enzymatic domains on mutated, overexpressed, or otherwise critical proteins within the cancer cell. Prominent and non-limiting examples are the tyrosine kinase inhibitors imatinib (Gleevec/Glivec) and gefitinib (Iressa). The use of small molecules e.g. sunitinib malate and/or sorafenib tosylate targeting some kinases in combination with vaccines for cancer therapy is also described in previous patent application US2009004213.

11. Virus-Based Vaccines

There are a number of virus-based cancer vaccines available or under development which can be used in a combined therapeutic approach together with the formulations of the present invention. One advantage of the use of such viral vectors is their intrinsic ability to initiate immune responses, with inflammatory reactions occurring as a result of the viral infection creating the danger signal necessary for immune activation. An ideal viral vector should be safe and should not introduce an anti-vector immune response to allow for boosting antitumour specific responses. Recombinant viruses such as vaccinia viruses, herpes simplex viruses, adenoviruses, adeno-associated viruses, retroviruses and avipox viruses have been used in animal tumor models and based on their encouraging results, human clinical trials have been initiated. Especially important virus-based vaccines are virus-like particles (VLPs), small particles that contain certain proteins from the outer coat of a virus. Virus-like particles do not contain any genetic material from the virus and cannot cause an infection but they can be constructed to present tumor antigens on their coat. VLPs can be derived from various viruses such as e.g. the hepatitis B virus or other virus families including Parvoviridae (e.g. adeno-associated virus), Retroviridae (e.g. HIV), and Flaviviridae (e.g. Hepatitis C virus). For a general review see Sorensen and Thompsen 2007: Virus-based immunotherapy of cancer: what do we know and where are we going? APMIS 115(11):1177-93; virus-like particles against cancer are reviewed in Buonaguro et al. 2011: Developments in virus-like particle-based vaccines for infectious diseases and cancer. Expert Rev Vaccines 10(11):1569-83; and in Guillen et al. 2010: Virus-like particles as vaccine antigens and adjuvants: application to chronic disease, cancer immunotherapy and infectious disease preventive strategies. Procedia in Vaccinology 2 (2), 128-133.

12. Multi-Epitope Strategies

The use of multi epitopes shows promising results for vaccination. Fast sequencing technologies combined with intelligent algorithm systems allow the exploitation of the tumor mutanome and may provide multi epitopes for individualized vaccines which can be combined with the present invention. For more information see 2007: Vaccination of metastatic colorectal cancer patients with matured dendritic cells loaded with multiple major histocompatibility complex class I peptides. J Immunother 30: 762-772; furthermore Castle et al. 2012: Exploiting the mutanome for tumor vaccination. Cancer Res 72 (5):1081-91.

13. Adoptive T-Cell Transfer

For example, a combination of a tumor antigen vaccination and T-cell transfer is described in: Rapoport et al. 2011: Combination immunotherapy using adoptive T-cell transfer and tumor antigen vaccination on the basis of hTERT and survivin after ASCT for myeloma. Blood 117(3):788-97.

14. Peptide-Based Target Therapies

Peptides can bind to cell surface receptors or affected extracellular matrix surrounding the tumor. Radionuclides which are attached to these peptides (e.g. RGDs) eventually kill the cancer cell if the nuclide decays in the vicinity of the cell. Especially oligo- or multimers of these binding motifs are of great interest, since this can lead to enhanced tumor specificity and avidity. For non-limiting examples see Yamada 2011: Peptide-based cancer vaccine therapy for prostate cancer, bladder cancer, and malignant glioma. Nihon Rinsho 69(9): 1657-61.

15. Other Therapies

There are numerous other cancer therapies which can be combined with the formulations and methods of the present invention in order to create synergistic effects. Non-limiting examples are treatments targeting apoptosis, hyperthermia, hormonal therapy, telomerase therapy, insulin potentiation therapy, gene therapy and photodynamic therapy.

The present invention is further illustrated by the following examples which are not be construed as limiting the scope of the invention.

EXAMPLES

Examples

Example 1: Generation, Purification and Analysis of Bispecific Antibody-Derivatives Targeting CLDN6 and CD3 (CLDN6×CD3)

a. Sequence Origin, Design of Bstb Constructs, and Cloning into Expression Vectors The bispecific chimeric TriMAB (bstb) constructs were designed as antigen binding fragments (Fab) equipped with two single-chain variable fragments (scFv) at the C-terminus of the constant regions. The Fab binding domain is specific for the human T-cell receptor component CD3ε. The anti-CD3 variable heavy chain region ($V_H$) and the corresponding variable light chain region (VL) domains are derived from murine IgG TR66 (Lanzavecchia und Scheidegger 1987). The cysteine at position 114 (according to IMGT nomenclature) has been substituted by serine. The constant heavy ($C_H1$) and constant light chain region ($C_L$) are of human origin. We chose kappa-type constant light chain region for our constructs. The two scFv-binding moieties are specific for the human tumor associated antigen (TAA) CLDN6. The corresponding $V_H$ and $V_L$ regions are derived from the chimeric IgG1 IMAB206-SUBW (Ganymed Pharmaceuticals AG, Mainz, Germany). FIG. 18 shows the amino acid sequences of VH and VL domains that were used in the course of the invention.

Two bstb molecules were generated differing in their $C_H1$ region. Bstb_369/367 contains a $C_H1$ region derived from human IgG1, whereas bstb_371/367 carries a $C_H1$ region from human IgG2. The rational was the comparison of heterodimer formation due to different disulfide-bond formation by $C_H1$ and $C_L$ of different subclasses (Röthlisberger et al. 2005). As the sequence for the kappa-type $C_L$ is conserved in IgG1 and IgG2, the same $C_L$ construct was used for the formation of the two constructs. The following molecules were obtained on protein level for the formation of bstb molecules:

| Bstb_369/367: | |
|---|---|
| N - $V_H^{\alpha CD3}$-$C_H1$(IgG1)-$V_H^{\alpha CLDN6}$-$V_L^{\alpha CLDN6}$-6xHis-tag - C | (Fd bstb_369/367) |
| N - $V_L^{\alpha CD3}$-$C_L$-$V_H^{\alpha CLDN6}$-$V_L^{\alpha CLDN6}$-Strep-tag - C | (L bstb_369/367) |
| Bstb_371/367: | |
| N - $V_H^{\alpha CD3}$-$C_H1$(IgG2)-$V_H^{\alpha CLDN6}$-$V_L^{\alpha CLDN6}$-6xHis-tag - C | (Fd bstb_371/367) |
| N - $V_L^{\alpha CD3}$-$C_L$-$V_H^{\alpha CLDN6}$-$V_L^{\alpha CLDN6}$-Strep-tag - C | (L bstb_371/367) |

C = C-terminus, $C_H$ = constant heavy chain region, $C_L$ = constant light chain region, Fd = digestible fragment (heavy chain portion of Fab), L = light chain portion of Fab, N = N-Terminus, $V_H$ = variable heavy chain domain, $V_L$ = variable light chain domain.

Table 1 summarizes the information about bstb constructs specific for the TAA CLDN6 that were generated in the course of the invention. The bstb construct fragments were generated by gene synthesis by GeneArt AG (GeneArt/Thermo Fisher Scientific, Regensburg, Germany) using the $V_H$ and $V_L$ sequences of the corresponding IgG antibodies and the conserved human $C_H$ and $C_L$ sequences as GeneArt Strings. CHO codon optimization was implemented by GeneArt's GeneOptimizer® software. Information on specificity, sequence origin from monoclonal antibodies (mAB), parameter for codon usage optimization and additional sequence features are listed in table 1. Sequences encoding the variable domains of the target cell binding moieties were originally from Ganymed Pharmaceuticals AG.

DNA cloning and expression vector construction was carried out with the Seamless PLUS Cloning and Assembly Kit (GeneArt/Thermo Fisher Scientific) known by the skilled person. A human IgG secretion signal sequence coding for MGWSCIILFLVATATGVHS (SEQ ID NO: 71) was introduced at the 5'-end upstream of the Fd- and L-bstb V-region sequences for protein secretion into the culture medium. A sequence coding for a 20 amino acid (AA) flexible glycine-serine (G-S) peptide linker ($(GGGGS)_4$) (SEQ ID NO: 68) was inserted to join the VH- and VL-domains for the composition of the anti-TAA scFv. Per VH- and VL-domain one substitution each to a cysteine was introduced for the formation of a scFv-stabilizing disulfide bridge. The one scFv domain sequence was connected to the Fd-portion (C-terminus of $C_H1$) by a sequence coding for an 18 AA linker ($SGPGGGRS(GGGGS)_2$) (SEQ ID NO: 66) and the other scFv was connected to the L-portion (C-terminus of $C_L$) by a sequence coding for a six AA linker (DVPGGS) (SEQ ID NO: 67). The different linker lengths allowed the discrimination of the Fd- and the L-portion by size. A 6xHis-tag sequence was added to the 3'-end of the Fd-scFv moiety and a Strep-tag to the 3'-end of the L-scFv moiety to facilitate purification of pure heterodimeric bstb of the first generation. In Table 2 the full bstb protein coding DNA sequences are listed. Table 3 shows the DNA sequence coding for the bi-(scFv)$_2$ used as reference.

The bstb antibody constructs were cloned into the standard mammalian pCEP4-based expression vector (Invitrogen/Thermo Fisher Scientific, Darmstadt, Germany) cleaved by NaeI and Pm/I resulting in a blunt ended linear plasmid. The C-terminal 6xHis-tag and Strep-tag served for affinity chromatographic purification of the proteins and for detection purposes. Constructs without tags were generated as well. All constructs were verified by external sequencing service.

Figure 1B:
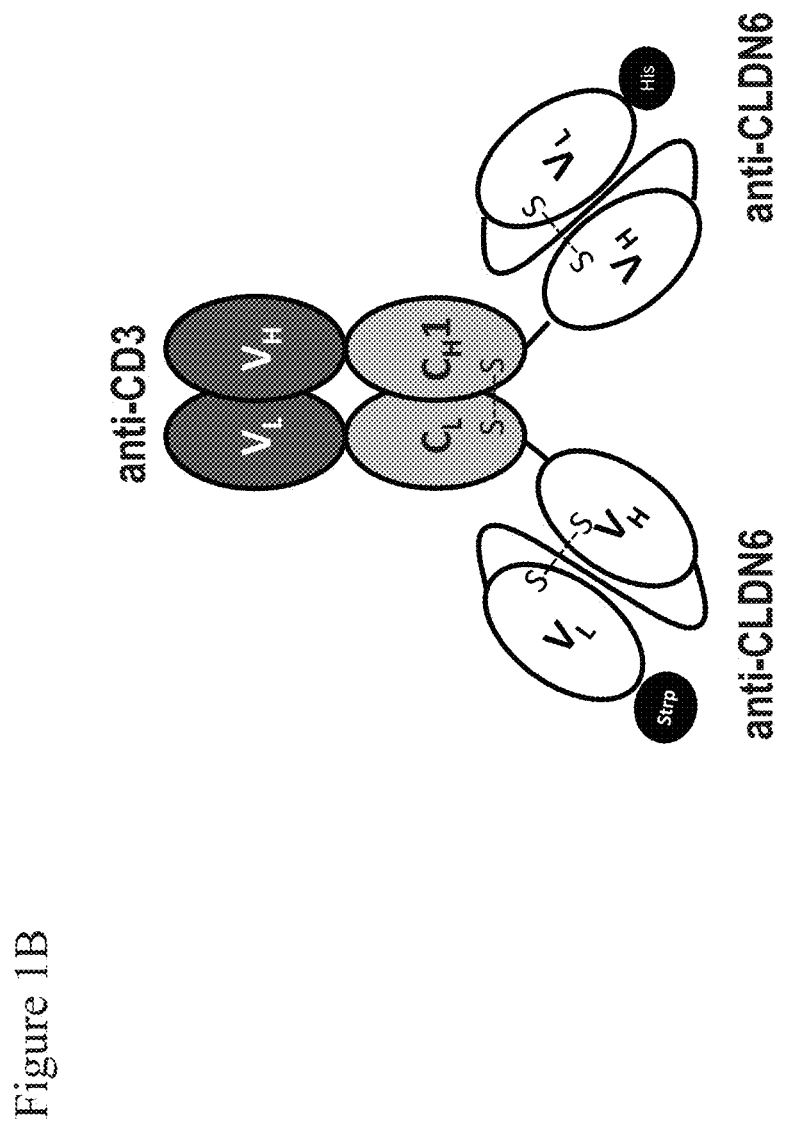

The construct and protein schemata are illustrated in FIG. 1.

TABLE 1

Summary of CLDN6 × CD3-bstb antibody features

| Internal name | Specificity | Origin of scFv $V_H$-$V_L$ regions | Origin of Fab $V_H$-$V_L$ region | Codon usage | $C_H1$ | Tag | ds bridge in scFv moiety |
|---|---|---|---|---|---|---|---|
| Bstb_369/367 (SEQ ID NO: 14/16) | HS | IMAB206-SUBW | TR66(C114S) | CG | IgG1 | His/Strp | + |
| Bstb_371/367 (SEQ ID NO: 15/16) | HS | IMAB206-SUBW | TR66(C114S) | CG | IgG2 | His/Strp | + |
| Bstb_5726/5725 (SEQ ID NO: 17/19) | HS | IMAB206-SUBW | TR66(C114S) | CG | IgG1 | — | + |
| Bstb_5727/5725 (SEQ ID NO: 18/19) | HS | IMAB206-SUBW | TR66(C114S) | CG | IgG2 | — | + |

Bstb indicates bispecific TriMAB;
C, cysteine;
CH1, constant heavy region 1;
CG, Cricetulus griseus;
IMAB, ideal monoclonal antibody;
His, 6xHis-tag;
HS, Homo sapiens;
IgG, immunoglobulin G;
S, serine;
Strp, Strep-tag;
W, tryptophan.

TABLE 2

CLDN6 x CD3-bstb_DNA coding sequences

| Plasmid internal name | Corresponding bstb fragment | DNA coding sequence |
|---|---|---|
| #367 | Lbstb_369/367, Lbstb_371/367 | ATGGGCTGGTCCTGCATCATCCTGTTTCTGGTGGCTACCGCCACCGGCGT GCACTCTCAGATCGTGCTGACCCAGTCTCCCGCCATCATGTCTGCTAGCC CTGGCGAGAAAGTGACAATGACCTGCCGGGCCTCCTCCTCCGTGTCCTAC ATGAACTGGTATCAGCAGAAGTCCGGCACCTCCCCCAAGCGGTGGATCTA CGACACCTCCAAGGTGGCCTCTGGCGTGCCCTACAGATTCTCCGGCTCTG GCTCTGGCACCTCCTACAGCCTGACCATCTCCAGCATGGAAGCCGAGGAT GCCGCCACCTACTACTGCCAGCAGTGGTCCTCCAACCCCCTGACCTTTGG CGCTGGCACCAAGCTGGAACTGAAGCGGACCGTGGCCGCTCCTTCCGTGT TCATCTTCCCTCCCTCCGACGAGCAGCTGAAGTCCGGCACCGCCTCCGTG GTGTGCCTGCTGAACAACTTCTACCCTCGGGAGGCCAAGGTGCAGTGGAA GGTGGACAACGCCCTGCAGTCCGGCAACTCCCAGGAAAGCGTCACCGAGC AGGACTCCAAGGACAGCACCTACTCCCTGTCCTCCACCCTGACCCTGTCC AAGGCCGACTACGAGAAGCACAAGGTGTACGCCTGCGAGGTGACCCACCA GGGCCTGTCCAGCCCTGTGACCAAGTCCTTCAACCGGGGCGAGTGTGACG TGCCTGGTGGTAGCGAAGTGCAGCTGCAGCAGAGCGGCCCTGAGCTGGTG AAACCCGGCGCTAGCATGAAGATCAGCTGCAAGGCCAGCGGCTACAGCTT CACCGGCTACACCATGAACTGGGTGAAACAGAGCCACGGCAAGTGCCTGG AATGGATCGGCCTGATCAACCCCTACAACGGCGGCACCATCTACAACCAG AAGTTCAAGGGCAAGGCCACACTGACCGTGGACAAGAGCAGCAGCACCGC CTACATGGAACTGCTGAGCCTGACCAGCGAGGACAGCGCCGTGTACTACT GCGCCAGAGACTACGGCTTCGTGCTGGACTACTGGGGCCAGGGCACCACC CTGACAGTGTCTAGCGGAGGCGGAGGATCTGGTGGTGGCGGATCTGGCGG CGGTGGAAGTGGCGGAGGTGGTAGCCAGATCGTGCTGACCCAGTCCCCCT CCATCATGTCCGTGTCTCCCGGCGAGAAAGTGACAATTACCTGCTCCGCC TCCTCCTCCGTGTCCTACATGCACTGGTTCCAGCAGAAGCCGGCACCTC CCCCAAGCTGTGGATCTACTCCACCTCCAACCTGGCCTCCGGCGTGCCCG CCAGATTCTCCGGAAGAGGCTCCGGCACCAGCTACTCCCTGACCATCTCC AGAGTGGCCGCCGAGGACGCCGCCACCTACTACTGCCAGCAGCGGTCCAA CTACCCCCCCTGGACCTTTGGCTGCGGCACCAAGCTGGAAATCAAGTCTG CCTGGAGCCACCCACAGTTCGAGAAGTGA |

TABLE 2-continued

CLDN6 x CD3-bstb_DNA coding sequences

| Plasmid internal name | Corresponding bstb fragment | DNA coding sequence |
|---|---|---|
| #369 | Fd bstb_369/367 | ATGGGCTGGTCCTGCATCATCCTGTTTCTGGTGGCTACCGCCACCGGCGT<br>GCACTCCCAGGTGCAGCTGCAGCAGTCTGGCGCTGAGCTGGCTAGACCTG<br>GCGCCTCCGTGAAGATGTCCTGCAAGACCTCCGGCTACACCTTCACCCGG<br>TACACCATGCACTGGGTCAAGCAGAGGCCTGGACAGGGCCTGGAATGGAT<br>CGGCTACATCAACCCCTCCCGGGGCTACACCAACTACAACCAGAAGTTCA<br>AGGACAAGGCCACCCTGACAACCGACAAGTCCTCCTCCACCGCCTACATG<br>CAGCTGTCCTCCCTGACCTCCGAGGACTCCGCCGTGTACTACTGCGCCCG<br>GTACTACGACGACCACTACTCCCTGGACTACTGGGGCCAGGGCACCACAC<br>TGACAGTGTCTAGCGCCTCCACCAAGGGCCCTTCCGTGTTCCCTCTGGCC<br>CCTTCCTCCAAGTCCACCTCCGGCGGCACCGCCGCTCTGGGCTGCCTGGT<br>GAAGGACTACTTCCCTGAGCCTGTGACCGTGAGCTGGAACTCTGGCGCCC<br>TGACCAGCGGCGTGCACACCTTCCCTGCCGTGCTGCAGTCCTCCGGCCTG<br>TACTCCCTGTCCTCCGTGGTGACCGTGCCTTCCTCCTCCCTGGGCACCCA<br>GACCTACATCTGCAACGTGAACCACAAGCCTTCCAACACCAAGGTGGACA<br>AGCGGGTGGAGCCTAAGTCCTGCTCCGGCCCTGGGGGCGGACGCAGCGGC<br>GGAGGCGGATCCGGCGGAGGAGGCTCTGAAGTGCAGCTGCAGCAGAGCGG<br>CCCTGAGCTGGTGAAACCCGGCGCTAGCATGAAGATCAGCTGCAAGGCCA<br>GCGGCTACAGCTTCACCGGCTACACCATGAACTGGGTGAAACAGAGCCAC<br>GGCAAGTGCCTGGAATGGATCGGCCTGATCAACCCCTACAACGGCGGCAC<br>CATCTACAACCAGAAGTTCAAGGGCAAGGCCACACTGACCGTGGACAAGA<br>GCAGCAGCACCGCCTACATGGAACTGCTGAGCCTGACCAGCGAGGACAGC<br>GCCGTGTACTACTGCGCCAGAGACTACGGCTTCGTGCTGGACTACTGGGG<br>CCAGGGCACCACCCTGACAGTGTCTAGCGGAGGCGGAGGATCTGGTGGTG<br>GCGGATCTGGCGGCGGTGGAAGTGGCGGAGGTGGTAGCCAGATCGTGCTG<br>ACCCAGTCCCCCTCCATCATGTCCGTGTCTCCCGGCGAGAAAGTGACAAT<br>TACCTGCTCCGCCTCCTCCGTGTCCTACATGCACTGGTTCCAGCAGA<br>AGCCCGGCACCTCCCCCAAGCTGTGGATCTACTCCACCTCCAACCTGGCC<br>TCCGGCGTGCCCGCCAGATTCTCCGGAAGAGGCTCCGGCACCAGCTACTC<br>CCTGACCATCTCCAGAGTGGCCGCCGAGGACGCCGCCACCTACTACTGCC<br>AGCAGCGGTCCAACTACCCCCCTGGACCTTTGGCTGCGGCACCAAGCTG<br>GAAATCAAGGGCGGCTCCCACCACCACCATCACCACTGA |
| #371 | Fd bstb_371/367 | ATGGGCTGGTCCTGCATCATCCTGTTTCTGGTGGCTACCGCCACCGGCGT<br>GCACTCCCAGGTGCAGCTGCAGCAGTCTGGCGCTGAGCTGGCTAGACCTG<br>GCGCCTCCGTGAAGATGTCCTGCAAGACCTCCGGCTACACCTTCACCCGG<br>TACACCATGCACTGGGTCAAGCAGAGGCCTGGACAGGGCCTGGAATGGAT<br>CGGCTACATCAACCCCTCCCGGGGCTACACCAACTACAACCAGAAGTTCA<br>AGGACAAGGCCACCCTGACAACCGACAAGTCCTCCTCCACCGCCTACATG<br>CAGCTGTCCTCCCTGACCTCCGAGGACTCCGCCGTGTACTACTGCGCCCG<br>GTACTACGACGACCACTACTCCCTGGACTACTGGGGCCAGGGCACCACAC<br>TGACAGTGTCTAGCGCCTCCACCAAGGGCCCTTCCGTGTTCCCTCTGGCC<br>CCTTGCTCCAAGTCCACCTCCGAAGGCACCGCCGCTCTGGGCTGCCTGGT<br>GAAGGACTACTTCCCTGAGCCTGTGACCGTGAGCTGGAACTCTGGCGCCC<br>TGACCAGCGGCGTGCACACCTTCCCTGCCGTGCTGCAGTCCTCCGGCCTG<br>TACTCCCTGTCCTCCGTGGTGACCGTGCCTTCCTCCAACTTCGGCACCCA<br>GACCTACACCTGCAACGTGGACCACAAGCCTTCCAACACCAAGGTGGACA<br>AGACCGTGGAGCCTAAGTCCGCCTCCGGCCCTGGGGGCGGACGCAGCGGC<br>GGAGGCGGATCCGGCGGAGGAGGCTCTGAAGTGCAGCTGCAGCAGAGCGG<br>CCCTGAGCTGGTGAAACCCGGCGCTAGCATGAAGATCAGCTGCAAGGCCA<br>GCGGCTACAGCTTCACCGGCTACACCATGAACTGGGTGAAACAGAGCCAC<br>GGCAAGTGCCTGGAATGGATCGGCCTGATCAACCCCTACAACGGCGCAC<br>CATCTACAACCAGAAGTTCAAGGGCAAGGCCACACTGACCGTGGACAAGA<br>GCAGCAGCACCGCCTACATGGAACTGCTGAGCCTGACCAGCGAGGACAGC<br>GCCGTGTACTACTGCGCCAGAGACTACGGCTTCGTGCTGGACTACTGGGG<br>CCAGGGCACCACCCTGACAGTGTCTAGCGGAGGCGGAGGATCTGGTGGTG<br>GCGGATCTGGCGGCGGTGGAAGTGGCGGAGGTGGTAGCCAGATCGTGCTG<br>ACCCAGTCCCCCTCCATCATGTCCGTGTCTCCCGGCGAGAAAGTGACAAT<br>TACCTGCTCCGCCTCCTCCTCCGTGTCCTACATGCACTGGTTCCAGCAGA<br>AGCCCGGCACCTCCCCCAAGCTGTGGATCTACTCCACCTCCAACCTGGCC<br>TCCGGCGTGCCCGCCAGATTCTCCGGAAGAGGCTCCGGCACCAGCTACTC<br>CCTGACCATCTCCAGAGTGGCCGCCGAGGACGCCGCCACCTACTACTGCC<br>AGCAGCGGTCCAACTACCCCCCTGGACCTTTGGCTGCGGCACCAAGCTG<br>GAAATCAAGGGCGGCTCCCACCACCACCATCACCACTGA |
| #5725 | L bstb_5726/5725,<br>L bstb_5727/5725 | ATGGGCTGGTCCTGCATCATCCTGTTTCTGGTGGCTACCGCCACCGGCGT<br>GCACTCTCAGATCGTGCTGACCCAGTCTCCCGCCATCATGTCTGCTAGCC<br>CTGGCGAGAAAGTGACAATGACCTGCCGGGCCTCCTCCTCCGTGTCCTAC<br>ATGAACTGGTATCAGCAGAAGTCCGGCACCTCCCCCAAGCGGTGGATCTA<br>CGACACCTCCAAGGTGGCCTCTGGCGTGCCCTACAGATTCTCCGGCTCTG<br>GCTCTGGCACCTCCTACAGCCTGACCATCTCCAGCATGGAAGCCGAGGAT<br>GCCGCCACCTACTACTGCCAGCAGTGGTCCTCCAACCCCCTGACCTTTGG<br>CGCTGGCACCAAGCTGGAACTGAAGCGGACCGTGGCCGCTCCTTCCGTGT<br>TCATCTTCCCTCCCTCCGACGAGCAGCTGAAGTCCGGCACCGCCTCCGTG |

TABLE 2-continued

CLDN6 x CD3-bstb_DNA coding sequences

| Plasmid internal name | Corresponding bstb fragment | DNA coding sequence |
|---|---|---|
| | | GTGTGCCTGCTGAACAACTTCTACCCTCGGGAGGCCAAGGTGCAGTGGAA<br>GGTGGACAACGCCCTGCAGTCCGGCAACTCCCAGGAAAGCGTCACCGAGC<br>AGGACTCCAAGGACAGCACCTACTCCCTGTCCTCCACCCTGACCCTGTCC<br>AAGGCCGACTACGAGAAGCACAAGGTGTACGCCTGCGAGGTGACCCACCA<br>GGGCCTGTCCAGCCCTGTGACCAAGTCCTTCAACCGGGGCGAGTGTGACG<br>TGCCTGGTGGTAGCGGAAGTGCAGCTGCAGCAGAGCGGCCCTGAGCTGGTG<br>AAACCCGGCGCTAGCATGAAGATCAGCTGCAAGGCCAGCGGCTACAGCTT<br>CACCGGCTACACCATGAACTGGGTGAAACAGAGCCACGGCAAGTGCCTGG<br>AATGGATCGGCCTGATCAACCCCTACAACGGCGGCACCATCTACAACCAG<br>AAGTTCAAGGGCAAGGCCACACTGACCGTGGACAAGAGCAGCAGCACCGC<br>CTACATGGAACTGCTGAGCCTGACCAGCGAGGACAGCGCCGTGTACTACT<br>GCGCCAGAGACTACGGCTTCGTGCTGGACTACTGGGGCCAGGGCACCACC<br>CTGACAGTGTCTAGCGGAGGCGGAGGATCTGGTGGTGGCGGATCTGGCGG<br>CGGTGGAAGTGGCGGAGGTGGTAGCCAGATCGTGCTGACCCAGTCCCCCT<br>CCATCATGTCCGTGTCTCCCGGCGAGAAAGTGACAATTACCTGCTCCGCC<br>TCCTCCTCCGTGTCCTACATGCACTGGTTCCAGCAGAAGCCCGGCACCTC<br>CCCCAAGCTGTGGATCTACTCCACCTCCAACCTGGCCTCCGGCGTGCCCG<br>CCAGATTCTCCGGAAGAGGCTCCGGCACCAGCTACTCCCTGACCATCTCC<br>AGAGTGGCCGCCGAGGACGCCGCCACCTACTACTGCCAGCAGCGGTCCAA<br>CTACCCCCCCTGGACCTTTGGCTGCGGCACCAAGCTGGAAATCAAGTGA |
| #5726 | Fd bstb_5726/5725 | ATGGGCTGGTCCTGCATCATCCTGTTTCTGGTGGCTACCGCCACCGGCGT<br>GCACTCCCAGGTGCAGCTGCAGCAGTCTGGCGCTGAGCTGGCTAGACCTG<br>GCGCCTCCGTGAAGATGTCCTGCAAGACCTCCGGCTACACCTTCACCCGG<br>TACACCATGCACTGGGTCAAGCAGAGGCCTGGACAGGGCCTGGAATGGAT<br>CGGCTACATCAACCCCTCCCGGGGCTACACCAACTACAACCAGAAGTTCA<br>AGGACAAGGCCACCCTGACAACCGACAAGTCCTCCTCCACCGCCTACATG<br>CAGCTGTCCTCCCTGACCTCCGAGGACTCCGCCGTGTACTACTGCGCCCG<br>GTACTACGACGACCACTACTCCCTGGACTACTGGGGCCAGGGCACCACAC<br>TGACAGTGTCTAGCGCCTCCACCAAGGGCCCTTCCGTGTTCCCTCTGGCC<br>CCTTCCTCCAAGTCCACCTCCGGCGGCACCGCCGCTCTGGGCTGCCTGGT<br>GAAGGACTACTTCCCTGAGCCTGTGACCGTGAGCTGGAACTCTGGCGCCC<br>TGACCAGCGGCGTGCACACCTTCCCTGCCGTGCTGCAGTCCTCCGGCCTG<br>TACTCCCTGTCCTCCGTGGTGACCGTGCCTTCCTCCTCCCTGGGCACCCA<br>GACCTACATCTGCAACGTGAACCACAAGCCTTCCAACACCAAGGTGGACA<br>AGCGGGTGGAGCCTAAGTCCTGCTCCGGCCCTGGGGGCGGACGCAGCGGC<br>GGAGGCGGATCCGGCGGAGGAGGCTCTGAAGTGCAGCTGCAGCAGAGCGG<br>CCCTGAGCTGGTGAAACCCGGCGCTAGCATGAAGATCAGCTGCAAGGCCA<br>GCGGCTACAGCTTCACCGGCTACACCATGAACTGGGTGAAACAGAGCCAC<br>GGCAAGTGCCTGGAATGGATCGGCCTGATCAACCCCTACAACGGCGGCAC<br>CATCTACAACCAGAAGTTCAAGGGCAAGGCCACACTGACCGTGGACAAGA<br>GCAGCAGCACCGCCTACATGGAACTGCTGAGCCTGACCAGCGAGGACAGC<br>GCCGTGTACTACTGCGCCAGAGACTACGGCTTCGTGCTGGACTACTGGGG<br>CCAGGGCACCACCCTGACAGTGTCTAGCGGAGGCGGAGGATCTGGTGGTG<br>GCGGATCTGGCGGCGGTGGAAGTGGCGGAGGTGGTAGCCAGATCGTGCTG<br>ACCCAGTCCCCCTCCATCATGTCCGTGTCTCCCGGCGAGAAAGTGACAAT<br>TACCTGCTCCGCCTCCTCCTCCGTGTCCTACATGCACTGGTTCCAGCAGA<br>AGCCCGGCACCTCCCCCAAGCTGTGGATCTACTCCACCTCCAACCTGGCC<br>TCCGGCGTGCCCGCCAGATTCTCCGGAAGAGGCTCCGGCACCAGCTACTC<br>CCTGACCATCTCCAGAGTGGCCGCCGAGGACGCCGCCACCTACTACTGCC<br>AGCAGCGGTCCAACTACCCCCCCTGGACCTTTGGCTGCGGCACCAAGCTG<br>GAAATCAAGTGA |
| #5727 | Fd bstb_5727/5725 | ATGGGCTGGTCCTGCATCATCCTGTTTCTGGTGGCTACCGCCACCGGCGT<br>GCACTCCCAGGTGCAGCTGCAGCAGTCTGGCGCTGAGCTGGCTAGACCTG<br>GCGCCTCCGTGAAGATGTCCTGCAAGACCTCCGGCTACACCTTCACCCGG<br>TACACCATGCACTGGGTCAAGCAGAGGCCTGGACAGGGCCTGGAATGGAT<br>CGGCTACATCAACCCCTCCCGGGGCTACACCAACTACAACCAGAAGTTCA<br>AGGACAAGGCCACCCTGACAACCGACAAGTCCTCCTCCACCGCCTACATG<br>CAGCTGTCCTCCCTGACCTCCGAGGACTCCGCCGTGTACTACTGCGCCCG<br>GTACTACGACGACCACTACTCCCTGGACTACTGGGGCCAGGGCACCACAC<br>TGACAGTGTCTAGCGCCTCCACCAAGGGCCCTTCCGTGTTCCCTCTGGCC<br>CCTTGCTCCAAGTCCACCTCCGAAGGCACCGCCGCTCTGGGCTGCCTGGT<br>GAAGGACTACTTCCCTGAGCCTGTGACCGTGAGCTGGAACTCTGGCGCCC<br>TGACCAGCGGCGTGCACACCTTCCCTGCCGTGCTGCAGTCCTCCGGCCTG<br>TACTCCCTGTCCTCCGTGGTGACCGTGCCTTCCTCCAACTTCGGCACCCA<br>GACCTACACCTGCAACGTGGACCACAAGCCTTCCAACACCAAGGTGGACA<br>AGACCGTGGAGCCTAAGTCCGCCTCCGGCCCTGGGGGCGGACGCAGCGGC<br>GGAGGCGGATCCGGCGGAGGAGGCTCTGAAGTGCAGCTGCAGCAGAGCGG<br>CCCTGAGCTGGTGAAACCCGGCGCTAGCATGAAGATCAGCTGCAAGGCCA<br>GCGGCTACAGCTTCACCGGCTACACCATGAACTGGGTGAAACAGAGCCAC<br>GGCAAGTGCCTGGAATGGATCGGCCTGATCAACCCCTACAACGGCGGCAC<br>CATCTACAACCAGAAGTTCAAGGGCAAGGCCACACTGACCGTGGACAAGA<br>GCAGCAGCACCGCCTACATGGAACTGCTGAGCCTGACCAGCGAGGACAGC |

TABLE 2-continued

CLDN6 x CD3-bstb DNA coding sequences

| Plasmid internal name | Corresponding bstb fragment | DNA coding sequence |
|---|---|---|
| | | GCCGTGTACTACTGCGCCAGAGACTACGGCTTCGTGCTGGACTACTGGGG<br>CCAGGGCACCACCCTGACAGTGTCTAGCGGAGGCGGAGGATCTGGTGGTG<br>GCGGATCTGGCGGCGGTGGAAGTGGCGGAGGTGGTAGCCAGATCGTGCTG<br>ACCCAGTCCCCCTCCATCATGTCCGTGTCTCCCGGCGAGAAAGTGACAAT<br>TACCTGCTCCGCCTCCTCCTCCGTGTCCTACATGCACTGGTTCCAGCAGA<br>AGCCCGGCACCTCCCCCAAGCTGTGGATCTACTCCACCTCCAACCTGGCC<br>TCCGGCGTGCCCGCCAGATTCTCCGGAAGAGGCTCCGGCACCAGCTACTC<br>CCTGACCATCTCCAGAGTGGCCGCCGAGGACGCCGCCACCTACTACTGCC<br>AGCAGCGGTCCAACTACCCCCCCTGGACCTTTGGCTGCGGCACCAAGCTG<br>GAAATCAAGTGA |

TABLE 3

CLDN6 x CD3-bi-(scFv)₂ DNA coding sequences

| Plasmid internal name | Corresponding bi-(scFv)₂ | DNA coding sequence |
|---|---|---|
| #123 | bi-scFv "reference" | ATGGGCTGGTCCTGCATCATCCTGTTTCTGGTGGCCACCGCCACCGGCGT<br>GCACAGCGACATCAAGCTGCAGCAGAGCGGAGCCGAGCTGGCCAGACCTG<br>GGGCCAGCGTGAAGATGAGCTGCAAGACCAGCGGCTACACCTTCACCCGG<br>TACACCATGCACTGGGTGAAACAGCGGCCTGGACAGGGCCTGGAATGGAT<br>CGGCTACATCAACCCCAGCCGGGGCTACACCAACTACAACCAGAAGTTCA<br>AGGACAAGGCCACCCTGACCACCGACAAGAGCAGCAGCACCGCCTACATG<br>CAGCTGAGCAGCCTGACCAGCGAGGACAGCGCCGTGTACTACTGCGCCCG<br>GTACTACGACGACCACTACAGCCTGGACTACTGGGGCCAGGGCACCACCC<br>TGACAGTGTCTAGCGTGGAAGGAGGAAGCGGAGGATCTGGCGGCTCTGGG<br>GGAAGCGGTGGCGTGGACGACATCCAGCTGACCCAGAGCCCCGCCATCAT<br>GTCTGCCAGCCCTGGCGAGAAAGTGACCATGACCTGCCGGGCCAGCAGCA<br>GCGTGTCCTACATGAACTGGTATCAGCAGAAGTCCGGCACCAGCCCCAAG<br>CGGTGGATCTACGACACCAGCAAGGTGGCAAGCGGCGTGCCCTACAGATT<br>CAGCGGCAGCGGCTCCGGCACCTCCTACTCCCTGACCATCAGCAGCATGG<br>AAGCCGAGGACGCCGCCACCTACTACTGCCAGCAGTGGTCCAGCAACCCC<br>CTGACCTTCGGAGCCGGCACCAAGCTGGAACTGAAGTCTGGCGGGGGAGG<br>ATCCGAGGTGCAGCTGCAGCAGTCCGGCCCTGAGCTGGTGAAACCCGGCG<br>CTAGCATGAAGATCTCTTGCAAGGCCTCCGGCTACAGCTTTACCGGCTAC<br>ACAATGAATTGGGTGAAGCAGAGCCACGGCAAGAATCTGGAATGGATTGG<br>CCTGATCAACCCTTACAACGGCGGCACAATCTATAATCAGAAGTTTAAAG<br>GGAAGGCCACACTGACAGTGGACAAGTCCAGCTCCACAGCCTACATGGAA<br>CTGCTGAGCCTGACCTCCGAGGACTCTGCCGTGTATTACTGTGCCAGAGA<br>CTACGGCTTCGTGCTGGATTATTGGGGACAGGGAACAACACTGACCGTGT<br>CCTCCGGGGGAGGGGGATCAGGTGGGGAGGTAGTGGGGGTGGCGGCTCT<br>GATATCGTGCTGACCCAGTCCCCTAGCATCATGAGCGTGTCCCCAGGCGA<br>AAAAGTGACAATCACTTGCAGCGCCAGCTCCTCCGTGTCTTATATGCATT<br>GGTTCCAGCAGAAGCCTGGCACATCCCCCAAACTGTTAATCTACAGCACC<br>TCCAACCTGGCTTCCGGCGTGCCCGCCAGATTTTCTGGCAGAGGCAGCGG<br>CACCAGCTACAGCCTGACAATCAGCCGGGTGGCCGCCGAAGATGCCGCCA<br>CATATTATTGTCAGCAGCGGAGCAACTACCCCCCCTGGACATTCGGGGGA<br>GGAACAAAGCTGGAAATCAAGCACCACCACCACCACCACTGA | b. Transient Transfection and Production

For transient production of CLDN6-specific bstb proteins the Expi293m Expression System (Thermo Fisher Scientific, Darmstadt, Germany)—a derivative of the human embryonic kidney cell line HEK293—was used according to the manufacturer's manual. To this end, Expi293F™ cells were pre-cultured to a density of $2.0 \times 10^6$ per ml Expi293m Expression Medium in cell culture suspension flasks for two days. At the day of transfection, $2.5 \times 10^6$ Expi293F™ cells per ml fresh Expi293™ Expression Medium were transferred into sterile Erlenmeyer glass flasks with a capacity for the 5-fold volume. The Fd- and L-fragment containing pCEP4 plasmids were mixed in a 1:1 ratio in Opti-MEM (Gibco/Thermo Fisher Scientific). Per ml cell suspension 1 µg DNA mixture was pre-diluted in 50 µl Opti-MEM and 2.7 µl ExpiFectamine™ 293 Reagent per ml cell suspension in 50 µl Opti-MEM in separated tubes and incubated for 5 min at RT. Subsequently, the pre-diluted DNA mixture was added to the pre-diluted ExpiFectamine™ 293 Reagent, mixed and incubated for 20 min at RT before adding to the cell suspension. The cell culture flask was agitated at 125 rpm in an 8% $CO_2$, 37° C. humidified Multitron Cell shaker (Infors HT, Bottmingen, Switzerland) for 16-18 h. Then, per ml cell suspension 3.9 µl Enhancer 1 and 39 µl Enhancer 2 were added and the cell culture flasks were further incubated. Protein containing supernatant was harvested seven days post transfection. Supernatants were filtered with 0.22 µm Nalgene Rapid Flow 90 mm Filter Units, Low Protein Binding (Thermo Fisher Scientific). The secreted protein content was estimated by BLItz quantitation using Protein L Biosensors (Pall/ForteBio, Dreieich, Germany) according to the manufacturer's protocol. Supernatant was stored at 2-8° C. until purification.

c. Purification of Tagged Proteins Bstb_369/367 and Bstb_371/367

Figure 2A:
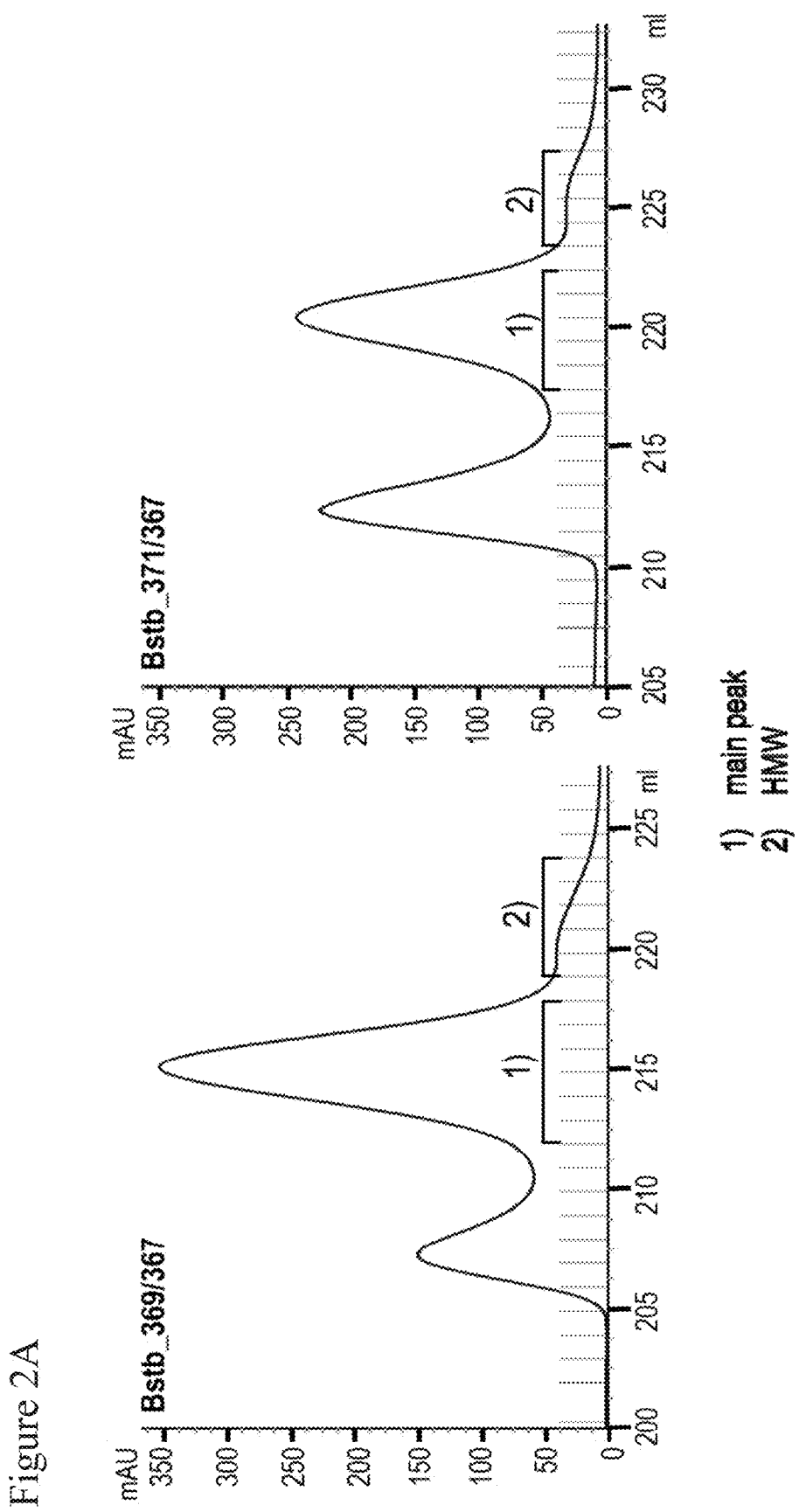

Cell culture supernatant of transiently transfected Expi293F™ cells containing protein bstb_369/367 or bstb_371/367 (described under Example 1b) was subjected to immobilized metal affinity chromatography (IMAC) using standard procedures (Coligan et al. 2001b). Briefly, cell culture supernatant supplemented with 10 mM Imidazole was loaded onto a HisTrap HP 1 ml column connected to an ÄKTA pure 25 FPLC system (both GE Healthcare Life Sciences, Freiburg, Germany) and equilibrated with wash buffer (20 mM $NaH_2PO_4$, 500 mM NaCl, 10 mM Imidazole, pH 7.5). Sample was loaded at a speed of 1 ml/min. The elution buffer differed from the wash buffer by an Imidazole concentration of 500 mM. After washing with ten column volumes (CV) the protein was eluted using a linear gradient of 0-100% elution buffer. The eluate was collected in 1 ml fractions at a speed of 1 ml/min. High molecular weight (HMW) and monomeric species (main peak) were collected (FIG. 2A). Eluted bstb protein was pooled and immediately dialyzed using a Slide-A-Lyzer G2 Dialysis Cassette 10K MWCO (Pierce/Thermo Fisher Scientific, Rockford, Ill., USA) against Strep-Tactin® binding buffer DPBS (Dulbecco's Phosphate-Buffered Saline, Gibco/Thermo Fisher Scientific) containing 137 mM NaCl, 2.7 mM KCl, 10 mM $Na_2HPO_4$, 2 mM $KH_2PO_4$ pH 7.4. Dialyzed bstb protein from the IMAC main peak was purified by further Strep-Tactin® affinity chromatography (GE Healthcare Life Sciences). All following Strep-Tactin® purification steps were run at a flow rate of 1 ml/min.

Figure 2B:
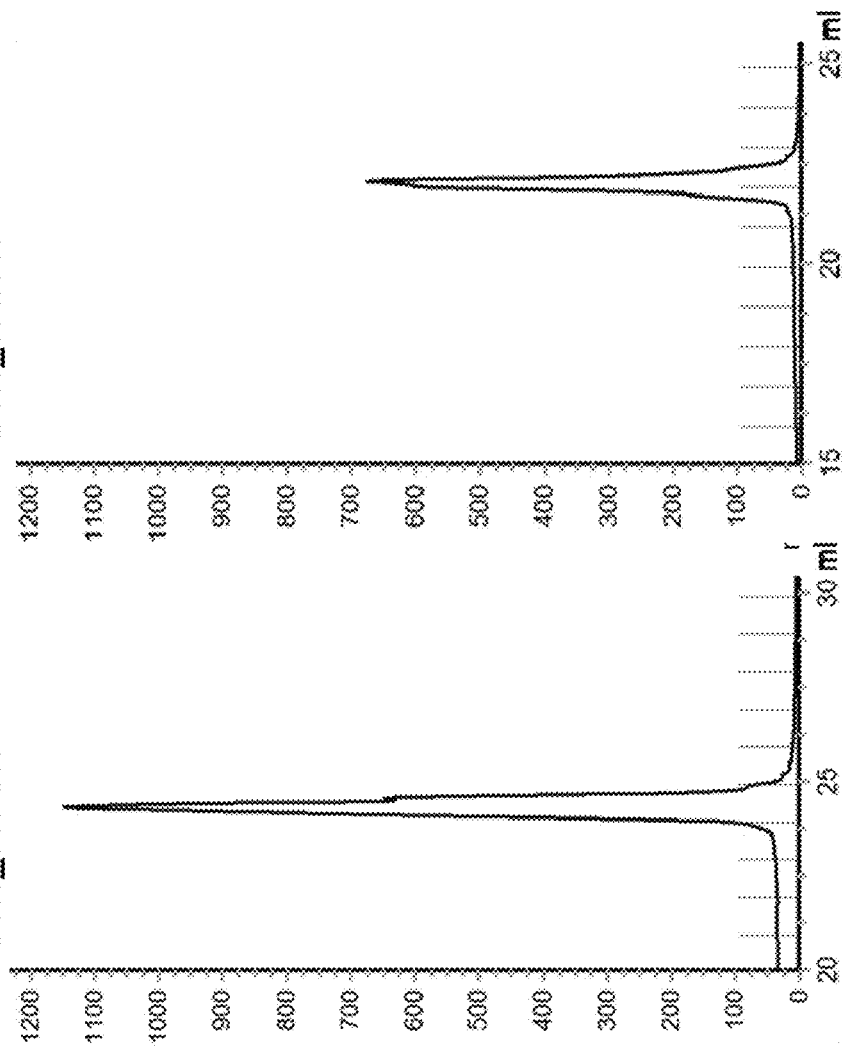

The Strep-Tactin® column was equilibrated with the binding buffer before application of the bstb protein. The elution of the bstb protein was performed by a linear gradient of 0-100% with 2.5 mM desthiobiotin (SigmaAldrich, Taufkirchen, Germany) containing binding buffer after a washing step of five CV binding buffer (FIG. 2B). Eluted bstb protein in 1 ml fractions was pooled and sub-injected onto an equilibrated size exclusion chromatography (SEC) HiLoad 16/600 Superdex 200 µg column (GE Healthcare Life Sciences) followed by isocratic elution with one CV DPBS.

The eluted HMW and monomeric bstb species were collected in 1 ml fractions (FIG. 2C) and pooled.

Bstb concentration was determined by measurement at 280 nm with a NanoDrop 2000c under consideration of the extinction coefficient and the theoretic molecular weight as determined via the ProtParam tool (web.expasy.org/protparam/). Purified protein was aliquoted and stored at 2-8° C.

d. Purification of Tag-Free Protein Bstb_5726/5725 and Bstb_5727/5725

Cell culture supernatant of transiently transfected Expi293F' cells containing protein bstb_5726/5725 and bstb_5727/5725 (described under Example 1b)—both without tags—were filtrated using Supracap™ 50 depth filter capsules (Pall corporation, Crailsheim, Germany) and subsequently subjected to a protein purification process. Purified bstb protein was analyzed by Size Exclusion-High Performance Liquid Chromatography, short SE-HPLC (FIG. 2D).

SE-HPLC was performed using a Dionex Ultimate 3000 (Thermo Scientific) with a size exclusion TSKgel G3000SW×1 column (300×7.8 mm, Tosoh Bioscience, Griesheim, Germany). Up to 100 µl was injected. The column was rinsed with the SE-HPLC buffer (0.3 M $Na_2HPO_4$, pH 7.2) and the bstb protein was separated by isocratic elution.

Figure 2D:
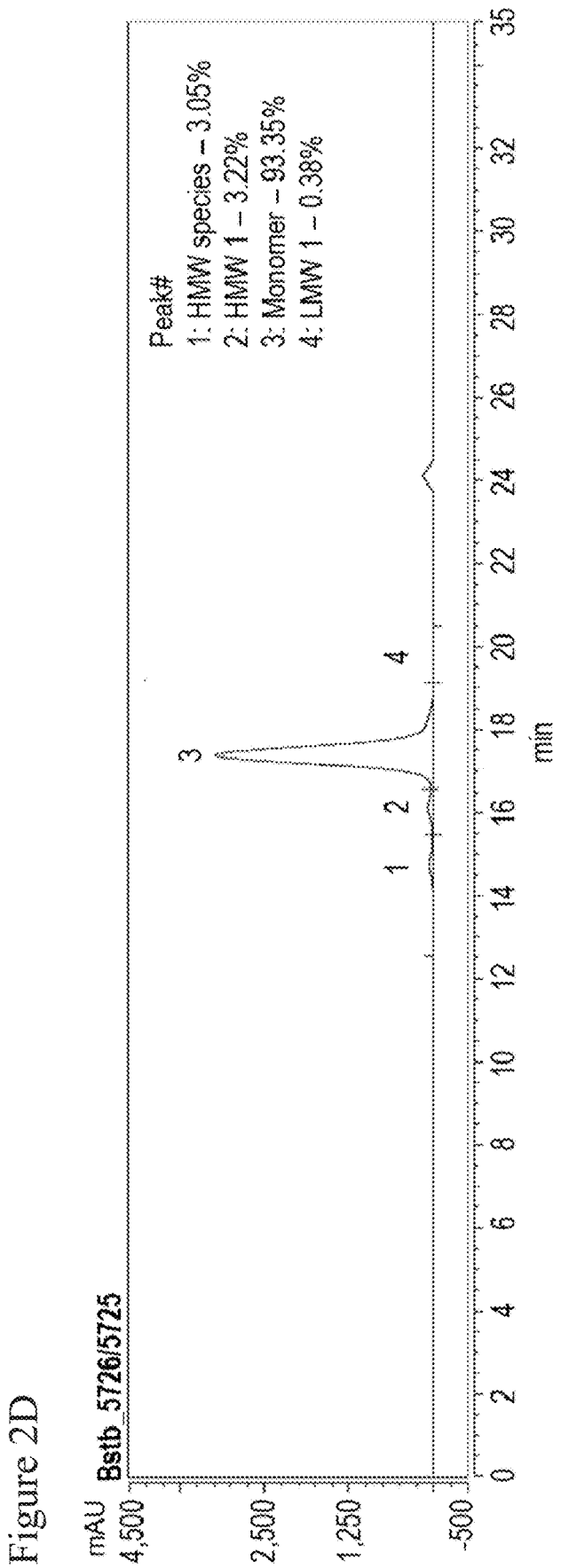

Both bstb_5726/5725 and bstb_5727/5725 (data not shown) could efficiently be purified with the established process and monomer contents were increased to >93% after the purification process (FIG. 2D). To further enrich the monomeric fraction to ~100%, samples dialyzed against PBS were finally subjected to a preparative SEC using a HiLoad 26/600 Superdex 200 µg column (GE Healthcare Life Sciences).

Herewith, a purification strategy for bstbs without tags could be shown.

e. Analysis of Tagged Proteins Bstb_369/367 and Bstb_371/367

Figure 3B:
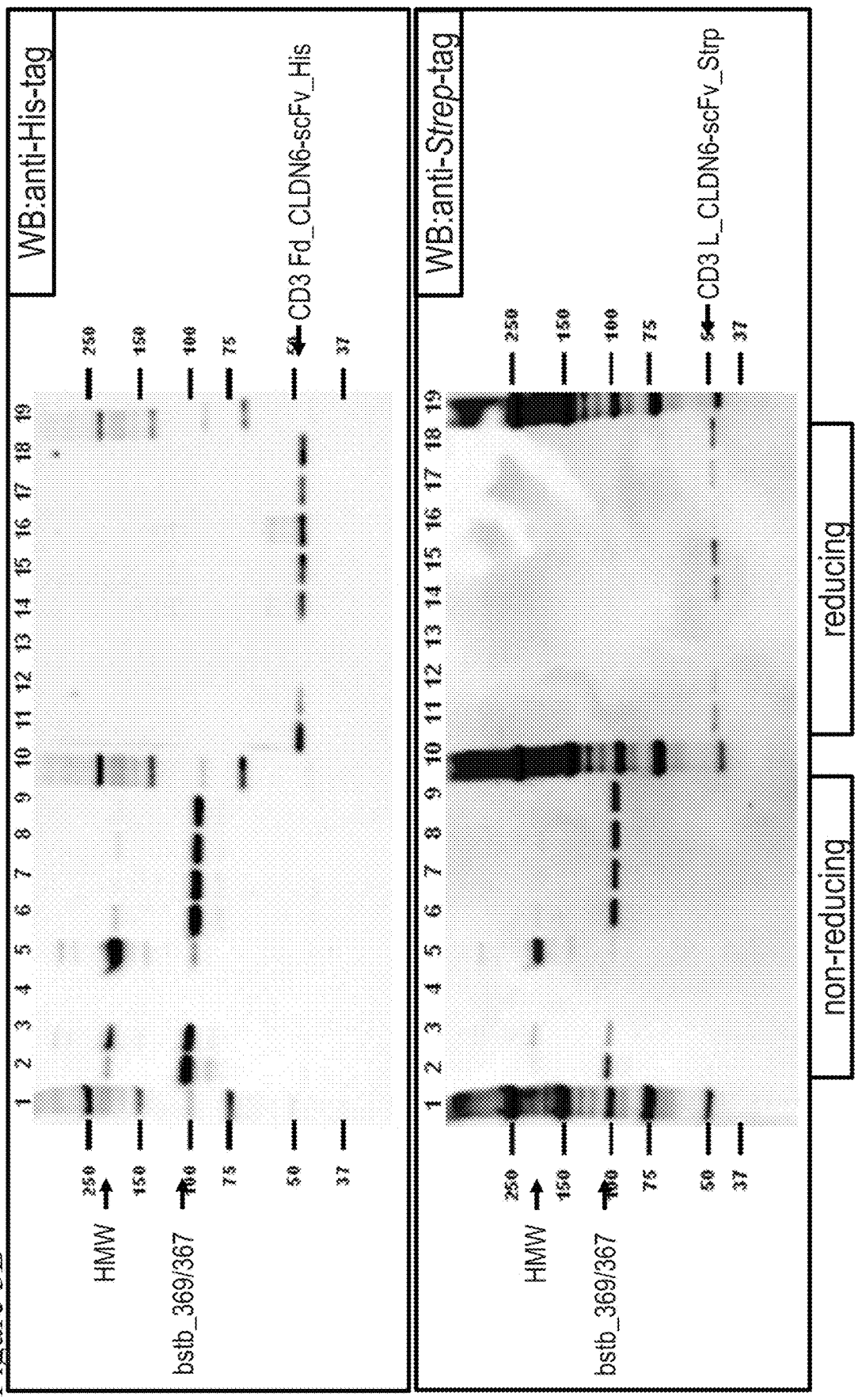

Quality and purity of bstb proteins with tags were tested by polyacrylamid gel electrophoresis using 4-15% Criterion™ TGX Stain-Free™ Gel (Bio-Rad Laboratories, Dreieich, Germany) followed by stain-free gel (FIG. 3A) and Western Blot analysis (FIG. 3B) according to standard procedures well known by the person skilled in the art. Antibodies used for Western Blot analysis were anti-6xHis tag® antibody (HRP) (1:10,000, Abcam, Cambridge, Mass., USA) and StrepMAB-Classic, HRP conjugate (1:10,000, IBA GmbH, Gottingen, Germany). Gel and Western Blot membranes were recorded with a Chemidoc MP Imaging System from Bio-Rad. Signals of bstb proteins were detected at 50-55 kD under reducing conditions (DTT addition) and at ~100 kD under non-reducing conditions as compared to the internal molecular weight standard (FIG. 3). The heterodimeric composition of the bstb becomes obvious under reducing conditions by the separation of the Fd- and L-fragment in the stain-free gel.

The aggregation state of purified proteins was determined by analytic SE-HPLC over time. SE-HPLC was performed using an Agilent 1260 Infinity system (Agilent Technologies, Waldbronn, Germany) with a size exclusion TSKgel G3000SW×1 column (300×7.8 mm, Tosoh Bioscience). Up to 100 µl was injected. The column was rinsed with SE-HPLC buffer (0.3 M $Na_2HPO_4$, pH 7.2) and the bstb protein was separated by isocratic elution. As summarized in Table 4, the purified bstb_369/367 protein has been tested over the course of more than six months by analytic SE-HPLC and showed a high stability at 2-8° C. in DPBS without any sign of aggregation or degradation.

TABLE 4

Stability of bstb_369/367 as analyzed by SE-HPLC

| Storage time at 2-8° C. in DPBS [days] | HMW [%] | Monomer [%] | LMW [%] |
|---|---|---|---|
| 0 | 0.59 | 99.41 | 0 |
| 7 | 0.54 | 99.46 | 0 |
| 30 | 0.76 | 99.24 | 0 |
| 56 | 0.74 | 99.26 | 0 |
| 203 | 0.66 | 99.34 | 0 |

Therewith, a high stability of the bstb molecule could be shown. Later purifications yielded even 100% monomeric bstb_369/367 protein.

Example 2: Determination of the Specific Lysis Activity of Bstb_369/367 and Bstb_371/367 in In Vitro Cytotoxicity Assays For the determination of specific lysis effects we used an in vitro luciferase cytotoxicity assay. As target cell lines the stably luciferase and endogenously CLDN6-expressing human ovarian cancer cell lines OV-90 (ATCC CRL-11732) and the teratocarcinoma cell line PA-1 (ATCC CRL-1572) were used. Human CLDN6-negative breast carcinoma cell line MDA-MB-231 (ATCC HTB-26)—also stably luciferase-expressing—served as specificity (off target) control.

Human peripheral blood mononuclear cells (PBMC), isolated from human blood of healthy donors (University Medicine of the JGU Mainz, Blood Transfusion Centre, Mainz, Germany) according to standard procedures (Coligan et al. 2001a), were chosen as effector cells.

a. EC50 Determination

For the determination of the half maximal effective concentration (EC50) of highly monomeric bstb_369/367, a titration row of the protein was tested in an in vitro luciferase cytotoxicity assay. In the described example, effector (E) and target (T) cells were mixed in an E:T ratio of 5:1 and seeded into white 96-well cell culture plates (Nunclon® Delta Surface, Thermo Scientific, Braunschweig, Germany) with a final cell number per well of $1 \times 10^4$ target cells and $5 \times 10^4$ effector cells. Cells were incubated with a 10-point, 10-fold serial dilution row of bstb_369/367 or bstb_371/367 protein in a concentration range of 4.85 aM to 48.50 nM. Wells serving as $L_{min}$ and $L_{max}$ values (see below) were supplemented with DPBS instead of bstb protein.

Cell culture microplates were incubated for 48 h at 37° C., 5% $CO_2$. For analysis, 50 µl of a water solution containing 1 mg/ml luciferin (BD Monolight, BD Biosciences, Heidelberg, Germany) and 50 mM HEPES were added per well and plates were subsequently incubated for 30 min in the dark at 37° C. Luminescence arising from oxidation of luciferin by luciferase-expressing viable cells was measured with an Infinite M200 Tecan microplate-reader (Tecan, Männedorf, Switzerland). Percentage of specific target cell lysis was calculated by the following formula:

% specific lysis=$[1-(\text{luminescence}_{test\ sample}-L_{max})/(L_{min}-L_{max})] \times 100$, whereas "L" indicates lysis. $L_{min}$ refers to the luminescence at minimum lysis in the absence of bstb and $L_{max}$ to the luminescence at maximum lysis (equal to spontaneous luminescence counts) in the absence of bstb achieved by addition of Triton X-100 (2% final concentration).

The EC50 value was calculated using a sigmoidal dose-response algorithm (log(agonist) vs. response (three parameters)) integrated into PRISM 6 software (GraphPad Software, San Diego, Calif., USA).

The determined EC50 of bstb_369/367 was 39.71 pM and therewith three times lower than the EC50 of bstb_371/367 with 117.00 pM (FIG. 4A) on CLDN6-positive OV-90 cells. No lysis was observed with the CLDN6-negative control cell line MDA-MB-231. The outcome of this assay depends strongly on the potency of the human PBMC which vary according to the immune status of the donor as also reported by others (see e.g. Lutterbuese et al. 2010). Thus, using eight different PBMC donors we determined an EC50 value range of bstb_369/367 protein from 0.98 fM to 39.71 pM (data not shown).

b. Comparison of Bstb_369/367 and a CLDN6×CD3 Bi-(scFv)$_2$

The bivalently CLDN6-binding bstb_369/367 was compared to a highly monomeric (99.5%) in-house generated CDLN6×CD3 bi-(scFv)$_2$ (BioNTech AG, Stadler et al. 2015) to investigate beneficial avidity effects of the bivalent anti-tumor targeting on the lysis potency.

For this purpose, the bstb and the bi-(scFv)$_2$ were used in equimolar concentrations and the lysis effects were tested on PA-1, OV-90 and MDA-MB-231 in a cytotoxicity assay (FIG. 4B) basically as described in Example 2a. PA-1 cells were co-incubated for only 24 h Strikingly, bstb_369/367 mediated PA-1 cell killing of 58% with only 0.24 pM, the lowest concentration used for PA-1, whereas the bi-(scFv)$_2$ reference showed a lysis curve starting at 0% killing. In the case of OV-90, the higher potency of bstb_369/367 compared to bi-(scFv)$_2$ becomes obvious by the 55-fold lower EC50 of the bstb. Both molecules did not exert off target lysis effects.

Hence, the bivalent CLDN6 binding by the bstb molecule strongly elevates the target cell killing potential compared to the monovalent CLDN6 binding by the bi-(scFv)$_2$ molecule.

c. Investigation of the Impact of Bstb_369/367 High Molecular Weight Species on the Lysis Activity HMW species such as dimers or multimers can exert a different activity compared to the monomeric species due to their multivalency for the corresponding antigens. Even though the molecules have been shown to be stable in their monomeric state the impact of HMW species on the activity was tested for future safety aspects.

To this end, HMW species were collected during the purification procedure, enriched by SEC and spiked into the monomeric preparation to a defined quantity of 5%. Subsequently, 99.3% monomer and 94.3% monomer supplemented with 5% HMW species were compared in a cytotoxicity assay as described in Example 2a., but in 15-point, 20-fold serial dilution rows. PA-1 and OV-90 served as target cells. Co-incubation with bstb_369/367 was carried out for 16 h with the rather sensitive cell line PA-1 and for 48 h with the more robust cell line OV-90. The EC50 values were calculated using a sigmoidal dose-response algorithm (log(agonist) vs. response—Variable slope (four parameters)) integrated into PRISM 6 software (GraphPad Software) as shown in FIG. 4C. The calculated EC50 of the 5% HMW bstb_369/367 sample was in case of PA-1 1.5-fold higher and in case of OV-90 2.3-fold lower. Hence, a slight activity decrease was observed with PA-1 and a slight activity increase with OV-90. Overall, the impact of 5% HMW species on the activity is low and might depend on the target cell line and/or incubation time. With regard to the stability of the bstb protein and the low impact of the rather high percentage of HMW species the bstb molecule qualifies for a therapeutic product development.

d. Comparison of Bstb_369/367 with the Tag-Free Variants Bstb_5726/5725 and Bstb_5727/5725

The tag-free bstb variants were evaluated in a cytotoxicity assay and compared to bstb_369/367. In addition, the influence of HMW species on the activity was tested. The assay set-up was as described in Example 2c, but the test items were applied in 10-point, 5-fold serial dilutions to OV-90 as CLDN6$^+$ target cells only.

Figure 4D:
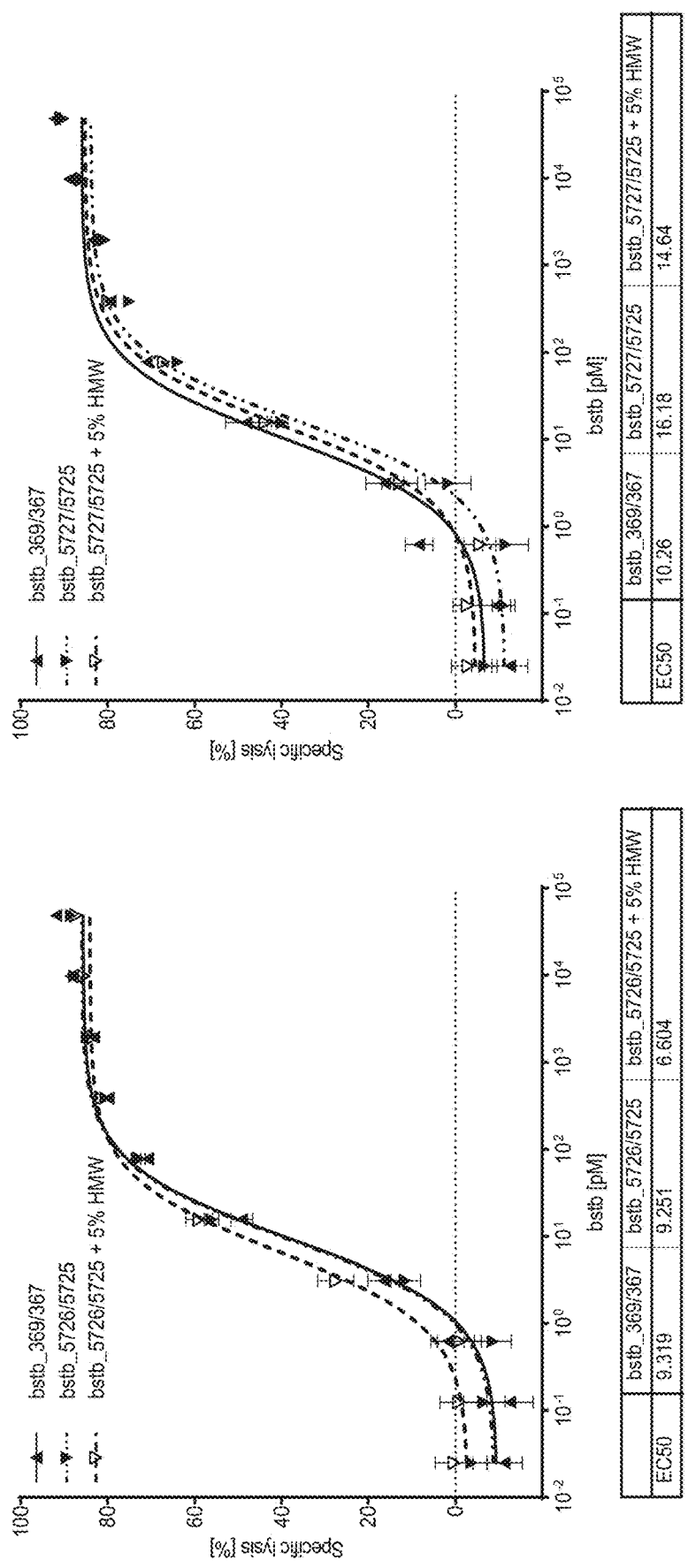

Bstb_369/367 and its tag-free analog bstb_5726/5725 (99.9% monomeric) presented equal lysis efficiency with an EC50 value of −9.3 pM. (FIG. 4D, left plot). 5% HMW led to a 1.4-fold lower EC50 value. The EC50 of $C_H1$(IgG2)-carrying variant bstb_5727/5725 (100% monomeric) was ~1.6-fold higher than the reference bstb_369/367, confirming the slightly lower potency of this variant as also shown for the tag-free variant in Example 2a. For bstb_5727/5725, 5% HMW barely influenced the potency (FIG. 4D, right plot). The EC50 with spiked HMW was only 1.1-fold lower as with the monomer in this exemplary study.

In conclusion, the tagged and the tag-free $C_H1$(IgG1)-carrying bstbs are equal in their functionality and exert a slightly higher potency compared to the $C_H1$(IgG2)-carrying bstbs. The influence of HMW species is low for both variants.

Example 3: T-Cell Modulation Mediated by Bstb_369/367 and Bstb_371/367

Modulation of T cells, precisely the activation and proliferation of T cells, as mediated by bstb_369/367 and bstb_371/367 was investigated in a similar set-up as described in Example 2 with the same target cell lines. Briefly, CLDN6+ target cells OV-90 and PA-1, and CLDN6- MDA-MB-231 control cells were seeded with human PBMC in 0.5 ml complete medium in 24-well plates in an E:T ratio of 5:1. To further confirm the target dependency, PBMC were subjected without target cells to co-incubation with bstb proteins. Bstb proteins bstb_369/367 and bstb_371/367 were added in a concentration range of 0.005-5,000 ng/ml in a 4-point, 100-fold serial dilution row. As positive control 100 ng/ml human anti-CD3 IgG2a clone OKT3 (BioXCell, West Lebanon, NH, USA), a target-independent T-cell activating murine IgG, was applied. As negative control we added DPBS, the bstb buffer.

a. T-Cell Activation

Effector and target cells were co-incubated with bstb for 48 h. PBMC were harvested, transferred to round bottom 96-wells (Fisher Scientific, Schwerte, Germany), centrifuged and washed. Cells were stained with anti-human fluorescence-labeled antibodies anti-CD5-PE-Cy7 (Abcam), CD69-APC, CD25-PE (BD Biosciences) and live/dead dye eFluor506 (eBioscience, Frankfurt am Main, Germany). Samples were measured with a BD FACSCantoII and 10,000 CD5+ viable singlet lymphocytes were recorded. Data was analyzed with FlowJo software V10 (Tree Star, San Carlos, Calif., USA) and Microsoft Excel 2010 (Microsoft Deutschland GmbH, UnterschleiBheim, Germany). Background signals from mock samples were subtracted.

As shown in FIG. 5A, both bstbs mediate strong CLDN6-dependent T-cell activation. After 48 h T cells reside in an intermediate activation stage as determined by the high percentage of double positivity for the early activation marker CD69 and the late activation marker CD25 and the absence of CD25 only positive T cells. Moreover, the data indicate that the lower the bstb concentration, the earlier is the activation state. Only at the high concentration of 5,000 ng/ml bstb proteins led to measurable target-independent T-cell activation which was below 5.5%. Bstb_369/367 shows slight but not significant higher potency than bstb_371/367 in the mediation of target-dependent T-cell activation (see also Table 5).

b. T-Cell Proliferation

PBMC were labeled with the CellTrace™ CFSE Cell Proliferation Kit (Thermo Fischer Scientific, Darmstadt, Germany) according to the manufacturer's protocol prior to assay set-up. Effector and target cells were co-incubated with bstb for 72 h. PBMC were harvested as described above in Example 3.a. Cells were stained with anti-human fluorescence-labeled antibodies anti-CD5-APC (BD Biosciences) and live/dead dye eFluor506 (eBioscience). Samples were measured with a BD FACSCantoII and 10,000 CD5+ viable singlet lymphocytes were recorded. Data was analyzed with FlowJo software V 10 from Tree Star and Microsoft Excel 2010.

As shown in Fig. ma, both bstbs mediate strong CLDN6-dependent T-cell proliferation as determined by fading CFSE positivity indicating cell division. A clear difference in potency of the two bstb molecules in terms of stronger proliferation could not be determined in the presence of PA-1. As also seen for the T-cell activation in the presence of OV-90, bstb_369/367 mediated stronger effects than bstb_371/367. No unspecific or target-independent T-cell proliferation was detected.

In summary, both bstb molecules mediate strong T-cell modulation in strict target dependency.

Example 4: Binding of Bstb_369/367 and Bstb_5726/5725 to CLDN6

Relative binding affinities of bi-(scFv)$_2$ reference protein, bstb_369/367 and its tag-free analog bstb_5726/5725 were determined using flow cytometric analysis. PA-1 cells endogenously expressing CLDN6 were harvested with 0.05% Trypsin/EDTA, washed with PBS and resuspended in FACS buffer (PBS containing 2% FCS and 0.1% sodium azide) at a concentration of $2 \times 10^6$ cells/ml. 100 µl of the cell suspension was incubated with a concentration series of the different respective antibodies diluted in FACS buffer (11-point, 2-fold dilution series 9.77-10,000 ng/ml) and incubated for 45 min at 4° C. The cells were then washed three times with FACS buffer and incubated for 45 min at 4° C. with Protein L (Pierce/Thermo Scientific) conjugated with FITC by Squarix (Squarix Biotechnology, Marl, Germany) at a concentration of 4 µg/ml. Subsequently, the cells were washed twice and resuspended in 100 µl FACS buffer. Binding was analyzed by flow cytometry using a BD

TABLE 5

T-cell activation by bstb_369/367 and bstb_371/367

| | Cell line | | | | | | | |
|---|---|---|---|---|---|---|---|---|
| | PA-1-SC12 | | OV-90-SC12 | | MDA-MB-231 | | No target cells | |
| | CLDN6 expression | | | | | | | |
| | + | | + | | − | | − | |
| | Test item | | | | | | | |
| | Bstb_369/367 | Bstb_371/367 | Bstb_369/367 | Bstb_371/367 | Bstb_369/367 | Bstb_371/367 | Bstb_369/367 | Bstb_371/367 |
| | Conc. [µg/ml] | | | | | | | |
| | 0.5 / 5000 | 0.5 / 5000 | 0.5 / 5000 | 0.5 / 5000 | 0.5 / 5000 | 0.5 / 5000 | 0.5 / 5000 | 0.5 / 5000 |
| Total activation [%] | 67.1 / 70.6 | 60.4 / 70.9 | 17.4 / 83.1 | 2.8 / 80.1 | 0.0 / 4.2 | 0.5 / 3.8 | 1.4 / 4.4 | 0.6 / 5.4 |
| CD69+/CD25+ [%] | 33.6 / 25.0 | 43.6 / 27.2 | 16.2 / 15.7 | 2.8 / 18.8 | 0.0 / 3.6 | 0.4 / 3.5 | 1.1 / 3.4 | 0.6 / 3.9 |
| CD69+/CD25+ [%] | 33.5 / 45.6 | 16.9 / 43.7 | 1.2 / 67.4 | 0.0 / 61.2 | 0.0 / 0.3 | 0.0 / 0.3 | 0.2 / 0.2 | 0.0 / 0.2 |
| CD69+/CD25+ [%] | 0.0 / 0.0 | 0.0 / 0.0 | 0.0 / 0.0 | 0.0 / 0.0 | 0.0 / 0.3 | 0.1 / 0.0 | 0.0 / 0.8 | 0.0 / 1.3 |

FACSArray (BD Biosciences). The EC50 of half maximal binding was determined using GraphPad Prism 6 One site—Specific binding.

Figure 6A:
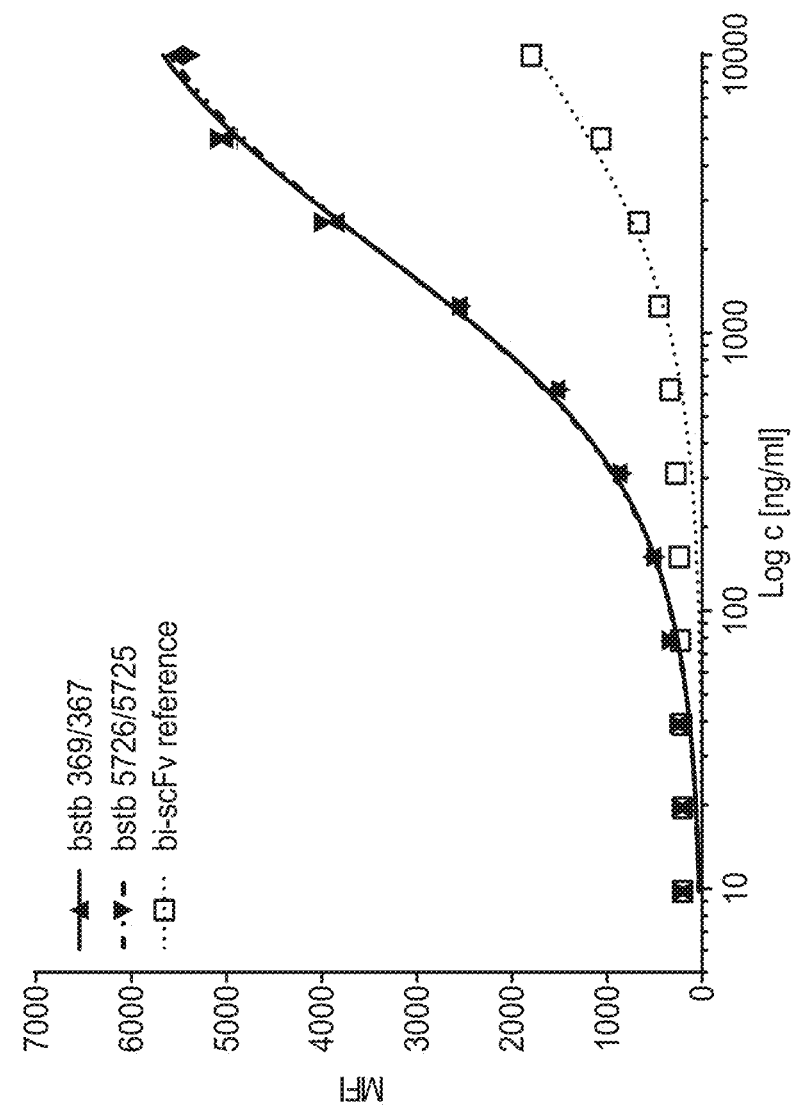
Figure 6B:
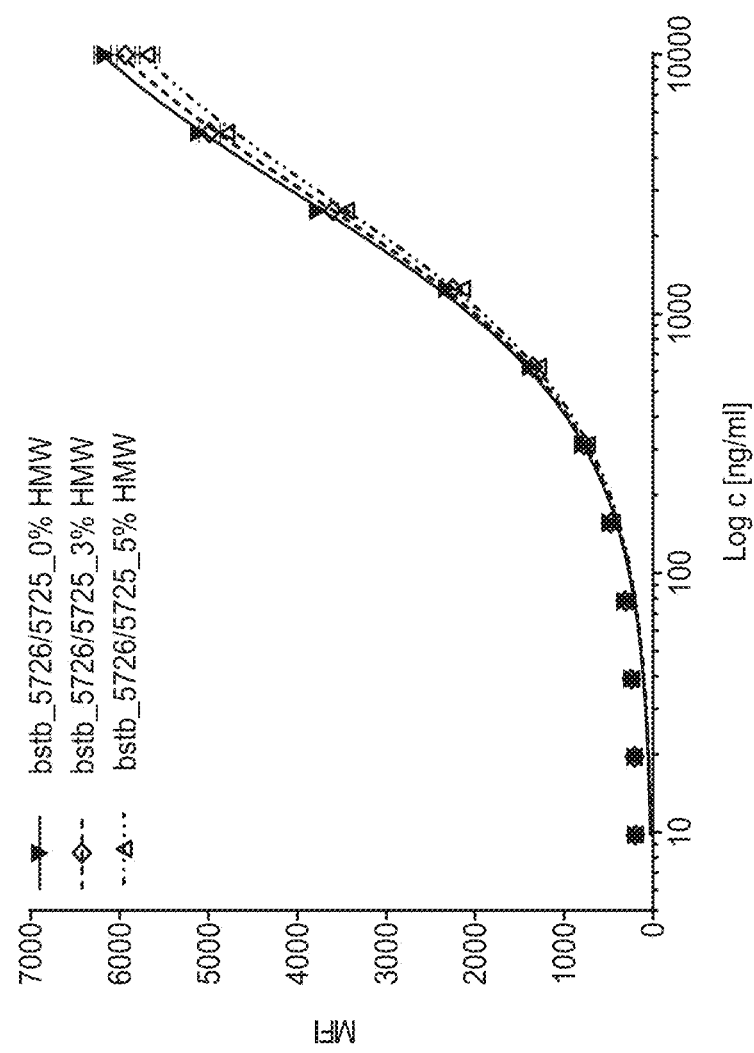

Bi-(scFv)$_2$ protein which possesses a monovalent CLDN6 binding site exhibited a low relative binding affinity (EC50: ~8.3 µg/ml corresponding to ~150 nM). In comparison, bstb_369/367 and bstb_5726/5725 demonstrated half maximal binding at a concentration of ~1.9 µg/ml corresponding to ~19 nM thus relative binding affinity was about 8-fold higher compared to the bi-(scFv)$_2$ reference protein (FIG. 6A). This indicates that binding to the target CLDN6 could be strongly improved by using bivalent binding sites thus increasing binding affinity by implementing avidity effects. Noteworthy, the binding curves of the tagged and tag-free bstbs are congruent. We further analyzed the influence of HMW species on the binding properties of bstb_5726/5725 monomers in flow cytometry using Protein L-FITC at a concentration of 4 µg/ml or PE-conjugated mouse anti-human IgG (Fab region) antibody (antikoerper-online, Aachen, Germany) at a concentration of 6 µg/ml as secondary detection reagents. The EC50 of half maximal binding did not differ between 100% monomer, 97% monomer/3% HMW and 95% monomer/5% HMW (varied between 28 nM and 31-34 nM depending on the secondary detection reagent). In FIG. 6B only the detection by Protein L-FITC is exemplary shown. These data are in accordance with data from cytotoxicity assays (see Example 2c) which clearly demonstrate that 5% HMW do not have relevant impact on the activity of the bstb_369/367 molecule thus favoring this format for a product development.

Example 5: Efficacy in a Mouse Xenograft Model

For the investigation of the therapeutic potential of the protein bstb_369/367 in vivo, the immunodeficient mouse strain NOD.Cg-Prkd$^{scid}$IL2rg$^{tm1Wjl}$/SzJ or short NSG (Jackson laboratory, Bar Harbour, ME, USA) was chosen. All mice were used in accordance with the guidelines from the Institutional Animal Care Committee of the Johannes Gutenberg University, Mainz, Germany.

a. Treatment of Advanced CLDN6-Expressing Tumors in Mice with Protein Bstb_369/367

In the exemplary study, male and female NSG mice at eight weeks of age and with a body weight of 21-36 g were used. CLDN6-positive OV-90 cells served as tumor cells and PBMC as effector cells.

Figure 7A:
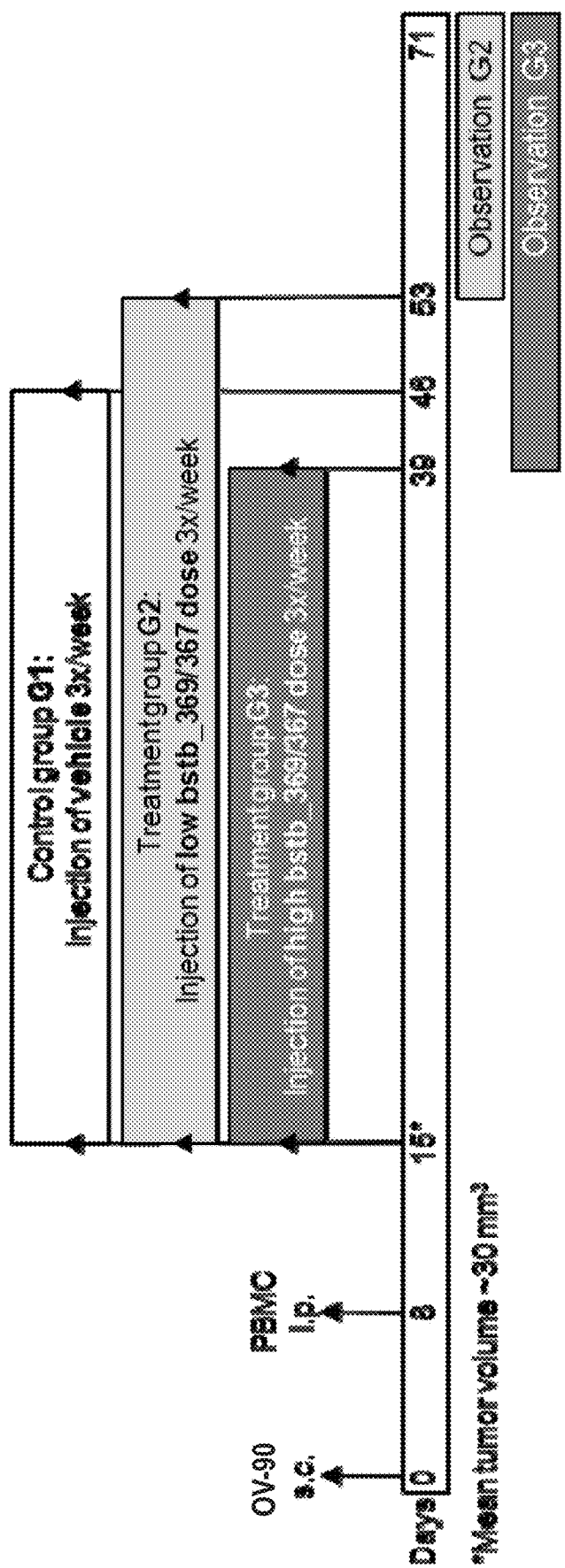

$5 \times 10^6$ tumor cells were inoculated subcutaneously (s.c.) and 1×107 PBMC were administered intraperitoneally (i.p.) eight days thereafter. Only PBMC engrafted mice—as analyzed in the peripheral blood five days post PBMC injection—were stratified into groups according to tumor volume and gender (both genders in all groups). The treatment was initiated at a mean tumor volume of ~30 mm$^3$ per group. Mice were treated three times per week (Mon-Wed-Fri) with vehicle (DPBS), 31 µg/kg bstb (low dose) or 308 µg/kg bstb (high dose) by i.p. injections. Group "G1-Vehicle" comprised four mice (n=4), "G2-bstb_369/367 (low dose)" eight mice (n=8) and "G3-bstb_369/367 (high dose)" nine mice (n=9). Treatment groups are summarized in Table 6. Administration was conducted intraperitoneally for five (G1), six (G2) or four (G3) consecutive weeks dependent on the tumor volume read-out (FIG. 7A). Twice per week tumor dimensions were measured with a digital calibrated caliper and the tumor volumes were calculated by the formula: tumor volume [mm$^3$]=length [mm]×(width [mm])$^2$/2. Mice were sacrificed by cervical dislocation when the tumor volume reached 1500 mm$^3$ or in case of severe morbidity (mainly symptoms of graft-versus-host disease (GVHD)).

Figure 7B:
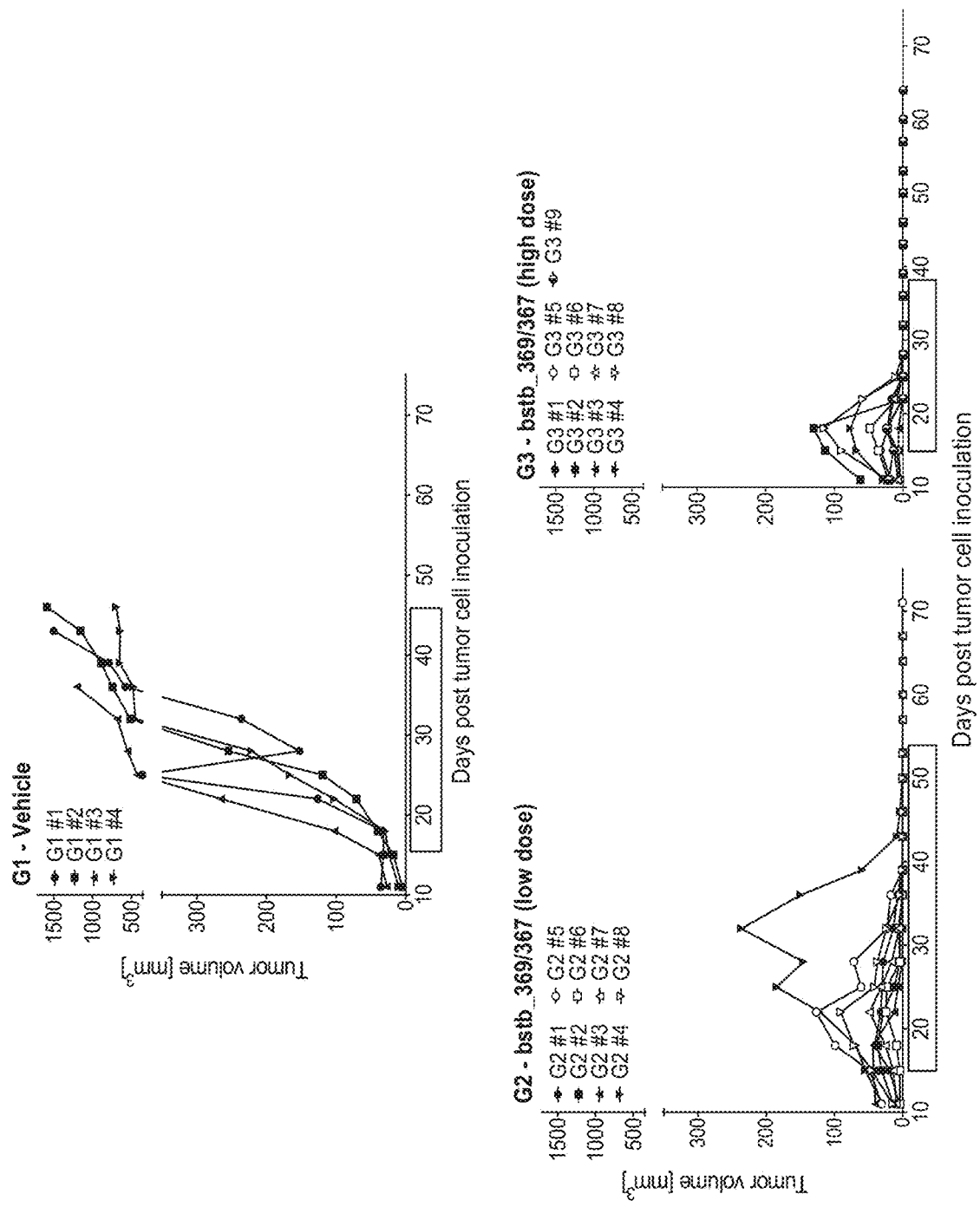

FIG. 7B illustrates the inhibition of tumor growth in all mice of the bstb-treated groups G2 and G3. Anti-tumor efficacy was measured as tumor growth inhibition/elimination and survival compared to the vehicle control G1. Treatment with test item bstb_369/367 resulted in tumor elimination in both dosing groups in contrast to the control group. All nine mice in the higher bstb_369/367 dose group (G3) were tumor-free after seven injections. All eight mice in the lower bstb_369/367 dose group (G2) were tumor-free after 15 injections. Tumor-free mice were observed for tumor relapse until GVHD symptoms occurred. No incidence of tumor relapse was registered in this period of time.

For the generation of a Kaplan-Meier survival plot (FIG. 7C) the day of treatment start was considered day 0. The survival was significantly prolonged in both bstb_369/367-treated groups compared to the control group G1 as determined by Kaplan-Meier survival statistics combined with the Mantel-Cox log-rank test for pairwise comparison. Comparison of G2 to G1 resulted in a p-value of p<0.0001 and comparison of G3 to G1 in p=0.0043. The median survival was 31 days in the control group G1 versus 52 and 42 days in treatment groups G2 and G3, respectively. In summary, bstb_369/367 demonstrated to be highly efficient in terms of tumor elimination and moreover beneficial in terms of survival in this GVHD-restricted mouse model.

TABLE 6

Treatment groups

| Treatment group (G) | # of mice (n) | Tumor cells | Effector cells | Bstb protein | Bstb protein dose [µg/kg] |
|---|---|---|---|---|---|
| G1 | 4 | OV-90 | PBMC | — | 0 |
| G2 | 8 | OV-90 | PBMC | 369/367 | 31 |
| G3 | 9 | OV-90 | PBMC | 369/367 | 308 | b. Determination of Therapy Influence on Body Weight

The body weight of each mouse was examined twice per week using a laboratory scale. No mouse in any group showed significant weight loss over the time of treatment (data not shown).

c. Splenocyte Isolation

After euthanasia of mice, spleens were dissected to detect the engraftment of human cells by flow cytometric analysis. Splenocyte isolation was performed immediately after spleen dissection by mashing the spleens through a 70 µm cell strainer placed into a 50 ml reaction tube with a sterile plunger of a 3-5 ml syringe and repeated flushing of the cell strainer with RT DPBS. Isolated splenocytes were centrifuged, DPBS decanted and the splenocyte pellets resuspended in 1 ml heat inactivated fetal bovine serum supplemented with 10% DMSO. Samples were immediately frozen at −65 to −85° C. and stored until splenocyte samples from all mice were complete.

d. Analysis of Engraftment of Human T Lymphocytes in Mouse Spleens

The complete collection of splenocyte samples was thawed at one time, all cells were washed twice with warm DPBS and $1 \times 10^6$ splenocytes per sample were incubated with fluorescence-conjugated antibodies (BD Biosciences) for 20 min at 4° C. in the dark to detect the engraftment of human cells by anti-hCD45-APC staining and the percentage of human T cells by anti-hCD3-FITC staining. Flow cytometric analysis was conducted with a FACSCanto II (BD Biosciences). Human T-cell engraftment could be confirmed by percentages of 50-95% hCD45/hCD3 double positive singlet splenocytes (data not shown).

Example 6: Estimation of Pharmacokinetic Behavior in Immunodeficient Mice

To determine the approximate half-life and clearance of bstb_369/367 protein in mice, we used female NSG mice at 9-49 weeks of age. 5 mg/kg highly monomeric (100%) bstb_369/367 in DPBS was i.p. injected per mouse. Group sizes comprised three mice with each group corresponding to one time point of blood retrieval. As basic value ("time after injection"=0 h) one group was injected with vehicle buffer (DPBS) only. Further time points for blood retrieval were set at 15 min, 1 h, 2 h, 3 h, 6 h and 8 h. Blood was directly collected in Li-Heparin tubes (Microvette 300 LH, Sarstedt, Nirmbrecht, Germany) and the plasma was separated by centrifugation as known by the person skilled in the art. Plasma was harvested, immediately shock frozen in liquid nitrogen and stored at ~65 to −85° C. until use.

An ELISA was performed for the quantitation of bstb_369/367 in plasma. To this end, a plasma aliquot of each group was thawed at RT and diluted in PBS/0.2% BSA. Diluted bstb_369/367-containing plasma and bstb_369/367 protein as standard row (0.39 ng/ml to 3.41 µg/ml) were added to MaxiSorp™ plates (Thermo Scientific) coated with goat-anti-human IgG F(ab')$_2$ antibody (Abd Serotec, Oxford, UK) and blocked with 3% milk. After a wash step, a murine IgG specific for the anti-CLDN6 binding site of bstb_369/367 (Ganymed Pharmaceuticals AG) at a concentration of 3.5 µg/ml was incubated followed by a wash step and the incubation with an alkaline-phosphatase conjugated goat-anti-mouse IgG (Fc) antibody (Dianova, Hamburg, Germany) in a 1:500 dilution. Finally, 4-Nitrophenyl Phosphate Disodium Salt 6-hydrate, short PNPP (PanReac AppliChem, Darmstadt, Germany), was added as substrate for alkaline-phosphatase and the reaction was stopped after 30 min with 3 M potassium hydroxide. The ELISA was measured with a microplate reader M200 Pro (Tecan) at 405/492 nm. On the basis of the bstb_369/367 standard curve the measured absorption values were transformed into concentration values.

As demonstrated in FIG. 8, the maximal bstb_369/367 plasma concentration of 34 µg/ml was reached within 1 h after i.p. injection. At the end point of analysis, 8 h after i.p. injection, the bstb_369/367 protein was still detectable in the serum (8 ng/ml).

Taking into account the binding to tumor target and T cells in patients which ensures a long-lasting circulation, injection cycles with bstb molecules once to twice per week are conceivable.

Example 7: In Vivo Dose-Finding Study with Tag-Free Bstb_5726/5725

Figure 9A:
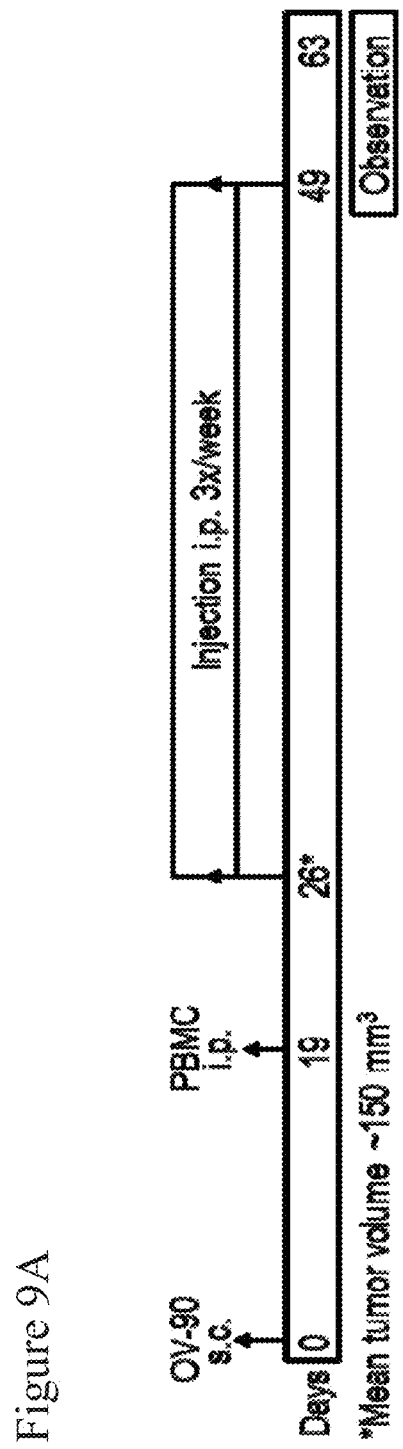

A xenograft model was set up as described in Example 5 according to the schedule illustrated in FIG. 9A. Briefly, 44 male and female NSG in the age of 10-36 weeks were engrafted with OV-90 (s.c.) and human PBMC (i.p.). Mice were randomized into seven groups with six treatment groups i six mice and one PBS control group á eight mice. To determine an optimal bstb_5726/5725 dose, concentrations above and below the effective doses of bstb_369/367 used in Example 5 (~300 and 30 µg/kg) were chosen, precisely 1,000 µg/kg, 300 µg/kg, 100 µg/kg, 30 µg/kg, 10 µg/kg and 3 µg/kg. At the day of treatment start the mean tumor volume was ~150 mm$^3$ in the randomized groups. Treatment was applied i.p. three times per week starting at day 28 post tumor cell inoculation. In total, 11 injections were given per group. Tumors were measured twice per week with a digital caliper.

Figure 9B:
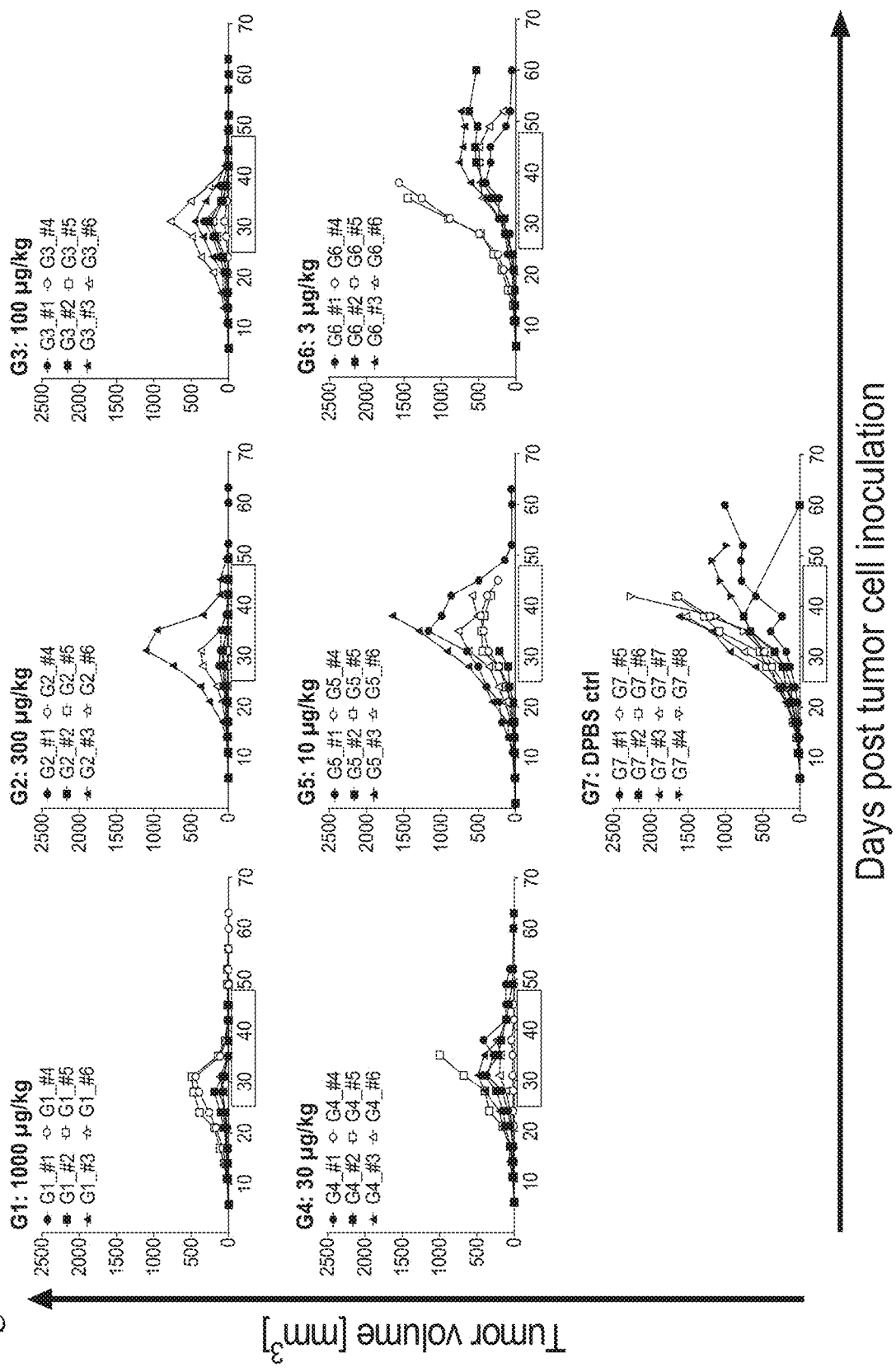

As shown in FIG. 9B, the tumor reduction rate correlates with the dose. A tumor volume of ~400 mm$^3$ at the start of treatment seems to present a critical size that is only eliminated by bstb doses>30 µg/kg. Interestingly, even 3 µg/kg led to tumor growth and size reduction over time assuming an accumulating effect of bstb in the tumor mass.

In this setting, 100 µg/kg were determined as a highly effective and safe dose. In the highest dose group of 1,000 µg/kg we observed adverse effects such as yellow discoloration of the skin and weight loss.

Example 8: Generation, Purification and Analysis of Bispecific Antibody-Derivatives Targeting CLDN18.2 and CD3 a. Sequence Origin, Design of Bstb Constructs, and Cloning into Expression Vectors The bispecific chimeric TriMAB (bstb) constructs were designed as antigen binding fragments (Fab) equipped with two single-chain variable fragments (scFv) at the C-terminus of the constant regions. The Fab binding domain is specific for the human T-cell receptor component CD3ε. The anti-CD3 variable heavy chain region ($V_H$) and the corresponding variable light chain region (VL) domains are derived from IgG TR66 (Lanzavecchia und Scheidegger 1987). The cysteine at position 114 has been substituted by serine. The constant heavy ($C_H1$) and constant light chain region ($C_L$) are of human origin. We chose kappa-type constant light region for our constructs. The two scFv-binding moieties are specific for the human tumor-associated antigen (TAA) CLDN18.2. The corresponding $V_H$ and $V_L$ regions are derived from the chimeric IgG1 IMAB362 (Ganymed Pharmaceuticals AG, Mainz, Germany) (e.g. Woll et al. 2014) that is currently in clinical trials such as NCT01630083 and NCT01671774. The orientation of the VH and VL regions and the selection of the linkers in the scFv moieties correlate to bi-(scFv)$_2$ molecules 5506 and 5538 described in patent application PCT/EP2013/003399. FIG. 18 shows the amino acid sequences of $V_H$ and $V_L$ domains that were used in the course of the invention. Four bstb molecules were generated as first generation differing in their $C_H1$ region and in the IMAB362 scFv moiety. Bstb_5730/5728 and bstb_5731/5729 contain the $C_H1$ region derived from human IgG1, bstb_5732/5728 and bstb_5733/5729 the $C_H1$ region derived from human IgG2. Furthermore, bstb_5730/5728 and bstb_5732/5728 carry the IMAB362 scFv-moiety in the VH-VL 5 orientation, whereas bstb_5731/5729 and bstb_5733/5728 carry the IMAB362 scFv-moiety in the $V_L$-$V_H$ orientation. The following molecules were obtained on protein level for the formation of bstb molecules:

Bstb_5730/5728:

N - $V_H^{\alpha CD3}$-$C_H$1(IgG1)-$V_H^{\alpha CLDN18.2}$-$V_L^{\alpha CLDN18.2}$-6xHis-tag - C (Fd bstb_5730/5728)
N - $V_L^{\alpha CD3}$-$C_L$-$V_H^{\alpha CLDN18.2}$-$V_L^{\alpha CLDN18.2}$-Strep-tag - C       (L bstb_5730/5728)

Bstb_5732/5728:

N - $V_H^{\alpha CD3}$-$C_H$1(IgG2)-$V_H^{\alpha CLDN18.2}$-$V_L^{\alpha CLDN18.2}$-6xHis-tag - C (Fd bstb_5732/5728)
N - $V_L^{\alpha CD3}$-$C_L$-$V_H^{\alpha CLDN18.2}$-$V_L^{\alpha CLDN18.2}$-Strep-tag - C       (L bstb_5732/5728)

Bstb_5731/5729:

N - $V_H^{\alpha CD3}$-$C_H$1(IgG1)-$V_L^{\alpha CLDN18.2}$-$V_H^{\alpha CLDN18.2}$-6xHis-tag - C (Fd bstb_5731/5729)
N - $V_L^{\alpha CD3}$-$C_L$-$V_L^{\alpha CLDN18.2}$-$V_H^{\alpha CLDN18.2}$-Strep-tag - C       (L bstb_5731/5729)

Bstb_5733/5729:

N - $V_H^{\alpha CD3}$-$C_H$1(IgG2)-$V_L^{\alpha CLDN18.2}$-$V_H^{\alpha CLDN18.2}$-6xHis-tag - C (Fd bstb_5733/5729)
N - $V_L^{\alpha CD3}$-$C_L$-$V_L^{\alpha CLDN18.2}$-$V_H^{\alpha CLDN18.2}$-Strep-tag - C       (L bstb_5733/5729)

C = C-terminus, $C_H$ = constant heavy chain region, $C_L$ = constant light chain region, Fd = digestible fragment (heavy chain portion of Fab), L = light chain portion of Fab, N = N-Terminus, $V_H$ = variable heavy chain domain, $V_L$ = variable light chain domain.

Table 7 summarizes the information about bstb constructs specific for the TAA CLDN18.2 that were generated in the course of the invention. Information on specificity, sequence origin from monoclonal antibodies (mAB), codon usage and additional sequence features are listed. Sequences encoding the variable domains of the target cell binding moieties were originally received from Ganymed Pharmaceuticals AG.

Figure 10A:
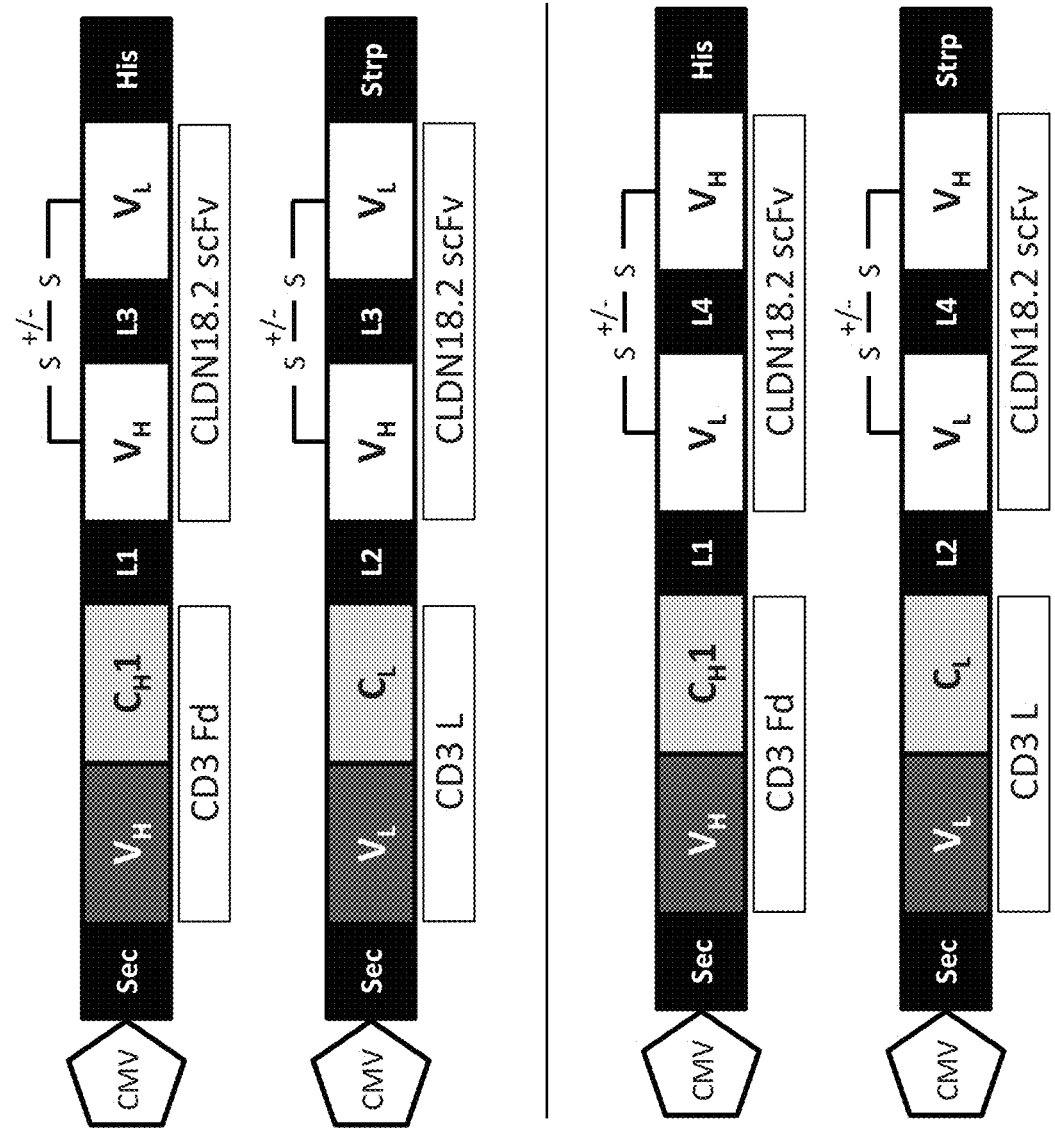
Figure 10B:
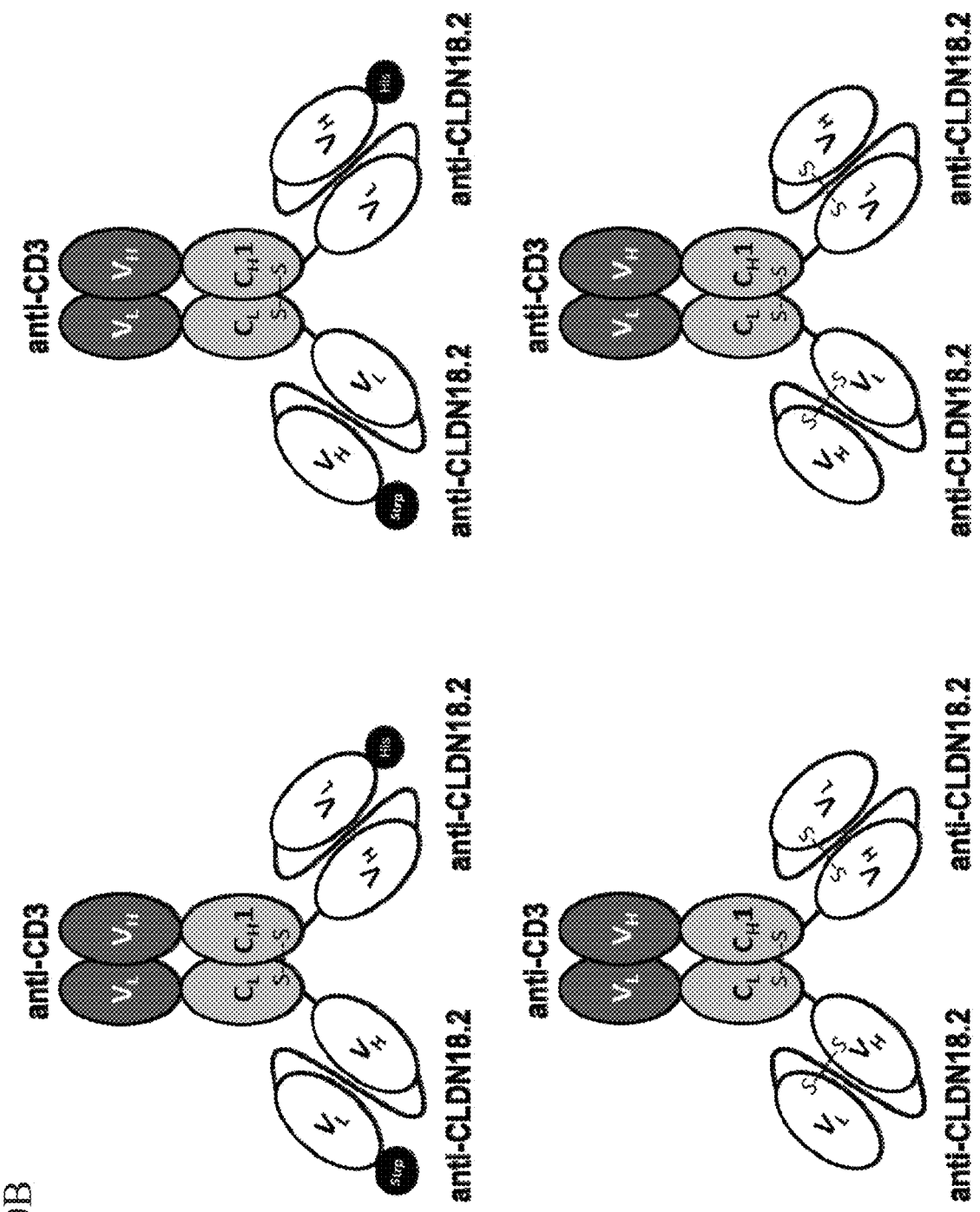

DNA cloning and pCEP4 expression vector construction was carried out by GeneArt (GeneArt/Thermo Fisher Scientific). A human IgG secretion signal sequence coding for MGWSCIILFLVATATGVHS (SEQ ID NO: 71) was introduced at the 5'-end upstream of the Fd—and L-bstb V-region sequences for protein secretion into the culture medium. A sequence coding for a 20 amino acid (AA) flexible glycine-serine (G-S) peptide linker ((GGGGS)$_4$) (SEQ ID NO: 68) was inserted to join the VH and VL domains for the composition of the anti-TAA scFv in VH-VL-orientation, whereas a 25 AA flexible (GGGGS)$_5$-peptide linker (SEQ ID NO: 69) was inserted for the composition of the anti-TAA scFv in $V_L$-$V_H$-orientation. The one scFv domain sequence was connected to the Fd-portion (C-terminus of $C_H$1) by a sequence coding for an 18 AA linker (SGPGG-GRS(GGGGS)$_2$) (SEQ ID NO: 66) and the other scFv was connected to the L-portion (C-terminus of $C_L$) by a sequence coding for a six AA linker (DVPGGS) (SEQ ID NO: 67). The different linker lengths allowed the discrimination of the Fd- and the L-portion by size. A 6xHis-tag sequence was added to the 3'-end of the Fd-scFv moiety and a Strep-tag to the 3-end of the L-scFv moiety to facilitate purification of pure heterodimeric bstb of the first generation. In Table 8 the full bstb protein coding DNA sequences are listed. In Table 9, the protein coding DNA sequences of the parental bi-(scFv)$_2$ and the reference bi-(scFv)$_2$ used for in vitro studies are listed. The C-terminal 6xHis-tag and Strep-tag served for affinity purification of the protein and for detection analysis. All constructs were verified by external sequencing service. The construct schemata are illustrated in FIG. 10A. Second generation bstbs were designed without tags and disulfide bridges were introduced into the scFv moieties.

TABLE 7

Summary of CLDN18.2 × CD3-bstb antibody features

| Internal name | Specificity | Origin of scFv $V_H$-$V_L$ regions | CLDN18.2-scFv $V_H$/$V_L$ orientation | CDLN18.2-scFv reference bi-(scFv)$_2$ | Origin of Fab $V_H$-$V_L$ region | Codon usage | $C_H$1 | Tag | ds bridge in scFv moiety |
|---|---|---|---|---|---|---|---|---|---|
| Bstb_5730/5728 (SEQ ID NO: 30/32) | HS | IMAB362 | $V_H$-$V_L$ | 5506 (SEQ ID NO: 76) | TR66(C114S) | CG | IgG1 | His/Strp | – |
| Bstb_5732/5728 (SEQ ID NO: 31/32) | HS | IMAB362 | $V_H$-$V_L$ | 5506 (SEQ ID NO: 76) | TR66(C114S) | CG | IgG2 | His/Strp | – |
| Bstb_5731/5729 (SEQ ID NO: 33/35) | HS | IMAB362 | $V_L$-$V_H$ | 5538 (SEQ ID NO: 77) | TR66(C114S) | CG | IgG1 | His/Strp | – |
| Bstb_5733/5729 (SEQ ID NO: 34/35) | HS | IMAB362 | $V_L$-$V_H$ | 5538 (SEQ ID NO: 77) | TR66(C114S) | CG | IgG2 | His/Strp | – |
| Bstb_5745/5747 (SEQ ID NO: 36/37) | HS | IMAB362 | $V_H$-$V_L$ | 5506 (SEQ ID NO: 76) | TR66(C114S) | CG | IgG1 | — | – |
| Bstb_5746/5748 (SEQ ID NO: 38/39) | HS | IMAB362 | $V_L$-$V_H$ | 5538 (SEQ ID NO: 77) | TR66(C114S) | CG | IgG1 | — | – |
| Bstb_5749/5751 (SEQ ID NO: 40/41) | HS | IMAB362 | $V_H$-$V_L$ | 5506 (SEQ ID NO: 76) | TR66(C114S) | CG | IgG1 | — | + |
| Bstb_5750/5752 (SEQ ID NO: 42/43) | HS | IMAB362 | $V_L$-$V_H$ | 5538 (SEQ ID NO: 77) | TR66(C114S) | CG | IgG1 | — | + |

$C_H$1 indicates constant heavy region 1;
CG, Cricetulus griseus;
ds, disulfide;
IMAB, ideal monoclonal antibody;
His, 6xHis-tag;
HS, *Homo sapiens*;
IgG, immunoglobulin G;
Strp, Strep-tag.

TABLE 8

CLDN18.2 × CD3-bstb DNA coding sequences

| Plasmid internal name | Corresponding bstb fragment | DNA coding sequence |
|---|---|---|
| #5728 | L bstb_5730/5728, L bstb_5732/5728 | ATGGGCTGGTCCTGCATCATCCTGTTTCTGGTGGCTACCGCCACCGGCGT GCACTCTCAGATCGTGCTGACCCAGTCTCCCGCCATCATGTCTGCTAGCC CTGGCGAGAAAGTGACAATGACCTGCCGGGCCTCCTCCTCCGTGTCCTAC ATGAACTGGTATCAGCAGAAGTCCGGCACCTCCCCCAAGCGGTGGATCTA CGACACCTCCAAGGTGGCCTCTGGCGTGCCCTACAGATTCTCCGGCTCTG GCTCTGGCACCTCCTACAGCCTGACCATCTCCAGCATGGAAGCCGAGGAT GCCGCCACCTACTACTGCCAGCAGTGGTCCTCCAACCCCCTGACCTTTGG CGCTGGCACCAAGCTGGAACTGAAGCGGACCGTGGCCGCTCCTTCCGTGT TCATCTTCCCTCCCTCCGACGAGCAGCTGAAGTCCGGCACCGCCTCCGTG GTGTGCCTGCTGAACAACTTCTACCCTCGGGAGGCCAAGGTGCAGTGGAA GGTGGACAACGCCCTGCAGTCCGGCAACTCCCAGGAAAGCGTCACCGAGC AGGACTCCAAGGACAGCACCTACTCCCTGTCCTCCACCCTGACCCTGTCC AAGGCCGACTACGAGAAGCACAAGGTGTACGCCTGCGAGGTGACCCACCA GGGCCTGTCCAGCCCTGTGACCAAGTCCTTCAACCGGGGCGAGTGTGACG TGCCTGGTGGTAGCCAGGTGCAGCTGCAGCAGCCTGGCGCTGAACTGGTC CGACCTGGCGCCTCCGTGAAGCTGTCCTGCAAGGCCTCCGGCTACACCTT CACCAGCTACTGGATCAACTGGGTCAAGCAGCGGCCTGGCCAGGGCCTGG AATGGATCGGCAACATCTACCCCTCCGACTCCTACACCAACTACAACCAG AAGTTCAAGGACAAGGCCACCCTGACCGTGGACAAGTCCTCCTCCACCGC CTACATGCAGCTGTCCAGCCCCACCTCCGAGGACTCCGCCGTGTACTACT GCACCCGGTCCTGGCGGGGCAACTCCTTCGACTATTGGGGCCAGGGCACC ACCCTGACAGTGTCCTCTGGAGGCGGAGGATCTGGTGGTGGCGGATCTGG CGGCGGTGGAAGTGGCGGAGGTGGTAGCGACATCGTGATGACCCAGTCCC CCTCCAGCCTGACCGTGACCGCTGGCGAGAAAGTGACCATGAGCTGCAAG TCCTCCCAGTCCCTGCTGAACTCCGGCAACCAGAAGAACTACCTGACCTG GTATCAGCAGAAGCCCGGCCAGCCCCCCAAGCTGCTGATCTACTGGGCCT CCACCCGCGAGTCTGGCGTGCCCGATAGATTCACCGGCTCCGGCAGCGGC ACCGACTTTACCCTGACCATCTCCAGCGTGCAGGCCGAGGACCTGGCCGT GTATTACTGTCAGAACGACTACTCCTACCCCTTCACCTTCGGCTCTGGCA CCAAGCTGGAAATCAAGTCTGCCTGGAGCCACCCACAGTTCGAGAAGTGA |
| #5729 | L bstb_5731/5729, L bstb_5733/5729 | ATGGGCTGGTCCTGCATCATCCTGTTTCTGGTGGCTACCGCCACCGGCGT GCACTCTCAGATCGTGCTGACCCAGTCTCCCGCCATCATGTCTGCTAGCC CTGGCGAGAAAGTGACAATGACCTGCCGGGCCTCCTCCTCCGTGTCCTAC ATGAACTGGTATCAGCAGAAGTCCGGCACCTCCCCCAAGCGGTGGATCTA CGACACCTCCAAGGTGGCCTCTGGCGTGCCCTACAGATTCTCCGGCTCTG GCTCTGGCACCTCCTACAGCCTGACCATCTCCAGCATGGAAGCCGAGGAT GCCGCCACCTACTACTGCCAGCAGTGGTCCTCCAACCCCCTGACCTTTGG CGCTGGCACCAAGCTGGAACTGAAGCGGACCGTGGCCGCTCCTTCCGTGT TCATCTTCCCTCCCTCCGACGAGCAGCTGAAGTCCGGCACCGCCTCCGTG GTGTGCCTGCTGAACAACTTCTACCCTCGGGAGGCCAAGGTGCAGTGGAA GGTGGACAACGCCCTGCAGTCCGGCAACTCCCAGGAAAGCGTCACCGAGC AGGACTCCAAGGACAGCACCTACTCCCTGTCCTCCACCCTGACCCTGTCC AAGGCCGACTACGAGAAGCACAAGGTGTACGCCTGCGAGGTGACCCACCA GGGCCTGTCCAGCCCTGTGACCAAGTCCTTCAACCGGGGCGAGTGTGACG TGCCTGGTGGTAGCGACATCGTGATGACCCAGTCCCCCTCCAGCCTGACC GTGACCGCTGGCGAGAAAGTGACCATGAGCTGCAAGTCCTCCCAGTCCCT GCTGAACTCCGGCAACCAGAAGAACTACCTGACCTGGTATCAGCAGAAGC CCGGCCAGCCCCCCAAGCTGCTGATCTACTGGGCCTCCACCCGCGAGTCT GGCGTGCCCGATAGATTCACCGGCTCCGGCAGCGGCACCGACTTTACCCT GACCATCTCCAGCGTGCAGGCCGAGGACCTGGCCGTGTATTACTGTCAGA ACGACTACTCCTACCCCTTCACCTTCGGCTCTGGCACCAAGCTGGAAATC AAGGGAGGCGGTGGTTCAGGCGGCGGAGGCAGCGGTGGAGGTGGTAGTGG CGGTGGCGGTTCAGGGGGAGGTGGCTCGCAGGTGCAGCTGCAGCAGCCTG GCGCTGAACTGGTCCGACCTGGCGCCTCCGTGAAGCTGTCCTGCAAGGCC TCCGGCTACACCTTCACCAGCTACTGGATCAACTGGGTCAAGCAGCGGCC TGGCCAGGGCCTGGAATGGATCGGCAACATCTACCCCTCCGACTCCTACA CCAACTACAACCAGAAGTTCAAGGACAAGGCCACCCTGACCGTGGACAAG TCCTCCTCCACCGCCTACATGCAGCTGTCCAGCCCCACCTCCGAGGACTC CGCCGTGTACTACTGCACCCGGTCCTGGCGGGGCAACTCCTTCGACTATT GGGGCCAGGGCACCACCCTGACAGTGTCCTCTTCTGCCTGGAGCCACCCA CAGTTCGAGAAGTGA |
| #5730 | Fd bstb_5730/5728 | ATGGGCTGGTCCTGCATCATCCTGTTTCTGGTGGCTACCGCCACCGGCGT GCACTCTCCAGGTGCAGCTGCAGCAGTCTGGCGCTGAGCTGGCTAGACCTG GCGCCTCCGTGAAGATGTCCTGCAAGACCTCCGGCTACACCTTCACCCGG TACACCATGCACTGGGTCAAGCAGAGGCCTGGACAGGGCCTGGAATGGAT CGGCTACATCAACCCCTCCCGGGGCTACACCAACTACAACCAGAAGTTCA AGGACAAGGCCACCCTGACAACCGACAAGTCCTCCTCCACCGCCTACATG CAGCTGTCCTCCCTGACCTCCGAGGACTCCGCCGTGTACTACTGCGCCCG GTACTACGACGACCACTACTCCCTGGACTACTGGGGCCAGGGCACCACAC TGACAGTGTCTAGCGCCTCCACCAAGGGCCCTTCCGTGTTCCCTCTGGCC CCTTCCTCCAAGTCCACCTCCGGCGGCACCGCCGCTCTGGGCTGCCTGGT GAAGGACTACTTCCCTGAGCCTGTGACCGTGAGCTGGAACTCTGGCGCCC |

TABLE 8-continued

CLDN18.2 x CD3-bstb DNA coding sequences

| Plasmid internal name | Corresponding bstb fragment | DNA coding sequence |
|---|---|---|
| | | TGACCAGCGGCGTGCACACCTTCCCTGCCGTGCTGCAGTCCTCCGGCCTG
TACTCCCTGTCCTCCGTGGTGACCGTGCCTTCCTCCTCCCTGGGCACCCA
GACCTACATCTGCAACGTGAACCACAAGCCTTCCAACACCAAGGTGGACA
AGCGGGTGGAGCCTAAGTCCTGCTCCGGCCCTGGGGGCGGACGCAGCGGC
GGAGGCGGATCCGGCGGAGGAGGCTCTCAGGTGCAGCTGCAGCAGCCTGG
CGCTGAACTGGTCCGACCTGGCGCCTCCGTGAAGCTGTCCTGCAAGGCCT
CCGGCTACACCTTCACCAGCTACTGGATCAACTGGGTCAAGCAGCGGCCT
GGCCAGGGCCTGGAATGGATCGGCAACATCTACCCCTCCGACTCCTACAC
CAACTACAACCAGAAGTTCAAGGACAAGGCCACCCTGACCGTGGACAAGT
CCTCCTCCACCGCCTACATGCAGCTGTCCAGCCCCACCTCCGAGGACTCC
GCCGTGTACTACTGCACCCGGTCCTGGCGGGGCAACTCCTTCGACTATTG
GGGCCAGGGCACCACCCTGACAGTGTCCTCTGGAGGCGGAGGATCTGGTG
GTGGCGGATCTGGCGGCGGTGGAAGTGGCGGAGGTGGTAGCGACATCGTG
ATGACCCAGTCCCCCTCCAGCCTGACCGTGACCGCTGGCGAGAAAGTGAC
CATGAGCTGCAAGTCCTCCCAGTCCCTGCTGAACTCCGGCAACCAGAAGA
ACTACCTGACCTGGTATCAGCAGAAGCCCGGCCAGCCCCCCAAGCTGCTG
ATCTACTGGGCCTCCACCCGCGAGTCTGGCGTGCCCGATAGATTCACCGG
CTCCGGCAGCGGCACCGACTTTACCCTGACCATCTCCAGCGTGCAGGCCG
AGGACCTGGCCGTGTATTACTGTCAGAACGACTACTCCTACCCCTTCACC
TTCGGCTCTGGCACCAAGCTGGAAATCAAGGGCGGCTCCCACCACCACCA
TCACCACTGA |
| #5731 | Fd bstb_5731/5729 | ATGGGCTGGTCCTGCATCATCCTGTTTCTGGTGGCTACCGCCACCGGCGT
GCACTCCCAGGTGCAGCTGCAGCAGTCTGGCGCTGAGCTGGCTAGACCTG
GCGCCTCCGTGAAGATGTCCTGCAAGACCTCCGGCTACACCTTCACCCGG
TACACCATGCACTGGGTCAAGCAGAGGCCTGGACAGGGCCTGGAATGGAT
CGGCTACATCAACCCCTCCCGGGGCTACACCAACTACAACCAGAAGTTCA
AGGACAAGGCCACCCTGACAACCGACAAGTCCTCCTCCACCGCCTACATG
CAGCTGTCCTCCCTGACCTCCGAGGACTCCGCCGTGTACTACTGCGCCCG
GTACTACGACGACCACTACTCCCTGGACTACGGGGCCAGGGCACCACAC
TGACAGTGTCTAGCGCCTCCACCAAGGGCCCTTCCGTGTTCCCTCTGGCC
CCTTCCTCCAAGTCCACCTCCGGCGGCACCGCCGCTCTGGGCTGCCTGGT
GAAGGACTACTTCCCTGAGCCTGTGACCGTGAGCTGGAACTCTGGCGCCC
TGACCAGCGGCGTGCACACCTTCCCTGCCGTGCTGCAGTCCTCCGGCCTG
TACTCCCTGTCCTCCGTGGTGACCGTGCCTTCCTCCTCCCTGGGCACCCA
GACCTACATCTGCAACGTGAACCACAAGCCTTCCAACACCAAGGTGGACA
AGCGGGTGGAGCCTAAGTCCTGCTCCGGCCCTGGGGGCGGACGCAGCGGC
GGAGGCGGATCCGGCGGAGGAGGCTCTGACATCGTGATGACCCAGTCCCC
CTCCAGCCTGACCGTGACCGCTGGCGAGAAAGTGACCATGAGCTGCAAGT
CCTCCCAGTCCCTGCTGAACTCCGGCAACCAGAAGAACTACCTGACCTGG
TATCAGCAGAAGCCCGGCCAGCCCCCCAAGCTGCTGATCTACTGGGCCTC
CACCCGCGAGTCTGGCGTGCCCGATAGATTCACCGGCTCCGGCAGCGGCA
CCGACTTTACCCTGACCATCTCCAGCGTGCAGGCCGAGGACCTGGCCGTG
TATTACTGTCAGAACGACTACTCCTACCCCTTCACCTTCGGCTCTGGCAC
CAAGCTGGAAATCAAGGGAGGCGGTGGTTCAGGCGGCGGAGGCAGCGGTG
GAGGTGGTAGTGGCGGTGGCGGTTCAGGGGGAGGTGGCTCGCAGGTGCAG
CTGCAGCAGCCTGGCGCTGAACTGGTCCGACCTGGCGCCTCCGTGAAGCT
GTCCTGCAAGGCCTCCGGCTACACCTTCACCAGCTACTGGATCAACTGGG
TCAAGCAGCGGCCTGGCCAGGGCCTGGAATGGATCGGCAACATCTACCCC
TCCGACTCCTACACCAACTACAACCAGAAGTTCAAGGACAAGGCCACCCT
GACCGTGGACAAGTCCTCCTCCACCGCCTACATGCAGCTGTCCAGCCCCA
CCTCCGAGGACTCCGCCGTGTACTACTGCACCCGGTCCTGGCGGGGCAAC
TCCTTCGACTATTGGGGCCAGGGCACCACCCTGACAGTGTCCTCTTCTCA
CCACCACCATCACCACTGA |
| #5732 | Fd bstb_5732/5728 | ATGGGCTGGTCCTGCATCATCCTGTTTCTGGTGGCTACCGCCACCGGCGT
GCACTCCCAGGTGCAGCTGCAGCAGTCTGGCGCTGAGCTGGCTAGACCTG
GCGCCTCCGTGAAGATGTCCTGCAAGACCTCCGGCTACACCTTCACCCGG
TACACCATGCACTGGGTCAAGCAGAGGCCTGGACAGGGCCTGGAATGGAT
CGGCTACATCAACCCCTCCCGGGGCTACACCAACTACAACCAGAAGTTCA
AGGACAAGGCCACCCTGACAACCGACAAGTCCTCCTCCACCGCCTACATG
CAGCTGTCCTCCCTGACCTCCGAGGACTCCGCCGTGTACTACTGCGCCCG
GTACTACGACGACCACTACTCCCTGGACTACGGGGCCAGGGCACCACAC
TGACAGTGTCTAGCGCCTCCACCAAGGGCCCTTCCGTGTTCCCTCTGGCC
CCTTGCTCCAAGTCCACCTCCGAAGGCACCGCCGCTCTGGGCTGCCTGGT
GAAGGACTACTTCCCTGAGCCTGTGACCGTGAGCTGGAACTCTGGCGCCC
TGACCAGCGGCGTGCACACCTTCCCTGCCGTGCTGCAGTCCTCCGGCCTG
TACTCCCTGTCCTCCGTGGTGACCGTGCCTTCCTCCAACTTCGGCACCCA
GACCTACACCTGCAACGTGGACCACAAGCCTTCCAACACCAAGGTGGACA
AGACCGTGGAGCCTAAGTCCGCCTCCGGCCCTGGGGGCGGACGCAGCGGC
GGAGGCGGATCCGGCGGAGGAGGCTCTCAGGTGCAGCTGCAGCAGCCTGG
CGCTGAACTGGTCCGACCTGGCGCCTCCGTGAAGCTGTCCTGCAAGGCCT
CCGGCTACACCTTCACCAGCTACTGGATCAACTGGGTCAAGCAGCGGCCT
GGCCAGGGCCTGGAATGGATCGGCAACATCTACCCCTCCGACTCCTACAC |

TABLE 8-continued

CLDN18.2 x CD3-bstb DNA coding sequences

| Plasmid internal name | Corresponding bstb fragment | DNA coding sequence |
|---|---|---|
|  |  | CAACTACAACCAGAAGTTCAAGGACAAGGCCACCCTGACCGTGGACAAGT<br>CCTCCTCCACCGCCTACATGCAGCTGTCCAGCCCCACCTCCGAGGACTCC<br>GCCGTGTACTACTGCACCCGGTCCTGGCGGGGCAACTCCTTCGACTATTG<br>GGGCCAGGGCACCACCCTGACAGTGTCCTCTGGAGGCGGAGGATCTGGTG<br>GTGGCGGATCTGGCGGCGGTGGAAGTGGCGGAGGTGGTAGCGACATCGTG<br>ATGACCCAGTCCCCCTCCAGCCTGACCGTGACCGCTGGCGAGAAAGTGAC<br>CATGAGCTGCAAGTCCTCCCAGTCCCTGCTGAACTCCGGCAACCAGAAGA<br>ACTACCTGACCTGGTATCAGCAGAAGCCCGGCCAGCCCCCCAAGCTGCTG<br>ATCTACTGGGCCTCCACCCGCGAGTCTGGCGTGCCCGATAGATTCACCGG<br>CTCCGGCAGCGGCACCGACTTTACCCTGACCATCTCCAGCGTGCAGGCCG<br>AGGACCTGGCCGTGTATTACTGTCAGAACGACTACTCCTACCCCTTCACC<br>TTCGGCTCTGGCACCAAGCTGGAAATCAAGGGCGGCTCCCACCACCACCA<br>TCACCACTGA |
| #5733 | Fd bstb_5733/5729 | ATGGGCTGGTCCTGCATCATCCTGTTTCTGGTGGCTACCGCCACCGGCGT<br>GCACTCCCAGGTGCAGCTGCAGCAGTCTGGCGCTGAGCTGGCTAGACCTG<br>GCGCCTCCGTGAAGATGTCCTGCAAGACCTCCGGCTACACCTTCACCCGG<br>TACACCATGCACTGGGTCAAGCAGAGGCCTGGACAGGGCCTGGAATGGAT<br>CGGCTACATCAACCCCTCCCGGGGCTACACCAACTACAACCAGAAGTTCA<br>AGGACAAGGCCACCCTGACAACCGACAAGTCCTCCTCCACCGCCTACATG<br>CAGCTGTCCTCCCTGACCTCCGAGGACTCCGCCGTGTACTACTGCGCCCG<br>GTACTACGACGACCACTACTCCCTGGACTACTGGGGCCAGGGCACCACAC<br>TGACAGTGTCTAGCGCCTCCACCAAGGGCCCTTCCGTGTTCCCTCTGGCC<br>CCTTGCTCCAAGTCCACCTCCGAAGGCACCGCCGCTCTGGGCTGCCTGGT<br>GAAGGACTACTTCCCTGAGCCTGTGACCGTGAGCTGGAACTCTGGCGCCC<br>TGACCAGCGGCGTGCACACCTTCCCTGCCGTGCTGCAGTCCTCCGGCCTG<br>TACTCCCTGTCCTCCGTGGTGACCGTGCCTTCCTCCAACTTCGGCACCCA<br>GACCTACACCTGCAACGTGGACCACAAGCCTTCCAACACCAAGGTGGACA<br>AGACCGTGGAGCCTAAGTCCGCCTCCGGCCCTGGGGGCGGACGCAGCGGC<br>GGAGGCGGATCCGGCGGAGGAGGCTCTGACATCGTGATGACCCAGTCCCC<br>CTCCAGCCTGACCGTGACCGCTGGCGAGAAAGTGACCATGAGCTGCAAGT<br>CCTCCCAGTCCCTGCTGAACTCCGGCAACCAGAAGAACTACCTGACCTGG<br>TATCAGCAGAAGCCCGGCCAGCCCCCCAAGCTGCTGATCTACTGGGCCTC<br>CACCCGCGAGTCTGGCGTGCCCGATAGATTCACCGGCTCCGGCAGCGGCA<br>CCGACTTTACCCTGACCATCTCCAGCGTGCAGGCCGAGGACCTGGCCGTG<br>TATTACTGTCAGAACGACTACTCCTACCCCTTCACCTTCGGCTCTGGCAC<br>CAAGCTGGAAATCAAGGGAGGCGGTGGTTCAGGCGGCGGAGGCAGCGGTG<br>GAGGTGGTAGTGGCGGTGGCGGTTCAGGGGGAGGTGGCTCGCAGGTGCAG<br>CTGCAGCAGCCTGGCGCTGAACTGGTCCGACCTGGCGCCTCCGTGAAGCT<br>GTCCTGCAAGGCCTCCGGCTACACCTTCACCAGCTACTGGATCAACTGGG<br>TCAAGCAGCGGCCTGGCCAGGGCCTGGAATGGATCGGCAACATCTACCCC<br>TCCGACTCCTACACCAACTACAACCAGAAGTTCAAGGACAAGGCCACCCT<br>GACCGTGGACAAGTCCTCCTCCACCGCCTACATGCAGCTGTCCAGCCCCA<br>CCTCCGAGGACTCCGCCGTGTACTACTGCACCCGGTCCTGGCGGGGCAAC<br>TCCTTCGACTATTGGGGCCAGGGCACCACCCTGACAGTGTCCTCTTCTCA<br>CCACCACCATCACCACTGA |
| #5745 | Fd bstb_5745/5747 | ATGGGCTGGTCCTGCATCATCCTGTTTCTGGTGGCTACCGCCACCGGCGT<br>GCACTCCCAGGTGCAGCTGCAGCAGTCTGGCGCTGAGCTGGCTAGACCTG<br>GCGCCTCCGTGAAGATGTCCTGCAAGACCTCCGGCTACACCTTCACCCGG<br>TACACCATGCACTGGGTCAAGCAGAGGCCTGGACAGGGCCTGGAATGGAT<br>CGGCTACATCAACCCCTCCCGGGGCTACACCAACTACAACCAGAAGTTCA<br>AGGACAAGGCCACCCTGACAACCGACAAGTCCTCCTCCACCGCCTACATG<br>CAGCTGTCCTCCCTGACCTCCGAGGACTCCGCCGTGTACTACTGCGCCCG<br>GTACTACGACGACCACTACTCCCTGGACTACTGGGGCCAGGGCACCACAC<br>TGACAGTGTCTAGCGCCTCCACCAAGGGCCCTTCCGTGTTCCCTCTGGCC<br>CCTTCCTCCAAGTCCACCTCCGGCGGCACCGCCGCTCTGGGCTGCCTGGT<br>GAAGGACTACTTCCCTGAGCCTGTGACCGTGAGCTGGAACTCTGGCGCCC<br>TGACCAGCGGCGTGCACACCTTCCCTGCCGTGCTGCAGTCCTCCGGCCTG<br>TACTCCCTGTCCTCCGTGGTGACCGTGCCTTCCTCCTCCCTGGGCACCCA<br>GACCTACATCTGCAACGTGAACCACAAGCCTTCCAACACCAAGGTGGACA<br>AGCGGGTGGAGCCTAAGTCCTGCTCCGGCCCTGGGGGCGGACGCAGCGGC<br>GGAGGCGGATCCGGCGGAGGAGGCTCTCAGGTGCAGCTGCAGCAGCCTGG<br>CGCTGAACTGGTCCGACCTGGCGCCTCCGTGAAGCTGTCCTGCAAGGCCT<br>CCGGCTACACCTTCACCAGCTACTGGATCAACTGGGTCAAGCAGCGGCCT<br>GGCCAGGGCCTGGAATGGATCGGCAACATCTACCCCTCCGACTCCTACAC<br>CAACTACAACCAGAAGTTCAAGGACAAGGCCACCCTGACCGTGGACAAGT<br>CCTCCTCCACCGCCTACATGCAGCTGTCCAGCCCCACCTCCGAGGACTCC<br>GCCGTGTACTACTGCACCCGGTCCTGGCGGGGCAACTCCTTCGACTATTG<br>GGGCCAGGGCACCACCCTGACAGTGTCCTCTGGAGGCGGAGGATCTGGTG<br>GTGGCGGATCTGGCGGCGGTGGAAGTGGCGGAGGTGGTAGCGACATCGTG<br>ATGACCCAGTCCCCCTCCAGCCTGACCGTGACCGCTGGCGAGAAAGTGAC<br>CATGAGCTGCAAGTCCTCCCAGTCCCTGCTGAACTCCGGCAACCAGAAGA<br>ACTACCTGACCTGGTATCAGCAGAAGCCCGGCCAGCCCCCCAAGCTGCTG |

TABLE 8-continued

CLDN18.2 x CD3-bstb DNA coding sequences

| Plasmid internal name | Corresponding bstb fragment | DNA coding sequence |
|---|---|---|
| | | ATCTACTGGGCCTCCACCCGCGAGTCTGGCGTGCCCGATAGATTCACCGG<br>CTCCGGCAGCGGCACCGACTTTACCCTGACCATCTCCAGCGTGCAGGCCG<br>AGGACCTGGCCGTGTATTACTGTCAGAACGACTACTCCTACCCCTTCACC<br>TTCGGCTCTGGCACCAAGCTGGAAATCAAGTGA |
| #5746 | Fd bstb_5746/5748 | ATGGGCTGGTCCTGCATCATCCTGTTTCTGGTGGCTACCGCCACCGGCGT<br>GCACTCCCAGGTGCAGCTGCAGCAGTCTGGCGCTGAGCTGGCTAGACCTG<br>GCGCCTCCGTGAAGATGTCCTGCAAGACCTCCGGCTACACCTTCACCCGG<br>TACACCATGCACTGGGTCAAGCAGAGGCCTGGACAGGGCCTGGAATGGAT<br>CGGCTACATCAACCCCTCCCGGGGCTACACCAACTACAACCAGAAGTTCA<br>AGGACAAGGCCACCCTGACAACCGACAAGTCCTCCTCCACCGCCTACATG<br>CAGCTGTCCTCCCTGACCTCCGAGGACTCCGCCGTGTACTACTGCGCCCG<br>GTACTACGACGACCACTACTCCCTGGACTACTGGGGCCAGGGCACCACAC<br>TGACAGTGTCTAGCGCCTCCACCAAGGGCCCTTCCGTGTTCCCTCTGGCC<br>CCTTCCTCCAAGTCCACCTCCGGCGGCACCGCCGCTCTGGGCTGCCTGGT<br>GAAGGACTACTTCCCTGAGCCTGTGACCGTGAGCTGGAACTCTGGCGCCC<br>TGACCAGCGGCGTGCACACCTTCCCTGCCGTGCTGCAGTCCTCCGGCCTG<br>TACTCCCTGTCCTCCGTGGTGACCGTGCCTTCCTCCTCCCTGGGCACCCA<br>GACCTACATCTGCAACGTGAACCACAAGCCTTCCAACACCAAGGTGGACA<br>AGCGGGTGGAGCCTAAGTCCTGCTCCGGCCCTGGGGCGGACGCAGCGGC<br>GGAGGCGGATCCGGCGGAGGAGGCTCTGACATCGTGATGACCCAGTCCCC<br>CTCCAGCCTGACCGTGACCGCTGGCGAGAAAGTGACCATGAGCTGCAAGT<br>CCTCCCAGTCCCTGCTGAACTCCGGCAACCAGAAGAACTACCTGACCTGG<br>TATCAGCAGAAGCCCGGCCAGCCCCCCAAGCTGCTGATCTACTGGGCCTC<br>CACCCGCGAGTCTGGCGTGCCCGATAGATTCACCGGCTCCGGCAGCGGCA<br>CCGACTTTACCCTGACCATCTCCAGCGTGCAGGCCGAGGACCTGGCCGTG<br>TATTACTGTCAGAACGACTACTCCTACCCCTTCACCTTCGGCTCTGGCAC<br>CAAGCTGGAAATCAAGGGAGGCGGTGGTTCAGGCGGCGGAGGCAGCGGTG<br>GAGGTGGTAGTGGCGGTGGCGGTTCAGGGGGAGGTGGCTCGCAGGTGCAG<br>CTGCAGCAGCCTGGCGCTGAACTGGTCCGACCTGGCGCCTCCGTGAAGCT<br>GTCCTGCAAGGCCTCCGGCTACACCTTCACCAGCTACTGGATCAACTGGG<br>TCAAGCAGCGGCCTGGCCAGGGCCTGGAATGGATCGGCAACATCTACCCC<br>TCCGACTCCTACACCAACTACAACCAGAAGTTCAAGGACAAGGCCACCCT<br>GACCGTGGACAAGTCCTCCTCCACCGCCTACATGCAGCTGTCCAGCCCCA<br>CCTCCGAGGACTCCGCCGTGTACTACTGCACCCGGTCCTGGCGGGGCAAC<br>TCCTTCGACTATTGGGGCCAGGGCACCACCCTGACAGTGTCCTCTTGA |
| #5747 | L bstb_5745/5747 | ATGGGCTGGTCCTGCATCATCCTGTTTCTGGTGGCTACCGCCACCGGCGT<br>GCACTCTCAGATCGTGCTGACCCAGTCTCCCGCCATCATGTCTGCTAGCC<br>CTGGCGAGAAAGTGACAATGACCTGCCGGGCCTCCTCCTCCGTGTCCTAC<br>ATGAACTGGTATCAGCAGAAGTCCGGCACCTCCCCCAAGCGGTGGATCTA<br>CGACACCTCCAAGGTGGCCTCTGGCGTGCCCTACAGATTCTCCGGCTCTG<br>GCTCTGGCACCTCCTACAGCCTGACCATCTCCAGCATGGAAGCCGAGGAT<br>GCCGCCACCTACTACTGCCAGCAGTGGTCCTCCAACCCCCTGACCTTTGG<br>CGCTGGCACCAAGCTGGAACTGAAGCGGACCGTGGCCGCTCCTTCCGTGT<br>TCATCTTCCCTCCCTCCGACGAGCAGCTGAAGTCCGGCACCGCCTCCGTG<br>GTGTGCCTGCTGAACAACTTCTACCCTCGGGAGGCCAAGGTGCAGTGGAA<br>GGTGGACAACGCCCTGCAGTCCGGCAACTCCCAGGAAAGCGTCACCGAGC<br>AGGACTCCAAGGACAGCACCTACTCCCTGTCCTCCACCCTGACCCTGTCC<br>AAGGCCGACTACGAGAAGCACAAGGTGTACGCCTGCGAGGTGACCCACCA<br>GGGCCTGTCCAGCCCTGTGACCAAGTCCTTCAACCGGGGCGAGTGTGACG<br>TGCCTGGTGGTAGCCAGGTGCAGCTGCAGCAGCCTGGCGCTGAACTGGTC<br>CGACCTGGCGCCTCCGTGAAGCTGTCCTGCAAGGCCTCCGGCTACACCTT<br>CACCAGCTACTGGATCAACTGGGTCAAGCAGCGGCCTGGCCAGGGCCTGG<br>AATGGATCGGCAACATCTACCCCTCCGACTCCTACACCAACTACAACCAG<br>AAGTTCAAGGACAAGGCCACCCTGACCGTGGACAAGTCCTCCTCCACCGC<br>CTACATGCAGCTGTCCAGCCCCACCTCCGAGGACTCCGCCGTGTACTACT<br>GCACCCGGTCCTGGCGGGGCAACTCCTTCGACTATTGGGGCCAGGGCACC<br>ACCCTGACAGTGTCCTCTGGAGGCGGAGGATCTGGTGGTGCGGATCTGG<br>CGGCGGTGGAAGTGGCGGAGGTGGTAGCGACATCGTGATGACCCAGTCCC<br>CCTCCAGCCTGACCGTGACCGCTGGCGAGAAAGTGACCATGAGCTGCAAG<br>TCCTCCCAGTCCCTGCTGAACTCCGGCAACCAGAAGAACTACCTGACCTG<br>GTATCAGCAGAAGCCCGGCCAGCCCCCCAAGCTGCTGATCTACTGGGCCT<br>CCACCCGCGAGTCTGGCGTGCCCGATAGATTCACCGGCTCCGGCAGCGGC<br>ACCGACTTTACCCTGACCATCTCCAGCGTGCAGGCCGAGGACCTGGCCGT<br>GTATTACTGTCAGAACGACTACTCCTACCCCTTCACCTTCGGCTCTGGCA<br>CCAAGCTGGAAATCAAGTGA |
| #5748 | L bstb_5746/5748 | ATGGGCTGGTCCTGCATCATCCTGTTTCTGGTGGCTACCGCCACCGGCGT<br>GCACTCTCAGATCGTGCTGACCCAGTCTCCCGCCATCATGTCTGCTAGCC<br>CTGGCGAGAAAGTGACAATGACCTGCCGGGCCTCCTCCTCCGTGTCCTAC<br>ATGAACTGGTATCAGCAGAAGTCCGGCACCTCCCCCAAGCGGTGGATCTA<br>CGACACCTCCAAGGTGGCCTCTGGCGTGCCCTACAGATTCTCCGGCTCTG<br>GCTCTGGCACCTCCTACAGCCTGACCATCTCCAGCATGGAAGCCGAGGAT |

TABLE 8-continued

CLDN18.2 x CD3-bstb DNA coding sequences

| Plasmid internal name | Corresponding bstb fragment | DNA coding sequence |
|---|---|---|
| | | GCCGCCACCTACTACTGCCAGCAGTGGTCCTCCAACCCCCTGACCTTTGG
CGCTGGCACCAAGCTGGAACTGAAGCGGACCGTGGCCGCTCCTTCCGTGT
TCATCTTCCCTCCCTCCGACGAGCAGCTGAAGTCCGGCACCGCCTCCGTG
GTGTGCCTGCTGAACAACTTCTACCCTCGGGAGGCCAAGGTGCAGTGGAA
GGTGGACAACGCCCTGCAGTCCGGCAACTCCCAGGAAAGCGTCACCGAGC
AGGACTCCAAGGACAGCACCTACTCCCTGTCCTCCACCCTGACCCTGTCC
AAGGCCGACTACGAGAAGCACAAGGTGTACGCCTGCGAGGTGACCCACCA
GGGCCTGTCCAGCCCTGTGACCAAGTCCTTCAACCGGGGCGAGTGTGACG
TGCCTGGTGGTAGCGACATCGTGATGACCCAGTCCCCCTCCAGCCTGACC
GTGACCGCTGGCGAGAAAGTGACCATGAGCTGCAAGTCCTCCCAGTCCCT
GCTGAACTCCGGCAACCAGAAGAACTACCTGACCTGGTATCAGCAGAAGC
CCGGCCAGCCCCCCAAGCTGCTGATCTACTGGGCCTCCACCCGCGAGTCT
GGCGTGCCCGATAGATTCACCGGCTCCGGCAGCGGCACCGACTTTACCCT
GACCATCTCCAGCGTGCAGGCCGAGGACCTGGCCGTGTATTACTGTCAGA
ACGACTACTCCTACCCCTTCACCTTCGGCTCTGGCACCAAGCTGGAAATC
AAGGGAGGCGGTGGTTCAGGCGGCGGAGGCAGCGGTGGAGGTGGTAGTGG
CGGTGGCGGTTCAGGGGGAGGTGGCTCGCAGGTGCAGCTGCAGCAGCCTG
GCGCTGAACTGGTCCGACCTGGCGCCTCCGTGAAGCTGTCCTGCAAGGCC
TCCGGCTACACCTTCACCAGCTACTGGATCAACTGGGTCAAGCAGCGGCC
TGGCCAGGGCCTGGAATGGATCGGCAACATCTACCCCTCCGACTCCTACA
CCAACTACAACCAGAAGTTCAAGGACAAGGCCACCCTGACCGTGGACAAG
TCCTCCTCCACCGCCTACATGCAGCTGTCCAGCCCCACCTCCGAGGACTC
CGCCGTGTACTACTGCACCCGGTCCTGGCGGGGCAACTCCTTCGACTATT
GGGGCCAGGGCACCACCCTGACAGTGTCCTCTTGA |
| #5749 | Fd bstb_5749/5751 | ATGGGCTGGTCCTGCATCATCCTGTTTCTGGTGGCTACCGCCACCGGCGT
GCACTCCCAGGTGCAGCTGCAGCAGTCTGGCGCTGAGCTGGCTAGACCTG
GCGCCTCCGTGAAGATGTCCTGCAAGACCTCCGGCTACACCTTCACCCGG
TACACCATGCACTGGGTCAAGCAGAGGCCTGGACAGGGCCTGGAATGGAT
CGGCTACATCAACCCCTCCCGGGGCTACACCAACTACAACCAGAAGTTCA
AGGACAAGGCCACCCTGACAACCGACAAGTCCTCCTCCACCGCCTACATG
CAGCTGTCCTCCCTGACCTCCGAGGACTCCGCCGTGTACTACTGCGCCCG
GTACTACGACGACCACTACTCCCTGGACTACTGGGGCCAGGGCACCACAC
TGACAGTGTCTAGCGCCTCCACCAAGGGCCCTTCCGTGTTCCCTCTGGCC
CCTTCCTCCAAGTCCACCTCCGGCGGCACCGCCGCTCTGGGCTGCCTGGT
GAAGGACTACTTCCCTGAGCCTGTGACCGTGAGCTGGAACTCTGGCGCCC
TGACCAGCGGCGTGCACACCTTCCCTGCCGTGCTGCAGTCCTCCGGCCTG
TACTCCCTGTCCTCCGTGGTGACCGTGCCTTCCTCCTCCCTGGGCACCCA
GACCTACATCTGCAACGTGAACCACAAGCCTTCCAACACCAAGGTGGACA
AGCGGGTGGAGCCTAAGTCCTGCTCCGGCCCTGGGGGCGGACGCAGCGGC
GGAGGCGGATCCGGCGGAGGAGGCTCTCAGGTGCAGCTGCAGCAGCCTGG
CGCTGAACTGGTCCGACCTGGCGCCTCCGTGAAGCTGTCCTGCAAGGCCT
CCGGCTACACCTTCACCAGCTACTGGATCAACTGGGTCAAGCAGCGGCCT
GGCCAGTGCCTGGAATGGATCGGCAACATCTACCCCTCCGACTCCTACAC
CAACTACAACCAGAAGTTCAAGGACAAGGCCACCCTGACCGTGGACAAGT
CCTCCTCCACCGCCTACATGCAGCTGTCCAGCCCCACCTCCGAGGACTCC
GCCGTGTACTACTGCACCCGGTCCTGGCGGGGCAACTCCTTCGACTATTG
GGGCCAGGGCACCACCCTGACAGTGTCCTCTGGAGGCGGAGGATCTGGTG
GTGGCGGATCTGGCGGCGGTGGAAGTGGCGGAGGTGGTAGCGACATCGTG
ATGACCCAGTCCCCCTCCAGCCTGACCGTGACCGCTGGCGAGAAAGTGAC
CATGAGCTGCAAGTCCTCCCAGTCCCTGCTGAACTCCGGCAACCAGAAGA
ACTACCTGACCTGGTATCAGCAGAAGCCCGGCCAGCCCCCCAAGCTGCTG
ATCTACTGGGCCTCCACCCGCGAGTCTGGCGTGCCCGATAGATTCACCGG
CTCCGGCAGCGGCACCGACTTTACCCTGACCATCTCCAGCGTGCAGGCCG
AGGACCTGGCCGTGTATTACTGTCAGAACGACTACTCCTACCCCTTCACC
TTCGGCTGCGGCACCAAGCTGGAAATCAAGTGA |
| #5750 | Fd bstb_5750/5752 | ATGGGCTGGTCCTGCATCATCCTGTTTCTGGTGGCTACCGCCACCGGCGT
GCACTCCCAGGTGCAGCTGCAGCAGTCTGGCGCTGAGCTGGCTAGACCTG
GCGCCTCCGTGAAGATGTCCTGCAAGACCTCCGGCTACACCTTCACCCGG
TACACCATGCACTGGGTCAAGCAGAGGCCTGGACAGGGCCTGGAATGGAT
CGGCTACATCAACCCCTCCCGGGGCTACACCAACTACAACCAGAAGTTCA
AGGACAAGGCCACCCTGACAACCGACAAGTCCTCCTCCACCGCCTACATG
CAGCTGTCCTCCCTGACCTCCGAGGACTCCGCCGTGTACTACTGCGCCCG
GTACTACGACGACCACTACTCCCTGGACTACTGGGGCCAGGGCACCACAC
TGACAGTGTCTAGCGCCTCCACCAAGGGCCCTTCCGTGTTCCCTCTGGCC
CCTTCCTCCAAGTCCACCTCCGGCGGCACCGCCGCTCTGGGCTGCCTGGT
GAAGGACTACTTCCCTGAGCCTGTGACCGTGAGCTGGAACTCTGGCGCCC
TGACCAGCGGCGTGCACACCTTCCCTGCCGTGCTGCAGTCCTCCGGCCTG
TACTCCCTGTCCTCCGTGGTGACCGTGCCTTCCTCCTCCCTGGGCACCCA
GACCTACATCTGCAACGTGAACCACAAGCCTTCCAACACCAAGGTGGACA
AGCGGGTGGAGCCTAAGTCCTGCTCCGGCCCTGGGGGCGGACGCAGCGGC
GGAGGCGGATCCGGCGGAGGAGGCTCTGACATCGTGATGACCCAGTCCCC
CTCCAGCCTGACCGTGACCGCTGGCGAGAAAGTGACCATGAGCTGCAAGT |

TABLE 8-continued

CLDN18.2 x CD3-bstb DNA coding sequences

| Plasmid internal name | Corresponding bstb fragment | DNA coding sequence |
|---|---|---|
| | | CCTCCCAGTCCCTGCTGAACTCCGGCAACCAGAAGAACTACCTGACCTGG<br>TATCAGCAGAAGCCCGGCCAGCCCCCCAAGCTGCTGATCTACTGGGCCTC<br>CACCCGCGAGTCTGGCGTGCCCGATAGATTCACCGGCTCCGGCAGCGGCA<br>CCGACTTTACCCTGACCATCTCCAGCGTGCAGGCCGAGGACCTGGCCGTG<br>TATTACTGTCAGAACGACTACTCCTACCCCTTCACCTTCGGCTGCGGCAC<br>CAAGCTGGAAATCAAGGGAGGCGGTGGTTCAGGCGGCGGAGGCAGCGGTG<br>GAGGTGGTAGTGGCGGTGGCGGTTCAGGGGGAGGTGGCTCGCAGGTGCAG<br>CTGCAGCAGCCTGGCGCTGAACTGGTCCGACCTGGCGCCTCCGTGAAGCT<br>GTCCTGCAAGGCCTCCGGCTACACCTTCACCAGCTACTGGATCAACTGGG<br>TCAAGCAGCGGCCTGGCCAGTGCCTGGAATGGATCGGCAACATCTACCCC<br>TCCGACTCCTACACCAACTACAACCAGAAGTTCAAGGACAAGGCCACCCT<br>GACCGTGGACAAGTCCTCCTCCACCGCCTACATGCAGCTGTCCAGCCCCA<br>CCTCCGAGGACTCCGCCGTGTACTACTGCACCCGGTCCTGGCGGGGCAAC<br>TCCTTCGACTATTGGGGCCAGGGCACCACCCTGACAGTGTCCTCTTGA |
| #5751 | L bstb_5749/5751 | ATGGGCTGGTCCTGCATCATCCTGTTTCTGGTGGCTACCGCCACCGGCGT<br>GCACTCTCAGATCGTGCTGACCCAGTCTCCCGCCATCATGTCTGCTAGCC<br>CTGGCGAGAAAGTGACAATGACCTGCCGGGCCTCCTCCTCCGTGTCCTAC<br>ATGAACTGGTATCAGCAGAAGTCCGGCACCTCCCCCAAGCGGTGGATCTA<br>CGACACCTCCAAGGTGGCCTCTGGCGTGCCCTACAGATTCTCCGGCTCTG<br>GCTCTGGCACCTCCTACAGCCTGACCATCTCCAGCATGGAAGCCGAGGAT<br>GCCGCCACCTACTACTGCCAGCAGTGGTCCTCCAACCCCCTGACCTTTGG<br>CGCTGGCACCAAGCTGGAACTGAAGCGGACCGTGGCCGCTCCTTCCGTGT<br>TCATCTTCCCTCCCTCCGACGAGCAGCTGAAGTCCGGCACCGCCTCCGTG<br>GTGTGCCTGCTGAACAACTTCTACCCTCGGGAGGCCAAGGTGCAGTGGAA<br>GGTGGACAACGCCCTGCAGTCCGGCAACTCCCAGGAAAGCGTCACCGAGC<br>AGGACTCCAAGGACAGCACCTACTCCCTGTCCTCCACCCTGACCCTGTCC<br>AAGGCCGACTACGAGAAGCACAAGGTGTACGCCTGCGAGGTGACCCACCA<br>GGGCCTGTCCAGCCCTGTGACCAAGTCCTTCAACCGGGGCGAGTGTGACG<br>TGCCTGGTGGTAGCCAGGTGCAGCTGCAGCAGCCTGGCGCTGAACTGGTC<br>CGACCTGGCGCCTCCGTGAAGCTGTCCTGCAAGGCCTCCGGCTACACCTT<br>CACCAGCTACTGGATCAACTGGGTCAAGCAGCGGCCTGGCCAGTGCCTGG<br>AATGGATCGGCAACATCTACCCCTCCGACTCCTACACCAACTACAACCAG<br>AAGTTCAAGGACAAGGCCACCCTGACCGTGGACAAGTCCTCCTCCACCGC<br>CTACATGCAGCTGTCCAGCCCCACCTCCGAGGACTCCGCCGTGTACTACT<br>GCACCCGGTCCTGGCGGGGCAACTCCTTCGACTATTGGGGCCAGGGCACC<br>ACCCTGACAGTGTCCTCTGGAGGCGGAGGATCTGGTGGTGGCGGATCTGG<br>CGGCGGTGGAAGTGGCGGAGGTGGTAGCGACATCGTGATGACCCAGTCCC<br>CCTCCAGCCTGACCGTGACCGCTGGCGAGAAAGTGACCATGAGCTGCAAG<br>TCCTCCCAGTCCCTGCTGAACTCCGGCAACCAGAAGAACTACCTGACCTG<br>GTATCAGCAGAAGCCCGGCCAGCCCCCAAGCTGCTGATCTACTGGGCCT<br>CCACCCGCGAGTCTGGCGTGCCCGATAGATTCACCGGCTCCGGCAGCGGC<br>ACCGACTTTACCCTGACCATCTCCAGCGTGCAGGCCGAGGACCTGGCCGT<br>GTATTACTGTCAGAACGACTACTCCTACCCCTTCACCTTCGGCTGCGGCA<br>CCAAGCTGGAAATCAAGTGA |
| #5752 | L bstb_5750/5752 | ATGGGCTGGTCCTGCATCATCCTGTTTCTGGTGGCTACCGCCACCGGCGT<br>GCACTCTCAGATCGTGCTGACCCAGTCTCCCGCCATCATGTCTGCTAGCC<br>CTGGCGAGAAAGTGACAATGACCTGCCGGGCCTCCTCCTCCGTGTCCTAC<br>ATGAACTGGTATCAGCAGAAGTCCGGCACCTCCCCCAAGCGGTGGATCTA<br>CGACACCTCCAAGGTGGCCTCTGGCGTGCCCTACAGATTCTCCGGCTCTG<br>GCTCTGGCACCTCCTACAGCCTGACCATCTCCAGCATGGAAGCCGAGGAT<br>GCCGCCACCTACTACTGCCAGCAGTGGTCCTCCAACCCCCTGACCTTTGG<br>CGCTGGCACCAAGCTGGAACTGAAGCGGACCGTGGCCGCTCCTTCCGTGT<br>TCATCTTCCCTCCCTCCGACGAGCAGCTGAAGTCCGGCACCGCCTCCGTG<br>GTGTGCCTGCTGAACAACTTCTACCCTCGGGAGGCCAAGGTGCAGTGGAA<br>GGTGGACAACGCCCTGCAGTCCGGCAACTCCCAGGAAAGCGTCACCGAGC<br>AGGACTCCAAGGACAGCACCTACTCCCTGTCCTCCACCCTGACCCTGTCC<br>AAGGCCGACTACGAGAAGCACAAGGTGTACGCCTGCGAGGTGACCCACCA<br>GGGCCTGTCCAGCCCTGTGACCAAGTCCTTCAACCGGGGCGAGTGTGACG<br>TGCCTGGTGGTAGCGACATCGTGATGACCCAGTCCCCCTCCAGCCTGACC<br>GTGACCGCTGGCGAGAAAGTGACCATGAGCTGCAAGTCCTCCCAGTCCCT<br>GCTGAACTCCGGCAACCAGAAGAACTACCTGACCTGGTATCAGCAGAAGC<br>CCGGCCAGCCCCCAAGCTGCTGATCTACTGGGCCTCCACCCGCGAGTCT<br>GGCGTGCCCGATAGATTCACCGGCTCCGGCAGCGGCACCGACTTTACCCT<br>GACCATCTCCAGCGTGCAGGCCGAGGACCTGGCCGTGTATTACTGTCAGA<br>ACGACTACTCCTACCCCTTCACCTTCGGCTCTGGCACCAAGCTGGAAATC<br>AAGGGAGGCGGTGGTTCAGGCGGCGGAGGCAGCGGTGGAGGTGGTAGTGG<br>CGGTGGCGGTTCAGGGGGAGGTGGCTCGCAGGTGCAGCTGCAGCAGCCTG<br>GCGCTGAACTGGTCCGACCTGGCGCCTCCGTGAAGCTGTCCTGCAAGGCC<br>TCCGGCTACACCTTCACCAGCTACTGGATCAACTGGGTCAAGCAGCGGCC<br>TGGCCAGGGCCTGGAATGGATCGGCAACATCTACCCCTCCGACTCCTACA<br>CCAACTACAACCAGAAGTTCAAGGACAAGGCCACCCTGACCGTGGACAAG<br>TCCTCCTCCACCGCCTACATGCAGCTGTCCAGCCCCACCTCCGAGGACTC |

TABLE 8-continued

CLDN18.2 x CD3-bstb DNA coding sequences

| Plasmid internal name | Corresponding bstb fragment | DNA coding sequence |
|---|---|---|
| | | CGCCGTGTACTACTGCACCCGGTCCTGGCGGGGCAACTCCTTCGACTATT GGGGCCAGGGCACCACCCTGACAGTGTCCTCTTGA |

TABLE 9

CLDN18.2 x CD3-bi-(scFv)$_2$ DNA coding sequences

| Plasmid internal name | Corresponding bi-(scFv)$_2$ | DNA coding sequence |
|---|---|---|
| #5506 | bi-scFv_5506 | ATGGGCTGGTCCTGCATCATCCTGTTTCTGGTGGCTACCGCCACCGGCGT GCACTCTCAGGTGCAGCTGCAGCAGCCTGGCGCTGAACTGGTCCGACCTG GCGCCTCCGTGAAGCTGTCCTGCAAGGCCTCCGGCTACACCTTCACCAGC TACTGGATCAACTGGGTCAAGCAGCGGCCTGGCCAGGGCCTGGAATGGAT CGGCAACATCTACCCCTCCGACTCCTACACCAACTACAACCAGAAGTTCA AGGACAAGGCCACCCTGACCGTGGACAAGTCCTCCTCCACCGCCTACATG CAGCTGTCCAGCCCCACCTCCGAGGACTCCGCCGTGTACTACTGCACCCG GTCCTGGCGGGGCAACTCCTTCGACTATTGGGGCCAGGGCACCACCCTGA CAGTGTCCTCTGGAGGCGGAGGATCTGGTGGTGGCGGATCTGGCGGCGGT GGAAGTGGCGGAGGTGGTAGCGACATCGTGATGACCCAGTCCCCCTCCAG CCTGACCGTGACCGCTGGCGAGAAAGTGACCATGAGCTGCAAGTCCTCCC AGTCCCTGCTGAACTCCGGCAACCAGAAGAACTACCTGACCTGGTATCAG CAGAAGCCCGGCCAGCCCCCCAAGCTGCTGATCTACTGGGCCTCCACCCG CGAGTCTGGCGTGCCCGATAGATTCACCGGCTCCGGCAGCGGCACCGACT TTACCCTGACCATCTCCAGCGTGCAGGCCGAGGACCTGGCCGTGTATTAC TGTCAGAACGACTACTCCTACCCCTTCACCTTCGGCTCTGGCACCAAGCT GGAAATCAAGTCTGGCGGAGGCGGATCCCAGGTGCAGCTGCAGCAGTCTG GCGCTGAGCTGGCTAGACCTGGCGCCTCCGTGAAGATGTCCTGCAAGACC TCCGGCTACACCTTCACCCGGTACACCATGCACTGGGTCAAGCAGAGGCC TGGACAGGGCCTGGAATGGATCGGCTACATCAACCCCTCCCGGGGCTACA CCAACTACAACCAGAAGTTCAAGGACAAGGCCACCCTGACAACCGACAAG TCCTCCTCCACCGCCTACATGCAGCTGTCCTCCCTGACCTCCGAGGACTC CGCCGTGTACTACTGCGCCCGGTACTACGACGACCACTACTCCCTGGACT ACTGGGGCCAGGGCACCACACTGACAGTGTCTAGCGGTGGTGGAGGAAGC GGAGGGGGTGGTAGCGGTGGTGGAGGCTCTGGCGGGGAGGGAGTCAGAT CGTGCTGACCCAGTCTCCCGCCATCATGTCTGCTAGCCCTGGCGAGAAAG TGACAATGACCTGCCGGGCCTCCTCCTCCGTGTCCTACATGAACTGGTAT CAGCAGAAGTCCGGCACCTCCCCCAAGCGGTGGATCTACGACACCTCCAA GGTGGCCTCTGGCGTGCCCTACAGATTCTCCGGCTCTGGCTCTGGCACCT CCTACAGCCTGACCATCTCCAGCATGGAAGCCGAGGATGCCGCCACCTAC TACTGCCAGCAGTGGTCCTCCAACCCCCTGACCTTTGGCGCTGGCACCAA GCTGGAACTGAAGGGCGGCTCTCACCACCACCATCACCACTGA |
| #5538 | bi-scFv_5538 | ATGGGCTGGTCCTGCATCATCCTGTTTCTGGTGGCTACCGCCACCGGCGT GCACTCTGACATCGTGATGACCCAGTCCCCCTCCAGCCTGACCGTGACCG CTGGCGAGAAAGTGACCATGAGCTGCAAGTCCTCCCAGTCCCTGCTGAAC TCCGGCAACCAGAAGAACTACCTGACCTGGTATCAGCAGAAGCCCGGCCA GCCCCCCAAGCTGCTGATCTACTGGGCCTCCACCCGCGAGTCTGGCGTGC CCGATAGATTCACCGGCTCCGGCAGCGGCACCGACTTTACCCTGACCATC TCCAGCGTGCAGGCCGAGGACCTGGCCGTGTATTACTGTCAGAACGACTA CTCCTACCCCTTCACCTTCGGCTCTGGCACCAAGCTGGAAATCAAGGGAG GCGGTGGTTCAGGCGGCGGAGGCAGCGGTGGAGGTGGTAGTGGCGGTGGC GGTTCAGGGGGAGGTGGCTCGCAGGTGCAGCTGCAGCAGCCTGGCGCTGA ACTGGTCCGACCTGGCGCCTCCGTGAAGCTGTCCTGCAAGGCCTCCGGCT ACACCTTCACCAGCTACTGGATCAACTGGGTCAAGCAGCGGCCTGGCCAG GGCCTGGAATGGATCGGCAACATCTACCCCTCCGACTCCTACACCAACTA CAACCAGAAGTTCAAGGACAAGGCCACCCTGACCGTGGACAAGTCCTCCT CCACCGCCTACATGCAGCTGTCCAGCCCCACCTCCGAGGACTCCGCCGTG TACTACTGCACCCGGTCCTGGCGGGGCAACTCCTTCGACTATTGGGGCCA GGGCACCACCCTGACAGTGTCCTCTTCTGGCGGAGGCGGATCCCAGGTGC AGCTGCAGCAGTCTGGCGCTGAGCTGGCTAGACCTGGCGCCTCCGTGAAG ATGTCCTGCAAGACCTCCGGCTACACCTTCACCCGGTACACCATGCACTG GGTCAAGCAGAGGCCTGGACAGGGCCTGGAATGGATCGGCTACATCAACC CCTCCCGGGGCTACACCAACTACAACCAGAAGTTCAAGGACAAGGCCACC CTGACAACCGACAAGTCCTCCTCCACCGCCTACATGCAGCTGTCCTCCCT GACCTCCGAGGACTCCGCCGTGTACTACTGCGCCCGGTACTACGACGACC ACTACTCCCTGGACTACTGGGGCCAGGGCACCACACTGACAGTGTCTAGC GGAGGCGGAGGATCTGGTGGTGGCGGATCTGGCGGCGGTGGAAGTGGCGG AGGTGGTAGCCAGATCGTGCTGACCCAGTCTCCCGCCATCATGTCTGCTA GCCCTGGCGAGAAAGTGACAATGACCTGCCGGGCCTCCTCCTCCGTGTCC |

TABLE 9-continued

CLDN18.2 x CD3-bi-(scFv)₂ DNA coding sequences

| Plasmid internal name | Corresponding bi-(scFv)₂ | DNA coding sequence |
|---|---|---|
|  |  | TACATGAACTGGTATCAGCAGAAGTCCGGCACCTCCCCCAAGCGGTGGAT<br>CTACGACACCTCCAAGGTGGCCTCTGGCGTGCCCTACAGATTCTCCGGCT<br>CTGGCTCTGGCACCTCCTACAGCCTGACCATCTCCAGCATGGAAGCCGAG<br>GATGCCGCCACCTACTACTGCCAGCAGTGGTCCTCCAACCCCCTGACCTT<br>TGGCGCTGGCACCAAGCTGGAACTGAAGGGCGGCTCTCACCACCACCATC<br>ACCACTGA |
| #5376 | bi-scFv "plate reference" | ATGGGATGGTCCTGCATCATCCTGTTTCTGGTGGCTACCGCCACCGGCGT<br>GCACAGCCAGGTGCAGCTGCAGCAGCCTGGAGCTGAACTGGTGCGGCCTG<br>GAGCCAGCGTGAAGCTGTCCTGCAAGGCCAGCGGCTACACCTTCACCAGC<br>TACTGGATCAACTGGGTGAAGCAGCGGCCTGGACAGGGCCTGGAATGGAT<br>CGGCAACATCTACCCCAGCGACAGCTACACCAACTACAACCAGAAGTTCA<br>AGGACAAGGCCACCCTGACCGTGGACAAGAGCAGCAGCACCGCCTACATG<br>CAGCTGTCCAGCCCCACCTCCGAGGACAGCGCCGTGTACTACTGCACCAG<br>AAGCTGGCGGGGCAACAGCTTCGACTACTGGGGCCAGGGCACCACACTGA<br>CAGTCAGCAGCGGAGGAGGGGGATCTGGCGGGGGAGGAAGCGGAGGGGGG<br>GGAAGCGACATCGTGATGACCCAGAGCCCCAGCAGCCTGACCGTGACAGC<br>CGGGGAAAAGGTGACCATGAGCTGCAAGAGCAGCCAGAGCCTGCTGAACA<br>GCGGCAACCAGAAGAACTACCTGACCTGGTATCAGCAGAAGCCCGGCCAG<br>CCCCCCAAGCTGCTGATCTACTGGGCCAGCACCCGGGAGAGCGGCGTGCC<br>CGACCGGTTTACCGGCTCCGGCTCCGGCACCGACTTCACCCTGACCATCA<br>GCAGCGTGCAGGCCGAGGACCTGGCCGTGTATTACTGTCAGAACGACTAC<br>AGCTACCCCTTCACCTTCGGCAGCGGCACCAAGCTGGAAATCAAGAGCGG<br>AGGGGGAGGATCCGATATCAAGCTGCAGCAGAGCGGAGCTGAACTGGCTA<br>GGCCAGGCGCCTCCGTGAAGATGAGCTGTAAGACCTCCGGCTATACCTTT<br>ACCCGGTACACCATGCACTGGGTGAAACAGAGGCCCGGACAGGGGCTGGA<br>ATGGATTGGCTATATCAACCCCTCCCGGGGCTACACAAATTACAATCAGA<br>AATTCAAAGATAAAGCCACACTGACAACCGACAAGTCCAGCTCCACAGCC<br>TATATGCAGCTGTCCTCCCTGACCAGCGAGGACTCTGCCGTGTACTATTG<br>CGCCCGGTACTACGACGACCACTACAGCCTGGATTATTGGGGGCAGGGGA<br>CAACACTGACAGTCTCCAGCGTGGAGGGCGGCAGCGGAGGATCTGGCGGG<br>AGCGGCGGCTCTGGGGGCGTCGACGACATCCAGCTGACCCAGTCCCCCGC<br>CATCATGAGCGCCAGCCCTGGCGAGAAGGTGACAATGACCTGCCGGGCCA<br>GCAGCAGCGTGAGCTACATGAATTGGTATCAGCAGAAAAGCGGCACCAGC<br>CCCAAGCGGTGGATCTACGACACCAGCAAGGTGGCCTCCGGCGTGCCCTA<br>CAGATTCTCCGGCTCCGGCTCTGGCACCAGCTACAGCCTGACAATTTCTA<br>GCATGGAAGCCGAGGACGCCGCCACCTACTACTGCCAGCAGTGGAGCAGC<br>AACCCCCTGACCTTTGGCGCCGGAACAAAGCTGGAACTGAAGTGA |

Example 9: Comparison of the Specific Lysis Activity of Four CLDN18.2×CD3-Bstbs in in Vitro Cytotoxicity Assays Proteins bstb_5730/5728, bstb_5731/5729, bstb_5732/5728 and bstb_5733/5729 (all including tags but no disulfide bridges in the scFv moieties) were produced and purified as described under Example 1b and c. Before separation of the highly monomeric species by SEC, the functionality of the proteins (50-77% monomeric species) was investigated in an in vitro luciferase cytotoxicity assay, basically as described under Example 2a. Deviations are described below.

In the exemplary study, the stably luciferase and CLDN18.2-expressing human gastric cancer cell line NUGC-4_hCLDN18.2 was used as target cell line. Human CLDN18.2-negative breast carcinoma cell line MDA-MB-231 served as specificity control. PBMC effector cells and target cells were incubated with a 10-point, 10-fold serial dilution row of the bstb proteins in a concentration range of 47.44 aM to 47.44 nM.

As shown in FIG. 11 all four CLDN18.2×CD3-bstb molecules (FIG. 10B) led to efficient lysis of NUGC-4_hCLDN18.2 cells after 48 h of co-incubation in the exemplary study. A maximum of 93% target cells was lysed. No lysis was observed with the CLDN18.2-negative control cell line MDA-MB-231. With respect to the monomer content before SEC and the efficiency in the cytotoxicity assay, the two bstb variants bstb_5730/5728 and bstb_5731/5729 carrying the $C_H1$ moiety of IgG1 were selected for further studies without tags and with or without disulfide bridges in the scFv moieties.

Figure 12A:
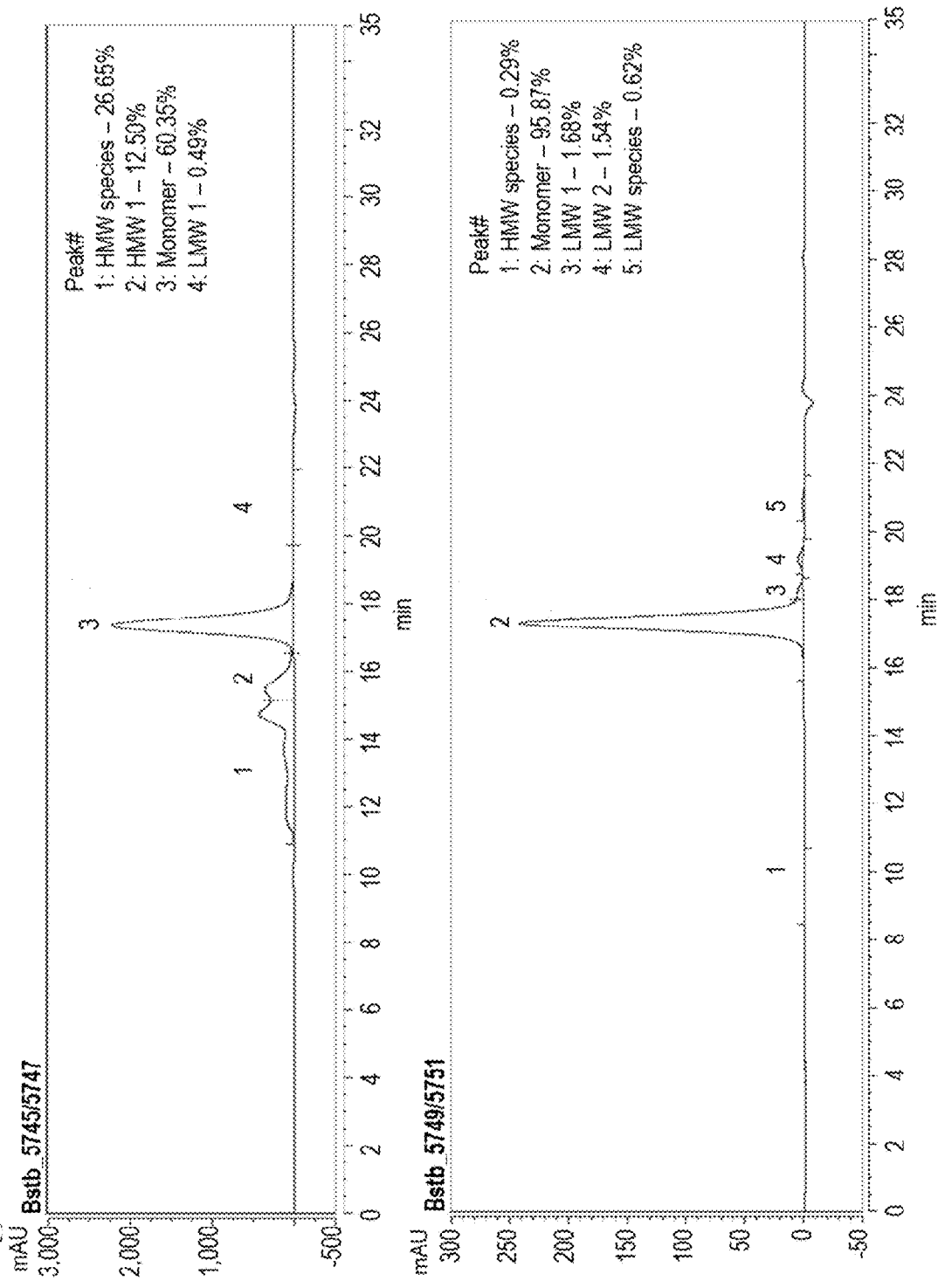

Example 10: Comparison of the Physicochemical Properties of Purified Tag-Free CLDN18.2×CD3-Bstbs Cell culture supernatants of transiently transfected Expi293F™ cells containing protein bstb_5745/5747, bstb_5746/5748, bstb_5749/5751 or bstb_5750/5752 were filtrated using Supracap™ 50 depth filter capsules (Pall Corporation, Port Washington, N.Y., USA) and subsequently subjected to a protein purification process To analyze the aggregation state of different purified CLDN18.2×CD3-bstb proteins we performed size exclusion-high performance liquid chromatography (SE-HPLC) using a Dionex Ultimate 3000 (Thermo Scientific) with a size exclusion TSKgel G3000SW×1 column (300×7.8 mm, Tosoh Bioscience). The column was rinsed with SE-HPLC buffer (0.3 M $Na_2HPO_4$, pH 7.2) and the bstb protein was separated by isocratic elution. While bstb_5745/5747 and bstb_5746/5748 demonstrated a relatively low amount of monomeric proteins (~60% and ~40%, respectively), bstb_5749/5751 and bstb_5750/5752 where highly monomeric after purification (~96% and ~89%, respectively) (FIGS. 12A and B). Furthermore, short time storage of bstb_5745/5747 and bstb_5746/5748 at RT resulted in the formation of visual aggregates.

Bstb_5745/5747 and bstb_5749/5751 as well as bstb_5746/5748 and bstb_5750/5752 each only differ in two amino acids of the respective anti-CLDN18.2 scFv moiety thereby allowing the formation of a disulfide bridge within the anti-CLDN18.2 scFv moieties of bstb_5749/5751 and bstb_5750/5752. This introduction of an additional disulfide bridge in the anti-CLDN18.2 scFv moieties favors the formation of the monomeric protein thus improves the physicochemical properties of the respective bstb.

All bstb variants after the initial purification were dialysed into PBS and finally subjected to a preparative SEC using a HiLoad 26/600 Superdex 200 µg column (GE Healthcare Life Sciences) to enrich the monomeric fraction to ~100% for further characterization of activity and binding.

Example 11: Direct Comparison of the Activity of CLDN18.2×CD3 Bstb and Bi-(scFv)$_2$ Proteins Monomeric proteins bstb_5749/5751 and bstb_5750/5752 (all including disulfide bridges in the scFv moieties) and their respective bi-(scFv)$_2$ analogs bi-scFv_5506 and bi-scFv_5538 (no disulfide bridges) were investigated in an in vitro luciferase cytotoxicity assay, basically as described under Example 9. Other than described before, a 10-point, 5-fold serial dilution row in a concentration range of 24.64 fM to 48.11 nM was applied. Moreover, a reference was included on each plate for normalization reasons. Bstb and bi-(scFv)$_2$ proteins were used in equimolar concentrations.

Figure 13B:
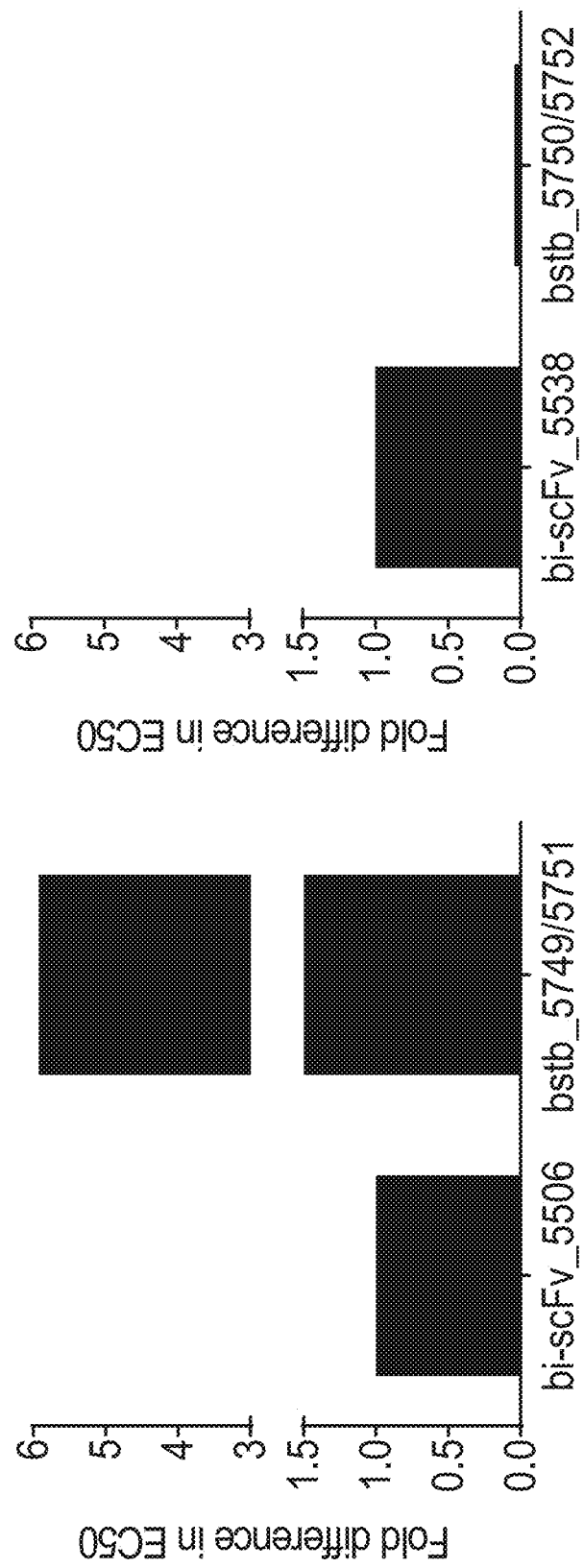

Bstb_5750/5752 shows a 1.8-fold lower EC50 (40.63 pM) than bstb_5749/5751 (70.94 pM) (FIG. 13A, left plot), thereby specifying a slightly higher activity of the first bstb. Both bstb proteins led to efficient lysis of ~95% target cells in the highest concentration. No lysis was observed with the CLDN18.2-negative control cell line MDA-MB-231 (data not shown). Interestingly, the respective bi-(scFv)$_2$-bi-scFv_5506 and 5538-analogs (FIG. 13A, right plot) represent a significant difference in the EC50 values of 9.99 pM and 777.20 pM, respectively. The EC50 values were subsequently normalized to the plate reference (bi-scFv_5376) and the fold difference calculated with the bi-(scFv)$_2$ EC50 set to 1. Surprisingly, the EC50 of bstb_5749/5751 is 6-fold higher compared to bi-scFv_5506, pointing to a loss in activity of ~80% of the first (FIG. 13B, left plot). On the other hand, the EC50 of bstb_5750/5752 is 23-fold lower compared to bi-scFv_5538, implying an activity increase of >2000% by the use of the bstb-format (FIG. 13B, right plot). Taken together, the switch from monovalency to bivalency depending on the used binding domains as well as their orientation can improve activity of a bispecific antibody as demonstrated with the dramatic activity increase of bstb_5750/5752 compared to bi-scFv_5538. In addition, the protein characteristics of the bstb format might be superior to the bi-(scFv)$_2$ format in terms of stability.

Example 12: Generation of IVT-mRNA Based Bispecific Antibody-Derivatives Targeting CLDN6 and CD3 a. Cloning of Bstb IVT-mRNA Template Vectors and IVT-mRNA Synthesis

For the generation of CLDN6×CD3 bispecific chimeric TriMABs (bstb) as in vitro transcribed messenger RNA (IVT-mRNA), we subcloned the DNA-sequences of bstb_369/367 and bstb_371/367 (described in Example 1) into the IVT-mRNA template vector pST1-TEV-MCS-F-I (BioNTech AG, Mainz, Germany) using standard techniques. The TEV leader sequence has been described elsewhere (Zeenko und Gallie 2005; Weingarten-Gabbay et al. 2016; Gallie et al. 1995) and the F-I sequence is described in patent application "3'UTR Sequences for Stabilization of RNA" (PCT/EP2015/073180). The following constructs were obtained for the formation of bstb molecules:

Bstb__435/434:

| | |
|---|---|
| pST1-5'TEV-Sec-$V_H^{\alpha CD3}$-$C_H1$(IgG1)-$V_H^{\alpha CLDN6}$-$V_L^{\alpha CLDN6}$-6xHis-tag-F-I-A30linkerA70 | (Fd) |
| pST1-5'TEV-Sec-$V_L^{\alpha CD3}$-$C_L$-$V_H^{\alpha CLDN6}$-$V_L^{\alpha CLDN6}$-Strep-tag-F-I-A30linkerA70 | (L) |

Bstb__436/434:

| | |
|---|---|
| pST1-5'TEV-Sec-$V_H^{\alpha CD3}$-$C_H1$(IgG2)-$V_H^{\alpha CLDN6}$-$V_L^{\alpha CLDN6}$-6xHis-tag-F-I-A30linkerA70 | (Fd) |
| pST1-5'TEV-Sec-$V_L^{\alpha CD3}$-$C_L$-$V_H^{\alpha CLDN6}$-$V_L^{\alpha CLDN6}$-Strep-tag-F-I-A30linkerA70 | (L) |

A = adenine, Fd = digestible fragment (heavy chain portion of Fab), F-I = 3'UTR sequence, L = light chain portion of Fab, Sec = secretion signal, 5'TEV = 5'UTR from tobacco etch virus.

Table 10 summarizes the information about bstb constructs specific for the TAA CLDN6 that were generated in the course of the invention. Information on specificity, sequence origin from monoclonal antibodies (mAB), codon usage, additional sequence features are listed. Sequences encoding the variable domains of the target cell binding moieties were originally received from Ganymed Pharmaceuticals AG.

TABLE 10

Summary of CLDN6 × CD3-bstb antibody features

| Internal name | Specificity | Origin of scFv $V_H$-$V_L$regions | Origin of Fab $V_H$-$V_L$region | Codon usage | $C_H1$ | Tag |
|---|---|---|---|---|---|---|
| Bstb_435/434 (SEQ ID NO: 79/78) | HS | IMAB206-SUBW | TR66(C114S) | CG | IgG1 | His/Strp |
| Bstb_436/434 (SEQ ID NO: 80/78) | HS | IMAB206-SUBW | TR66(C114S) | CG | IgG2 | His/Strp |

Bstb indicates bispecific TriMABs;
C, cysteine;
$C_H1$, constant heavy chain region 1;
CG, Cricetulus griseus;
IMAB, ideal monoclonal antibody;
His, 6xHis-tag;
HS, Homo sapiens;
IgG, immunoglobulin G;
S, serine;
Strp, Strep-tag;
W, tryptophan.

b. IVT-mRNA Synthesis

To generate templates for in vitro transcription, plasmid DNAs were linearized downstream of the poly(A) tail-encoding region using a class IIs restriction endonuclease, thereby generating a template to transcribe RNAs with no additional nucleotides past the poly(A)-tail (Holtkamp et al. 2006). Linearized template DNAs were purified, spectrophotometrically quantified, and then subjected to in vitro transcription with T7 RNA polymerase essentially as previously described (Grudzien-Nogalska et al. 2013) in the presence of 7.5 mM each of ATP, CTP, UTP, 1.5 mM GTP, and 6 mM beta-S-ARCA(D2) cap analog (Kuhn et al. 2010). RNA was purified using magnetic particles (Berensmeier 2006). For in vivo studies, non-immunogenic RNA was used. To this end, N1-Methylpseudouridine-5'-Triphosphate (TriLink Biotechnologies, San Diega, CA, USA) was incorporated instead of UTP and double-stranded RNA was removed. RNA was enzymatically capped with the Script-Cap m7G Capping System and 2'O-Methyltransferase (CellScript, Madison, Wis., USA). RNA concentration and quality were assessed by spectrophotometry and analysis on a 2100 Bioanalyzer (Agilent, Santa Clara, Calif., USA). A sketch of the two IVT-mRNAs needed for the formation of a complete bstb molecule is depicted in FIG. 14.

Example 13: Determination of the Specific Lysis Activity of Bstb_435/434 and Bstb_436/434 in In Vitro Cytotoxicity Assays a. Electroporation of Producer Cells For the production of bstb protein from IVT-mRNA, 4×106 K-562 cells (ATCC CCL-243, LGC Standards GmbH, Wesel, Germany) per ml growing in log-phase were electroporated with $H_2O$ (Mock) or with 25 µg/ml IVT-mRNA per bstb chain in 0.4 mm cuvettes using a GenePulser MXCell (Bio-Rad Laboratories Dreieich, Germany) with the following setting: 200 V, 2 pulses, 8 ms. Cells were subsequently seeded in complete culture medium at a density of $5\times10^5$/ml into 6-well tissue culture plates. After 48 h of incubation, the supernatant was harvested by centrifugation and sterile filtered with 0.2 µm Minisart NML Syringe Filters (Sartorius, Gottingen, Germany).

b. Quantitation of Bstb in Producer Cell Supernatant Via ELISA

Supernatants from electroporated K-562 were subjected to an in-house designed ELISA for quantitation. In brief, 96-well MaxiSorp™ plates (Thermo Scientific, Braunschweig, Germany) were coated with 4.5 µg/ml goat anti-human IgG F(ab')$_2$ antibody (Abd Serotec, Puchheim, Germany) in DPBS for 1 h at 37° C., washed three times (wash buffer: PBS/0.05% Tween-20) and blocked at 2-8° C. with 3% milk powder in DPBS overnight. After a wash step a serial dilution of bstb_369/367 and bstb_371/367 proteins as reference and a serial dilution of the bstb_435/434 and bstb_436/434 containing K-562 supernatants (diluent: 0.2% BSA) were added to the coated plate in triplicates. After 2 h at RT the plate was washed three times. For the detection of bstb bound to anti-F(ab')$_2$, 3.5 µg/ml murine anti-IMAB206 (Ganymed Pharmaceuticals AG, Mainz, Germany) was added, incubated for 1 h at RT and the plate washed again three times. An AP-conjugated goat-anti-mouse IgG Fc antibody (Jackson ImmunoResearch, Newmarket, UK) in a dilution of 1:500 was incubated for 1 h at RT. For visualization the plate was incubated with a self-made pNPP-substrate solution for 30 min at RT in the dark and the reaction finally stopped with 3 M KOH. Analysis was conducted in a Tecan M200 microplate-reader (Tecan, Mdnnedorf, Switzerland) at 405/492 nm. Data was analyzed with GraphPad Prism software 6 and Microsoft Excel 2010 (data not shown).

A concentration of 253 ng/ml bstb_435/434 and 427 ng/ml bstb_436/434 could be determined in K-562 supernatant. Accordingly, both bstb were translated and secreted but in different amounts. Obtained protein amounts greatly depend on the electroporation and vary each time. In the course of various experiments, 1.0-1.7-fold bstb_436/434 has been produced compared to bstb_435/434.

c. Western Blot Analysis of Producer Cell Lysate and Supernatant

Supernatant and cell lysate of K-562 cells (Example 13 a.) were used for the analysis of translation and secretion of bstb proteins. Cell lysates were obtained by incubation of $1\times10^6$ washed cells in 200 µl 4× Laemmli buffer (Bio-Rad Laboratories) including 20 units Benzonase (Merck Millipore, Darmstadt, Germany). Subsequently, the samples were heated to 95° C. for 10 min with (reducing) or without (non-reducing) 1M Dithiothreitol (DTT, final concentration 0.1M). Supernatants were treated likewise with Laemmli buffer. Prepared cell lysates and supernatants and the corresponding purified bstb proteins were separated by polyacrylamid gel electrophoresis using 4-15% Criterion™ TGX Stain-Free™ Gel (Bio-Rad Laboratories) followed by Western Blot analysis (FIG. 15) according to standard procedures known by the person skilled in the art. For Western Blot analysis the horseradish peroxidase (HRP) conjugated antibodies anti-6×His-tag (1:10,000, Abcam, Cambridge, Mass., USA), StrepMAB-Classic (1:10,000, IBA GmbH, Gottingen, Germany) and anti-beta-Actin (1:25,000, Abcam) were used. Western Blot membranes were recorded with a Chemidoc MP Imaging System from Bio-Rad. Signals of bstb proteins were detected at 50-55 kD under reducing and at ~100 kD under non-reducing conditions as compared to the internal molecular weight standard. Bstb_435/436 (FIG. 15A) and bstb_436/434 (FIG. 15B) were mainly detected in supernatant but also in cell lysate indicating an incomplete secretion at the time point of harvest. The heterodimeric composition of the bstb proteins becomes obvious under reducing conditions and detection with a mixture of the anti-6×His-tag HRP and StrepMAB-Classic HRP (FIG. 15C): The Fd- and L-fragment differ by ~2 kD in size (~51 kD and ~49 kD, respectively). By quantitation of the protein bands corresponding to HMW and monomeric bstb detected under non-reducing conditions, we determined 3% HMW and 88% monomeric bstb_435/434 species and 1.4% HMW and 92% monomeric bstb_436/434 species. Only a few smaller bands (total of ~8% and ~6%, respectively) indicating slight degradation during cell culture were detected. In summary, both bstb can be efficiently translated from IVT-mRNA and are secreted to the cell culture supernatant. Bstb_436/434 shows a somewhat more favourable protein pattern regarding HMW species and degradation products but the percentage of HMW species is low for both bstb molecules.

d. Luciferase Cytotoxicity Assay and EC50 Determination

The cytotoxicity assay was in principle performed as described in Example 2a. Bstb proteins were used as reference. K-562 supernatant samples from Example 13 a were diluted in K-562 mock supernatant (electroporation without IVT-mRNA). $L_{min}$ and $L_{max}$ of K-562 supernatant samples were supplemented with K-562 mock supernatant. 20 µl bstb in supernatant had been applied in a 7-point, 5-fold serial dilution row from 33.1 fM to 516.5 pM to OV-90 and MDA-MB-231 cancer cells (stably transduced with luciferase) that were plated together with PBMC as effector cells (E:T 5:1). After 48 h of co-incubation luciferase solution was added for measurement and the plate was analyzed.

As shown in FIG. 16, both bstb mediate efficient lysis of CLDN6$^+$ OV-90 but not of CLDN6-MDA-MB-231. A maximum lysis of app. 77-80% was reached with 516.5 pM bstb_436/434 and bstb_435/434, respectively. EC50 values indicate a 1.3-fold higher activity of bstb_435/434. EC50 values of the RNA-translated bstbs were 4-fold and 7.5-fold lower in comparison to the corresponding protein items bstb_369/367 and bstb_371/367, respectively. This effect might originate from a higher protein activity due to the lack of any further protein manipulation, from an influence of HMW species, from deviations of quantitation or a combination thereof.

In summary, the RNA approach is feasible, highly efficient and time-saving regarding the omission of protein expression, purification, stability and analysis matters.

Example 14: Efficacy of IVT-RNA Encoding Bispecific Antibodies in Comparison to Protein References in a Mouse Xenograft Model For the investigation of the therapeutic potential of IVT-mRNA encoding bispecific bstb and bi-(scFv)$_2$ antibodies in comparison to protein references in vivo, the immunodeficient mouse strain NOD.Cg-Prkd$^{scid}$ IL2rg$^{tm1Wjl}$/SzJ or short NSG (Jackson laboratory, Bar Harbour, ME, USA) was chosen again. All mice were used in accordance with the guidelines from the Institutional Animal Care Committee of the Johannes Gutenberg University, Mainz, Germany.

a. Treatment of Advanced CLDN6-Expressing Tumors in Mice with Bstb and Bi-(scFv)$_2$ Encoding IVT-RNA in Comparison to Protein In the exemplary study, male and female NSG mice at 6-25 weeks of age and with a body weight of 18-38 g were used. CLDN6-positive OV-90 cells served as tumor cells and PBMC as effector cells. 5×10$^6$ tumor cells were inoculated subcutaneously (s.c.) and 1×10$^7$ PBMC were administered intraperitoneally (i.p.) 19 days thereafter. PBMC engrafted mice—as analyzed in the peripheral blood six days post PBMC injection—were stratified into groups according to tumor volume and gender (both genders in all groups). The treatment was initiated eight days post PBMC administration at a rather advanced tumor stage with a mean tumor volume of ~250 mm$^3$ per group. Mice were treated once per week by intravenous (i.v.) injections (injection schedule FIG. 17A) into the retroorbital venous plexus. Group "G1-RNA control", "G2-bstb RNA" and "G3-bi-scFv RNA" received 3 µg IVT-mRNA complexed with TransIT®-mRNA Transfection Kit (Mirus Bio, Madison, Wis., USA) in 200 µl volume per mouse. As RNA control luciferase IVT-mRNA was used, bstb-encoding RNAs were CDLN6×CD3 bstb Fd and LC chain IVT-mRNAs 435 and 434 (mixed 1:1) and bi-(scFv)$_2$-encoding RNA was CDLN6×CD3 bi-(scFv)$_2$ IVT-RNA 123r. All IVT-RNAs were synthesized according to Example 12 b, in vivo. "G4-Vehicle control" comprised six mice treated with DPBS and six mice treated with 10 mM NaOAc buffer, pH5.5 (bstb and bi-(scFv)$_2$ formulation buffers, respectively). "G5-bstb protein" and "G6-bi-scFv protein" were treated with the protein analogs to the IVT-mRNA items. Bstb protein was bstb_369/367 (dose of 100 µg/kg, 5 µl/g body weight) and bi-(scFv)$_2$ protein bi-scFv_123 (dose of 200 µg/kg, 5 µl/g body weight). Treatment groups are summarized in Table 11. Administration was conducted for four consecutive weeks. Twice per week tumor dimensions were measured with a digital calibrated caliper and the tumor volumes were calculated by the formula: tumor volume [mm$^3$]=length [mm]× (width [mm])$^2$/2. Mice were sacrificed by cervical dislocation when the tumor volume reached 1500 mm$^3$ or in case of severe morbidity (mainly symptoms of graft-versus-host disease (GVHD)).

Figure 17B:
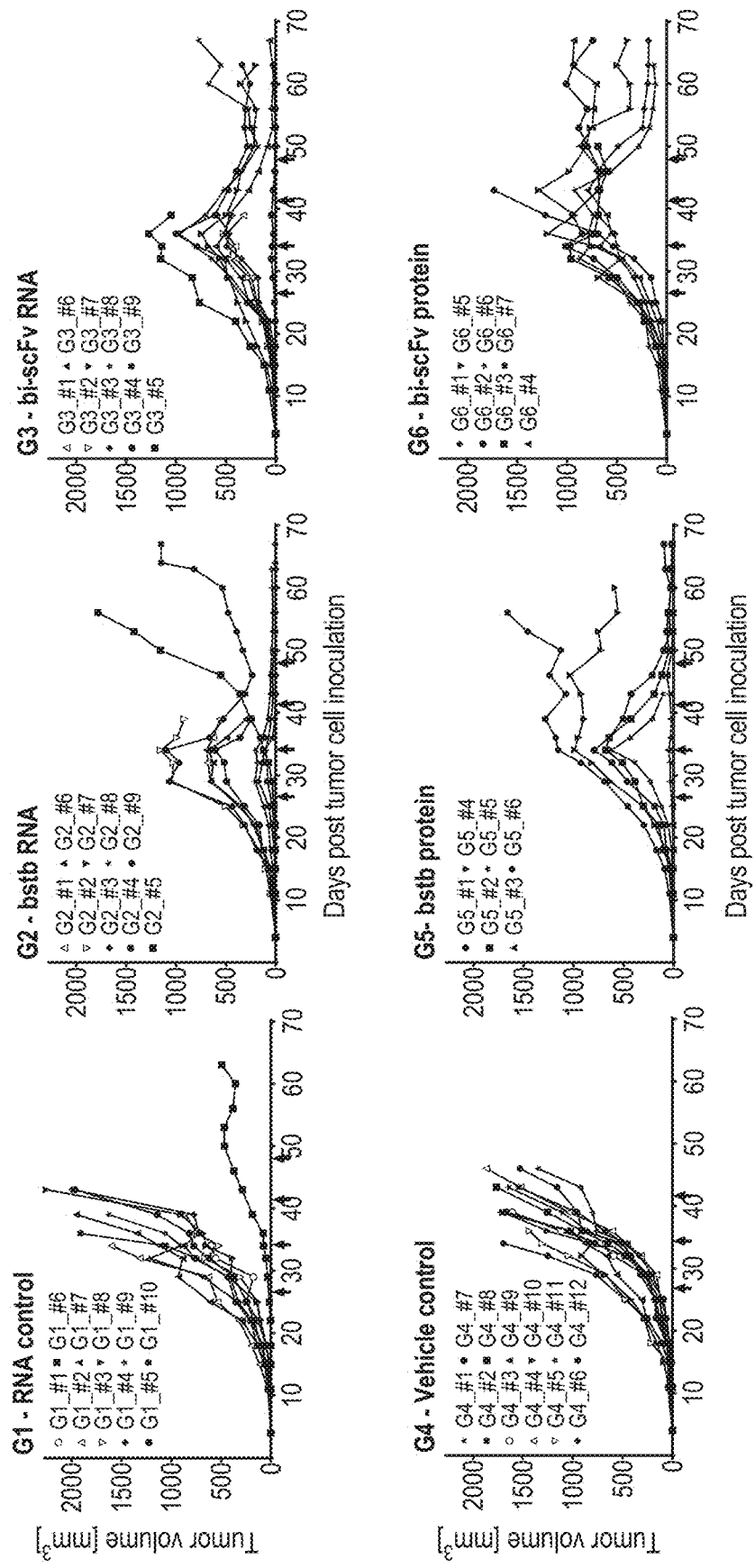
Figure 17C:
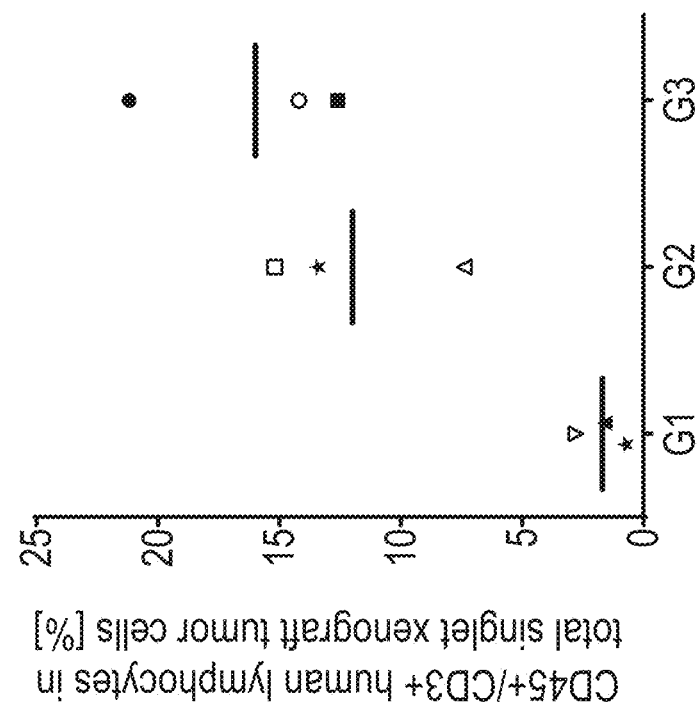

FIG. 17B illustrates the treatment effects on tumor growth. Anti-tumor efficacy was measured as tumor growth inhibition/reduction and survival compared to the RNA control group G1 or the vehicle control G4. Treatment with test item bstb_435/434 (G2) resulted in tumor reduction in 8/9 mice and with test item bi-scFv_123r (G3) in 9/9 mice in contrast to the control group G1 in which 0/10 mice had reduced tumor growth. Treatment with the protein analogs (G5, G6) was similar for bstb but less efficient for bi-(scFv)$_2$. Importantly, proteins were administered according to the RNA injection scheme (once per week, i.v., meaning retroorbitally) for direct comparison and not to the established protein treatment schedule of three-times per week, i.p. The higher efficiency of RNA is probably caused by a longer lasting translation and secretion of protein over several days whereas injected protein is quickly eliminated. The protein blood concentrations in vivo after RNA injection are unknown. Three mice of G1-G3 were sacrificed earlier to investigate tumor-infiltrating lymphocytes (TIL) by flow cytometric analysis. To this end, single cell suspensions of tumors were stained with anti-human CD45 and CD3 fluorescently-labeled antibodies (BD Biosciences, Heidelberg, Germany) and singlet cells of total tumors analyzed with a BD FACS CantoII flow cytometer. In the RNA control group<3% infiltrated human T cells were detected whereas>7% and >12% human T cells were detected in the bstb- and bi-(scFv)$_2$-RNA group, respectively (FIG. 17C). These data show the directed infiltration of human T cells engaged by bispecific RNA-encoded antibodies.

b. Determination of Therapy Influence on Body Weight

The body weight of each mouse was examined once per week using a laboratory scale. No treatment related weight loss was observed (data not shown).

REFERENCES

Berensmeier, Sonja (2006): Magnetic particles for the separation and purification of nucleic acids. In: *Applied microbiology and biotechnology* 73 (3), S. 495-504. DOI: 10.1007/s00253-006-0675-0.

Coligan, John E.; Bierer, Barbara E.; Margulies, David H.; Shevach, Ethan M.; Strober, Warren (2001a): Current Protocols in Immunology. Hoboken, N.J., USA: John Wiley & Sons, Inc.

Coligan, John E.; Dunn, Ben M.; Speicher, David W.; Wingfield, Paul T. (2001b): Current Protocols in Protein Science. Hoboken, N.J., USA: John Wiley & Sons, Inc.

Gallie, D. R.; Tanguay, R. L.; Leathers, V. (1995): The tobacco etch viral 5' leader and poly(A) tail are functionally synergistic regulators of translation. In: Gene 165 (2), S. 233-238. DOI: 10.1016/0378-1119(95)00521-7.

Grudzien-Nogalska, Ewa; Kowalska, Joanna; Su, Wei; Kuhn, Andreas N.; Slepenkov, Sergey V.; Darzynkiewicz, Edward et al. (2013): Synthetic mRNAs with superior translation and stability properties. In: *Methods in molecular biology* (Clifton, N.J.) 969, S. 55-72. DOI: 10.1007/978-1-62703-260-5_4.

Holtkamp, S.; Kreiter, S.; Selmi, A.; Simon, P.; Koslowski, M.; Huber, C. et al. (2006): Modification of antigen-encoding RNA increases stability, translational efficacy, and T-cell stimulatory capacity of dendritic cells. In: *Blood* 108 (13), S. 4009-4017. DOI: 10.1182/blood-2006-04-015024.

Kuhn, A. N.; Diken, M.; Kreiter, S.; Selmi, A.; Kowalska, J.; Jemielity, J. et al. (2010): Phosphorothioate cap analogs increase stability and translational efficiency of RNA vaccines in immature dendritic cells and induce superior immune responses in vivo. In: *Gene Ther* 17 (8), S. 961-971. DOI: 10.1038/gt.2010.52.

Lanzavecchia, A.; Scheidegger, D. (1987): The use of hybrid hybridomas to target human cytotoxic T lymphocytes. In: *Eur. J Immunol.* 17 (1), S. 105-111. DOI: 10.1002/eji.1830170118.

Lutterbuese, Ralf; Raum, Tobias; Kischel, Roman; Hoffmann, Patrick; Mangold, Susanne; Rattel, Benno et al. (2010): T cell-engaging BiTE antibodies specific for EGFR potently eliminate KRAS- and BRAF-mutated colorectal cancer cells. In: *Proceedings of the National Academy of Sciences of the United States of America* 107 (28), S. 12605-12610. DOI: 10.1073/pnas.1000976107.

Röthlisberger, Daniela; Honegger, Annemarie; Pluckthun, Andreas (2005): Domain interactions in the Fab fragment: a comparative evaluation of the single-chain Fv and Fab format engineered with variable domains of different stability. In: *Journal of molecular biology* 347 (4), S. 773-789. DOI: 10.1016/j.jmb.2005.01.053.

Stadler, Christiane R.; Bahr-Mahmud, Hayat; Plum, Laura M.; Schmoldt, Kathrin; Kolsch, Anne C.; Tureci, Özlem; Sahin, Ugur (2015): Characterization of the first-in-class T-cell-engaging bispecific single-chain antibody for targeted immunotherapy of solid tumors expressing the oncofetal protein claudin 6. In: *OncoImmunology* 5 (3), S. e1091555. DOI: 10.1080/2162402X.2015.1091555.

Weingarten-Gabbay, Shira; Elias-Kirma, Shani; Nir, Ronit; Gritsenko, Alexey A.; Stem-Ginossar, Noam; Yakhini, Zohar et al. (2016): Comparative genetics. Systematic discovery of cap-independent translation sequences in human and viral genomes. In: *Science* (New York, N. Y) 351 (6270). DOI: 10.1126/science.aad4939.

Woll, Stefan; Schlitter, Anna Melissa; Dhaene, Karl; Roller, Marc; Esposito, Irene; Sahin, Ugur; Tureci, Ozlem (2014): Claudin 18.2 is a target for IMAB362 antibody in pancreatic neoplasms. In: *International journal of cancer* 134 (3), S. 731-739. DOI: 10.1002/ijc.28400.

Zeenko, Vladimir; Gallie, Daniel R. (2005): Cap-independent translation of tobacco etch virus is conferred by an RNA pseudoknot in the 5'-leader. In: *The Journal of biological chemistry* 280 (29), S. 26813-26824. DOI: 10.1074/jbc.M503576200.

The invention claimed is:

1. A nucleic acid encoding a binding agent comprising at least three binding domains, wherein a first binding domain binds to a T cell-specific antigen and a second binding domain and a third binding domain bind to a claudin, wherein the binding agent comprises
(a) a first polypeptide comprising a VH domain with a specificity for the T cell-specific antigen (VH(T)), a VH domain with a specificity for the claudin (VH(CLDN)) and a VL domain with a specificity for the claudin (VL(CLDN)); and
(b) a second polypeptide comprising a VL domain with a specificity for the T cell-specific antigen (VL(T)), a VH domain with a specificity for the claudin (VH(CLDN)) and a VL domain with a specificity for the claudin (VL(CLDN)); and
wherein
each VH(CLDN) comprises:
a HCDR1 having the amino acid sequence set forth in SEQ ID NO: 44,
a HCDR2 having the amino acid sequence set forth in SEQ ID NO: 45, and
a HCDR3 having the amino acid sequence set forth in SEQ ID NO: 46; and
each VL(CLDN) comprises:
a LCDR1 having the amino acid sequence set forth in SEQ ID NO: 50,
a LCDR2 having the amino acid sequence set forth in SEQ ID NO: 51, and
a LCDR3 having the amino acid sequence set forth in SEQ ID NO: 52; and wherein each VH(CLDN) comprises the amino acid sequence set forth in SEQ ID NO: 8 and each VL(CLDN) comprises the amino acid sequence set forth in SEQ ID NO: 9 or a variant thereof, wherein said variant comprises no more than two amino acid substitutions relative to SEQ ID NO: 9.

2. The nucleic acid of claim 1, wherein said variant of SEQ ID NO: 9 comprises two amino acid substitutions relative to SEQ ID NO: 9.

3. The nucleic acid of claim 2, wherein VH(T) comprises the amino acid sequence set forth in SEQ ID NO: 5 and VL(T) comprises the amino acid sequence set forth in SEQ ID NO: 6.

4. The nucleic acid of claim 1, wherein the first polypeptide further comprises a constant domain 1 of a heavy chain of an immunoglobulin (CH1) and the second polypeptide further comprises a constant domain of a light chain of an immunoglobulin (CL), wherein both domains are able to associate.

5. The nucleic acid of claim 4, wherein, in the first polypeptide and the second polypeptide, the VH domain(s), the VL domain(s), the CH1 domain and the CL domain are arranged, from N-terminus to C-terminus, in the order
a. VH(T)-CH1-VH(CLDN)-VL(CLDN) and VL(T)-CL-VH(CLDN)-VL(CLDN); or
b. VH(T)-CH1-VL(CLDN)-VH(CLDN) and VL(T)-CL-VL(CLDN)-VH(CLDN).

6. The nucleic acid of claim 5, wherein VH(T) comprises the amino acid sequence set forth in SEQ ID NO: 5 and VL(T) comprises the amino acid sequence set forth in SEQ ID NO: 6.

7. The nucleic acid of claim 5, wherein said variant of SEQ ID NO: 9 comprises two amino acid substitutions relative to SEQ ID NO: 9.

8. The nucleic acid of claim 5, wherein the VH-VL or VL-VH domains are connected to the CH1 domain or CL domain via a peptide linker.

9. The nucleic acid of claim 5, wherein the VH and VL domains are connected via a peptide linker to form the VH-VL or VL-VH domains.

10. A nucleic acid encoding a binding agent comprising at least three binding domains, wherein a first binding domain binds to a T cell-specific antigen and a second binding domain and a third binding domain bind to a claudin, wherein the binding agent comprises
 (a) a first polypeptide comprising a VH domain with a specificity for the T cell-specific antigen (VH(T)), a VH domain with a specificity for the claudin (VH(CLDN)) and a VL domain with a specificity for the claudin (VL(CLDN)); and
 (b) a second polypeptide comprising a VL domain with a specificity for the T cell-specific antigen (VL(T)), a VH domain with a specificity for the claudin (VH(CLDN)) and a VL domain with a specificity for the claudin (VL(CLDN)); and
 wherein
  each VH(CLDN) comprises:
   a HCDR1 having the amino acid sequence set forth in SEQ ID NO: 44,
   a HCDR2 having the amino acid sequence set forth in SEQ ID NO: 45, and
   a HCDR3 having the amino acid sequence set forth in SEQ ID NO: 46; and
  each VL(CLDN) comprises:
   a LCDR1 having the amino acid sequence set forth in SEQ ID NO: 50,
   a LCDR2 having the amino acid sequence set forth in SEQ ID NO: 51, and
   a LCDR3 having the amino acid sequence set forth in SEQ ID NO: 52, and
 wherein
  VH(T) comprises:
   a HCDR1 of positions 26-33 of SEQ ID NO: 5 (GYTFTRYT),
   a HCDR2 of positions 51-58 of SEQ ID NO: 5 (INPSRGYT), and
   a HCDR3 of positions 97-108 of SEQ ID NO: 5 (ARYYDDHYSLDY); and
  VL(T) comprises:
   a LCDR1 of positions 27-31 of SEQ ID NO: 6 (SSVSY),
   a LCDR2 of positions 49-51 of SEQ ID NO: 6 (DTS), and
   a LCDR3 of positions 88-96 of SEQ ID NO: 6 (QQWSSNPLT); and
 wherein the first polypeptide comprises the amino acid sequence set forth in SEQ ID NO: 17 or a variant thereof and the second polypeptide comprises the amino acid sequence set forth in SEQ ID NO: 19 or a variant thereof, wherein said variant of SEQ ID NO: 17 consists of one amino acid substitution relative to SEQ ID NO: 17 and wherein said variant of SEQ ID NO: 19 consists of one amino acid substitution relative to SEQ ID NO: 19.

11. A nucleic acid encoding a binding agent comprising at least three binding domains, wherein a first binding domain binds to a T cell-specific antigen and a second binding domain and a third binding domain bind to a claudin, wherein the binding agent comprises
 (a) a first polypeptide comprising a VH domain with a specificity for the T cell-specific antigen (VH(T)), a VH domain with a specificity for the claudin (VH(CLDN)) and a VL domain with a specificity for the claudin (VL(CLDN)); and
 (b) a second polypeptide comprising a VL domain with a specificity for the T cell-specific antigen (VL(T)), a VH domain with a specificity for the claudin (VH(CLDN)) and a VL domain with a specificity for the claudin (VL(CLDN));
 wherein
  each VH(CLDN) comprises:
   a HCDR1 having the amino acid sequence set forth in SEQ ID NO: 44,
   a HCDR2 having the amino acid sequence set forth in SEQ ID NO: 45, and
   a HCDR3 having the amino acid sequence set forth in SEQ ID NO: 46; and
  each VL(CLDN) comprises:
   a LCDR1 having the amino acid sequence set forth in SEQ ID NO: 50,
   a LCDR2 having the amino acid sequence set forth in SEQ ID NO: 51, and
   a LCDR3 having the amino acid sequence set forth in SEQ ID NO: 52; and
 wherein
  VH(T) comprises:
   a HCDR1 of positions 26-33 of SEQ ID NO: 5 (GYTFTRYT),
   a HCDR2 of positions 51-58 of SEQ ID NO: 5 (INPSRGYT), and
   a HCDR3 of positions 97-108 of SEQ ID NO: 5 (ARYYDDHYSLDY); and
  VL(T) comprises:
   a LCDR1 of positions 27-31 of SEQ ID NO: 6 (SSVSY),
   a LCDR2 of positions 49-51 of SEQ ID NO: 6 (DTS), and
   a LCDR3 of positions 88-96 of SEQ ID NO: 6 (QQWSSNPLT); and
 wherein the first polypeptide comprises the amino acid sequence set forth in SEQ ID NO: 17 or a variant thereof and the second polypeptide comprises the amino acid sequence set forth in SEQ ID NO: 19 or a variant thereof, wherein said variant of SEQ ID NO: 17 has a degree of identity of at least 95% to SEQ ID NO: 17 and wherein said variant of SEQ ID NO: 19 has a degree of identity of at least 95% to SEQ ID NO: 19.

12. A nucleic acid encoding a binding agent comprising at least three binding domains, wherein a first binding domain binds to a T cell-specific antigen and a second binding domain and a third binding domain bind to a claudin, wherein:
 (a) the first binding domain specifically binds human CD3 and comprises a first heavy chain variable domain and a first light chain variable domain;
 (b) the second binding domain specifically binds human claudin 6 (CLDN6) and comprises a second heavy chain variable domain and a second light chain variable domain; and
 (c) the third binding domain specifically binds human CLDN6 and comprises a third heavy chain variable domain and a third light chain variable domain; and wherein
  each of the second heavy chain variable domain and the third heavy chain variable domain comprises:
    a HCDR1 having the amino acid sequence set forth in SEQ ID NO: 44,
    a HCDR2 having the amino acid sequence set forth in SEQ ID NO: 45, and
    a HCDR3 having the amino acid sequence set forth in SEQ ID NO: 46; and
  each of the second light chain variable domain and the third light chain variable domain comprises:
    a LCDR1 having the amino acid sequence set forth in SEQ ID NO: 50,
    a LCDR2 having the amino acid sequence set forth in SEQ ID NO: 51, and
    a LCDR3 having the amino acid sequence set forth in SEQ ID NO: 52; and
  wherein the second and third heavy chain variable domains each comprise the amino acid sequence set forth in SEQ ID NO: 8 and the second and third light chain variable domains each comprise the amino acid sequence set forth in SEQ ID NO: 9 or a variant thereof, wherein said variant comprises no more than two amino acid substitutions relative to SEQ ID NO: 9.

13. The nucleic acid of claim 12, wherein said variant of SEQ ID NO: 9 comprises two amino acid substitutions relative to SEQ ID NO: 9.

14. The nucleic acid of claim 13, wherein the first heavy chain variable domain comprises the amino acid sequence set forth in SEQ ID NO: 5 and the first light chain variable domain comprises the amino acid sequence set forth in SEQ ID NO: 6.

15. The nucleic acid of claim 12, wherein the first heavy chain variable domain comprises the amino acid sequence set forth in SEQ ID NO: 5 and the first light chain variable domain comprises the amino acid sequence set forth in SEQ ID NO: 6.

16. A host cell comprising the nucleic acid of claim 12.

17. The nucleic acid of claim 5, wherein the VH-VL or VL-VH domains are connected to the CH1 domain or CL domain via a peptide linker comprising the amino acid sequence $DVPG_2S$ (SEQ ID NO: 67) or $SGPG_3RS(G_4S)_2$ (SEQ ID NO: 66).

18. The nucleic acid of claim 5, wherein the VH and VL domains are connected via a peptide linker to form the VH-VL or VL-VH domains, wherein the peptide linker comprises the amino acid sequence $(G_4S)_x$ (SEQ ID NO: 70), wherein x is 3, 4, 5 or 6.

19. A host cell comprising the nucleic acid of claim 10.

20. A host cell comprising the nucleic acid of claim 11.

21. The nucleic acid of claim 1, wherein the first polypeptide and the second polypeptide are encoded on different nucleic acids.

22. The nucleic acid of claim 1, wherein the first polypeptide and the second polypeptide are encoded on the same nucleic acid.

23. The nucleic acid of claim 10, wherein the first polypeptide and the second polypeptide are encoded on different nucleic acids.

24. The nucleic acid of claim 10, wherein the first polypeptide and the second polypeptide are encoded on the same nucleic acid.

25. The nucleic acid of claim 11, wherein the first polypeptide and the second polypeptide are encoded on different nucleic acids.

26. The nucleic acid of claim 11, wherein the first polypeptide and the second polypeptide are encoded on the same nucleic acid.

27. The nucleic acid of claim 1, wherein
  VH(T) comprises:
    a HCDR1 of positions 26-33 of SEQ ID NO: 5 (GYTFTRYT),
    a HCDR2 of positions 51-58 of SEQ ID NO: 5 (INPSRGYT), and
    a HCDR3 of positions 97-108 of SEQ ID NO: 5 (ARYYDDHYSLDY); and
  VL(T) comprises:
    a LCDR1 of positions 27-31 of SEQ ID NO: 6 (SSVSY),
    a LCDR2 of positions 49-51 of SEQ ID NO: 6 (DTS), and
    a LCDR3 of positions 88-96 of SEQ ID NO: 6 (QQWSSNPLT).

28. The nucleic acid of claim 12, wherein
  the first heavy chain variable domain comprises:
    a HCDR1 of positions 26-33 of SEQ ID NO: 5 (GYTFTRYT),
    a HCDR2 of positions 51-58 of SEQ ID NO: 5 (INPSRGYT), and
    a HCDR3 of positions 97-108 of SEQ ID NO: 5 (ARYYDDHYSLDY); and
  the first light chain variable domain comprises:
    a LCDR1 of positions 27-31 of SEQ ID NO: 6 (SSVSY),
    a LCDR2 of positions 49-51 of SEQ ID NO: 6 (DTS), and
    a LCDR3 of positions 88-96 of SEQ ID NO: 6 (QQWSSNPLT).

29. The nucleic acid of claim 1, which is in the form of a vector or in the form of RNA.

30. A host cell comprising the nucleic acid of claim 1.

31. The nucleic acid of claim 1, wherein VH(T) comprises the amino acid sequence set forth in SEQ ID NO: 5 and VL(T) comprises the amino acid sequence set forth in SEQ ID NO: 6.

32. The nucleic acid of claim 12, wherein the first heavy chain variable domain comprises the amino acid sequence set forth in SEQ ID NO: 5 and the first light chain variable domain comprises the amino acid sequence set forth in SEQ ID NO: 6.

* * * * *